United States Patent
Ratcliffe et al.

(10) Patent No.: US 7,148,215 B2
(45) Date of Patent: Dec. 12, 2006

(54) CHEMICAL COMPOUNDS

(75) Inventors: Andrew James Ratcliffe, Brentwood (GB); Roger John Aitchison Walsh, Chelmsford (GB); Tahir Nadeem Majid, Hoboken, NJ (US); Sukanthini Thurairatnam, Bedminster, NJ (US); Shelley Amendola, Bedminster, NJ (US); David John Aldous, Gillette, NJ (US); John Edward Souness, Morristown, NJ (US); Conception Nemecek, Thiais (FR); Sylvie Wentzler, Fresnes (FR); Corinne Venot, Paris (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 10/803,566

(22) Filed: Mar. 18, 2004

(65) Prior Publication Data

US 2005/0009831 A1 Jan. 13, 2005

Related U.S. Application Data

(63) Continuation of application No. PCT/EP02/11131, filed on Sep. 17, 2002.

(60) Provisional application No. 60/355,860, filed on Feb. 11, 2002.

(30) Foreign Application Priority Data

Sep. 19, 2001 (GB) .................................. 0122560.6

(51) Int. Cl.
| | | |
|---|---|---|
| *A01N 43/62* | (2006.01) | |
| *A01N 43/58* | (2006.01) | |
| *A01N 43/60* | (2006.01) | |
| *A61N 31/55* | (2006.01) | |
| *A61N 31/50* | (2006.01) | |

(52) U.S. Cl. ...................... 514/221; 514/249; 514/393; 540/476; 540/579; 540/580; 544/349; 548/302.7

(58) Field of Classification Search ................ 514/221, 514/249, 393; 540/476, 579, 580; 544/349; 548/302.7

See application file for complete search history.

(56) References Cited

FOREIGN PATENT DOCUMENTS

| IT | 1214644 | 9/1985 |
| JP | 57-123183 | 7/1982 |
| JP | 07-053511 | 2/1995 |
| WO | WO 01/72752 | * 10/2001 |
| WO | WO 03/024967 | 3/2003 |

OTHER PUBLICATIONS

Al-Dabbagh and Smith, "Species differences in oxidative drug metabolism: some basic considerations." Archives of toxicology. Supplement. Archiv fur Toxikologie. supplement, vol. 7, pp. 219-231 (1984).*

(Continued)

*Primary Examiner*—James O. Wilson
*Assistant Examiner*—Zachary C. Tucker
(74) *Attorney, Agent, or Firm*—James W. Bolcsak

(57) ABSTRACT

The present invention concerns compounds of general formula (I):

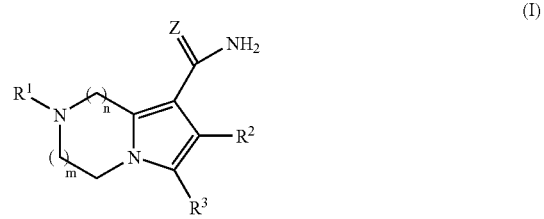

in which the substituents are as described herein.

10 Claims, 1 Drawing Sheet

: Neurotoxic effect of LY294002.

These 2 graphs represent typical experiments. Each point is the mean of six different wells.
The control corresponds to cells that have only received buffer.

OTHER PUBLICATIONS

Hans Bundgaard, Design of Prodrugs, p. 1. © 1985 Elsevier Science Publishers.*

Richard B. Silverman, The Organic Chemistry of Drug Design and Drug Action, pp. 352-400. © 1992 Academic Press, Inc.*

Vippagunta et al, "Crystalline Solids" Advanced Drug Delivery Reviews, vol. 48, pp. 3-26 (2001).*

Gavezzotti, "Are Crystal Structures Predictable?" Accounts of Chemical Research, vol. 27, pp. 309-314 (1994).*

Kennedy et al, "Suppresion of Ras-stimulated transformation by the JNK signal transduction pathway" Genes & Development, vol. 17, pp. 629-637 (2003).*

Harper and LoGrasso, "Inhibitors of the JNK Signaling Pathways" Drugs of the Future, vol. 26(10), pp. 957-973 (2001).*

Manning and Davis, "Targeting JNK for Therapeutic Benefit: From Junk to Gold?" Nature, vol. 2, pp. 554-565 (Jul. 2003).*

J.R. Ross et al., Synthesis of a Series of Pyrole-1-Acetic Acids as Potential Antiinflammatory Agents, Journal Heterocycl. Chem (1987, pp. 757-765, vol. 24-Issue 3).

* cited by examiner

Figure 1 : Neurotoxic effect of LY294002.
Figure 2 : Protective effect of Example 9(a) against LY294002-induced toxicity.
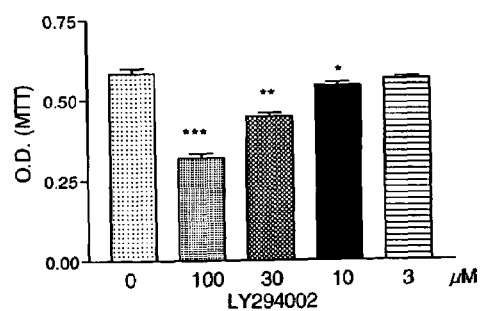
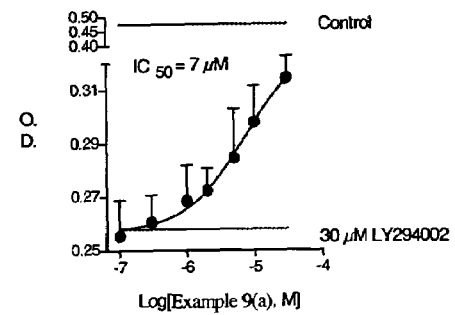
These 2 graphs represent typical experiments. Each point is the mean of six different wells.
The control corresponds to cells that have only received buffer.

CHEMICAL COMPOUNDS

This application is a Continuation of PCT Application No. PCT/EP02/11131, filed Sep. 17, 2002. Priority is claimed from British Application No. GB0122560.6, filed Sep. 19, 2001; and from U.S. Provisional Application No. 60/355,860, filed Feb. 11, 2002. The foregoing applications are hereby incorporated by reference into the present application.

This invention is directed to indolizines, their preparation, pharmaceutical compositions containing these compounds, and their pharmaceutical use in the treatment of disease states capable of being modulated by the inhibition of JNK activity. These disease states include inflammatory and proliferative disorders as well as those in which tissue degeneration occurs as a consequence of excessive metalloproteinase release and/or apoptosis.

The present invention concerns too particularly novel indolizine derivatives with inhibitory effects towards kinase proteins. Such kinase proteins belong especially to the following group: EGFR, Fak, FLK-1, FGFR1, FGFR2, FGFR3, FGFR4, FGFR5, flt-1, IGF-1R, KDR, PDGFR, tie2, and VEGFR. The indolizines of the present patent application may thus especially be used for preventing or treating diseases that may be modulated by the inhibition of such kinase proteins and particularly solid tumours.

Many proteins including cytokines, adhesion molecules and proteolytic enzymes contribute to the pathology of chronic inflammatory disorders. During inflammation, the transcription and synthesis of inflammatory proteins is increased. This is achieved by the activation of several families of proteins called transcription factors which bind to specific regions of the DNA juxtaposed to the gene to induce transcription and consequently synthesis of the protein.

The Jun family of transcription factors is involved in controlling the transcription of important pro-inflammatory proteins including tumour necrosis factor (TNF), interleukin (IL)-2, γ-interferon and E-selectin.

Jun family members form homodimers and heterodimers with other transcription factors, notably members of the fos family to form an AP-1 binding complex. Recent reports indicate that c-Jun also forms heterodimers with ATF-2 and can interact with the p50/p65 subunits of NF-κB. These complexes bind to consensus sequences upstream of the promoters of genes of pro-inflammatory proteins to direct transcription.

Phosphorylation on two serine residues ($Ser^{63}$, $Ser^{73}$) at the N-terminus of c-Jun greatly increases its ability to induce transcription of pro-inflammatory proteins, a process known as transactivation. Upon exposure of cells to a variety of stress—(heat, U.V. light, osmotic stress etc) and inflammatory-stimuli, phosphorylation of c-Jun is increased. An AP-1 site lies in the promotor region of cJun and the same stimuli that increase c-Jun phosphorylation also cause an increase in the intracellular levels of this transcription factor. This, in turn, induces the expression of pro-inflammatory cytokines which possess sites in their upstream promoters which bind homo- or hetero-dimers of c-Jun and related proteins.

N-terminal phosphorylation and transactivation of c-Jun is a consequence of the activation of c-Jun-N-terminal kinase (JNK), the only enzyme known to possess this activity. Upon exposure of cells to a variety of inflammatory stimuli, JNK is activated and migrates to the nucleus where it phosphorylates c-Jun and induces the expression of pro-inflammatory genes. As well as inflammatory agents, a number of cellular stresses (heat, U.V. light, osmotic stress etc) activate JNK, hence the alternative name of this enzyme family, stress-activated protein kinase (SAPK). JNK is phosphorylated and activated following the triggering of a kinase cascade (stress-activated protein kinase cascade) by inflammatory stimuli, with the final step being catalysed by upstream MAP kinase kinases (MKK)4 and/or 7. There are three distinct JNK genes, JNK-1, JNK-2 and JNK-3. There are four splice of variants each of both JNK-1 and JNK-2 and two of JNK-3. JNK-1 and JNK-2 are widely distributed while JNK-3 is localised predominantly in the brain.

The expression of important pro-inflammatory cytokines including TNF as well as proteolytic enzymes and adhesion molecules is regulated by AP-1-sites or other consensus sequences to which c-Jun binds that are present in the upstream promotor of these genes. Lipopolysaccharide (LPS), which stimulates release of TNF and other pro-inflammatory proteins, increases JNK activity as well as cJun phosphorylation and expression. Furthermore, LPS increases the binding of c-Jun to AP-1 and other sites that appear to be essential for full expression of pro-inflammatory proteins. c-Jun phosphorylation also plays an important role in signalling by TNF and other pro-inflammatory cytokines. JNK activation, phosphorylation of c-Jun, c-Jun binding to an AP-1 site in the promoter of target genes and AP-1-dependent transcriptional activity are also induced in certain cell-types such as fibroblasts by TNF itself. JNK is also important in regulating the synthesis of metalloproteinases that contribute to the pathology of diseases such as rheumatoid arthritis. Knockout mice lacking JNK-3 show reduced apoptosis of hippocampal neurons and a reduced incidence of seizures induced by kainic acid, a glutamate-receptor agonist. Furthermore, knockout mice that lack the N-terminal phosphorylation sites on c-Jun are similarly resistant to the apoptosis of hippocampal neurons and seizures induced by kainic acid. JNK-3 and c-Jun phosphorylation are therefore of significant medical interest in disorders in which neuronal damage occurs, such as stroke. In addition, JNK inhibitors are also of value in other diseases and disorders in which neuronal damage occurs as a consequence of JNK activation occurring as a consequence of aberrant signaling, abnormal protein processing, deprivation of growth factors, osmotic changes and free-radical generation. These include Alzheimer's disease, Parkinson's disease, and Huntington's disease as well as brain trauma and neuronal damage resulting from cardiac surgery or cardiac arrest.

Thus, inhibition of JNK activity and suppression of cJun phosphorylation is a very attractive target to inhibit release of and responses to pro-inflammatory cytokines such as TNF, production of metalloproteinases and neuronal apoptosis. Compounds which inhibit JNK will be useful for the treatment of inflammatory diseases in which TNF plays a major pathological role as well as diseases in which tissue distruction occurs as a consequence of excessive metalloproteinase release and apoptosis.

TNF is an important pro-inflammatory cytokine which causes hemorrhagic necrosis of tumours and possesses other important biological activities. TNF is released by activated macrophages, activated T-lymphocytes, natural killer cells, mast cells and basophils, fibroblasts, endothelial cells and brain astrocytes among other cells.

The principal in vivo actions of TNF can be broadly classified as inflammatory and catabolic. It has been implicated as a mediator of endotoxic shock, inflammation of joints and of the airways, immune deficiency states, allograft rejection, and in the cachexia associated with malignant disease and some parasitic infections. In view of the association of high serum levels of TNF with poor prognosis in sepsis, graft versus host disease and adult respiratory distress syndrome, and its role in many other immunologic processes, this factor is regarded as an important mediator of general inflammation.

TNF primes or activates neutrophils, eosinophils, and endothelial cells to release tissue damaging mediators such as adhesion molecules. In fibroblasts, TNF stimulates the production of collagenase, an enzyme implicated in the joint destruction in rheumatoid arthritis. TNF also activates monocytes, macrophages and T-lymphocytes to cause the production of colony stimulating factors and other pro-inflammatory cytokines such IL-1, IL-6, IL-8 and GM-CSF, which in some case mediate the end effects of TNF. The ability of TNF to activate T-lymphocytes, monocytes, macrophages and related cells has been implicated in the progression of Human Immunodeficiency Virus (HIV) infection. In order for these cells to become infected with HIV and for HIV replication to take place the cells must be maintained in an activated state. Cytokines such as TNF have been shown to activate HIV replication in monocytes and macrophages. Features of endotoxic shock such as fever, metabolic acidosis, hypotension and intravascular coagulation are thought to be mediated through the actions of TNF on the hypothalamus and in reducing the anti-coagulant activity of vascular endothelial cells. The cachexia associated with certain disease states is mediated through indirect effects on protein catabolism. TNF also promotes bone resorption and acute phase protein synthesis.

TNF-alpha inhibits surfactant protein C gene transcription, which may contribute to abnormalities of surfactant homeostasis associated with pulmonary injury and infection, induces mucin hypersecretion and mediates the recruitment of neutrophils and eosinophils during airway inflammation. Although TNF-alpha inhibits collagen synthesis in fibroblasts, a number of studies point to it being pro-fibrotic in vivo. Thus, by inhibiting TNF-alpha production, the compounds of the invention have potential in suppressing the airways remodelling that occurs in asthma.

Myocyte apoptosis occurs in myocardial infarction and heart failure. Locally produced cytokines such as Fas or TNFα may contribute to myocyte apoptosis and are upregulated in failing myocardium. In addition, TNFα may play a role in heart failure through it's ability to stimulate remodelling and inhibit contractility. Strategies to inhibit TNFα may be therapeutically useful in heart failure and myocardial infarction. Thus, the compounds of the invention, by inhibiting TNFα release and apoptosis, have potential in the in the treatment of myocardial infarction and heart failure.

The discussion herein relates to disease states associated with TNF including those disease states related to the production of TNF itself, and disease states associated with other cytokines, such as, but not limited to IL-1 or IL-6, that are modulated by associated with TNF. For Example, a IL-1 associated disease state, where IL-1 production or action is exacerbated or secreted in response to TNF, would therefore be considered a disease state associated with TNF. TNF-alpha and TNF-beta are also herein referred to collectively as "TNF" unless specifically delineated otherwise, since there is a close structural homology between TNF-alpha (cachectin) and TNF-beta (lymphotoxin) and each of them has a capacity to induce similar biological responses and bind to the same cellular receptor.

We have now found a novel group of indolizines which have valuable pharmaceutical properties, in particular the ability to inhibit JNK, cJun phosphorylation and the consequential effect in suppressing the expression of proteins (for Example TNF) involved in mediating inflammatory and proliferative disorders.

The present invention concerns then particularly compounds capable to inhibit protein kinases.

Protein kinases participate in the signalling events which control the activation, growth and differentiation of cells in response to extracellular mediators and to changes in the environment. In general, these kinases fall into several groups; those which preferentially phosphorylate serine and/or threonine residues and those which preferentially phosphorylate tyrosine residues [S. K. Hanks and T. Hunter, FASEB. J., 1995, 9, pages 576–596]. The serine/threonine kinases include for Example, protein kinase C isoforms [A. C. Newton, J. Biol. Chem., 1995, 270, pages 28495–28498] and a group of cyclin-dependent kinases such as cdc2 [J. Pines, Trends in Biochemical Sciences, 1995, 18, pages 195–197]. The tyrosine kinases include membrane-spanning growth factor receptors such as the epidermal growth factor receptor [S. Iwashita and M. Kobayashi, Cellular Signalling, 1992, 4, pages 123–132], and cytosolic non-receptor kinases such as p56tck, p59fYn, ZAP-70 and csk kinases [C. Chan et. al., Ann. Rev. Immunol., 1994, 12, pages 555–592].

Inappropriately high protein kinase activity has been implicated in many diseases resulting from abnormal cellular function. This might arise either directly or indirectly, for Example by failure of the proper control mechanisms for the kinase, related for Example to mutation, over-expression or inappropriate activation of the enzyme; or by over- or underproduction of cytokines or growth factors also participating in the transduction of signals upstream or downstream of the kinase. In all of these instances, selective inhibition of the action of the kinase might be expected to have a beneficial effect.

The type 1 insulin-like growth factor receptor (IGF-I-R) is a transmembrane receptor tyrosine kinase that binds primarily to IGF-I but also to IGF-II and insulin with lower affinity. Binding of IGF-I to its receptor results in receptor oligomerization, activation of tyrosine kinase, intermolecular receptor autophosphorylation and phosphorylation of cellular substrates (major substrates are IRS 1 and Shc). The ligand-activated IGF-I-R induces mitogenic activity in normal cells. Meanwhile IGF-I-R plays also an important role in abnormal growth.

Several clinical reports underline the important role of the IGF-I pathway in human tumor development:

IGF-I-R overexpression is frequently found in various tumors (breast, colon, lung, sarcoma . . . ) and is often associated with an aggressive phenotype.

High circulating IGF1 concentrations are strongly correlated with prostate, lung and breast cancer risk.

Furthermore, IGF-I-R requirement for establishment and maintenance of the transformed phenotype in vitro and in vivo has been largely documented [Baserga R, Exp. Cell. Res., 1999, 253, pages 1–6]. The kinase activity of IGF-I-R is essential for the transforming activity of several oncogenes: EGFR, PDGFR, SV40 T antigen, activated Ras, Raf, and v-Src. The expression of IGF-I-R in normal fibroblasts induces neoplastic phenotypes, which can then form tumor in vivo. IGF-I-R expression plays an important role in anchorage-independent growth. IGF-I-R has also been shown to protect cells from chemotherapy-, radiation-, and cytokine-induced apoptosis. Conversely, inhibition of endogenous IGF-I-R by dominant negative IGF-I-R, triple helix formation or antisense expression vector has been shown to repress transforming activity in vitro and tumor growth in animal models.

Focal adhesion kinase (FAK) is a non-receptor tyrosine kinase involved in integrin-mediated signal transduction pathways. FAK colocalizes with integrins in focal contact sites and FAK activation and its tyrosine phosphorylation have been shown in many cell types to be dependent on integrins binding to their extracellular ligands. Results from several studies support the hypothesis that FAK inhibitors could be useful in cancer treatment. For Example, Fak-deficient cells migrate poorly in response to chemotactic signals and overexpression of FAK C-terminal dominant negative construct blocks cell spreading as well as chemotactic migration (Sieg et al, J. Cell Science, 1999, 112, 2677–2691; Richardson A. and Parsons T., Cell, 1997, 97, 221–231); in addition, tumor cells treated with FAK antisense oligonucleotides lost their attachment and underwent apoptosis (Xu et al, Cell Growth Differ. 1996, 4, 413–418). FAK has been reported to be overexpressed in many tumor types as prostate, breast, thyroid, colon lung, brain and melanoma cancers. In addition, the level of expression of FAK is directly correlated with tumors demonstrating the most aggressive phenotype.

One subject of the invention is thus novel indolizines derivatives with inhibitory effects towards kinase proteins.

The indolizines of the present patent application may thus especially be used for preventing or treating diseases that may be modulated by the inhibition of kinase proteins.

Such kinase proteins belong especially to the following group: EGFR, Fak, FLK-1, FGFR1, FGFR2, FGFR3, FGFR4, FGFR5, flt-1, IGF-1R, KDR, PDGFR, tie2, VEGFR.

Mention is made particularly of the kinase protein IGF1-R.

Mention is made particularly of the kinase protein FAK.

The inhibition or regulation of such kinases proteins thus provides a powerful new mechanism of action for the treatment of a large number of solid tumours.

The present patent application thus relates particularly to novel inhibitors of the IGF-1R receptor that may be used especially for treatment in oncology.

The present patent application thus relates particularly to novel inhibitors of the FAK receptor that may be used especially for treatment in oncology.

The products of the present patent application as IGF-1R inhibitors may be used especially for the treatment or prevention of diseases chosen from the following group: cancers, especially breast, colon, lung and prostate cancer.

The products of the present patent application as FAK inhibitors may be used especially for the treatment or prevention of diseases chosen from the following group: cancers, especially breast, colon, lung and prostate cancer.

Thus, according to one aspect of the present invention, we provide the compounds of general formula (I):

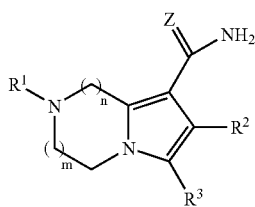

(I)

optionally further substituted in the saturated ring by one or more alkyl substituents, in which:

$R^1$ represents hydrogen, $R^4$, —C(=Y)—NHR$^4$, —SO$_2$NHR$^4$, —C(=Z$^1$)—R$^4$, —SO$_2$—R$^4$ or —C(=Z$^1$)—OR$^4$;

$R^2$ represents hydrogen, cyano, halogen or —C≡C—R$^5$;

$R^3$ represents hydrogen, acyl, alkoxycarbonyl, alkyl, aroyl, aryl, aryloxycarbonyl, carboxy, cycloalkenyl, cycloalkyl, heteroaroyl, heteroaryl, heterocycloalkyl or —C(=O)—NY$^1$Y$^2$;

$R^4$ represents alkyl, cycloalkyl, cycloalkenyl or heterocycloalkyl each optionally substituted by one or more groups selected from aryl, cycloalkenyl, cycloalkyl, heteroaryl, heterocycloalkyl, —C(=O)—OR$^8$, —C(=O)—R$^9$, —C(=O)—NY$^3$Y$^4$, —NY$^1$Y$^2$, —N(R$^{10}$)—C(=O)—R$^9$, —N(R$^{10}$)—C(=O)—OR$^9$, —N(R$^{10}$)—SO$_2$—R$^9$ or -Z$^2$R$^8$; or R$^4$ represents aryl or heteroaryl each optionally substituted by one or more groups selected from alkylenedioxy, alkenyl, alkenyloxy, alkynyl, aryl, cyano, halo, hydroxy, heteroaryl, heterocycloalkyl, nitro, R$^7$, —C(=O)—NY$^3$Y$^4$, —C(=O)—OR$^8$, —C(=O)—R$^{11}$, —NY$^3$Y$^4$, —N(R$^{10}$)—C(=O)—R$^9$, —N(R$^{10}$)—C(=O)—NY$^5$Y$^6$, —N(R$^{10}$)—C(=O)—OR$^9$, —N(R$^{10}$)—SO$_2$—R$^9$, —N(R$^{10}$)—SO$_2$—NY$^5$Y$^6$, —SO$_2$—NY$^3$Y$^4$ and -Z$^2$R$^{12}$;

$R^5$ represents hydrogen or alkyl;

$R^6$ represents alkyl, acyl, alkoxycarbonyl, alkylsulfonyl, aryl, arylsulfonyl, aroyl, cycloalkyl, cycloalkenyl, heteroaryl, heteroarylsulfonyl, heteroaroyl and heterocycloalkyl;

$R^7$ represents alkyl, cycloalkyl or cycloalkylalkyl each optionally substituted by one or more substituents selected from aryl, cycloalkyl, cyano, halo, heteroaryl, heterocycloalkyl, hydroxy, —CHO (or a 5-, 6- or 7-membered cyclic acetal derivative thereof), —C(=O)—NY$^1$Y$^2$, —C(=O)—OR$^8$, —NY$^3$Y$^4$, —N(R$^{10}$)—C(=O)—R$^9$, —N(R$^{10}$)—C(=O)—NY$^3$Y$^4$, —N(R$^{10}$)—SO$_2$—R$^9$, —N(R$^{10}$)—SO$_2$—NY$^3$Y$^4$ and —OR$^9$;

$R^8$ represents hydrogen, alkyl, alkenyl, aryl, arylalkyl, heteroaryl or heteroarylalkyl;

$R^9$ represents alkyl, aryl, arylalkyl, cycloalkyl, cycloalkylalkyl, heteroaryl, heteroarylalkyl, heterocycloalkyl or heterocycloalkylalkyl;

$R^{10}$ represents hydrogen or lower alkyl;

$R^{11}$ represents alkyl, aryl, arylalkyl, cycloalkyl, cycloalkylalkyl, heteroaryl, heteroarylalkyl, heterocycloalkyl or heterocycloalkylalkyl; or alkyl optionally substituted by —NY$^1$Y$^2$;

$R^{12}$ represents aryl or heteroaryl; or alkyl, cycloalkyl, cycloalkylalkyl, heterocycloalkyl or heterocycloalkylalkyl each optionally substituted by one or more substituents selected from aryl, cycloalkyl, cyano, halo, heteroaryl, heterocycloalkyl, hydroxy, —CHO (or a 5-, 6- or 7-membered cyclic acetal derivative thereof), —C(=O)—NY$^1$Y$^2$, —C(=O)—OR$^8$, —NY$^1$Y$^2$, —N(R$^{10}$)—C(=O)—R$^9$, —N(R$^{10}$)—C(=O)—NY$^3$Y$^4$, —N(R$^{10}$)—SO$_2$—R$^9$, —N(R$^{10}$)—SO$_2$—NY$^3$Y$^4$ and —OR$^9$;

Y represents O, S or NCN;

$Y^1$ and $Y^2$ are independently hydrogen, alkyl, aryl, cycloalkyl, cycloalkenyl, heteroaryl or heterocycloalkyl; or the group —NY$^1$Y$^2$ may form 5-7 membered ring which optionally contains an additional heteroatom selected from O, S or NR$^6$;

$Y^3$ and $Y^4$ are independently hydrogen, alkenyl, aryl, cycloalkyl, heteroaryl or alkyl optionally substituted by one or more groups selected from aryl, halo, heteroaryl, hydroxy, —C(=O)—NY$^5$Y$^6$, —C(=O)—OR$^8$, —NY$^5$Y$^6$, —N(R$^6$)—C(=O)R$^9$, —N(R$^6$)—C(=O)—NY$^5$Y$^6$, —N(R$^6$)—SO$_2$—R$^9$, —N(R$^6$)—SO$_2$—NY$^5$Y$^6$ and —OR$^9$; or the group —NY$^3$Y$^4$ may form a cyclic amine;

Y$^5$ and Y$^6$ are independently hydrogen, alkenyl, alkyl, aryl, arylalkyl, cycloalkyl, heteroaryl or heteroarylalkyl; or the group —NY$^5$Y$^6$ may form a cyclic amine;

Z represents O or S;

Z$^1$ represents O or S;

Z$^2$ represents O or S(O)$_p$;

n is zero or an integer 1 or 2;

m is 1 or 2;

p is 1 or 2;

and their corresponding N-oxides, and their prodrugs; and pharmaceutically acceptable salts and solvates (e.g. hydrates) of such compounds and their N-oxides and their prodrugs; optionally together with one or more pharmaceutically acceptable carriers or excipients.

BRIEF DESCRIPTION OF THE DRAWINGS

FIG. 1 is a depiction of the neurotoxic effect of LY294002.

FIG. 2 is a depiction of the protective effect of the compound of Example 9(a) against LY294002 induced toxicity.

As used above, and throughout the description of the invention, the following terms, unless otherwise indicated, shall be understood to have the following meanings:

"Acyl" means an H—CO— or alkyl-CO— or cycloalkenyl-CO— or cycloalkyl-CO— or heterocycloalkyl-CO— group in which the alkyl, cycloalkyl, cycloalkenyl and heterocycloalkyl moieties are as described herein.

"Acylamino" is an acyl-NH— group wherein acyl is as defined herein.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably 2 to about 6 carbon atoms (e.g. 2 to 4 carbon atoms) in the chain. "Branched," as used herein and throughout the text, means that one or more lower alkyl groups such as methyl, ethyl or propyl are attached to a linear chain; here a linear alkenyl chain. "Lower alkenyl" means about 2 to about 4 carbon atoms in the chain, which may be straight or branched. Exemplary alkenyl groups include ethenyl, propenyl, n-butenyl, i-butenyl, 3-methylbut-2-enyl, n-pentenyl, heptenyl, octenyl, cyclohexylbutenyl and decenyl.

"Alkoxy" means an alkyl-O— group in which the alkyl group is as described herein. Exemplary alkoxy groups include difluoromethoxy, methoxy, trifluoromethoxy, ethoxy, n-propoxy, i-propoxy, n-butoxy and heptoxy.

"Alkoxycarbonyl" means an alkyl-O—CO— group in which the alkyl group is as described herein. Exemplary alkoxycarbonyl groups include methoxy- and ethoxycarbonyl.

"Alkyl" means, unless otherwise specified, an aliphatic hydrocarbon group which may be straight or branched chain having about 1 to about 15 carbon atoms in the chain, optionally substituted by one or more halogen atoms. Particular alkyl groups have from 1 to about 6 carbon atoms. "Lower alkyl" as a group or part of a lower alkoxy, lower alkylthio, lower alkylsulfinyl or lower alkylsulfonyl group means unless otherwise specified, an aliphatic hydrocarbon group which may be a straight or branched chain having 1 to about 4 carbon atoms in the chain. Exemplary alkyl groups include methyl, ethyl, n-propyl, i-propyl, n-butyl, s-butyl, t-butyl, n-pentyl, 3-pentyl, heptyl, octyl, nonyl, decyl and dodecyl. Exemplary alkyl groups substituted by one or more halogen atoms include trifluoromethyl.

"Alkylenedioxy" means an —O-alkylene-O— group in which alkylene is as defined above. Exemplary alkylenedioxy groups include methylenedioxy and ethylenedioxy.

"Alkylsulfinyl" means an alkyl-SO— group in which the alkyl group is as previously described. Preferred alkylsulfinyl groups are those in which the alkyl group is C$_{1-4}$alkyl.

"Alkylsulfonyl" means an alkyl-SO$_2$— group in which the alkyl group is as previously described. Preferred alkylsulfonyl groups are those in which the alkyl group is C$_{1-4}$alkyl.

"Alkylsulfonylcarbamoyl" means an alkyl-SO$_2$—NH—C(=O)— group in which the alkyl group is as previously described. Preferred alkylsulfonylcarbamoyl groups are those in which the alkyl group is C$_{1-4}$alkyl.

"Alkylthio" means an alkyl-S— group in which the alkyl group is as previously described. Exemplary alkylthio groups include methylthio, ethylthio, isopropylthio and heptylthio.

"Alkynyl" means an aliphatic hydrocarbon group containing a carbon-carbon triple bond and which group may be a straight or branched chain having about 2 to about 15 carbon atoms in the chain. Preferred alkynyl groups have 2 to about 12 carbon atoms in the chain; and more preferably 2 to about 6 carbon atoms (e.g. 2 to 4 carbon atoms) in the chain. Exemplary alkynyl groups include ethynyl, propynyl, n-butynyl, i-butynyl, 3-methylbut-2-ynyl, and n-pentynyl.

"Aroyl" means an aryl-CO— group in which the aryl group is as described herein. Exemplary aroyl groups include benzoyl and 1- and 2-naphthoyl.

"Aroylamino" is an aroyl-NH— group wherein aroyl is as previously defined.

"Aryl" as a group or part of a group denotes: (i) an optionally substituted monocyclic or multicyclic aromatic carbocyclic moiety of about 6 to about 14 carbon atoms, such as phenyl or naphthyl; or (ii) an optionally substituted partially saturated multicyclic aromatic carbocyclic moiety in which an aryl and a cycloalkyl or cycloalkenyl group are fused together to form a cyclic structure, such as a tetrahydronaphthyl, indenyl or indanyl ring. Except where otherwise defined, aryl groups may be substituted with one or more aryl group substituents, which may be the same or different, where "aryl group substituent" includes, for example, acyl, acylamino, alkoxy, alkoxycarbonyl, alkylenedioxy, alkylsulfinyl, alkylsulfonyl, alkylthio, aroyl, aroylamino, aryl, arylalkyloxy, arylalkyloxycarbonyl, arylalkylthio, aryloxy, aryloxycarbonyl, arylsulfinyl, arylsulfonyl, arylthio, carboxy, cyano, halo, heteroaroyl, heteroaryl, heteroarylalkyloxy, heteroaroylamino, heteroaryloxy, hydroxy, nitro, trifluoromethyl, —NY$^5$Y$^6$, —CONY$^5$Y$^6$, —SO$_2$NY$^5$Y$^6$, —NY$^5$—C(=O)alkyl, —NY$^5$SO$_2$alkyl or alkyl optionally substituted with aryl, heteroaryl, hydroxy, or —NY$^5$Y$^6$.

"Arylalkyl" means an aryl-alkyl-group in which the aryl and alkyl moieties are as previously described. Preferred arylalkyl groups contain a C$_{1-4}$alkyl moiety. Exemplary arylalkyl groups include benzyl, 2-phenethyl and naphthlenemethyl.

"Arylalkyloxy" means an arylalkyl-O— group in which the arylalkyl groups is as previously described. Exemplary arylalkyloxy groups include benzyloxy and 1- or 2-naphthalenemethoxy.

"Arylalkyloxycarbonyl" means an arylalkyl-O—CO— group in which the arylalkyl group is as previously described. An exemplary arylalkyloxycarbonyl group is benzyloxycarbonyl.

"Arylalkylthio" means an arylalkyl-S— group in which the arylalkyl group is as previously described. An exemplary arylalkylthio group is benzylthio.

"Aryloxy" means an aryl-O— group in which the aryl group is as previously described. Exemplary aryloxy groups include phenoxy and naphthoxy, each optionally substituted.

"Aryloxycarbonyl" means an aryl-O—CO— group in which the aryl group is as previously described. Exemplary aryloxycarbonyl groups include phenoxycarbonyl and naphthoxycarbonyl.

"Arylsulfinyl" means an aryl-SO— group in which the aryl group is as previously described.

"Arylsulfonyl" means an aryl-$SO_2$— group in which the aryl group is as previously described.

"Arylsulfonylcarbamoyl" means an aryl-$SO_2$—NH—C(=O)— group in which the aryl group is as previously described.

"Arylthio" means an aryl-S— group in which the aryl group is as previously described. Exemplary arylthio groups include phenylthio and naphthylthio.

"Azaheteroaryl" means an aromatic carbocyclic moiety of about 5 to about 10 ring members, optionally substituted by one or more "aryl group substituents" as defined above, and in which one of the ring members is nitrogen and the other ring members are chosen from carbon, oxygen, sulfur, or nitrogen. Examples of optionally substituted azaheteroaryl groups include optionally substituted benzimidazolyl, imidazolyl, isoquinolinyl, isoxazolyl, isothiazolyl, oxadiazolyl, pyrazinyl, pyrazolyl, pyridazinyl, pyridyl, pyrimidinyl, pyrrolyl, quinazolinyl, quinolinyl, thiadiazolyl, thiazolyl, and triazolyl. Preferred azaheteroaryl groups within $R^3$ include optionally substituted pyridyl.

"Cyclic amine" means a 3 to 8 membered monocyclic cycloalkyl ring system (in which the cycloalkyl group is as described herein) wherein one of the ring carbon atoms is replaced by nitrogen and which (i) may also contain a further heteroatom-containing group selected from O, S, $SO_2$, or $NY^7$ (where $Y^7$ is hydrogen, alkyl, aryl, arylalkyl, —C(=O)—$R^9$, —C(=O)—$OR^9$ or —$SO_2R^9$); and (ii) may be fused to additional aryl (e.g. phenyl), heteroaryl (e.g. pyridyl), heterocycloalkyl or cycloalkyl rings to form a bicyclic or tricyclic ring system. Exemplary cyclic amines include pyrrolidine, piperidine, piperazinyl, morpholine, piperazine, indoline, pyrindoline, tetrahydroquinoline and the like groups.

"Cycloalkenyl" means an optionally substituted, non-aromatic monocyclic or multicyclic ring system containing at least one carbon-carbon double bond and having about 3 to about 10 carbon atoms. Exemplary monocyclic cycloalkenyl rings include $C_{3-8}$cycloalkenyl rings such as cyclobutenyl, cyclopentenyl, or cyclohexenyl.

"Cycloalkyl" means a saturated monocyclic or bicyclic ring system of about 3 to about 10 carbon atoms. Exemplary monocyclic cycloalkyl rings include $C_{3-8}$cycloalkyl rings such as cyclopropyl, cyclobutyl, cyclopentyl and cyclohexyl.

"Cycloalkylalkyl" means a cycloalkyl-alkyl-group in which the cycloalkyl and alkyl moieties are as previously described. Exemplary monocyclic cycloalkylalkyl groups include cyclopropylmethyl, cyclopentylmethyl, cyclohexylmethyl and cycloheptylmethyl.

"Halo" or "halogen" means fluoro, chloro, bromo, or iodo. Preferred are fluoro or chloro.

"Heteroaroyl" means a heteroaryl-CO— group in which the heteroaryl group is as described herein. Exemplary groups include pyridylcarbonyl.

"Heteroaroylamino" means a heteroaroyl-NH— group in which the heteroaryl moiety is as previously described.

"Heteroaryl" as a group or part of a group denotes: (i) an optionally substituted aromatic monocyclic or multicyclic organic moiety of about 5 to about 10 ring members in which one or more of the ring members is/are element(s) other than carbon, for Example nitrogen, oxygen or sulfur (Examples of such groups include benzimidazolyl, benzthiazolyl, furyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl groups, optionally substituted by one or more aryl group substituents as defined above except where otherwise defined); (ii) an optionally substituted partially saturated multicyclic heterocarbocyclic moiety in which a heteroaryl and a cycloalkyl or cycloalkenyl group are fused together to form a cyclic structure (Examples of such groups include pyrindanyl groups, optionally substituted by one or more "aryl group substituents" as defined above, except where otherwise defined). Optional substituents include one or more "aryl group substituents" as defined above, except where otherwise defined. When $R^1$ contains an optionally substituted heteroaryl group this may particularly represent an optionally substituted "azaheteroaryl" group as defined above.

"Heteroarylalkyloxy" means a heteroarylalkyl-O— group in which the heteroarylalkyl group is as previously described. Exemplary heteroaryloxy groups include optionally substituted pyridylmethoxy.

"Heteroaryloxy" means a heteroaryl-O— group in which the heteroaryl group is as previously described. Exemplary heteroaryloxy groups include optionally substituted pyridyloxy.

"Heteroarylsulfinyl" means a heteroaryl-SO— group in which the aryl group is as previously described.

"Heteroarylsulfonyl" means a heteroaryl-$SO_2$— group in which the aryl group is as previously described.

"Heteroarylsulfonylcarbamoyl" means a heteroaryl-$SO_2$—NH—C(=O)— group in which the heteroaryl group is as previously described.

"Heteroarylthio" means a heteroaryl-S— group in which the aryl group is as previously described.

"Heterocycloalkyl" means: (i) a cycloalkyl group of about 3 to 7 ring members which contains one or more heteroatoms or heteroatom-containing groups selected from O, S and $NY^7$ (where $Y^7$ is hydrogen, alkyl, aryl, arylalkyl, —C(=O)—$R^9$, —C(=O)—$OR^9$, —C(=O)—$NY^5Y^6$ or —$SO_2R^9$) and may be optionally substituted by oxo; (ii) a partially saturated multicyclic heterocarbocyclic moiety in which an aryl (or heteroaryl) ring, each optionally substituted by one or more "aryl group substituents," and a cycloalkyl group of about 3 to 7 ring members, which contains one or more heteroatoms or heteroatom-containing groups selected from O, S and $NY^7$ and may be optionally substituted by oxo, are fused together to form a cyclic structure. The heterocycloalkyl group may be attached to the rest of the molecule via a ring carbon atom or, when one or more nitrogen atoms are present, via a ring carbon or nitrogen atom. Exemplary heterocycloalkyl groups include chromanyl, dihydrobenzofuranyl, indolinyl, morpholinyl, piperidinyl, piperazinyl, perhydropyranyl, pyrindolinyl, tetrahydroquinolinyl and tetrahydroisoquinolinyl.

"Heterocycloalkylalkyl" means a heterocycloalkyl-alkyl-group in which the heterocycloalkyl and alkyl moieties are as previously described.

"Patient" includes both human and other mammals.

"Prodrug" means a compound which is convertible in vivo by metabolic means (e.g. by hydrolysis) to a compound of formula (I). For Example an ester of a compound of formula (I) containing a hydroxy group may be convertible by hydrolysis in vivo to the parent molecule. Alternatively an ester of a compound of formula (I) containing a carboxy group may be convertible by hydrolysis in vivo to the parent molecule.

Suitable esters of compounds of formula (I) containing a hydroxy group are for Example acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates and quinates.

An especially useful class of esters of compounds of formula (I) containing a hydroxy group, may be formed from acid moieties selected from those described by Bundgaard et. al., J. Med. Chem., 1989, 32, page 2503–2507, and include substituted (aminomethyl)-benzoates, for Example dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

Some of the compounds of the present invention are basic, and such compounds are useful in the form of the free base or in the form of a pharmaceutically acceptable acid addition salt thereof.

Acid addition salts are a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for Example, when the salt is formed only for purposes of purification, and identification, or when it is used as intermediate in preparing a pharmaceutically acceptable salt by ion exchange procedures. Pharmaceutically acceptable salts within the scope of the invention include those derived from mineral acids and organic acids, and include hydrohalides, e.g. hydrochlorides and hydrobromides, sulfates, phosphates, nitrates, sulfamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulfonates, ethanesulfonates, benzenesulfonates, p-toluenesulfonates, cyclohexylsulfamates and quinates and the like.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the patient in pharmaceutical doses of the salts, so that the beneficial inhibitory effects inherent in the free base are not vitiated by side effects ascribable to the cations. Pharmaceutically acceptable salts, including those derived from alkali and alkaline earth metal salts, within the scope of the invention include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, tetramethylammonium hydroxide, and the like.

As well as being useful in themselves as active compounds, salts of compounds of the invention are useful for the purposes of purification of the compounds, for Example by exploitation of the solubility differences between the salts and the parent compounds, side products and/or starting materials by techniques well known to those skilled in the art.

With reference to formula (I) above, the following are particular and preferred groupings:

$R^1$ may particularly represent hydrogen.

$R^1$ may also particularly represent $R^4$, especially heteroaryl, more especially benzothiazolyl or benzooxazolyl.

$R^1$ may also represent particularly —C(=Y)—NH—$R^4$ in which $R^4$ represents alkyl, cycloalkyl, heterocycloalkyl, arylalkyl, cycloalkylalkyl, heteroarylalkyl, heterocycloalkylalkyl, aryl or heteroaryl, each optionally substituted.

$R^1$ may also particularly represent —C(=Y)—NH—$R^4$ in which $R^4$ is optionally substituted aryl, more especially (i) indanyl or (ii) phenyl optionally substituted by one or more groups selected from halo, cyano, —C(=O)—$OR^8$, —C(=O)—$R^{11}$, -$Z^2R^{12}$, $R^7$, —$NY^3Y^4$ and —C(=O)—$NY^3Y^4$.

$R^1$ may also particularly represent —C(=Y)—NH—$R^4$ in which $R^4$ is optionally substituted heteroaryl. Exemplary optionally substituted heteroaryls include benzthiazolyl, furanyl, pyridyl, quinolinyl, thiazolyl and thienyl. Optional substituents include heteroaryl and $R^7$.

$R^1$ may also particularly represent —C(=Y)—NH—$R^4$ in which $R^4$ is optionally substituted alkyl. Optional substituents include aryl, heteroaryl, —C(=O)—$OR^8$ and $R^7$.

$R^1$ may also particularly represent —C(=Y)—NH—$R^4$ in which $R^4$ is optionally substituted cycloalkyl. Exemplary optionally substituted cycloalkyls include cyclopropyl, cyclopentyl, cyclohexyl, cycloheptyl and norbornyl. Optional substituents include aryl, —C(=O)—$OR^8$ and -$Z^2R^{12}$.

$R^1$ may also particularly represent —C(=Y)—NH—$R^4$ in which $R^4$ is optionally substituted heterocycloalkyl, more especially tetrahydropyranyl or optionally substituted piperidinyl. Optional substituents include $R^7$, —C(=O)—$R^9$, —C(=O)—$OR^8$ and -$Z^2R^{12}$.

$R^1$ may also particularly represent —$SO_2$—$NHR^4$ in which $R^4$ is optionally substituted aryl, more especially optionally substituted phenyl. Optional substituents include halo, $R^7$ and -$Z^2R^{12}$.

$R^1$ may also particularly represent —C(=$Z^1$)—$R^4$ in which $Z^1$ is O and $R^4$ is optionally substituted alkyl. Optional substituents include aryl, cyclolalkyl, heteroaryl, $-Z^2R^8$, $-C(=O)-R^9$ and $-C(=O)-NY^3Y^4$.

$R^1$ may also particularly represent $-C(=Z^1)-R^4$ in which $Z^1$ is O and $R^4$ is optionally substituted aryl, more especially optionally substituted phenyl. Optional substituents include one or more groups selected from halo, cyano, $-C(=O)-OR^8$, $-C(=O)-R^{11}$, $-Z^2R^{12}$, $R^7$, $-NY^3Y^4$ and $-C(=O)-NY^3Y^4$.

$R^1$ may also particularly represent $-C(=Z^1)-R^4$ in which $Z^1$ is O and $R^4$ is optionally substituted heteroaryl. Exemplary optionally substituted heteroaryls include imidazolyl, furanyl, pyridyl and thienyl. Optional substituents include heteroaryl and $R^7$.

$R^1$ may also particularly represent $-SO_2-R^4$ in which $R^4$ is optionally substituted aryl, more especially optionally substituted phenyl. Optional substituents include cyano, halo, heteroaryl, nitro, $R^7$ and $-Z^2R^{12}$.

$R^1$ may also particularly represent $-SO_2-R^4$ in which $R^4$ is optionally substituted heteroaryl.

Exemplary optionally substituted heteroaryls include imidazolyl, furanyl, pyridyl and thienyl. Optional substituents include heteroaryl and $R^7$.

$R^1$ may also particularly represent $-C(=Z^1)-OR^4$ in which $Z^1$ is O and $R^4$ is alkyl, especially tert-butyl.

$R^2$ may also particularly represent chloro.

$R^2$ may also particularly represent cyano.

$R^3$ may particularly represent hydrogen.

$R^3$ may also particularly represent alkyl, especially methyl or trifluoromethyl.

$R^3$ may also particularly represent aryl, especially phenyl.

$R^3$ may also particularly represent heteroaryl, especially optionally substituted pyridyl, more especially optionally substituted pyrid-3-yl.

$R^3$ may also particularly represent cycloalkyl, especially cyclopropyl.

$R^3$ may also particularly represent heterocycloalkyl, especially tetrahydropyranyl, more especially tetrahydropyran-4-yl, or substituted piperidinyl, more especially methanesulfonylpiperidin-4-yl.

Y may particularly represent O.

Z may particularly represent O.

n may particularly represent 1.

m may particularly represent 1.

It is to be understood that this invention covers all appropriate combinations of the particular and preferred groupings referred to herein.

A particular preferred group of compounds of the invention are compounds of formula (Ia):

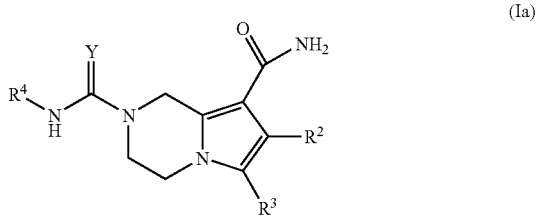

(Ia)

in which $R^2$, $R^3$, $R^4$ and Y are as hereinbefore defined; and their corresponding N-oxides, and their prodrugs; and pharmaceutically acceptable salts and solvates (e.g. hydrates) of compounds of formula (Ia) and their N-oxides and their prodrugs.

Compounds of formula (Ia) in which $R^2$ represents chloro or cyano are preferred.

Compounds of formula (Ia) in which $R^3$ represents hydrogen, methyl, trifluoromethyl, optionally substituted phenyl (more especially phenyl), cyclopropyl, tetrahydropyran-4-yl, optionally substituted pyridinyl (more especially pyrid-3-yl or 4-methyl-pyrid-3-yl) or 1 methanesulfonylpiperidin-4-yl are preferred.

Compounds of formula (Ia) in which $R^4$ represents:

(i) optionally substituted aryl, especially indanyl, phenyl or phenyl substituted by one or more groups selected from halo, cyano, $-C(=O)-OR^8$, $-C(=O)-R^{11}$, $-Z^2R^{12}$, $R^7$, $-NY^3Y^4$ and $-C(=O)-NY^3Y^4$ [e.g. 4-acetylphenyl, 4-(3-amino-pyrrolidin-1-yl)phenyl, 3-(3-amino-pyrrolidin-1-yl)phenyl, 4-benzyloxyphenyl, 4-carboxymethylphenyl, 4-carboxymethyloxyphenyl, 4-carboxyphenyl, 3-carboxyphenyl, 4-chlorophenyl, 3-chlorophenyl, 3-chloro-4-fluorophenyl, 4-chloro-3-trifluoromethylphenyl, 4-cyanophenyl, 3-cyanophenyl, 3,4-dichlorophenyl, 2,5-difluorophenyl, 3,4-difluorophenyl, 4-(3-dimethylaminopropoxy) phenyl, di-(2-methoxyethyl)aminomethylphenyl, 4-(3, 5-ditrifluoromethyl)phenyl, 4-ethoxyphenyl, 4-ethoxycarbonylphenyl, 3-ethylphenyl, 3-ethoxycarbonylphenyl, 4-ethoxycarbonylmethylphenyl, 4-fluorophenyl, 3-fluorophenyl, 2-fluorophenyl, 4-(4-fluorophenoxy)phenyl, 4-hydroxyphenyl, 3-hydroxyphenyl, 4-iodophenyl, 4-isopropylphenyl, 4-(4-isopropylpiperazine-1-carbonyl)phenyl, 4-methanesulfonamidophenyl, 4-methanesulfonylphenyl, 4-methoxyphenyl, 3-methoxyphenyl, 4-methylphenyl, 3-methylphenyl, 4-(4-methylpiperazinyl)phenyl, 3-(4-methylpiperazinyl)phenyl, 4-(4-methylpiperazine-1-carbonyl)phenyl, 4-(4-methylpiperazin-1-ylmethyl) phenyl, 4-(4-isopropyl[1,4]diazepane-1-carbonyl) phenyl, 4-(4-methyl[1,4]diazepane-1-carbonyl)phenyl, 3-(4-methyl[1,4]diazepane-1-carbonyl)phenyl, 3-(4-methylpiperazine-1-carbonyl)phenyl, 3-methyl-4-(piperazin-1-yl)phenyl, 4-(N-methylpiperidin-4-ylmethyl) phenyl, 4-(N-methylpiperidine-4-carbonyl)phenyl, 4-(morpholine-4-carbonyl)phenyl, 4-(2-(morpholin-4-yl)ethyloxy)phenyl, 4-(morpholin-4-ylmethyl)phenyl, 4-(morpholin-4-ethylaminocarbonyl)phenyl, 3-(morpholin-4-ylmethyl)phenyl, 4-nitrophenyl, 4-(piperazine-1-carbonyl)phenyl, 4-phenoxyphenyl, 4-thiomethylphenyl, 4-(3,4,5-trimethylpiperazine-1-carbonyl) phenyl, 2,3,4-trifluorophenyl, 4-trifluoromethylphenyl, 3-trifluoromethylphenyl and 4-trifluoromethoxyphenyl];

(ii) optionally substituted heteroaryl [e.g. furan-2-yl, 5-methyl-thien-2-yl, pyrid-2-yl, pyrid-3-yl, pyrid-4-yl, 5-(pyrid-2-yl)-thien-2-yl), quinolin-6-yl, thiazol-2-yl and 6-trifluoromethylpyridin-3-yl];

(iii) optionally substituted $C_{1-4}$alkyl [e.g. ethyl, isopropyl, 1-phenylethyl, phenethyl, benzyl, $-CH_2-CO_2Et$, $-CH_2-CH_2-CO_2Et$,

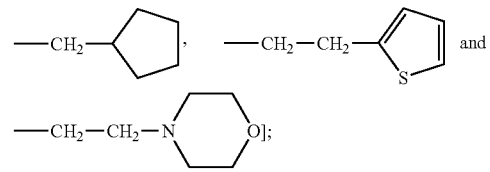

(iv) optionally substituted cycloalkyl [e.g. cyclohexyl, cyclopentyl, cyclopropyl, 4-hydroxycyclohex-1-yl, norbornyl, 4-phenylcyclohex-1-yl, or 2-phenylcyclopropyl]; or (v) optionally substituted heterocycloalkyl (e.g. 1-benzoylpiperidin-4-yl, 1-(1-ethoxycarbonylpiperazine-4-carbonyl)piperidin-4-yl, 3-(4-fluorophenyl) cyclobutyl, 1-isopropoxycarbonyl-piperidin-4-yl, 1-methanesulfonylpiperidin-4-yl, 1-(2-methylphenyl)sulfonylpiperidin-4-yl, 1-methyl-1,2,3,4-tetrahydroisoquinolin-6-yl, 1-(morpholine-4-carbonyl)piperidin-4-yl, 1-phenylsulfonylpiperidin-4-yl, piperidin-4-yl, 1,2,3,4-tetrahydroisoquinolin-6-yl and tetrahydropyran-4-yl);

are preferred.

Compounds of formula (Ia) in which $R^4$ represents 4-(4-methylpiperazine-1-carbonyl)phenyl

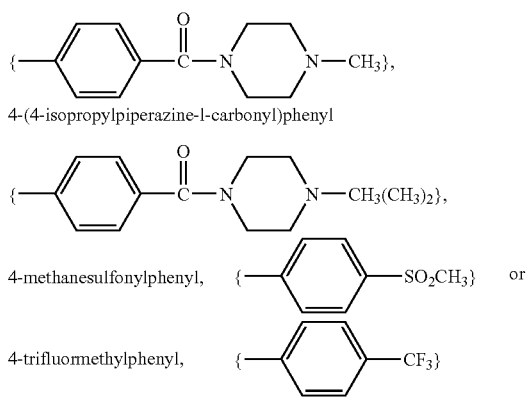

are especially preferred.

Compounds of formula (Ia) in which Y represents O are preferred.

A preferred group of compounds of the invention are compounds of formula (Ia) in which: $R^2$ is chloro or cyano; $R^3$ is hydrogen, methyl, trifluoromethyl, optionally substituted phenyl (especially phenyl), cyclopropyl, tetrahydropyran-4-yl, optionally substituted pyridinyl (especially pyrid-3-yl or 4-methyl-pyrid-3-yl) or 1-methanesulfonylpiperidin-4-yl; $R^4$ is (i) optionally substituted aryl, especially indanyl, phenyl or phenyl substituted by one or more groups selected from halo, cyano, —C(=O)—$OR^8$, —C(=O)—$R^{11}$, -$Z^2R^{12}$, $R^7$, —$NY^3Y^4$ and —C(=O)—$NY^3Y^4$ (especially 4-acetylphenyl, 4-(3-amino-pyrrolidin-1-yl)phenyl, 3-(3-aminopyrrolidin-1-yl)phenyl, 4-benzyloxyphenyl, 4-carboxymethylphenyl, 4-carboxymethyloxyphenyl, 4-carboxyphenyl, 3-carboxyphenyl, 4-chlorophenyl, 3-chlorophenyl, 3-chloro-4-fluorophenyl, 4-chloro-3-trifluoromethylphenyl, 4-cyanophenyl, 3-cyanophenyl, 3,4-dichlorophenyl, 2,5-difluorophenyl, 3,4-difluorophenyl, 4-(3-dimethylaminopropoxy) phenyl, di-(2-methoxyethyl)aminomethylphenyl, 4-(3,5-ditrifluoromethyl)phenyl, 4-ethoxyphenyl, 4-ethoxycarbonylphenyl, 3-ethoxycarbonylphenyl, 4-ethoxycarbonylmethylphenyl, 3-ethylphenyl, 4-fluorophenyl, 3-fluorophenyl, 2-fluorophenyl, 4-(4-fluorophenoxy)phenyl, 4-hydroxyphenyl, 3-hydroxyphenyl, 4-iodophenyl, 4-isopropylphenyl, 4-(4-isopropylpiperazine-1-carbonyl)phenyl, 4-methanesulfonamidophenyl, 4-methanesulfonylphenyl, 4-methoxyphenyl, 3-methoxyphenyl, 4-methylphenyl, 3-methylphenyl, 4-(4-methylpiperazinyl) phenyl, 3-(4-methylpiperazinyl) phenyl, 4-(4-methylpiperazine-1-carbonyl)phenyl, 4-(4-methylpiperazin-1-ylmethyl) phenyl, 4-(4-isopropyl[1,4]diazepane-1-carbonyl)phenyl, 4-(4-methyl[1,4]diazepane-1-carbonyl) phenyl, 3-(4-methyl[1,4]diazepane-1-carbonyl)phenyl, 3-(4-methylpiperazine-1-carbonyl) phenyl, 3-methyl-4-(piperazin-1-yl)phenyl, 4-(N-methylpiperidin-4-ylmethyl)phenyl, 4-(N-methylpiperidine-4-carbonyl)phenyl, 4-(morpholine-4-carbonyl)phenyl, 4-(2-(morpholin-4-yl)ethyloxy)phenyl, 4-(morpholin-4-ylmethyl)phenyl, 4-(morpholin-4-ethylaminocarbonyl) phenyl, 3-(morpholin-4-ylmethyl)phenyl, 4-nitrophenyl, 4-(piperazine-1-carbonyl)phenyl, 4-phenoxyphenyl, 4-thiomethylphenyl, 4-(3,4,5-trimethylpiperazine-1-carbonyl) phenyl, 2,3,4-trifluorophenyl, 4-trifluoromethylphenyl, 3-trifluoromethylphenyl and 4-trifluoromethoxyphenyl); (ii) optionally substituted heteroaryl [e.g. furan-2-yl, 5-methylthien-2-yl, pyrid-2-yl, pyrid-3-yl, pyrid-4-yl, 5-(pyrid-2-yl)-thien-2-yl), quinolin-6-yl, thiazol-2-yl and 6-trifluoromethylpyridin-3-yl]; (iii) optionally substituted $C_{1-4}$alkyl [e.g. ethyl, isopropyl, 1-phenylethyl, phenethyl, benzyl, —$CH_2$—$CO_2Et$, —$CH_2$—$CH_2$—$CO_2Et$,

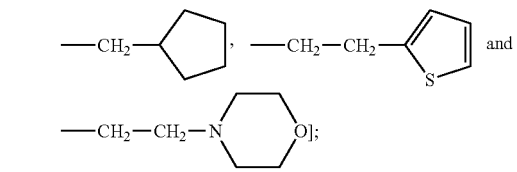

(iv) optionally substituted cycloalkyl [e.g. cyclohexyl, cyclopentyl, cyclopropyl, 4-hydroxycyclohex-1-yl, norbornyl, 4-phenylcyclohex-1-yl, or 2-phenylcyclopropyl]; or (v) optionally substituted heterocycloalkyl (e.g. 1-benzoylpiperidin-4-yl, 1-(1-ethoxycarbonylpiperazine-4-carbonyl)piperidin-4-yl, 3-(4-fluorophenyl)cyclobutyl, 1-isopropoxycarbonyl-piperidin-4-yl, 1-methanesulfonylpiperidin-4-yl, 1-(2-methylphenyl)sulfonylpiperidin-4-yl, 1-methyl-1, 2,3,4-tetrahydroisoquinolin-6-yl, 1-(morpholine-4-carbonyl)piperidin-4-yl, 1-phenylsulfonylpiperidin-4-yl, piperidin-4-yl, 1,2,3,4-tetrahydroisoquinolin-6-yl and tetrahydropyran-4-yl); and Y is O; and the corresponding N-oxides, and their prodrugs; and pharmaceutically acceptable salts and solvates (e.g. hydrates) of such compounds and their N-oxides and their prodrugs.

An especially preferred group of compounds of the invention are compounds of formula (Ia) in which: $R^2$ is chloro or cyano; $R^3$ is hydrogen, methyl, trifluoromethyl, optionally substituted phenyl (especially phenyl), cyclopropyl, tetrahydropyran-4-yl, optionally substituted pyridinyl (especially pyrid-3-yl or 4-methyl-pyrid-3-yl) or 1-methanesulfonylpiperidin-4-yl; $R^4$ is 4-(4-methylpiperazine-1-carbonyl)phenyl

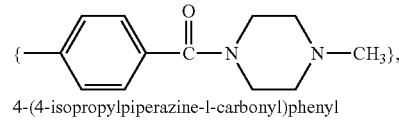

-continued

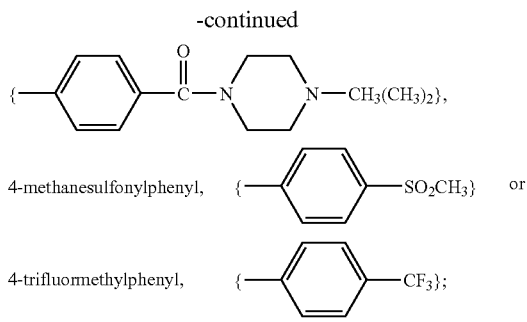

and Y is O; and the corresponding N-oxides, and their prodrugs; and pharmaceutically acceptable salts and solvates (e.g. hydrates) of such compounds and their N-oxides and their prodrugs.

Another particular group of compounds of the invention are compounds of formula (Ib):

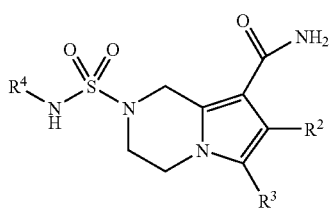

in which $R^2$, $R^3$ and $R^4$ are as hereinbefore defined; and their corresponding N-oxides, and their prodrugs; and pharmaceutically acceptable salts and solvates (e.g. hydrates) of compounds of formula (Ib) and their N-oxides and their prodrugs.

Compounds of formula (Ib) in which $R^2$ represents chloro or cyano are preferred.

Compounds of formula (Ib) in which $R^3$ represents hydrogen, methyl, trifluoromethyl, optionally substituted phenyl (more especially phenyl), cyclopropyl, tetrahydropyran-4-yl, optionally substituted pyridinyl (more especially pyrid-3-yl or 4-methyl-pyrid-3-yl) or 1-methanesulfonylpiperidin-4-yl are preferred.

Compounds of formula (Ib) in which $R^4$ represents optionally substituted aryl, especially optionally substituted phenyl [e.g. phenyl, 4-trifluoromethylphenyl, 4-fluorophenyl and 4-methoxyphenyl] are preferred.

A preferred group of compounds of the invention are compounds of formula (Ib) in which: $R^2$ is chloro or cyano; $R^3$ is hydrogen, methyl, trifluoromethyl, optionally substituted phenyl (especially phenyl), cyclopropyl, tetrahydropyran-4-yl, optionally substituted pyridinyl (especially pyrid-3-yl or 4-methyl-pyrid-3-yl) or 1-methanesulfonylpiperidin-4-yl; and $R^4$ is optionally substituted phenyl (especially phenyl, 4-trifluoromethylphenyl, 4-fluoromethyl and 4-methoxyphenyl); and their corresponding N-oxides, and their prodrugs; and pharmaceutically acceptable salts and solvates (e.g. hydrates) of such compounds and their N-oxides and their prodrugs.

Another particular group of compounds of the invention are compounds of formula (Ic):

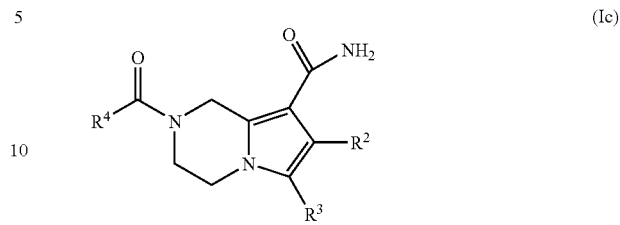

(in which $R^2$, $R^3$ and $R^4$ are as hereinbefore defined; and their corresponding N-oxides, and their prodrugs; and pharmaceutically acceptable salts and solvates (e.g. hydrates) of compounds of formula (Ic) and their N-oxides and their prodrugs.

Compounds of formula (Ic) in which $R^2$ represents chloro or cyano are preferred.

Compounds of formula (Ic) in which $R^3$ represents hydrogen, methyl, trifluoromethyl, optionally substituted phenyl (more especially phenyl), cyclopropyl, tetrahydropyran-4-yl, optionally substituted pyridinyl (more especially pyrid-3-yl or 4-methyl-pyrid-3-yl) or 1-methanesulfonylpiperidin-4-yl are preferred.

Compounds of formula (Ic) in which $R^4$ represents:
(i) optionally substituted aryl, especially optionally substituted phenyl [e.g. 4-trifluoromethylphenyl]; or
(ii) optionally substituted heteroaryl [e.g. 5-(pyrid-2-yl)thien-2-yl] are preferred.

A preferred group of compounds of the invention are compounds of formula (Ic) in which: $R^2$ is chloro or cyano; $R^3$ is hydrogen, methyl, trifluoromethyl, optionally substituted phenyl (especially phenyl), cyclopropyl, tetrahydropyran-4-yl, optionally substituted pyridinyl (especially pyrid-3-yl or 4-methyl-pyrid-3-yl) or 1-methanesulfonylpiperidin-4-yl; and $R^4$ is (i) optionally substituted phenyl [especially 4-trifluoromethylphenyl] or (ii) optionally substituted heteroaryl [especially 5-(pyrid-2-yl)thien-2-yl]; and their corresponding N-oxides, and their prodrugs; and pharmaceutically acceptable salts and solvates (e.g. hydrates) of such compounds and their N-oxides and their prodrugs.

The present invention concerns particularly the compounds of general formula (I) as defined above which are compounds of formula (ICC):

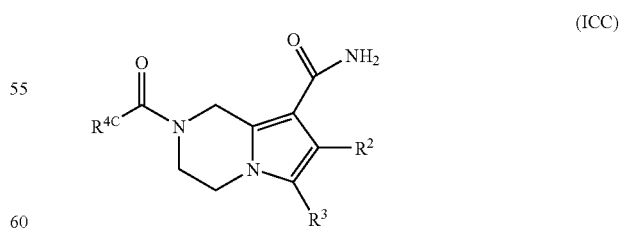

in which $R^2$, $R^3$ and $R^{4C}$ represents NHR4 with $R^4$ as hereinbefore defined; and their corresponding N-oxides, and their prodrugs; and pharmaceutically acceptable salts and solvates (e.g. hydrates) of compounds of formula (Ic) and their N-oxides and their prodrugs.

The present invention concerns particularly the compounds of formula (ICC) as defined above in which $R^2$ represents halogeno (Br, Cl, I or F) or cyano.

The present invention concerns particularly the compounds of formula (ICC) as defined above in which $R^3$ represents hydrogen, methyl, trifluoromethyl, optionally substituted aryl, cyclopropyl, tetrahydropyran-4-yl, optionally substituted pyridinyl (more especially pyrid-3-yl or 4-methyl-pyrid-3-yl) or 1-methanesulfonylpiperidin-4-yl.

The present invention concerns particularly the compounds of formula (ICC) as defined above in which $R^3$ represents optionally substituted aryl.

The present invention concerns particularly the compounds of formula (ICC) as defined above in which $R^3$ represents phenyl.

The present invention concerns particularly the compounds of formula (ICC) as defined above in which $R^{4C}$ represents NH $R^4$ in which $R^4$ represents alkyl, cycloalkyl, heterocycloalkyl, arylalkyl, cycloalkylalkyl, heteroarylalkyl, heterocycloalkylalky, aryl or heteroaryl, each optionally substituted.

The present invention concerns particularly the compounds of formula (ICC) as defined above in which $R^{4C}$ represents NH $R^4$ in which $R^4$ represents alkyl, aryl or cycloalkyl, all optionally substituted.

The present invention concerns particularly the compounds of formula (ICC) as defined in the previous claims in which: $R^2$ is halogeno or cyano; $R^3$ is optionally substituted aryl (especially phenyl), and $R^{4C}$ represents NH $R^4$ in which $R^4$ represents alkyl, cycloalkyl, heterocycloalkyl, arylalkyl, cycloalkylalkyl, heteroarylalkyl, heterocycloalkylalkyl, aryl or heteroaryl, each optionally substituted, and their corresponding N-oxides, and their prodrugs; and pharmaceutically acceptable salts and solvates (e.g. hydrates) of such compounds and their N-oxides and their prodrugs.

The present invention concerns particularly the compounds of formula (ICC) as defined above in which: $R^2$ is chloro or cyano; $R^3$ is phenyl and $R^{4C}$ represents NH $R^4$ in which $R^4$ represents alkyl, cycloalkyl, heterocycloalkyl (especially hexahydropyranne), phenylalkyl, cycloalkylalkyl, heteroarylalkyl, heterocycloalkylalkyl, phenyl or heteroaryl (especially tetrahydroquinoleine), each optionally substituted, and their corresponding N-oxides, and their prodrugs; and pharmaceutically acceptable salts and solvates (e.g. hydrates) of such compounds and their N-oxides and their prodrugs.

The present invention concerns particularly the compounds of formula (ICC) as defined above in which $R^2$ is chloro or cyano; $R^3$ is phenyl $R^{4C}$ represents NH $R^4$ in which $R^4$ represents optionally substituted alkyl; cycloalkyl optionally substituted by phenyl itself optionally substituted; heterocycloalkyl; phenylalkyl; cycloalkylalkyl; heteroarylalkyl; heterocycloalkylalkyl; heteroaryl; or phenyl optionally substituted by one or more substituants chosen among optionally substituted alkyle, optionally substituted piperidyl and morpholino; halogen; carboxy free, salified or esterified; optionally substituted alcoxy; optionally substituted carbonyl; and their corresponding N-oxides, and their prodrugs; and pharmaceutically acceptable salts and solvates (e.g. hydrates) of such compounds and their N-oxides and their prodrugs.

The present invention concerns particularly the compounds of formula (ICC) as defined above in which $R^2$ is chloro or cyano; $R^3$ is phenyl $R^{4C}$ represents NH $R^4$ in which $R^4$ represents alkyl optionally substituted by carboxy free, salified or esterified by alkyl C1–4; cycloalkyl (especially cyclopentyle or cyclopropyl optionally substituted by phenyl itself optionally substituted; heterocycloalkyl (especially tetrahydropyranne); phenylalkyl; cycloalkylalkyl (especially cyclopentylalkyl); heteroarylalkyl; heterocycloalkylalkyl; heteroaryl (especially furyl, dihydroisoquinoleinyl optionally substituted by alkyle or hydroxyalkyle); or phenyl optionally substituted by one or more substituants chosen among alkyle itself optionally substituted by piperidyl, alkylpiperidyl and morpholino; halogen; carboxy free, salified or esterified; alcoxy itself optionally substituted by carboxy free, salified or esterified or morpholino; alkylpiperazinylcarbonyl; alkylpiperidylcarbonyl; alkyldiazepancarbonyl and their corresponding N-oxides, and their prodrugs; and pharmaceutically acceptable salts and solvates (e.g. hydrates) of such compounds and their N-oxides and their prodrugs.

Another particular group of compounds of the invention are compounds of formula (Id):

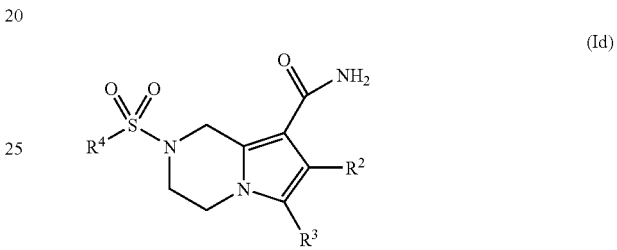

in which $R^2$, $R^3$ and $R^4$ are as hereinbefore defined; and their corresponding N-oxides, and their prodrugs; and pharmaceutically acceptable salts and solvates (e.g. hydrates) of compounds of formula (Id) and their N-oxides and their prodrugs.

Compounds of formula (Id) in which $R^2$ represents chloro or cyano are preferred.

Compounds of formula (Id) in which $R^3$ represents hydrogen, methyl, trifluoromethyl, optionally substituted phenyl (more especially phenyl), cyclopropyl, tetrahydropyran-4-yl, optionally substituted pyridinyl (more especially pyrid-3-yl or 4-methyl-pyrid-3-yl) or 1-methanesulfonylpiperidin-4-yl are preferred.

Compounds of formula (Id) in which $R^4$ represents:
(i) optionally substituted aryl, especially optionally substituted phenyl (e.g. 4-chlorophenyl, 4-cyanophenyl, 4-fluorophenyl, 4-methanesulfonylphenyl, 4-methoxyphenyl, 4-methylphenyl, 4-nitrophenyl, 4-trifluoromethylphenyl); or
(ii) optionally substituted heteroaryl (e.g. 5-(oxazol-3-yl)-thien-2-yl, pyrid-4-yl and 5-pyrid-2-ylthien-5-yl);

are preferred.

A preferred group of compounds of the invention are compounds of formula (Id) in which: $R^2$ is chloro or cyano; $R^3$ is hydrogen, methyl, trifluoromethyl, optionally substituted phenyl (especially phenyl), cyclopropyl, tetrahydropyran-4-yl, optionally substituted pyridinyl (especially pyrid-3-yl or 4-methyl-pyrid-3-yl) or 1-methanesulfonylpiperidin-4-yl; and $R^4$ is (i) optionally substituted phenyl (especially 4-chlorophenyl, 4-cyanophenyl, 4-fluorophenyl, 4-methanesulfonylphenyl, 4-methoxyphenyl, 4-methylphenyl, 4-nitrophenyl, 4-trifluoromethylphenyl) or (ii) optionally substituted heteroaryl (especially 5-(oxazol-3-yl)-thien-2-yl, pyrid-4-yl and 5-pyrid-2-ylthien-5-yl); and their corresponding N-oxides, and their prodrugs; and pharmaceutically acceptable salts and solvates (e.g. hydrates) of such compounds and their N-oxides and their prodrugs.

Another particular group of compounds of the invention are compounds of formula (Ie):

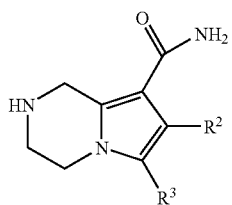

(Ie)

in which $R^2$ and $R^3$ are as hereinbefore defined; and their corresponding N-oxides, and their prodrugs; and pharmaceutically acceptable salts and solvates (e.g. hydrates) of compounds of formula (Ie) and their N-oxides and their prodrugs.

Compounds of formula (Ie) in which $R^2$ represents chloro or cyano are preferred.

Compounds of formula (Ie) in which $R^3$ represents cyclopropyl are preferred.

A preferred group of compounds of the invention are compounds of formula (Ie) in which: $R^2$ is chloro or cyano; and $R^3$ is cyclopropyl; and their corresponding N-oxides, and their prodrugs; and pharmaceutically acceptable salts and solvates (e.g. hydrates) of such compounds and their N-oxides and their prodrugs.

Another particular group of compounds of the invention are compounds of formula (If):

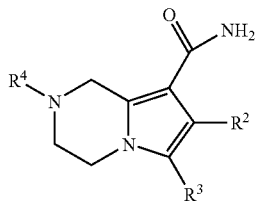

(If)

in which $R^2$, $R^3$ and $R^4$ are as hereinbefore defined; and their corresponding N-oxides, and their prodrugs; and pharmaceutically acceptable salts and solvates (e.g. hydrates) of compounds of formula (If) and their N-oxides and their prodrugs.

Compounds of formula (If) in which $R^2$ represents chloro or cyano are preferred.

Compounds of formula (If) in which $R^3$ represents hydrogen, methyl, trifluoromethyl, optionally substituted phenyl (more especially phenyl), cyclopropyl, tetrahydropyran-4-yl, optionally substituted pyridinyl (more especially pyrid-3-yl or 4-methyl-pyrid-3-yl) or 1-methanesulfonylpiperidin-4-yl are preferred.

Compounds of formula (If) in which $R^4$ represents optionally substituted heteroaryl (e.g. benzothiaz-2-yl and benzooxazol-2-yl) are preferred.

A preferred group of compounds of the invention are compounds of formula (If) in which: $R^2$ is chloro or cyano; $R^3$ is hydrogen, methyl, trifluoromethyl, optionally substituted phenyl (especially phenyl), cyclopropyl, tetrahydropyran-4-yl, optionally substituted pyridinyl (especially pyrid-3-yl or 4-methyl-pyrid-3-yl) or 1-methanesulfonylpiperidin-4-yl; and $R^4$ is optionally substituted heteroaryl (especially benzothiaz-2-yl and benzooxazol-2-yl); and their corresponding N-oxides, and their prodrugs; and pharmaceutically acceptable salts and solvates (e.g. hydrates) of such compounds and their N-oxides and their prodrugs.

Particular compounds of the invention of formula (I) are selected from the compounds formed by joining (i) the carbon atom (C*) of one of the fragments A1 to A118, (ii) the sulfur atom (S*) of one of the fragments A119 to A128 or (iii) the hydrogen atom (*H) of fragment A129 shown in Table 1 to the nitrogen atom (*N) in the dihydro-1H-pyrrolo[1,2-a]pyrazine ring of one of the fragments (B1 or B2) shown in Table 2, and joining the carbon atom (C*) in the dihydro-1H-pyrrolo[1,2-a]pyrazine ring of one of the fragments (B1 or B2) shown in Table 2 to the carbon atom (*C) of one of the fragments (C1 to C10) or to a hydrogen atom (*H, fragment (C11)) depicted in Table 3.

TABLE 1

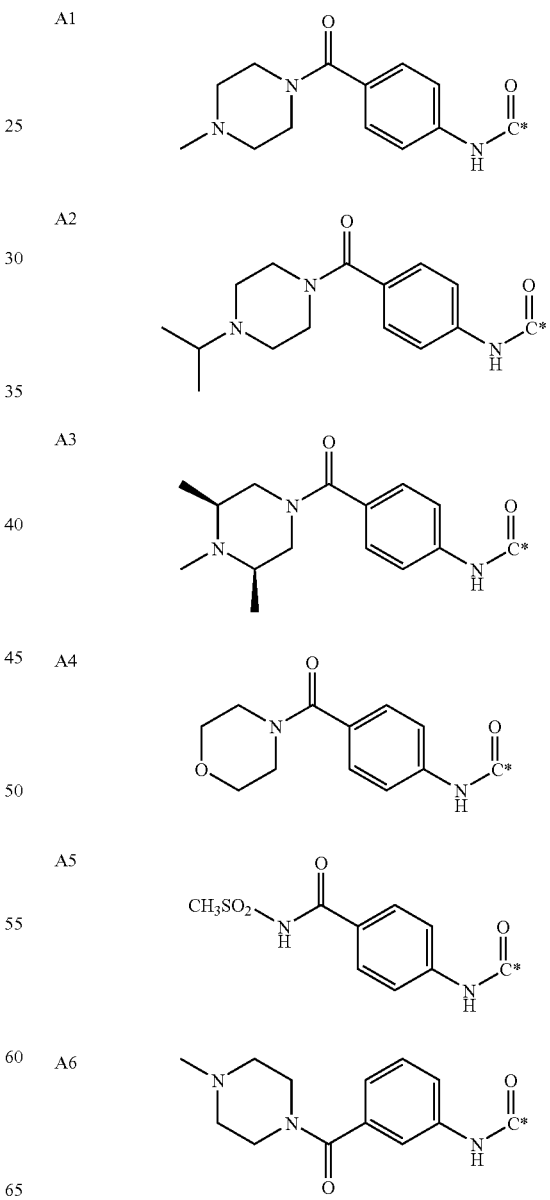

TABLE 1-continued
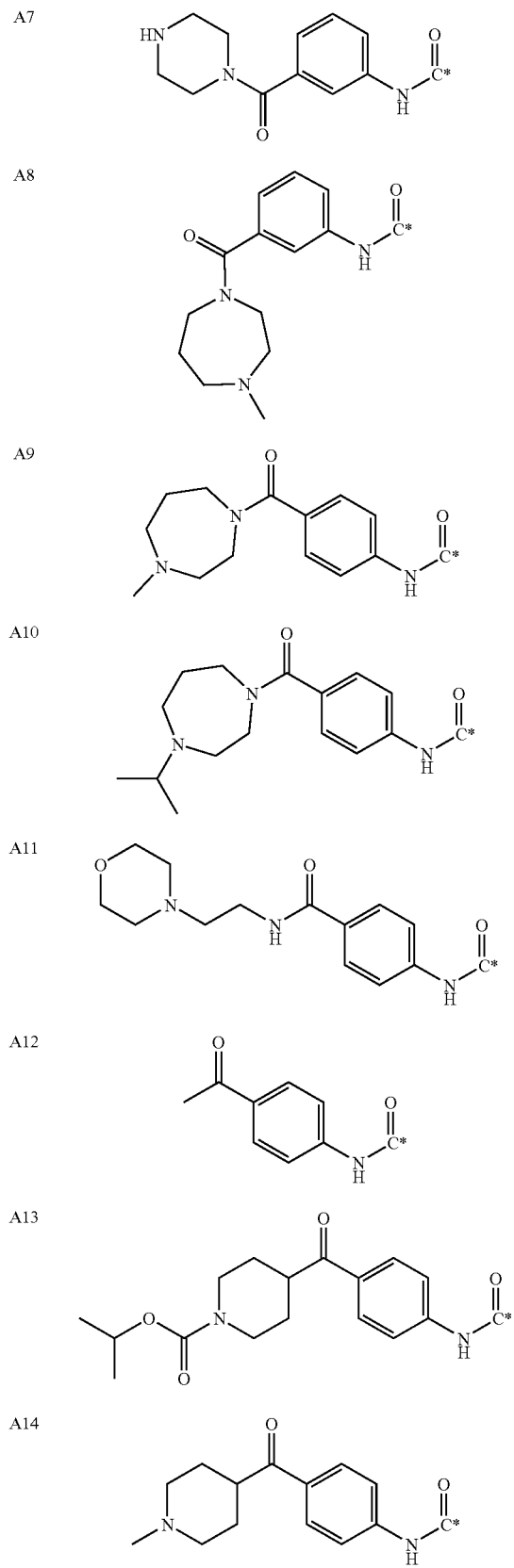
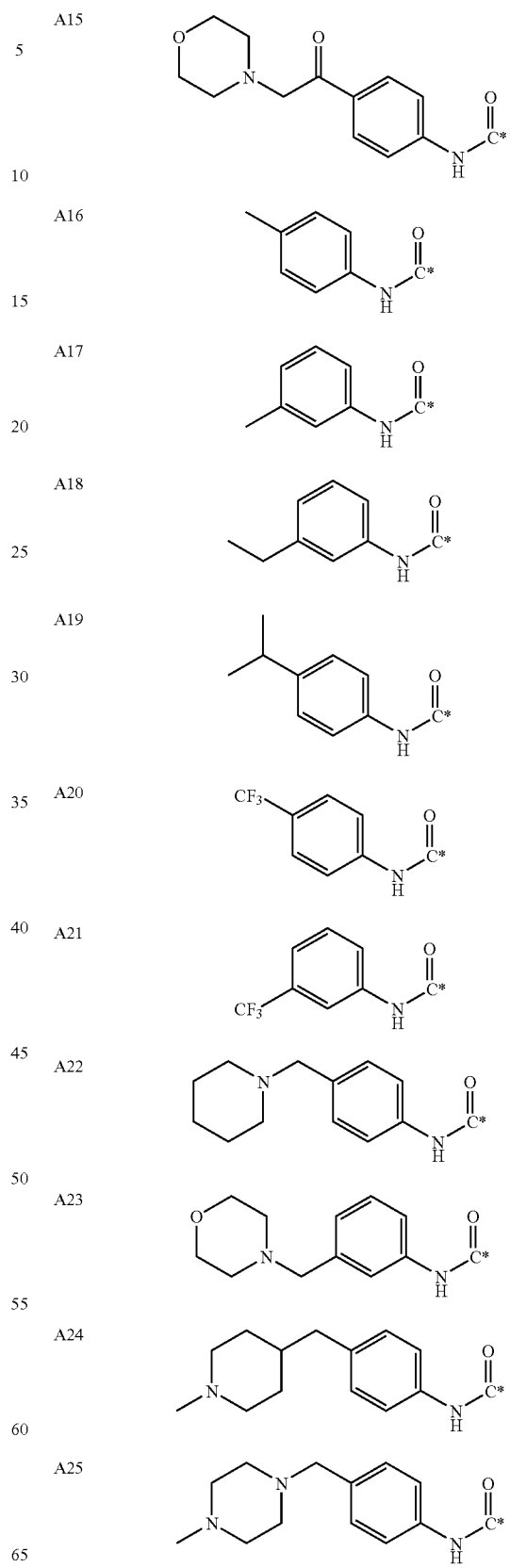

TABLE 1-continued
| | |
|---|---|
| A26 | 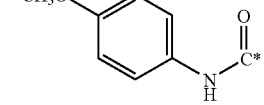 |
| A27 | 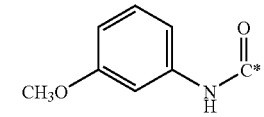 |
| A28 | 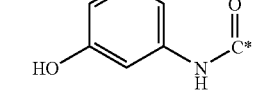 |
| A29 | 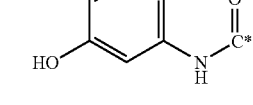 |
| A30 | 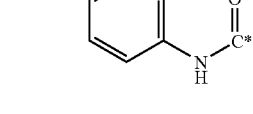 |
| A31 | 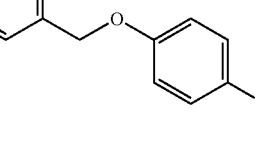 |
| A32 | 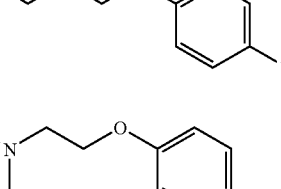 |
| A33 | 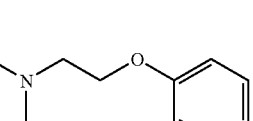 |
| A34 | 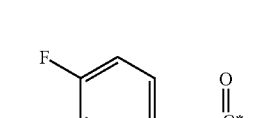 |
| A35 |  |
| A36 | |
TABLE 1-continued
| | |
|---|---|
| A37 | |
| A38 | |
| A39 | |
| A40 | |
| A41 | |
| A42 | |
| A43 | |
| A44 | |
| A45 | |
| A46 | |
| A47 | |

TABLE 1-continued
| | |
|---|---|
| A48 | 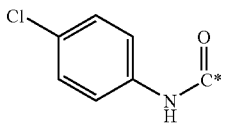 |
| A49 | 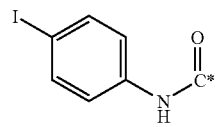 |
| A50 | 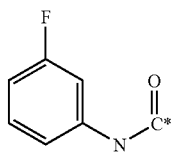 |
| A51 | 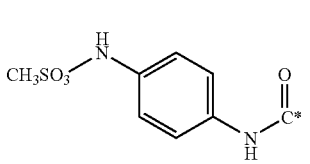 |
| A52 | 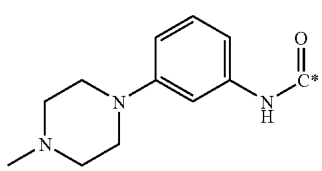 |
| A53 | 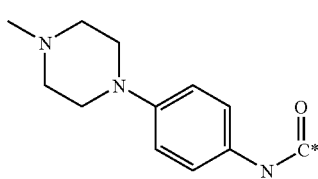 |
| A54 | 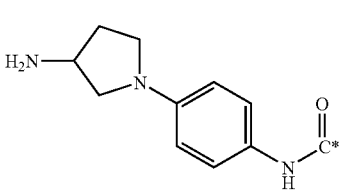 |
| A55 | 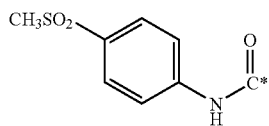 |
| A56 | 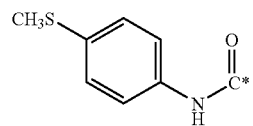 |
| A57 | 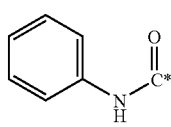 |
TABLE 1-continued
| | |
|---|---|
| A58 | 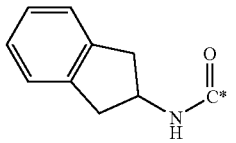 |
| A59 | 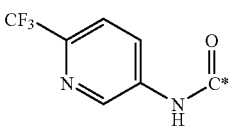 |
| A60 | 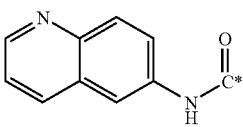 |
| A61 | 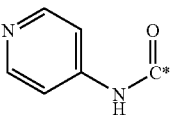 |
| A62 | 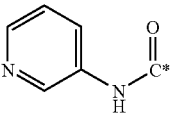 |
| A63 | 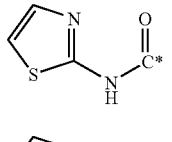 |
| A64 | 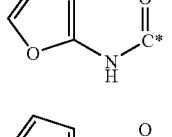 |
| A65 | 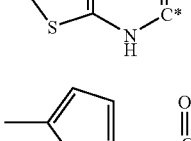 |
| A66 | 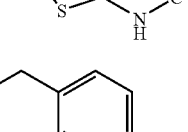 |
| A67 | 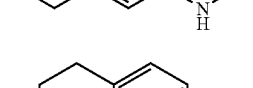 |
| A68 | 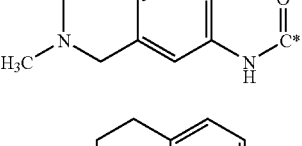 |
| A69 | 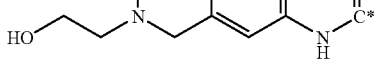 |

TABLE 1-continued
| | |
|---|---|
| A70 | 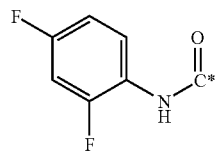 |
| A71 | 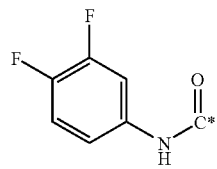 |
| A72 | 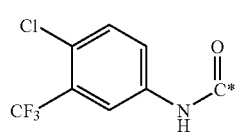 |
| A73 | 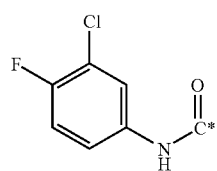 |
| A74 | 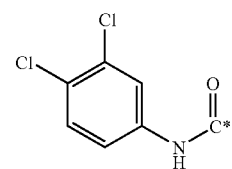 |
| A75 | 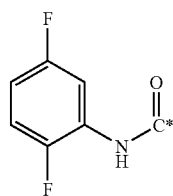 |
| A76 | 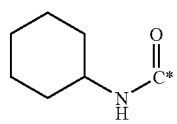 |
| A77 | 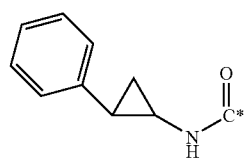 |
| A78 | 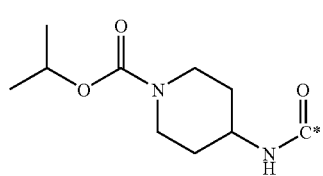 |
TABLE 1-continued
| | |
|---|---|
| A79 | 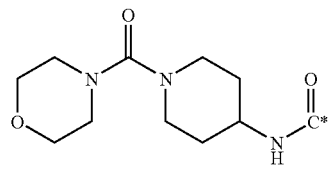 |
| A80 | 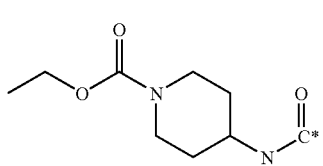 |
| A81 | 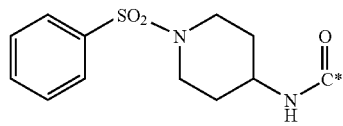 |
| A82 | 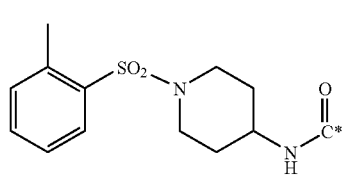 |
| A83 | 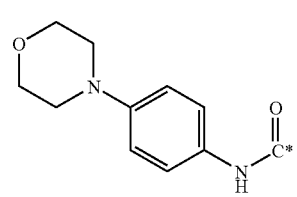 |
| A84 | 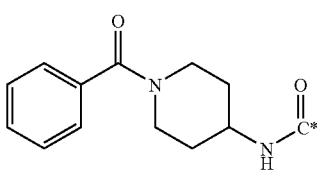 |
| A85 | 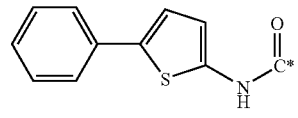 |
| A86 | 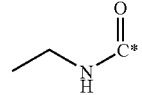 |
| A87 | 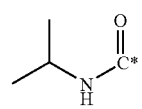 |
| A88 | 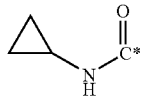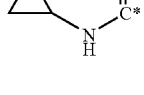 |

TABLE 1-continued
| | |
|---|---|
| A89 | 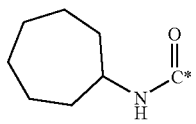 |
| A90 | 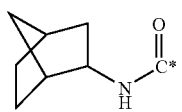 |
| A91 | 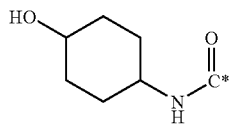 |
| A92 | 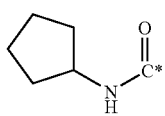 |
| A93 | 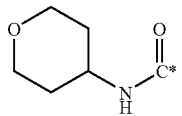 |
| A94 | 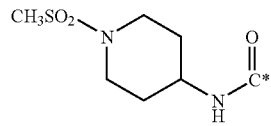 |
| A95 | 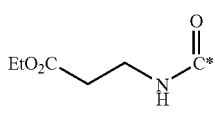 |
| A96 | 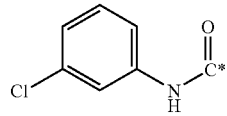 |
| A97 | 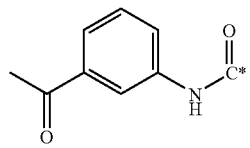 |
| A98 | 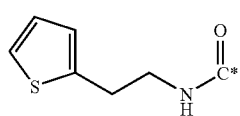 |
| A99 | 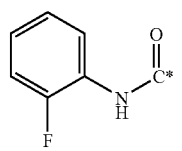 |
| A100 | 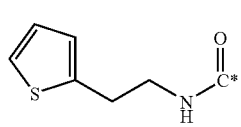 |
TABLE 1-continued
| | |
|---|---|
| A101 | 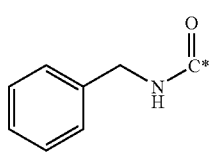 |
| A102 | 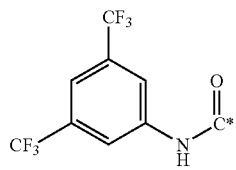 |
| A103 | 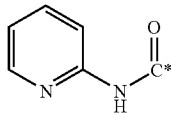 |
| A104 | 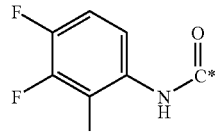 |
| A105 | 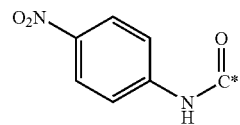 |
| A106 | 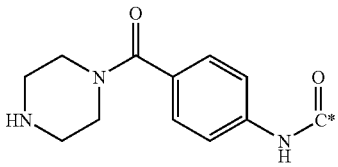 |
| A107 | 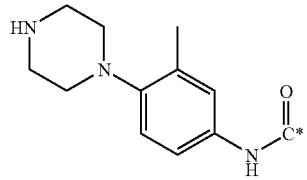 |
| A108 | 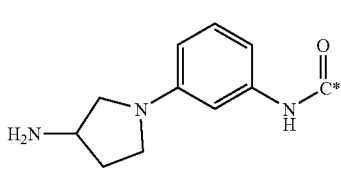 |
| A109 | 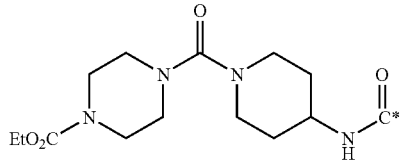 |

TABLE 1-continued
| A110 | 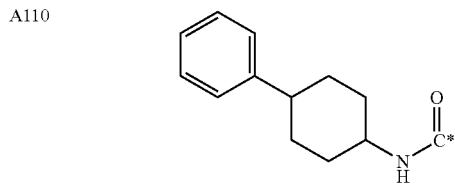 |
| A111 | 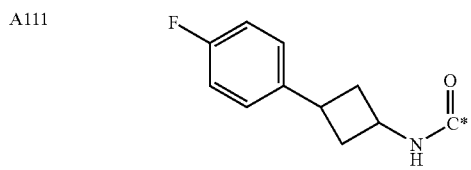 |
| A112 | 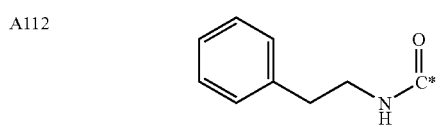 |
| A113 | 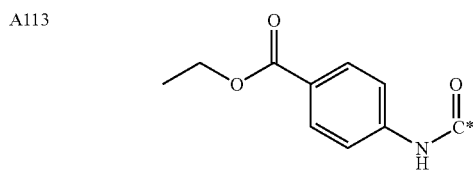 |
| A114 | 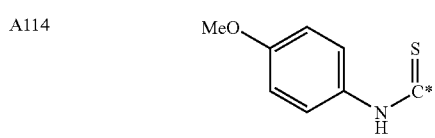 |
| A115 | 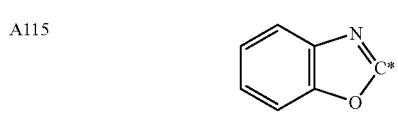 |
| A116 | 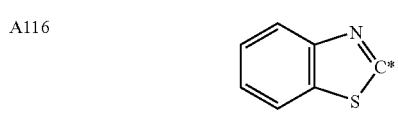 |
| A117 | 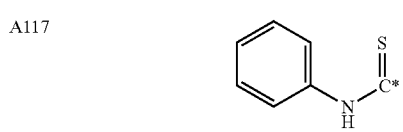 |
| A118 | 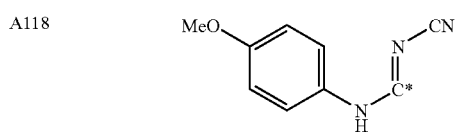 |
| A119 | 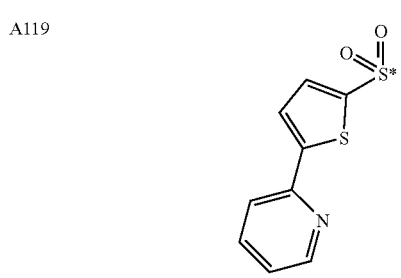 |
TABLE 1-continued
| A120 |  |
| A121 | 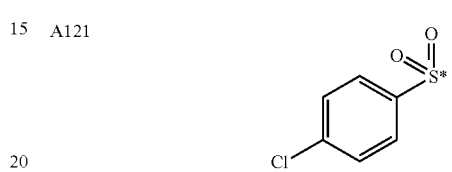 |
| A122 |  |
| A123 |  |
| A124 | 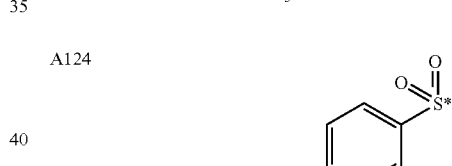 |
| A125 |  |
| A126 | 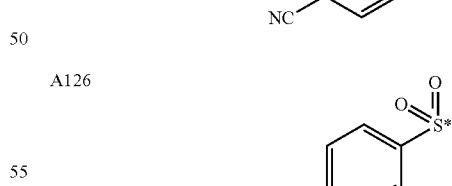 |
| A127 | 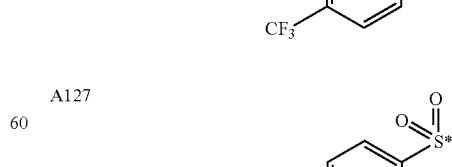 |

TABLE 1-continued

A128 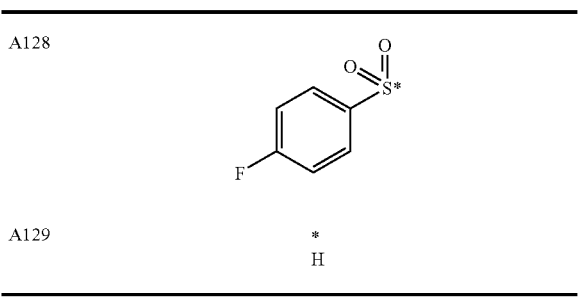

A129 *—H

TABLE 2

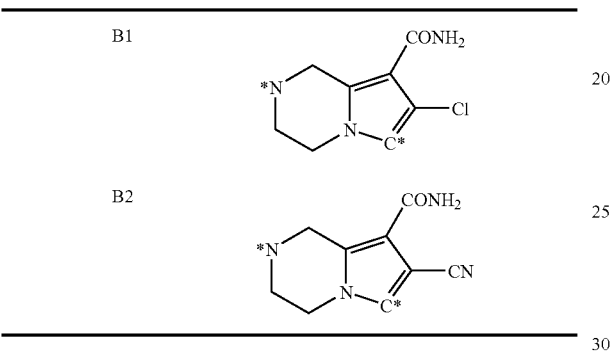

TABLE 3

C1 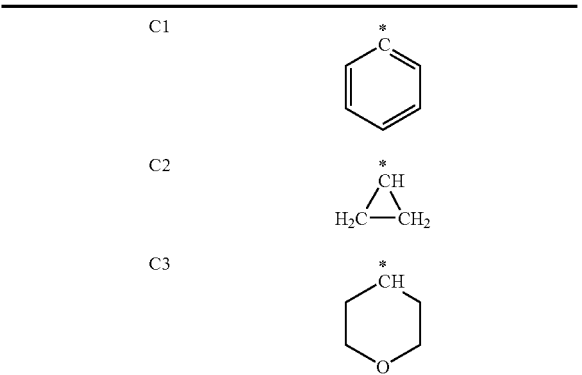

C2

C3

TABLE 3-continued

C4

C5

C6

C7 *—CH₃

C8 *—CF₃

C9

C10

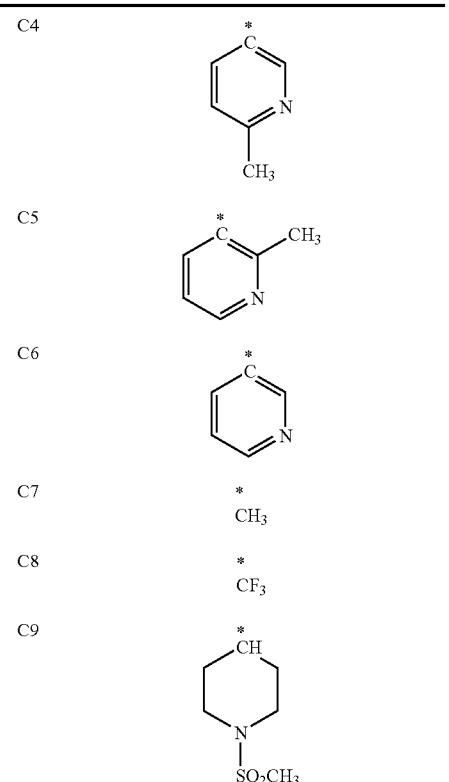

C11 *—H

Particular compounds of the invention of formula (I) denoted as the product of the combination of one of the fragments A1 to A129 in Table 1 and one of the fragments B1 to B2 in Table 2 and one of the fragments C1 to C11 in Table 3 are illustrated below:

| | | | | |
|---|---|---|---|---|
| A1-B1-C1; | A1-B1-C2; | A1-B1-C3; | A1-B1-C4; | A1-B1-C5; |
| A1-B1-C6; | A1-B1-C7; | A1-B1-C8; | A1-B1-C9; | A1-B1-C10; |
| A1-B1-C11; | A2-B1-C1; | A2-B1-C2; | A2-B1-C3; | A2-B1-C4; |
| A2-B1-C5; | A2-B1-C6; | A2-B1-C7; | A2-B1-C8; | A2-B1-C9; |
| A2-B1-C10; | A2-B1-C11; | A3-B1-C1; | A3-B1-C2; | A3-B1-C3; |
| A3-B1-C4; | A3-B1-C5; | A3-B1-C6; | A3-B1-C7; | A3-B1-C8; |
| A3-B1-C9; | A3-B1-C10; | A3-B1-C11; | A4-B1-C1; | A4-B1-C2; |
| A4-B1-C3; | A4-B1-C4; | A4-B1-C5; | A4-B1-C6; | A4-B1-C7; |
| A4-B1-C8; | A4-B1-C9; | A4-B1-C10; | A4-B1-C11; | A5-B1-C1; |
| A5-B1-C2; | A5-B1-C3; | A5-B1-C4; | A5-B1-C5; | A5-B1-C6; |
| A5-B1-C7; | A5-B1-C8; | A5-B1-C9; | A5-B1-C10; | A5-B1-C11; |
| A6-B1-C1; | A6-B1-C2; | A6-B1-C3; | A6-B1-C4; | A6-B1-C5; |
| A6-B1-C6; | A6-B1-C7; | A6-B1-C8; | A6-B1-C9; | A6-B1-C10; |
| A6-B1-C11; | A7-B1-C1; | A7-B1-C2; | A7-B1-C3; | A7-B1-C4; |
| A7-B1-C5; | A7-B1-C6; | A7-B1-C7; | A7-B1-C8; | A7-B1-C9; |
| A7-B1-C10; | A7-B1-C11; | A8-B1-C1; | A8-B1-C2; | A8-B1-C3; |
| A8-B1-C4; | A8-B1-C5; | A8-B1-C6; | A8-B1-C7; | A8-B1-C8; |

-continued

| | | | | |
|---|---|---|---|---|
| A8-B1-C9; | A8-B1-C10; | A8-B1-C11; | A9-B1-C1; | A9-B1-C2; |
| A9-B1-C3; | A9-B1-C4; | A9-B1-C5; | A9-B1-C6; | A9-B1-C7; |
| A9-B1-C8; | A9-B1-C9; | A9-B1-C10; | A9-B1-C11; | A10-B1-C1; |
| A10-B1-C2; | A10-B1-C3; | A10-B1-C4; | A10-B1-C5; | A10-B1-C6; |
| A10-B1-C7; | A10-B1-C8; | A10-B1-C9; | A10-B1-C10; | A10-B1-C11; |
| A11-B1-C1; | A11-B1-C2; | A11-B1-C3; | A11-B1-C4; | A11-B1-C5; |
| A11-B1-C6; | A11-B1-C7; | A11-B1-C8; | A11-B1-C9; | A11-B1-C10; |
| A11-B1-C11; | A12-B1-C1; | A12-B1-C2; | A12-B1-C3; | A12-B1-C4; |
| A12-B1-C5; | A12-B1-C6; | A12-B1-C7; | A12-B1-C8; | A12-B1-C9; |
| A12-B1-C10; | A12-B1-C11; | A13-B1-C1; | A13-B1-C2; | A13-B1-C3; |
| A13-B1-C4; | A13-B1-C5; | A13-B1-C6; | A13-B1-C7; | A13-B1-C8; |
| A13-B1-C9; | A13-B1-C10; | A13-B1-C11; | A14-B1-C1; | A14-B1-C2; |
| A14-B1-C3; | A14-B1-C4; | A14-B1-C5; | A14-B1-C6; | A14-B1-C7; |
| A14-B1-C8; | A14-B1-C9; | A14-B1-C10; | A14-B1-C11; | A15-B1-C1; |
| A15-B1-C2; | A15-B1-C3; | A15-B1-C4; | A15-B1-C5; | A15-B1-C6; |
| A15-B1-C7; | A15-B1-C8; | A15-B1-C9; | A15-B1-C10; | A15-B1-C11; |
| A16-B1-C1; | A16-B1-C2; | A16-B1-C3; | A16-B1-C4; | A16-B1-C5; |
| A16-B1-C6; | A16-B1-C7; | A16-B1-C8; | A16-B1-C9; | A16-B1-C10; |
| A16-B1-C11; | A17-B1-C1; | A17-B1-C2; | A17-B1-C3; | A17-B1-C4; |
| A17-B1-C5; | A17-B1-C6; | A17-B1-C7; | A17-B1-C8; | A17-B1-C9; |
| A17-B1-C10; | A17-B1-C11; | A18-B1-C1; | A18-B1-C2; | A18-B1-C3; |
| A18-B1-C4; | A18-B1-C5; | A18-B1-C6; | A18-B1-C7; | A18-B1-C8; |
| A18-B1-C9; | A18-B1-C10; | A18-B1-C11; | A19-B1-C1; | A19-B1-C2; |
| A19-B1-C3; | A19-B1-C4; | A19-B1-C5; | A19-B1-C6; | A19-B1-C7; |
| A19-B1-C8; | A19-B1-C9; | A19-B1-C10; | A19-B1-C11; | A20-B1-C1; |
| A20-B1-C2; | A20-B1-C3; | A20-B1-C4; | A20-B1-C5; | A20-B1-C6; |
| A20-B1-C7; | A20-B1-C8; | A20-B1-C9; | A20-B1-C10; | A20-B1-C11; |
| A21-B1-C1; | A21-B1-C2; | A21-B1-C3; | A21-B1-C4; | A21-B1-C5; |
| A21-B1-C6; | A21-B1-C7; | A21-B1-C8; | A21-B1-C9; | A21-B1-C10; |
| A21-B1-C11; | A22-B1-C1; | A22-B1-C2; | A22-B1-C3; | A22-B1-C4; |
| A22-B1-C5; | A22-B1-C6; | A22-B1-C7; | A22-B1-C8; | A22-B1-C9; |
| A22-B1-C10; | A22-B1-C11; | A23-B1-C1; | A23-B1-C2; | A23-B1-C3; |
| A23-B1-C4; | A23-B1-C5; | A23-B1-C6; | A23-B1-C7; | A23-B1-C8; |
| A23-B1-C9; | A23-B1-C10; | A23-B1-C11; | A24-B1-C1; | A24-B1-C2; |
| A24-B1-C3; | A24-B1-C4; | A24-B1-C5; | A24-B1-C6; | A24-B1-C7; |
| A24-B1-C8; | A24-B1-C9; | A24-B1-C10; | A24-B1-C11; | A25-B1-C1; |
| A25-B1-C2; | A25-B1-C3; | A25-B1-C4; | A25-B1-C5; | A25-B1-C6; |
| A25-B1-C7; | A25-B1-C8; | A25-B1-C9; | A25-B1-C10; | A25-B1-C11; |
| A26-B1-C1; | A26-B1-C2; | A26-B1-C3; | A26-B1-C4; | A26-B1-C5; |
| A26-B1-C6; | A26-B1-C7; | A26-B1-C8; | A26-B1-C9; | A26-B1-C10; |
| A26-B1-C11; | A27-B1-C1; | A27-B1-C2; | A27-B1-C3; | A27-B1-C4; |
| A27-B1-C5; | A27-B1-C6; | A27-B1-C7; | A27-B1-C8; | A27-B1-C9; |
| A27-B1-C10; | A27-B1-C11; | A28-B1-C1; | A28-B1-C2; | A28-B1-C3; |
| A28-B1-C4; | A28-B1-C5; | A28-B1-C6; | A28-B1-C7; | A28-B1-C8; |
| A28-B1-C9; | A28-B1-C10; | A28-B1-C11; | A29-B1-C1; | A29-B1-C2; |
| A29-B1-C3; | A29-B1-C4; | A29-B1-C5; | A29-B1-C6; | A29-B1-C7; |
| A29-B1-C8; | A29-B1-C9; | A29-B1-C10; | A29-B1-C11; | A30-B1-C1; |
| A30-B1-C2; | A30-B1-C3; | A30-B1-C4; | A30-B1-C5; | A30-B1-C6; |
| A30-B1-C7; | A30-B1-C8; | A30-B1-C9; | A30-B1-C10; | A30-B1-C11; |
| A31-B1-C1; | A31-B1-C2; | A31-B1-C3; | A31-B1-C4; | A31-B1-C5; |
| A31-B1-C6; | A31-B1-C7; | A31-B1-C8; | A31-B1-C9; | A31-B1-C10; |
| A31-B1-C11; | A32-B1-C1; | A32-B1-C2; | A32-B1-C3; | A32-B1-C4; |
| A32-B1-C5; | A32-B1-C6; | A32-B1-C7; | A32-B1-C8; | A32-B1-C9; |
| A32-B1-C10; | A32-B1-C11; | A33-B1-C1; | A33-B1-C2; | A33-B1-C3; |
| A33-B1-C4; | A33-B1-C5; | A33-B1-C6; | A33-B1-C7; | A33-B1-C8; |
| A33-B1-C9; | A33-B1-C10; | A33-B1-C11; | A34-B1-C1; | A34-B1-C2; |
| A34-B1-C3; | A34-B1-C4; | A34-B1-C5; | A34-B1-C6; | A34-B1-C7; |
| A34-B1-C8; | A34-B1-C9; | A34-B1-C10; | A34-B1-C11; | A35-B1-C1; |
| A35-B1-C2; | A35-B1-C3; | A35-B1-C4; | A35-B1-C5; | A35-B1-C6; |
| A35-B1-C7; | A35-B1-C8; | A35-B1-C9; | A35-B1-C10; | A35-B1-C11; |
| A36-B1-C1; | A36-B1-C2; | A36-B1-C3; | A36-B1-C4; | A36-B1-C5; |
| A36-B1-C6; | A36-B1-C7; | A36-B1-C8; | A36-B1-C9; | A36-B1-C10; |
| A36-B1-C11; | A37-B1-C1; | A37-B1-C2; | A37-B1-C3; | A37-B1-C4; |
| A37-B1-C5; | A37-B1-C6; | A37-B1-C7; | A37-B1-C8; | A37-B1-C9; |
| A37-B1-C10; | A37-B1-C11; | A38-B1-C1; | A38-B1-C2; | A38-B1-C3; |
| A38-B1-C4; | A38-B1-C5; | A38-B1-C6; | A38-B1-C7; | A38-B1-C8; |
| A38-B1-C9; | A38-B1-C10; | A38-B1-C11; | A39-B1-C1; | A39-B1-C2; |
| A39-B1-C3; | A39-B1-C4; | A39-B1-C5; | A39-B1-C6; | A39-B1-C7; |
| A39-B1-C8; | A39-B1-C9; | A39-B1-C10; | A39-B1-C11; | A40-B1-C1; |
| A40-B1-C2; | A40-B1-C3; | A40-B1-C4; | A40-B1-C5; | A40-B1-C6; |
| A40-B1-C7; | A40-B1-C8; | A40-B1-C9; | A40-B1-C10; | A40-B1-C11; |
| A41-B1-C1; | A41-B1-C2; | A41-B1-C3; | A41-B1-C4; | A41-B1-C5; |
| A41-B1-C6; | A41-B1-C7; | A41-B1-C8; | A41-B1-C9; | A41-B1-C10; |
| A41-B1-C11; | A42-B1-C1; | A42-B1-C2; | A42-B1-C3; | A42-B1-C4; |
| A42-B1-C5; | A42-B1-C6; | A42-B1-C7; | A42-B1-C8; | A42-B1-C9; |
| A42-B1-C10; | A42-B1-C11; | A43-B1-C1; | A43-B1-C2; | A43-B1-C3; |
| A43-B1-C4; | A43-B1-C5; | A43-B1-C6; | A43-B1-C7; | A43-B1-C8; |
| A43-B1-C9; | A43-B1-C10; | A43-B1-C11; | A44-B1-C1; | A44-B1-C2; |
| A44-B1-C3; | A44-B1-C4; | A44-B1-C5; | A44-B1-C6; | A44-B1-C7; |

-continued

| | | | | |
|---|---|---|---|---|
| A44-B1-C8; | A44-B1-C9; | A44-B1-C10; | A44-B1-C11; | A45-B1-C1; |
| A45-B1-C2; | A45-B1-C3; | A45-B1-C4; | A45-B1-C5; | A45-B1-C6; |
| A45-B1-C7; | A45-B1-C8; | A45-B1-C9; | A45-B1-C10; | A45-B1-C11; |
| A46-B1-C1; | A46-B1-C2; | A46-B1-C3; | A46-B1-C4; | A46-B1-C5; |
| A46-B1-C6; | A46-B1-C7; | A46-B1-C8; | A46-B1-C9; | A46-B1-C10; |
| A46-B1-C11; | A47-B1-C1; | A47-B1-C2; | A47-B1-C3; | A47-B1-C4; |
| A47-B1-C5; | A47-B1-C6; | A47-B1-C7; | A47-B1-C8; | A47-B1-C9; |
| A47-B1-C10; | A47-B1-C11; | A48-B1-C1; | A48-B1-C2; | A48-B1-C3; |
| A48-B1-C4; | A48-B1-C5; | A48-B1-C6; | A48-B1-C7; | A48-B1-C8; |
| A48-B1-C9; | A48-B1-C10; | A48-B1-C11; | A49-B1-C1; | A49-B1-C2; |
| A49-B1-C3; | A49-B1-C4; | A49-B1-C5; | A49-B1-C6; | A49-B1-C7; |
| A49-B1-C8; | A49-B1-C9; | A49-B1-C10; | A49-B1-C11; | A50-B1-C1; |
| A50-B1-C2; | A50-B1-C3; | A50-B1-C4; | A50-B1-C5; | A50-B1-C6; |
| A50-B1-C7; | A50-B1-C8; | A50-B1-C9; | A50-B1-C10; | A50-B1-C11; |
| A51-B1-C1; | A51-B1-C2; | A51-B1-C3; | A51-B1-C4; | A51-B1-C5; |
| A51-B1-C6; | A51-B1-C7; | A51-B1-C8; | A51-B1-C9; | A51-B1-C10; |
| A51-B1-C11; | A52-B1-C1; | A52-B1-C2; | A52-B1-C3; | A52-B1-C4; |
| A52-B1-C5; | A52-B1-C6; | A52-B1-C7; | A52-B1-C8; | A52-B1-C9; |
| A52-B1-C10; | A52-B1-C11; | A53-B1-C1; | A53-B1-C2; | A53-B1-C3; |
| A53-B1-C4; | A53-B1-C5; | A53-B1-C6; | A53-B1-C7; | A53-B1-C8; |
| A53-B1-C9; | A53-B1-C10; | A53-B1-C11; | A54-B1-C1; | A54-B1-C2; |
| A54-B1-C3; | A54-B1-C4; | A54-B1-C5; | A54-B1-C6; | A54-B1-C7; |
| A54-B1-C8; | A54-B1-C9; | A54-B1-C10; | A54-B1-C11; | A55-B1-C1; |
| A55-B1-C2; | A55-B1-C3; | A55-B1-C4; | A55-B1-C5; | A55-B1-C6; |
| A55-B1-C7; | A55-B1-C8; | A55-B1-C9; | A55-B1-C10; | A55-B1-C11; |
| A56-B1-C1; | A56-B1-C2; | A56-B1-C3; | A56-B1-C4; | A56-B1-C5; |
| A56-B1-C6; | A56-B1-C7; | A56-B1-C8; | A56-B1-C9; | A56-B1-C10; |
| A56-B1-C11; | A57-B1-C1; | A57-B1-C2; | A57-B1-C3; | A57-B1-C4; |
| A57-B1-C5; | A57-B1-C6; | A57-B1-C7; | A57-B1-C8; | A57-B1-C9; |
| A57-B1-C10; | A57-B1-C11; | A58-B1-C1; | A58-B1-C2; | A58-B1-C3; |
| A58-B1-C4; | A58-B1-C5; | A58-B1-C6; | A58-B1-C7; | A58-B1-C8; |
| A58-B1-C9; | A58-B1-C10; | A58-B1-C11; | A59-B1-C1; | A59-B1-C2; |
| A59-B1-C3; | A59-B1-C4; | A59-B1-C5; | A59-B1-C6; | A59-B1-C7; |
| A59-B1-C8; | A59-B1-C9; | A59-B1-C10; | A59-B1-C11; | A60-B1-C1; |
| A60-B1-C2; | A60-B1-C3; | A60-B1-C4; | A60-B1-C5; | A60-B1-C6; |
| A60-B1-C7; | A60-B1-C8; | A60-B1-C9; | A60-B1-C10; | A60-B1-C11; |
| A61-B1-C1; | A61-B1-C2; | A61-B1-C3; | A61-B1-C4; | A61-B1-C5; |
| A61-B1-C6; | A61-B1-C7; | A61-B1-C8; | A61-B1-C9; | A61-B1-C10; |
| A61-B1-C11; | A62-B1-C1; | A62-B1-C2; | A62-B1-C3; | A62-B1-C4; |
| A62-B1-C5; | A62-B1-C6; | A62-B1-C7; | A62-B1-C8; | A62-B1-C9; |
| A62-B1-C10; | A62-B1-C11; | A63-B1-C1; | A63-B1-C2; | A63-B1-C3; |
| A63-B1-C4; | A63-B1-C5; | A63-B1-C6; | A63-B1-C7; | A63-B1-C8; |
| A63-B1-C9; | A63-B1-C10; | A63-B1-C11; | A64-B1-C1; | A64-B1-C2; |
| A64-B1-C3; | A64-B1-C4; | A64-B1-C5; | A64-B1-C6; | A64-B1-C7; |
| A64-B1-C8; | A64-B1-C9; | A64-B1-C10; | A64-B1-C11; | A65-B1-C1; |
| A65-B1-C2; | A65-B1-C3; | A65-B1-C4; | A65-B1-C5; | A65-B1-C6; |
| A65-B1-C7; | A65-B1-C8; | A65-B1-C9; | A65-B1-C10; | A65-B1-C11; |
| A66-B1-C1; | A66-B1-C2; | A66-B1-C3; | A66-B1-C4; | A66-B1-C5; |
| A66-B1-C6; | A66-B1-C7; | A66-B1-C8; | A66-B1-C9; | A66-B1-C10; |
| A66-B1-C11; | A67-B1-C1; | A67-B1-C2; | A67-B1-C3; | A67-B1-C4; |
| A67-B1-C5; | A67-B1-C6; | A67-B1-C7; | A67-B1-C8; | A67-B1-C9; |
| A67-B1-C10; | A67-B1-C11; | A68-B1-C1; | A68-B1-C2; | A68-B1-C3; |
| A68-B1-C4; | A68-B1-C5; | A68-B1-C6; | A68-B1-C7; | A68-B1-C8; |
| A68-B1-C9; | A68-B1-C10; | A68-B1-C11; | A69-B1-C1; | A69-B1-C2; |
| A69-B1-C3; | A69-B1-C4; | A69-B1-C5; | A69-B1-C6; | A69-B1-C7; |
| A69-B1-C8; | A69-B1-C9; | A69-B1-C10; | A69-B1-C11; | A70-B1-C1; |
| A70-B1-C2; | A70-B1-C3; | A70-B1-C4; | A70-B1-C5; | A70-B1-C6; |
| A70-B1-C7; | A70-B1-C8; | A70-B1-C9; | A70-B1-C10; | A70-B1-C11; |
| A71-B1-C1; | A71-B1-C2; | A71-B1-C3; | A71-B1-C4; | A71-B1-C5; |
| A71-B1-C6; | A71-B1-C7; | A71-B1-C8; | A71-B1-C9; | A71-B1-C10; |
| A71-B1-C11; | A72-B1-C1; | A72-B1-C2; | A72-B1-C3; | A72-B1-C4; |
| A72-B1-C5; | A72-B1-C6; | A72-B1-C7; | A72-B1-C8; | A72-B1-C9; |
| A72-B1-C10; | A72-B1-C11; | A73-B1-C1; | A73-B1-C2; | A73-B1-C3; |
| A73-B1-C4; | A73-B1-C5; | A73-B1-C6; | A73-B1-C7; | A73-B1-C8; |
| A73-B1-C9; | A73-B1-C10; | A73-B1-C11; | A74-B1-C1; | A74-B1-C2; |
| A74-B1-C3; | A74-B1-C4; | A74-B1-C5; | A74-B1-C6; | A74-B1-C7; |
| A74-B1-C8; | A74-B1-C9; | A74-B1-C10; | A74-B1-C11; | A75-B1-C1; |
| A75-B1-C2; | A75-B1-C3; | A75-B1-C4; | A75-B1-C5; | A75-B1-C6; |
| A75-B1-C7; | A75-B1-C8; | A75-B1-C9; | A75-B1-C10; | A75-B1-C11; |
| A76-B1-C1; | A76-B1-C2; | A76-B1-C3; | A76-B1-C4; | A76-B1-C5; |
| A76-B1-C6; | A76-B1-C7; | A76-B1-C8; | A76-B1-C9; | A76-B1-C10; |
| A76-B1-C11; | A77-B1-C1; | A77-B1-C2; | A77-B1-C3; | A77-B1-C4; |
| A77-B1-C5; | A77-B1-C6; | A77-B1-C7; | A77-B1-C8; | A77-B1-C9; |
| A77-B1-C10; | A77-B1-C11; | A78-B1-C1; | A78-B1-C2; | A78-B1-C3; |
| A78-B1-C4; | A78-B1-C5; | A78-B1-C6; | A78-B1-C7; | A78-B1-C8; |
| A78-B1-C9; | A78-B1-C10; | A78-B1-C11; | A79-B1-C1; | A79-B1-C2; |
| A79-B1-C3; | A79-B1-C4; | A79-B1-C5; | A79-B1-C6; | A79-B1-C7; |
| A79-B1-C8; | A79-B1-C9; | A79-B1-C10; | A79-B1-C11; | A80-B1-C1; |
| A80-B1-C2; | A80-B1-C3; | A80-B1-C4; | A80-B1-C5; | A80-B1-C6; |

-continued

| | | | | |
|---|---|---|---|---|
| A80-B1-C7; | A80-B1-C8; | A80-B1-C9; | A80-B1-C10; | A80-B1-C11; |
| A81-B1-C1; | A81-B1-C2; | A81-B1-C3; | A81-B1-C4; | A81-B1-C5; |
| A81-B1-C6; | A81-B1-C7; | A81-B1-C8; | A81-B1-C9; | A81-B1-C10; |
| A81-B1-C11; | A82-B1-C1; | A82-B1-C2; | A82-B1-C3; | A82-B1-C4; |
| A82-B1-C5; | A82-B1-C6; | A82-B1-C7; | A82-B1-C8; | A82-B1-C9; |
| A82-B1-C10; | A82-B1-C11; | A83-B1-C1; | A83-B1-C2; | A83-B1-C3; |
| A83-B1-C4; | A83-B1-C5; | A83-B1-C6; | A83-B1-C7; | A83-B1-C8; |
| A83-B1-C9; | A83-B1-C10; | A83-B1-C11; | A84-B1-C1; | A84-B1-C2; |
| A84-B1-C3; | A84-B1-C4; | A84-B1-C5; | A84-B1-C6; | A84-B1-C7; |
| A84-B1-C8; | A84-B1-C9; | A84-B1-C10; | A84-B1-C11; | A85-B1-C1; |
| A85-B1-C2; | A85-B1-C3; | A85-B1-C4; | A85-B1-C5; | A85-B1-C6; |
| A85-B1-C7; | A85-B1-C8; | A85-B1-C9; | A85-B1-C10; | A85-B1-C11; |
| A86-B1-C1; | A86-B1-C2; | A86-B1-C3; | A86-B1-C4; | A86-B1-C5; |
| A86-B1-C6; | A86-B1-C7; | A86-B1-C8; | A86-B1-C9; | A86-B1-C10; |
| A86-B1-C11; | A87-B1-C1; | A87-B1-C2; | A87-B1-C3; | A87-B1-C4; |
| A87-B1-C5; | A87-B1-C6; | A87-B1-C7; | A87-B1-C8; | A87-B1-C9; |
| A87-B1-C10; | A87-B1-C11; | A88-B1-C1; | A88-B1-C2; | A88-B1-C3; |
| A88-B1-C4; | A88-B1-C5; | A88-B1-C6; | A88-B1-C7; | A88-B1-C8; |
| A88-B1-C9; | A88-B1-C10; | A88-B1-C11; | A89-B1-C1; | A89-B1-C2; |
| A89-B1-C3; | A89-B1-C4; | A89-B1-C5; | A89-B1-C6; | A89-B1-C7; |
| A89-B1-C8; | A89-B1-C9; | A89-B1-C10; | A89-B1-C11; | A90-B1-C1; |
| A90-B1-C2; | A90-B1-C3; | A90-B1-C4; | A90-B1-C5; | A90-B1-C6; |
| A90-B1-C7; | A90-B1-C8; | A90-B1-C9; | A90-B1-C10; | A90-B1-C11; |
| A91-B1-C1; | A91-B1-C2; | A91-B1-C3; | A91-B1-C4; | A91-B1-C5; |
| A91-B1-C6; | A91-B1-C7; | A91-B1-C8; | A91-B1-C9; | A91-B1-C10; |
| A91-B1-C11; | A92-B1-C1; | A92-B1-C2; | A92-B1-C3; | A92-B1-C4; |
| A92-B1-C5; | A92-B1-C6; | A92-B1-C7; | A92-B1-C8; | A92-B1-C9; |
| A92-B1-C10; | A92-B1-C11; | A93-B1-C1; | A93-B1-C2; | A93-B1-C3; |
| A93-B1-C4; | A93-B1-C5; | A93-B1-C6; | A93-B1-C7; | A93-B1-C8; |
| A93-B1-C9; | A93-B1-C10; | A93-B1-C11; | A94-B1-C1; | A94-B1-C2; |
| A94-B1-C3; | A94-B1-C4; | A94-B1-C5; | A94-B1-C6; | A94-B1-C7; |
| A94-B1-C8; | A94-B1-C9; | A94-B1-C10; | A94-B1-C11; | A95-B1-C1; |
| A95-B1-C2; | A95-B1-C3; | A95-B1-C4; | A95-B1-C5; | A95-B1-C6; |
| A95-B1-C7; | A95-B1-C8; | A95-B1-C9; | A95-B1-C10; | A95-B1-C11; |
| A96-B1-C1; | A96-B1-C2; | A96-B1-C3; | A96-B1-C4; | A96-B1-C5; |
| A96-B1-C6; | A96-B1-C7; | A96-B1-C8; | A96-B1-C9; | A96-B1-C10; |
| A96-B1-C11; | A97-B1-C1; | A97-B1-C2; | A97-B1-C3; | A97-B1-C4; |
| A97-B1-C5; | A97-B1-C6; | A97-B1-C7; | A97-B1-C8; | A97-B1-C9; |
| A97-B1-C10; | A97-B1-C11; | A98-B1-C1; | A98-B1-C2; | A98-B1-C3; |
| A98-B1-C4; | A98-B1-C5; | A98-B1-C6; | A98-B1-C7; | A98-B1-C8; |
| A98-B1-C9; | A98-B1-C10; | A98-B1-C11; | A99-B1-C1; | A99-B1-C2; |
| A99-B1-C3; | A99-B1-C4; | A99-B1-C5; | A99-B1-C6; | A99-B1-C7; |
| A99-B1-C8; | A99-B1-C9; | A99-B1-C10; | A99-B1-C11; | A100-B1-C1; |
| A100-B1-C2; | A100-B1-C3; | A100-B1-C4; | A100-B1-C5; | A100-B1-C6; |
| A100-B1-C7; | A100-B1-C8; | A100-B1-C9; | A100-B1-C10; | A100-B1-C11; |
| A101-B1-C1; | A101-B1-C2; | A101-B1-C3; | A101-B1-C4; | A101-B1-C5; |
| A101-B1-C6; | A101-B1-C7; | A101-B1-C8; | A101-B1-C9; | A101-B1-C10; |
| A101-B1-C11; | A102-B1-C1; | A102-B1-C2; | A102-B1-C3; | A102-B1-C4; |
| A102-B1-C5; | A102-B1-C6; | A102-B1-C7; | A102-B1-C8; | A102-B1-C9; |
| A102-B1-C10; | A102-B1-C11; | A103-B1-C1; | A103-B1-C2; | A103-B1-C3; |
| A103-B1-C4; | A103-B1-C5; | A103-B1-C6; | A103-B1-C7; | A103-B1-C8; |
| A103-B1-C9; | A103-B1-C10; | A103-B1-C11; | A104-B1-C1; | A104-B1-C2; |
| A104-B1-C3; | A104-B1-C4; | A104-B1-C5; | A104-B1-C6; | A104-B1-C7; |
| A104-B1-C8; | A104-B1-C9; | A104-B1-C10; | A104-B1-C11; | A105-B1-C1; |
| A105-B1-C2; | A105-B1-C3; | A105-B1-C4; | A105-B1-C5; | A105-B1-C6; |
| A105-B1-C7; | A105-B1-C8; | A105-B1-C9; | A105-B1-C10; | A105-B1-C11; |
| A106-B1-C1; | A106-B1-C2; | A106-B1-C3; | A106-B1-C4; | A106-B1-C5; |
| A106-B1-C6; | A106-B1-C7; | A106-B1-C8; | A106-B1-C9; | A106-B1-C10; |
| A106-B1-C11; | A107-B1-C1; | A107-B1-C2; | A107-B1-C3; | A107-B1-C4; |
| A107-B1-C5; | A107-B1-C6; | A107-B1-C7; | A107-B1-C8; | A107-B1-C9; |
| A107-B1-C10; | A107-B1-C11; | A108-B1-C1; | A108-B1-C2; | A108-B1-C3; |
| A108-B1-C4; | A108-B1-C5; | A108-B1-C6; | A108-B1-C7; | A108-B1-C8; |
| A108-B1-C9; | A108-B1-C10; | A108-B1-C11; | A109-B1-C1; | A109-B1-C2; |
| A109-B1-C3; | A109-B1-C4; | A109-B1-C5; | A109-B1-C6; | A109-B1-C7; |
| A109-B1-C8; | A109-B1-C9; | A109-B1-C10; | A109-B1-C11; | A110-B1-C1; |
| A110-B1-C2; | A110-B1-C3; | A110-B1-C4; | A110-B1-C5; | A110-B1-C6; |
| A110-B1-C7; | A110-B1-C8; | A110-B1-C9; | A110-B1-C10; | A110-B1-C11; |
| A111-B1-C1; | A111-B1-C2; | A111-B1-C3; | A111-B1-C4; | A111-B1-C5; |
| A111-B1-C6; | A111-B1-C7; | A111-B1-C8; | A111-B1-C9; | A111-B1-C10; |
| A111-B1-C11; | A112-B1-C1; | A112-B1-C2; | A112-B1-C3; | A112-B1-C4; |
| A112-B1-C5; | A112-B1-C6; | A112-B1-C7; | A112-B1-C8; | A112-B1-C9; |
| A112-B1-C10; | A112-B1-C11; | A113-B1-C1; | A113-B1-C2; | A113-B1-C3; |
| A113-B1-C4; | A113-B1-C5; | A113-B1-C6; | A113-B1-C7; | A113-B1-C8; |
| A113-B1-C9; | A113-B1-C10; | A113-B1-C11; | A114-B1-C1; | A114-B1-C2; |
| A114-B1-C3; | A114-B1-C4; | A114-B1-C5; | A114-B1-C6; | A114-B1-C7; |
| A114-B1-C8; | A114-B1-C9; | A114-B1-C10; | A114-B1-C11; | A115-B1-C1; |
| A115-B1-C2; | A115-B1-C3; | A115-B1-C4; | A115-B1-C5; | A115-B1-C6; |
| A115-B1-C7; | A115-B1-C8; | A115-B1-C9; | A115-B1-C10; | A115-B1-C11; |
| A116-B1-C1; | A116-B1-C2; | A116-B1-C3; | A116-B1-C4; | A116-B1-C5; |

-continued

A116-B1-C6; A116-B1-C7; A116-B1-C8; A116-B1-C9; A116-B1-C10;
A116-B1-C11; A117-B1-C1; A117-B1-C2; A117-B1-C3; A117-B1-C4;
A117-B1-C5; A117-B1-C6; A117-B1-C7; A117-B1-C8; A117-B1-C9;
A117-B1-C10; A117-B1-C11; A118-B1-C1; A118-B1-C2; A118-B1-C3;
A118-B1-C4; A118-B1-C5; A118-B1-C6; A118-B1-C7; A118-B1-C8;
A118-B1-C9; A118-B1-C10; A118-B1-C11; A119-B1-C1; A119-B1-C2;
A119-B1-C3; A119-B1-C4; A119-B1-C5; A119-B1-C6; A119-B1-C7;
A119-B1-C8; A119-B1-C9; A119-B1-C10; A119-B1-C11; A120-B1-C1;
A120-B1-C2; A120-B1-C3; A120-B1-C4; A120-B1-C5; A120-B1-C6;
A120-B1-C7; A120-B1-C8; A120-B1-C9; A120-B1-C10; A120-B1-C11;
A121-B1-C1; A121-B1-C2; A121-B1-C3; A121-B1-C4; A121-B1-C5;
A121-B1-C6; A121-B1-C7; A121-B1-C8; A121-B1-C9; A121-B1-C10;
A121-B1-C11; A122-B1-C1; A122-B1-C2; A122-B1-C3; A122-B1-C4;
A122-B1-C5; A122-B1-C6; A122-B1-C7; A122-B1-C8; A122-B1-C9;
A122-B1-C10; A122-B1-C11; A123-B1-C1; A123-B1-C2; A123-B1-C3;
A123-B1-C4; A123-B1-C5; A123-B1-C6; A123-B1-C7; A123-B1-C8;
A123-B1-C9; A123-B1-C10; A123-B1-C11; A124-B1-C1; A124-B1-C2;
A124-B1-C3; A124-B1-C4; A124-B1-C5; A124-B1-C6; A124-B1-C7;
A124-B1-C8; A124-B1-C9; A124-B1-C10; A124-B1-C11; A125-B1-C1;
A125-B1-C2; A125-B1-C3; A125-B1-C4; A125-B1-C5; A125-B1-C6;
A125-B1-C7; A125-B1-C8; A125-B1-C9; A125-B1-C10; A125-B1-C11;
A126-B1-C1; A126-B1-C2; A126-B1-C3; A126-B1-C4; A126-B1-C5;
A126-B1-C6; A126-B1-C7; A126-B1-C8; A126-B1-C9; A126-B1-C10;
A126-B1-C11; A127-B1-C1; A127-B1-C2; A127-B1-C3; A127-B1-C4;
A127-B1-C5; A127-B1-C6; A127-B1-C7; A127-B1-C8; A127-B1-C9;
A127-B1-C10; A127-B1-C11; A128-B1-C1; A128-B1-C2; A128-B1-C3;
A128-B1-C4; A128-B1-C5; A128-B1-C6; A128-B1-C7; A128-B1-C8;
A128-B1-C9; A128-B1-C10; A128-B1-C11; A129-B1-C1; A129-B1-C2;
A129-B1-C3; A129-B1-C4; A129-B1-C5; A129-B1-C6; A129-B1-C7;
A129-B1-C8; A129-B1-C9; A129-B1-C10; A129-B1-C11; A1-B2-C1;
A1-B2-C2; A1-B2-C3; A1-B2-C4; A1-B2-C5; A1-B2-C6;
A1-B2-C7; A1-B2-C8; A1-B2-C9; A1-B2-C10; A1-B2-C11;
A2-B2-C1; A2-B2-C2; A2-B2-C3; A2-B2-C4; A2-B2-C5;
A2-B2-C6; A2-B2-C7; A2-B2-C8; A2-B2-C9; A2-B2-C10;
A2-B2-C11; A3-B2-C1; A3-B2-C2; A3-B2-C3; A3-B2-C4;
A3-B2-C5; A3-B2-C6; A3-B2-C7; A3-B2-C8; A3-B2-C9;
A3-B2-C10; A3-B2-C11; A4-B2-C1; A4-B2-C2; A4-B2-C3;
A4-B2-C4; A4-B2-C5; A4-B2-C6; A4-B2-C7; A4-B2-C8;
A4-B2-C9; A4-B2-C10; A4-B2-C11; A5-B2-C1; A5-B2-C2;
A5-B2-C3; A5-B2-C4; A5-B2-C5; A5-B2-C6; A5-B2-C7;
A5-B2-C8; A5-B2-C9; A5-B2-C10; A5-B2-C11; A6-B2-C1;
A6-B2-C2; A6-B2-C3; A6-B2-C4; A6-B2-C5; A6-B2-C6;
A6-B2-C7; A6-B2-C8; A6-B2-C9; A6-B2-C10; A6-B2-C11;
A7-B2-C1; A7-B2-C2; A7-B2-C3; A7-B2-C4; A7-B2-C5;
A7-B2-C6; A7-B2-C7; A7-B2-C8; A7-B2-C9; A7-B2-C10;
A7-B2-C11; A8-B2-C1; A8-B2-C2; A8-B2-C3; A8-B2-C4;
A8-B2-C5; A8-B2-C6; A8-B2-C7; A8-B2-C8; A8-B2-C9;
A8-B2-C10; A8-B2-C11; A9-B2-C1; A9-B2-C2; A9-B2-C3;
A9-B2-C4; A9-B2-C5; A9-B2-C6; A9-B2-C7; A9-B2-C8;
A9-B2-C9; A9-B2-C10; A9-B2-C11; A10-B2-C1; A10-B2-C2;
A10-B2-C3; A10-B2-C4; A10-B2-C5; A10-B2-C6; A10-B2-C7;
A10-B2-C8; A10-B2-C9; A10-B2-C10; A10-B2-C11; A11-B2-C1;
A11-B2-C2; A11-B2-C3; A11-B2-C4; A11-B2-C5; A11-B2-C6;
A11-B2-C7; A11-B2-C8; A11-B2-C9; A11-B2-C10; A11-B2-C11;
A12-B2-C1; A12-B2-C2; A12-B2-C3; A12-B2-C4; A12-B2-C5;
A12-B2-C6; A12-B2-C7; A12-B2-C8; A12-B2-C9; A12-B2-C10;
A12-B2-C11; A13-B2-C1; A13-B2-C2; A13-B2-C3; A13-B2-C4;
A13-B2-C5; A13-B2-C6; A13-B2-C7; A13-B2-C8; A13-B2-C9;
A13-B2-C10; A13-B2-C11; A14-B2-C1; A14-B2-C2; A14-B2-C3;
A14-B2-C4; A14-B2-C5; A14-B2-C6; A14-B2-C7; A14-B2-C8;
A14-B2-C9; A14-B2-C10; A14-B2-C11; A15-B2-C1; A15-B2-C2;
A15-B2-C3; A15-B2-C4; A15-B2-C5; A15-B2-C6; A15-B2-C7;
A15-B2-C8; A15-B2-C9; A15-B2-C10; A15-B2-C11; A16-B2-C1;
A16-B2-C2; A16-B2-C3; A16-B2-C4; A16-B2-C5; A16-B2-C6;
A16-B2-C7; A16-B2-C8; A16-B2-C9; A16-B2-C10; A16-B2-C11;
A17-B2-C1; A17-B2-C2; A17-B2-C3; A17-B2-C4; A17-B2-C5;
A17-B2-C6; A17-B2-C7; A17-B2-C8; A17-B2-C9; A17-B2-C10;
A17-B2-C11; A18-B2-C1; A18-B2-C2; A18-B2-C3; A18-B2-C4;
A18-B2-C5; A18-B2-C6; A18-B2-C7; A18-B2-C8; A18-B2-C9;
A18-B2-C10; A18-B2-C11; A19-B2-C1; A19-B2-C2; A19-B2-C3;
A19-B2-C4; A19-B2-C5; A19-B2-C6; A19-B2-C7; A19-B2-C8;
A19-B2-C9; A19-B2-C10; A19-B2-C11; A20-B2-C1; A20-B2-C2;
A20-B2-C3; A20-B2-C4; A20-B2-C5; A20-B2-C6; A20-B2-C7;
A20-B2-C8; A20-B2-C9; A20-B2-C10; A20-B2-C11; A21-B2-C1;
A21-B2-C2; A21-B2-C3; A21-B2-C4; A21-B2-C5; A21-B2-C6;
A21-B2-C7; A21-B2-C8; A21-B2-C9; A21-B2-C10; A21-B2-C11;
A22-B2-C1; A22-B2-C2; A22-B2-C3; A22-B2-C4; A22-B2-C5;
A22-B2-C6; A22-B2-C7; A22-B2-C8; A22-B2-C9; A22-B2-C10;
A22-B2-C11; A23-B2-C1; A23-B2-C2; A23-B2-C3; A23-B2-C4;

-continued

| | | | | |
|---|---|---|---|---|
| A23-B2-C5; | A23-B2-C6; | A23-B2-C7; | A23-B2-C8; | A23-B2-C9; |
| A23-B2-C10; | A23-B2-C11; | A24-B2-C1; | A24-B2-C2; | A24-B2-C3; |
| A24-B2-C4; | A24-B2-C5; | A24-B2-C6; | A24-B2-C7; | A24-B2-C8; |
| A24-B2-C9; | A24-B2-C10; | A24-B2-C11; | A25-B2-C1; | A25-B2-C2; |
| A25-B2-C3; | A25-B2-C4; | A25-B2-C5; | A25-B2-C6; | A25-B2-C7; |
| A25-B2-C8; | A25-B2-C9; | A25-B2-C10; | A25-B2-C11; | A26-B2-C1; |
| A26-B2-C2; | A26-B2-C3; | A26-B2-C4; | A26-B2-C5; | A26-B2-C6; |
| A26-B2-C7; | A26-B2-C8; | A26-B2-C9; | A26-B2-C10; | A26-B2-C11; |
| A27-B2-C1; | A27-B2-C2; | A27-B2-C3; | A27-B2-C4; | A27-B2-C5; |
| A27-B2-C6; | A27-B2-C7; | A27-B2-C8; | A27-B2-C9; | A27-B2-C10; |
| A27-B2-C11; | A28-B2-C1; | A28-B2-C2; | A28-B2-C3; | A28-B2-C4; |
| A28-B2-C5; | A28-B2-C6; | A28-B2-C7; | A28-B2-C8; | A28-B2-C9; |
| A28-B2-C10; | A28-B2-C11; | A29-B2-C1; | A29-B2-C2; | A29-B2-C3; |
| A29-B2-C4; | A29-B2-C5; | A29-B2-C6; | A29-B2-C7; | A29-B2-C8; |
| A29-B2-C9; | A29-B2-C10; | A29-B2-C11; | A30-B2-C1; | A30-B2-C2; |
| A30-B2-C3; | A30-B2-C4; | A30-B2-C5; | A30-B2-C6; | A30-B2-C7; |
| A30-B2-C8; | A30-B2-C9; | A30-B2-C10; | A30-B2-C11; | A31-B2-C1; |
| A31-B2-C2; | A31-B2-C3; | A31-B2-C4; | A31-B2-C5; | A31-B2-C6; |
| A31-B2-C7; | A31-B2-C8; | A31-B2-C9; | A31-B2-C10; | A31-B2-C11; |
| A32-B2-C1; | A32-B2-C2; | A32-B2-C3; | A32-B2-C4; | A32-B2-C5; |
| A32-B2-C6; | A32-B2-C7; | A32-B2-C8; | A32-B2-C9; | A32-B2-C10; |
| A32-B2-C11; | A33-B2-C1; | A33-B2-C2; | A33-B2-C3; | A33-B2-C4; |
| A33-B2-C5; | A33-B2-C6; | A33-B2-C7; | A33-B2-C8; | A33-B2-C9; |
| A33-B2-C10; | A33-B2-C11; | A34-B2-C1; | A34-B2-C2; | A34-B2-C3; |
| A34-B2-C4; | A34-B2-C5; | A34-B2-C6; | A34-B2-C7; | A34-B2-C8; |
| A34-B2-C9; | A34-B2-C10; | A34-B2-C11; | A35-B2-C1; | A35-B2-C2; |
| A35-B2-C3; | A35-B2-C4; | A35-B2-C5; | A35-B2-C6; | A35-B2-C7; |
| A35-B2-C8; | A35-B2-C9; | A35-B2-C10; | A35-B2-C11; | A36-B2-C1; |
| A36-B2-C2; | A36-B2-C3; | A36-B2-C4; | A36-B2-C5; | A36-B2-C6; |
| A36-B2-C7; | A36-B2-C8; | A36-B2-C9; | A36-B2-C10; | A36-B2-C11; |
| A37-B2-C1; | A37-B2-C2; | A37-B2-C3; | A37-B2-C4; | A37-B2-C5; |
| A37-B2-C6; | A37-B2-C7; | A37-B2-C8; | A37-B2-C9; | A37-B2-C10; |
| A37-B2-C11; | A38-B2-C1; | A38-B2-C2; | A38-B2-C3; | A38-B2-C4; |
| A38-B2-C5; | A38-B2-C6; | A38-B2-C7; | A38-B2-C8; | A38-B2-C9; |
| A38-B2-C10; | A38-B2-C11; | A39-B2-C1; | A39-B2-C2; | A39-B2-C3; |
| A39-B2-C4; | A39-B2-C5; | A39-B2-C6; | A39-B2-C7; | A39-B2-C8; |
| A39-B2-C9; | A39-B2-C10; | A39-B2-C11; | A40-B2-C1; | A40-B2-C2; |
| A40-B2-C3; | A40-B2-C4; | A40-B2-C5; | A40-B2-C6; | A40-B2-C7; |
| A40-B2-C8; | A40-B2-C9; | A40-B2-C10; | A40-B2-C11; | A41-B2-C1; |
| A41-B2-C2; | A41-B2-C3; | A41-B2-C4; | A41-B2-C5; | A41-B2-C6; |
| A41-B2-C7; | A41-B2-C8; | A41-B2-C9; | A41-B2-C10; | A41-B2-C11; |
| A42-B2-C1; | A42-B2-C2; | A42-B2-C3; | A42-B2-C4; | A42-B2-C5; |
| A42-B2-C6; | A42-B2-C7; | A42-B2-C8; | A42-B2-C9; | A42-B2-C10; |
| A42-B2-C11; | A43-B2-C1; | A43-B2-C2; | A43-B2-C3; | A43-B2-C4; |
| A43-B2-C5; | A43-B2-C6; | A43-B2-C7; | A43-B2-C8; | A43-B2-C9; |
| A43-B2-C10; | A43-B2-C11; | A44-B2-C1; | A44-B2-C2; | A44-B2-C3; |
| A44-B2-C4; | A44-B2-C5; | A44-B2-C6; | A44-B2-C7; | A44-B2-C8; |
| A44-B2-C9; | A44-B2-C10; | A44-B2-C11; | A45-B2-C1; | A45-B2-C2; |
| A45-B2-C3; | A45-B2-C4; | A45-B2-C5; | A45-B2-C6; | A45-B2-C7; |
| A45-B2-C8; | A45-B2-C9; | A45-B2-C10; | A45-B2-C11; | A46-B2-C1; |
| A46-B2-C2; | A46-B2-C3; | A46-B2-C4; | A46-B2-C5; | A46-B2-C6; |
| A46-B2-C7; | A46-B2-C8; | A46-B2-C9; | A46-B2-C10; | A46-B2-C11; |
| A47-B2-C1; | A47-B2-C2; | A47-B2-C3; | A47-B2-C4; | A47-B2-C5; |
| A47-B2-C6; | A47-B2-C7; | A47-B2-C8; | A47-B2-C9; | A47-B2-C10; |
| A47-B2-C11; | A48-B2-C1; | A48-B2-C2; | A48-B2-C3; | A48-B2-C4; |
| A48-B2-C5; | A48-B2-C6; | A48-B2-C7; | A48-B2-C8; | A48-B2-C9; |
| A48-B2-C10; | A48-B2-C11; | A49-B2-C1; | A49-B2-C2; | A49-B2-C3; |
| A49-B2-C4; | A49-B2-C5; | A49-B2-C6; | A49-B2-C7; | A49-B2-C8; |
| A49-B2-C9; | A49-B2-C10; | A49-B2-C11; | A50-B2-C1; | A50-B2-C2; |
| A50-B2-C3; | A50-B2-C4; | A50-B2-C5; | A50-B2-C6; | A50-B2-C7; |
| A50-B2-C8; | A50-B2-C9; | A50-B2-C10; | A50-B2-C11; | A51-B2-C1; |
| A51-B2-C2; | A51-B2-C3; | A51-B2-C4; | A51-B2-C5; | A51-B2-C6; |
| A51-B2-C7; | A51-B2-C8; | A51-B2-C9; | A51-B2-C10; | A51-B2-C11; |
| A52-B2-C1; | A52-B2-C2; | A52-B2-C3; | A52-B2-C4; | A52-B2-C5; |
| A52-B2-C6; | A52-B2-C7; | A52-B2-C8; | A52-B2-C9; | A52-B2-C10; |
| A52-B2-C11; | A53-B2-C2; | A53-B2-C3; | A53-B2-C4; | |
| A53-B2-C5; | A53-B2-C6; | A53-B2-C7; | A53-B2-C8; | A53-B2-C9; |
| A53-B2-C10; | A53-B2-C11; | A54-B2-C1; | A54-B2-C2; | A54-B2-C3; |
| A54-B2-C4; | A54-B2-C5; | A54-B2-C6; | A54-B2-C7; | A54-B2-C8; |
| A54-B2-C9; | A54-B2-C10; | A54-B2-C11; | A55-B2-C1; | A55-B2-C2; |
| A55-B2-C3; | A55-B2-C4; | A55-B2-C5; | A55-B2-C6; | A55-B2-C7; |
| A55-B2-C8; | A55-B2-C9; | A55-B2-C10; | A55-B2-C11; | A56-B2-C1; |
| A56-B2-C2; | A56-B2-C3; | A56-B2-C4; | A56-B2-C5; | A56-B2-C6; |
| A56-B2-C7; | A56-B2-C8; | A56-B2-C9; | A56-B2-C10; | A56-B2-C11; |
| A57-B2-C1; | A57-B2-C2; | A57-B2-C3; | A57-B2-C4; | A57-B2-C5; |
| A57-B2-C6; | A57-B2-C7; | A57-B2-C8; | A57-B2-C9; | A57-B2-C10; |
| A57-B2-C11; | A58-B2-C1; | A58-B2-C2; | A58-B2-C3; | A58-B2-C4; |
| A58-B2-C5; | A58-B2-C6; | A58-B2-C7; | A58-B2-C8; | A58-B2-C9; |
| A58-B2-C10; | A58-B2-C11; | A59-B2-C1; | A59-B2-C2; | A59-B2-C3; |

-continued

| | | | | |
|---|---|---|---|---|
| A59-B2-C4; | A59-B2-C5; | A59-B2-C6; | A59-B2-C7; | A59-B2-C8; |
| A59-B2-C9; | A59-B2-C10; | A59-B2-C11; | A60-B2-C1; | A60-B2-C2; |
| A60-B2-C3; | A60-B2-C4; | A60-B2-C5; | A60-B2-C6; | A60-B2-C7; |
| A60-B2-C8; | A60-B2-C9; | A60-B2-C10; | A60-B2-C11; | A61-B2-C1; |
| A61-B2-C2; | A61-B2-C3; | A61-B2-C4; | A61-B2-C5; | A61-B2-C6; |
| A61-B2-C7; | A61-B2-C8; | A61-B2-C9; | A61-B2-C10; | A61-B2-C11; |
| A62-B2-C1; | A62-B2-C2; | A62-B2-C3; | A62-B2-C4; | A62-B2-C5; |
| A62-B2-C6; | A62-B2-C7; | A62-B2-C8; | A62-B2-C9; | A62-B2-C10; |
| A62-B2-C11; | A63-B2-C1; | A63-B2-C2; | A63-B2-C3; | A63-B2-C4; |
| A63-B2-C5; | A63-B2-C6; | A63-B2-C7; | A63-B2-C8; | A63-B2-C9; |
| A63-B2-C10; | A63-B2-C11; | A64-B2-C1; | A64-B2-C2; | A64-B2-C3; |
| A64-B2-C4; | A64-B2-C5; | A64-B2-C6; | A64-B2-C7; | A64-B2-C8; |
| A64-B2-C9; | A64-B2-C10; | A64-B2-C11; | A65-B2-C1; | A65-B2-C2; |
| A65-B2-C3; | A65-B2-C4; | A65-B2-C5; | A65-B2-C6; | A65-B2-C7; |
| A65-B2-C8; | A65-B2-C9; | A65-B2-C10; | A65-B2-C11; | A66-B2-C1; |
| A66-B2-C2; | A66-B2-C3; | A66-B2-C4; | A66-B2-C5; | A66-B2-C6; |
| A66-B2-C7; | A66-B2-C8; | A66-B2-C9; | A66-B2-C10; | A66-B2-C11; |
| A67-B2-C1; | A67-B2-C2; | A67-B2-C3; | A67-B2-C4; | A67-B2-C5; |
| A67-B2-C6; | A67-B2-C7; | A67-B2-C8; | A67-B2-C9; | A67-B2-C10; |
| A67-B2-C11; | A68-B2-C1; | A68-B2-C2; | A68-B2-C3; | A68-B2-C4; |
| A68-B2-C5; | A68-B2-C6; | A68-B2-C7; | A68-B2-C8; | A68-B2-C9; |
| A68-B2-C10; | A68-B2-C11; | A69-B2-C1; | A69-B2-C2; | A69-B2-C3; |
| A69-B2-C4; | A69-B2-C5; | A69-B2-C6; | A69-B2-C7; | A69-B2-C8; |
| A69-B2-C9; | A69-B2-C10; | A69-B2-C11; | A70-B2-C1; | A70-B2-C2; |
| A70-B2-C3; | A70-B2-C4; | A70-B2-C5; | A70-B2-C6; | A70-B2-C7; |
| A70-B2-C8; | A70-B2-C9; | A70-B2-C10; | A70-B2-C11; | A71-B2-C1; |
| A71-B2-C2; | A71-B2-C3; | A71-B2-C4; | A71-B2-C5; | A71-B2-C6; |
| A71-B2-C7; | A71-B2-C8; | A71-B2-C9; | A71-B2-C10; | A71-B2-C11; |
| A72-B2-C1; | A72-B2-C2; | A72-B2-C3; | A72-B2-C4; | A72-B2-C5; |
| A72-B2-C6; | A72-B2-C7; | A72-B2-C8; | A72-B2-C9; | A72-B2-C10; |
| A72-B2-C11; | A73-B2-C1; | A73-B2-C2; | A73-B2-C3; | A73-B2-C4; |
| A73-B2-C5; | A73-B2-C6; | A73-B2-C7; | A73-B2-C8; | A73-B2-C9; |
| A73-B2-C10; | A73-B2-C11; | A74-B2-C1; | A74-B2-C2; | A74-B2-C3; |
| A74-B2-C4; | A74-B2-C5; | A74-B2-C6; | A74-B2-C7; | A74-B2-C8; |
| A74-B2-C9; | A74-B2-C10; | A74-B2-C11; | A75-B2-C1; | A75-B2-C2; |
| A75-B2-C3; | A75-B2-C4; | A75-B2-C5; | A75-B2-C6; | A75-B2-C7; |
| A75-B2-C8; | A75-B2-C9; | A75-B2-C10; | A75-B2-C11; | A76-B2-C1; |
| A76-B2-C2; | A76-B2-C3; | A76-B2-C4; | A76-B2-C5; | A76-B2-C6; |
| A76-B2-C7; | A76-B2-C8; | A76-B2-C9; | A76-B2-C10; | A76-B2-C11; |
| A77-B2-C1; | A77-B2-C2; | A77-B2-C3; | A77-B2-C4; | A77-B2-C5; |
| A77-B2-C6; | A77-B2-C7; | A77-B2-C8; | A77-B2-C9; | A77-B2-C10; |
| A77-B2-C11; | A78-B2-C1; | A78-B2-C2; | A78-B2-C3; | A78-B2-C4; |
| A78-B2-C5; | A78-B2-C6; | A78-B2-C7; | A78-B2-C8; | A78-B2-C9; |
| A78-B2-C10; | A78-B2-C11; | A79-B2-C1; | A79-B2-C2; | A79-B2-C3; |
| A79-B2-C4; | A79-B2-C5; | A79-B2-C6; | A79-B2-C7; | A79-B2-C8; |
| A79-B2-C9; | A79-B2-C10; | A79-B2-C11; | A80-B2-C1; | A80-B2-C2; |
| A80-B2-C3; | A80-B2-C4; | A80-B2-C5; | A80-B2-C6; | A80-B2-C7; |
| A80-B2-C8; | A80-B2-C9; | A80-B2-C10; | A80-B2-C11; | A81-B2-C1; |
| A81-B2-C2; | A81-B2-C3; | A81-B2-C4; | A81-B2-C5; | A81-B2-C6; |
| A81-B2-C7; | A81-B2-C8; | A81-B2-C9; | A81-B2-C10; | A81-B2-C11; |
| A82-B2-C1; | A82-B2-C2; | A82-B2-C3; | A82-B2-C4; | A82-B2-C5; |
| A82-B2-C6; | A82-B2-C7; | A82-B2-C8; | A82-B2-C9; | A82-B2-C10; |
| A82-B2-C11; | A83-B2-C1; | A83-B2-C2; | A83-B2-C3; | A83-B2-C4; |
| A83-B2-C5; | A83-B2-C6; | A83-B2-C7; | A83-B2-C8; | A83-B2-C9; |
| A83-B2-C10; | A83-B2-C11; | A84-B2-C1; | A84-B2-C2; | A84-B2-C3; |
| A84-B2-C4; | A84-B2-C5; | A84-B2-C6; | A84-B2-C7; | A84-B2-C8; |
| A84-B2-C9; | A84-B2-C10; | A84-B2-C11; | A85-B2-C1; | A85-B2-C2; |
| A85-B2-C3; | A85-B2-C4; | A85-B2-C5; | A85-B2-C6; | A85-B2-C7; |
| A85-B2-C8; | A85-B2-C9; | A85-B2-C10; | A85-B2-C11; | A86-B2-C1; |
| A86-B2-C2; | A86-B2-C3; | A86-B2-C4; | A86-B2-C5; | A86-B2-C6; |
| A86-B2-C7; | A86-B2-C8; | A86-B2-C9; | A86-B2-C10; | A86-B2-C11; |
| A87-B2-C1; | A87-B2-C2; | A87-B2-C3; | A87-B2-C4; | A87-B2-C5; |
| A87-B2-C6; | A87-B2-C7; | A87-B2-C8; | A87-B2-C9; | A87-B2-C10; |
| A87-B2-C11; | A88-B2-C1; | A88-B2-C2; | A88-B2-C3; | A88-B2-C4; |
| A88-B2-C5; | A88-B2-C6; | A88-B2-C7; | A88-B2-C8; | A88-B2-C9; |
| A88-B2-C10; | A88-B2-C11; | A89-B2-C1; | A89-B2-C2; | A89-B2-C3; |
| A89-B2-C4; | A89-B2-C5; | A89-B2-C6; | A89-B2-C7; | A89-B2-C8; |
| A89-B2-C9; | A89-B2-C10; | A89-B2-C11; | A90-B2-C1; | A90-B2-C2; |
| A90-B2-C3; | A90-B2-C4; | A90-B2-C5; | A90-B2-C6; | A90-B2-C7; |
| A90-B2-C8; | A90-B2-C9; | A90-B2-C10; | A90-B2-C11; | A91-B2-C1; |
| A91-B2-C2; | A91-B2-C3; | A91-B2-C4; | A91-B2-C5; | A91-B2-C6; |
| A91-B2-C7; | A91-B2-C8; | A91-B2-C9; | A91-B2-C10; | A91-B2-C11; |
| A92-B2-C1; | A92-B2-C2; | A92-B2-C3; | A92-B2-C4; | A92-B2-C5; |
| A92-B2-C6; | A92-B2-C7; | A92-B2-C8; | A92-B2-C9; | A92-B2-C10; |
| A92-B2-C11; | A93-B2-C1; | A93-B2-C2; | A93-B2-C3; | A93-B2-C4; |
| A93-B2-C5; | A93-B2-C6; | A93-B2-C7; | A93-B2-C8; | A93-B2-C9; |
| A93-B2-C10; | A93-B2-C11; | A94-B2-C1; | A94-B2-C2; | A94-B2-C3; |
| A94-B2-C4; | A94-B2-C5; | A94-B2-C6; | A94-B2-C7; | A94-B2-C8; |
| A94-B2-C9; | A94-B2-C10; | A94-B2-C11; | A95-B2-C1; | A95-B2-C2; |

-continued

| | | | | |
|---|---|---|---|---|
| A95-B2-C3; | A95-B2-C4; | A95-B2-C5; | A95-B2-C6; | A95-B2-C7; |
| A95-B2-C8; | A95-B2-C9; | A95-B2-C10; | A95-B2-C11; | A96-B2-C1; |
| A96-B2-C2; | A96-B2-C3; | A96-B2-C4; | A96-B2-C5; | A96-B2-C6; |
| A96-B2-C7; | A96-B2-C8; | A96-B2-C9; | A96-B2-C10; | A96-B2-C11; |
| A97-B2-C1; | A97-B2-C2; | A97-B2-C3; | A97-B2-C4; | A97-B2-C5; |
| A97-B2-C6; | A97-B2-C7; | A97-B2-C8; | A97-B2-C9; | A97-B2-C10; |
| A97-B2-C11; | A98-B2-C1; | A98-B2-C2; | A98-B2-C3; | A98-B2-C4; |
| A98-B2-C5; | A98-B2-C6; | A98-B2-C7; | A98-B2-C8; | A98-B2-C9; |
| A98-B2-C10; | A98-B2-C11; | A99-B2-C1; | A99-B2-C2; | A99-B2-C3; |
| A99-B2-C4; | A99-B2-C5; | A99-B2-C6; | A99-B2-C7; | A99-B2-C8; |
| A99-B2-C9; | A99-B2-C10; | A99-B2-C11; | A100-B2-C1; | A100-B2-C2; |
| A100-B2-C3; | A100-B2-C4; | A100-B2-C5; | A100-B2-C6; | A100-B2-C7; |
| A100-B2-C8; | A100-B2-C9; | A100-B2-C10; | A100-B2-C11; | A101-B2-C1; |
| A101-B2-C2; | A101-B2-C3; | A101-B2-C4; | A101-B2-C5; | A101-B2-C6; |
| A101-B2-C7; | A101-B2-C8; | A101-B2-C9; | A101-B2-C10; | A101-B2-C11; |
| A102-B2-C1; | A102-B2-C2; | A102-B2-C3; | A102-B2-C4; | A102-B2-C5; |
| A102-B2-C6; | A102-B2-C7; | A102-B2-C8; | A102-B2-C9; | A102-B2-C10; |
| A102-B2-C11; | A103-B2-C1; | A103-B2-C2; | A103-B2-C3; | A103-B2-C4; |
| A103-B2-C5; | A103-B2-C6; | A103-B2-C7; | A103-B2-C8; | A103-B2-C9; |
| A103-B2-C10; | A103-B2-C11; | A104-B2-C1; | A104-B2-C2; | A104-B2-C3; |
| A104-B2-C4; | A104-B2-C5; | A104-B2-C6; | A104-B2-C7; | A104-B2-C8; |
| A104-B2-C9; | A104-B2-C10; | A104-B2-C11; | A105-B2-C1; | A105-B2-C2; |
| A105-B2-C3; | A105-B2-C4; | A105-B2-C5; | A105-B2-C6; | A105-B2-C7; |
| A105-B2-C8; | A105-B2-C9; | A105-B2-C10; | A105-B2-C11; | A106-B2-C1; |
| A106-B2-C2; | A106-B2-C3; | A106-B2-C4; | A106-B2-C5; | A106-B2-C6; |
| A106-B2-C7; | A106-B2-C8; | A106-B2-C9; | A106-B2-C10; | A106-B2-C11; |
| A107-B2-C1; | A107-B2-C2; | A107-B2-C3; | A107-B2-C4; | A107-B2-C5; |
| A107-B2-C6; | A107-B2-C7; | A107-B2-C8; | A107-B2-C9; | A107-B2-C10; |
| A107-B2-C11; | A108-B2-C1; | A108-B2-C2; | A108-B2-C3; | A108-B2-C4; |
| A108-B2-C5; | A108-B2-C6; | A108-B2-C7; | A108-B2-C8; | A108-B2-C9; |
| A108-B2-C10; | A108-B2-C11; | A109-B2-C1; | A109-B2-C2; | A109-B2-C3; |
| A109-B2-C4; | A109-B2-C5; | A109-B2-C6; | A109-B2-C7; | A109-B2-C8; |
| A109-B2-C9; | A109-B2-C10; | A109-B2-C11; | A110-B2-C1; | A110-B2-C2; |
| A110-B2-C3; | A110-B2-C4; | A110-B2-C5; | A110-B2-C6; | A110-B2-C7; |
| A110-B2-C8; | A110-B2-C9; | A110-B2-C10; | A110-B2-C11; | A111-B2-C1; |
| A111-B2-C2; | A111-B2-C3; | A111-B2-C4; | A111-B2-C5; | A111-B2-C6; |
| A111-B2-C7; | A111-B2-C8; | A111-B2-C9; | A111-B2-C10; | A111-B2-C11; |
| A112-B2-C1; | A112-B2-C2; | A112-B2-C3; | A112-B2-C4; | A112-B2-C5; |
| A112-B2-C6; | A112-B2-C7; | A112-B2-C8; | A112-B2-C9; | A112-B2-C10; |
| A112-B2-C11; | A113-B2-C1; | A113-B2-C2; | A113-B2-C3; | A113-B2-C4; |
| A113-B2-C5; | A113-B2-C6; | A113-B2-C7; | A113-B2-C8; | A113-B2-C9; |
| A113-B2-C10; | A113-B2-C11; | A114-B2-C1; | A114-B2-C2; | A114-B2-C3; |
| A114-B2-C4; | A114-B2-C5; | A114-B2-C6; | A114-B2-C7; | A114-B2-C8; |
| A114-B2-C9; | A114-B2-C10; | A114-B2-C11; | A115-B2-C1; | A115-B2-C2; |
| A115-B2-C3; | A115-B2-C4; | A115-B2-C5; | A115-B2-C6; | A115-B2-C7; |
| A115-B2-C8; | A115-B2-C9; | A115-B2-C10; | A115-B2-C11; | A116-B2-C1; |
| A116-B2-C2; | A116-B2-C3; | A116-B2-C4; | A116-B2-C5; | A116-B2-C6; |
| A116-B2-C7; | A116-B2-C8; | A116-B2-C9; | A116-B2-C10; | A116-B2-C11; |
| A117-B2-C1; | A117-B2-C2; | A117-B2-C3; | A117-B2-C4; | A117-B2-C5; |
| A117-B2-C6; | A117-B2-C7; | A117-B2-C8; | A117-B2-C9; | A117-B2-C10; |
| A117-B2-C11; | A118-B2-C1; | A118-B2-C2; | A118-B2-C3; | A118-B2-C4; |
| A118-B2-C5; | A118-B2-C6; | A118-B2-C7; | A118-B2-C8; | A118-B2-C9; |
| A118-B2-C10; | A118-B2-C11; | A119-B2-C1; | A119-B2-C2; | A119-B2-C3; |
| A119-B2-C4; | A119-B2-C5; | A119-B2-C6; | A119-B2-C7; | A119-B2-C8; |
| A119-B2-C9; | A119-B2-C10; | A119-B2-C11; | A120-B2-C1; | A120-B2-C2; |
| A120-B2-C3; | A120-B2-C4; | A120-B2-C5; | A120-B2-C6; | A120-B2-C7; |
| A120-B2-C8; | A120-B2-C9; | A120-B2-C10; | A120-B2-C11; | A121-B2-C1; |
| A121-B2-C2; | A121-B2-C3; | A121-B2-C4; | A121-B2-C5; | A121-B2-C6; |
| A121-B2-C7; | A121-B2-C8; | A121-B2-C9; | A121-B2-C10; | A121-B2-C11; |
| A122-B2-C1; | A122-B2-C2; | A122-B2-C3; | A122-B2-C4; | A122-B2-C5; |
| A122-B2-C6; | A122-B2-C7; | A122-B2-C8; | A122-B2-C9; | A122-B2-C10; |
| A122-B2-C11; | A123-B2-C1; | A123-B2-C2; | A123-B2-C3; | A123-B2-C4; |
| A123-B2-C5; | A123-B2-C6; | A123-B2-C7; | A123-B2-C8; | A123-B2-C9; |
| A123-B2-C10; | A123-B2-C11; | A124-B2-C1; | A124-B2-C2; | A124-B2-C3; |
| A124-B2-C4; | A124-B2-C5; | A124-B2-C6; | A124-B2-C7; | A124-B2-C8; |
| A124-B2-C9; | A124-B2-C10; | A124-B2-C11; | A125-B2-C1; | A125-B2-C2; |
| A125-B2-C3; | A125-B2-C4; | A125-B2-C5; | A125-B2-C6; | A125-B2-C7; |
| A125-B2-C8; | A125-B2-C9; | A125-B2-C10; | A125-B2-C11; | A126-B2-C1; |
| A126-B2-C2; | A126-B2-C3; | A126-B2-C4; | A126-B2-C5; | A126-B2-C6; |
| A126-B2-C7; | A126-B2-C8; | A126-B2-C9; | A126-B2-C10; | A126-B2-C11; |
| A127-B2-C1; | A127-B2-C2; | A127-B2-C3; | A127-B2-C4; | A127-B2-C5; |
| A127-B2-C6; | A127-B2-C7; | A127-B2-C8; | A127-B2-C9; | A127-B2-C10; |
| A127-B2-C11; | A128-B2-C1; | A128-B2-C2; | A128-B2-C3; | A128-B2-C4; |
| A128-B2-C5; | A128-B2-C6; | A128-B2-C7; | A128-B2-C8; | A128-B2-C9; |
| A128-B2-C10; | A128-B2-C11; | A129-B2-C1; | A129-B2-C2; | A129-B2-C3; |
| A129-B2-C4; | A129-B2-C5; | A129-B2-C6; | A129-B2-C7; | A129-B2-C8; |
| A129-B2-C9; | A129-B2-C10; | A129-B2-C11; | | |

Thus, for Example, in the above list the compound denoted as A1-B1-C1 is the product of the combination of group A1 in Table 1 and B1 in Table 2 and C1 in Table 3, namely

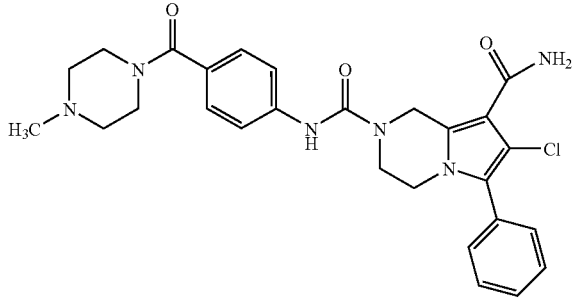

Example 2(l) hereinafter described.

Particular compounds of the invention are:

7-chloro-6-phenyl-3,4-dihydro-1H-pyrrolo[1,2-a]pyrazine-2,8-dicarboxylic acid 8-amide 2-[(4-methoxyphenyl)amide], Example 1(a):

7-chloro-6-phenyl-3,4-dihydro-1H-pyrrolo[1,2-a]pyrazine-2,8-dicarboxylic acid 8-amide 2-p-tolylamide, Example 1(b);

7-chloro-6-phenyl-3,4-dihydro-1H-pyrrolo[1,2-a]pyrazine-2,8-dicarboxylic acid 8-amide 2-phenylamide, Example 1(c);

7-chloro-6-phenyl-3,4-dihydro-1H-pyrrolo[1,2-a]pyrazine-2,8-dicarboxylic acid 8-amide 2-[(4-trifluoromethoxyphenyl)amide], Example 1(d);

7-chloro-6-phenyl-3,4-dihydro-1H-pyrrolo[1,2-a]pyrazine-2,8-dicarboxylic acid 8-amide 2-[(3-fluorophenyl)amide], Example 1(e);

7-chloro-6-phenyl-3,4-dihydro-1H-pyrrolo[1,2-a]pyrazine-2,8-dicarboxylic acid 8-amide 2-[(3-ethylphenyl)amide], Example 1(f);

7-chloro-6-phenyl-3,4-dihydro-1H-pyrrolo[1,2-a]pyrazine-2,8-dicarboxylic acid 8-amide 2-[(3-methoxyphenyl)amide], Example 1(g);

7-chloro-6-phenyl-3,4-dihydro-1H-pyrrolo[1,2-a]pyrazine-2,8-dicarboxylic acid 8-amide 2-[(3-trifluoromethylphenyl)amide], Example 1(h);

(±) trans-7-chloro-6-phenyl-3,4-dihydro-1H-pyrrolo[1,2-a]pyrazine-2,8-dicarboxylic acid 8-amide 2-[2-phenylcyclopropyl)amide], Example 1(i);

7-chloro-6-phenyl-3,4-dihydro-1H-pyrrolo[1,2-a]pyrazine-2,8-dicarboxylic acid 8-amide 2-furan-2-ylamide, Example 1(j);

7-chloro-6-phenyl-3,4-dihydro-1H-pyrrolo[1,2-a]pyrazine-2,8-dicarboxylic acid 8-amide 2-[(4-isopropylphenyl)amide], Example 1(k);

7-chloro-6-phenyl-3,4-dihydro-1H-pyrrolo[1,2-a]pyrazine-2,8-dicarboxylic acid 8-amide 2-[(2-fluorophenyl)amide], Example 1(l);

7-chloro-6-phenyl-3,4-dihydro-1H-pyrrolo[1,2-a]pyrazine-2,8-dicarboxylic acid 8-amide 2-[(2-chlorophenyl)amide], Example 1(m);

7-chloro-6-phenyl-3,4-dihydro-1H-pyrrolo[1,2-a]pyrazine-2,8-dicarboxylic acid 2-[(4-acetylphenyl)amide] 8-amide, Example 1(n);

7-chloro-6-phenyl-3,4-dihydro-1H-pyrrolo[1,2-a]pyrazine-2,8-dicarboxylic acid 8-amide 2-[(4-fluorophenyl)amide], Example 1(o);

7-chloro-6-phenyl-3,4-dihydro-1H-pyrrolo[1,2-a]pyrazine-2,8-dicarboxylic acid 8-amide 2-[(2,6-difluorophenyl)amide], Example 1(p);

7-chloro-6-phenyl-3,4-dihydro-1H-pyrrolo[1,2-a]pyrazine-2,8-dicarboxylic acid 8-amide 2-[(3-chlorophenyl)amide], Example 1(q);

7-chloro-6-phenyl-3,4-dihydro-1H-pyrrolo[1,2-a]pyrazine-2,8-dicarboxylic acid 8-amide 2-benzylamide, Example 1(r);

7-chloro-6-phenyl-3,4-dihydro-1H-pyrrolo[1,2-a]pyrazine-2,8-dicarboxylic acid 2-[(3-acetylphenyl)amide] 8-amide, Example 1(s);

7-chloro-6-phenyl-3,4-dihydro-1H-pyrrolo[1,2-a]pyrazine-2,8-dicarboxylic acid 8-amide 2-cyclohexylamide, Example 1(t);

7-chloro-6-phenyl-3,4-dihydro-1H-pyrrolo[1,2-a]pyrazine-2,8-dicarboxylic acid 8-amide 2-[(3-cyanophenyl)amide], Example 1(u);

3-[(8-carbamoyl-7-chloro-6-phenyl-3,4-dihydro-1H-pyrrolo[1,2-a]pyrazine-2-carbonyl)amino]propionic acid ethyl ester, Example 1(v);

7-chloro-6-phenyl-3,4-dihydro-1H-pyrrolo[1,2-a]pyrazine-2,8-dicarboxylic acid 8-amide 2-ethylamide, Example 1(w);

7-chloro-6-phenyl-3,4-dihydro-1H-pyrrolo[1,2-a]pyrazine-2,8-dicarboxylic acid 8-amide 2-m-tolylamide, Example 1(x);

7-chloro-6-phenyl-3,4-dihydro-1H-pyrrolo[1,2-a]pyrazine-2,8-dicarboxylic acid 8-amide 2-isopropylamide, Example 1(y);

7-chloro-6-phenyl-3,4-dihydro-1H-pyrrolo[1,2-a]pyrazine-2,8-dicarboxylic acid 8-amide 2-[(3,4-dichlorophenyl)amide], Example 1(z);

7-chloro-6-phenyl-3,4-dihydro-1H-pyrrolo[1,2-a]pyrazine-2,8-dicarboxylic acid 8-amide 2-cyclopentylmethylamide, Example 1(aa);

7-chloro-6-phenyl-3,4-dihydro-1H-pyrrolo[1,2-a]pyrazine-2,8-dicarboxylic acid 8-amide 2-[(4-phenoxyphenyl)amide], Example 1(ab);

7-chloro-6-phenyl-3,4-dihydro-1H-pyrrolo[1,2-a]pyrazine-2,8-dicarboxylic acid 8-amide 2-[(4-chlorophenyl)amide], Example 1(ac);

7-chloro-6-phenyl-3,4-dihydro-1H-pyrrolo[1,2-a]pyrazine-2,8-dicarboxylic acid 8-amide 2-[(4-chloro-3-trifluoromethylphenyl)amide], Example 1(ad);

7-chloro-6-phenyl-3,4-dihydro-1H-pyrrolo[1,2-a]pyrazine-2,8-dicarboxylic acid 8-amide 2-[(2-thiophen-2-ylethyl)amide], Example 1(ae);

7-chloro-6-phenyl-3,4-dihydro-1H-pyrrolo[1,2-a]pyrazine-2,8-dicarboxylic acid 8-amide 2-[(2-methoxyphenyl)amide], Example 1(af);

7-chloro-6-phenyl-3,4-dihydro-1H-pyrrolo[1,2-a]pyrazine-2,8-dicarboxylic acid 8-amide 2-[(3,5-bistrifluoromethylphenyl)amide], Example 1(ag);

7-chloro-6-phenyl-3,4-dihydro-1H-pyrrolo[1,2-a]pyrazine-2,8-dicarboxylic acid 8-amide 2-[(2,4-difluorophenyl)amide], Example 1(ah);

7-chloro-6-phenyl-3,4-dihydro-1H-pyrrolo[1,2-a]pyrazine-2,8-dicarboxylic acid 8-amide 2-[(2,5-difluorophenyl)amide], Example 1(ai);

4-[(8-carbamoyl-7-chloro-6-phenyl-3,4-dihydro-1H-pyrrolo[1,2-a]pyrazine-2-carbonyl)amino]benzoic acid ethyl ester, Example 1(aj);

7-chloro-6-phenyl-3,4-dihydro-1H-pyrrolo[1,2-a]pyrazine-2,8-dicarboxylic acid 8-amide 2-[(4-benzyloxyphenyl)amide], Example 1(ak);

7-chloro-6-phenyl-3,4-dihydro-1H-pyrrolo[1,2-a]pyrazine-2,8-dicarboxylic acid 8-amide 2-[(tetrahydropyran-4-yl)amide], Example 1(al);

7-chloro-6-phenyl-3,4-dihydro-1H-pyrrolo[1,2-a]pyrazine-2,8-dicarboxylic acid 8-amide 2-[(4-methanesulfonylphenyl)amide], Example 1(am);

7-chloro-6-phenyl-3,4-dihydro-1H-pyrrolo[1,2-a]pyrazine-2,8-dicarboxylic acid 8-amide 2-naphthalen-1-ylamide, Example 1(an);

[(8-carbamoyl-7-chloro-6-phenyl-3,4-dihydro-1H-pyrrolo[1,2-a]pyrazine-2-carbonyl)amino] acetic acid ethyl ester, Example 1(ao);

7-chloro-6-phenyl-3,4-dihydro-1H-pyrrolo[1,2-a]pyrazine-2,8-dicarboxylic acid 8-amide 2-{[4-(6-methylbenzothiazol-2-yl)phenyl]amide}, Example 1(ap);

7-chloro-6-phenyl-3,4-dihydro-1H-pyrrolo[1,2-a]pyrazine-2,8-dicarboxylic acid 8-amide 2-thiophen-2-ylamide, Example 1(aq);

7-chloro-6-phenyl-3,4-dihydro-1H-pyrrolo[1,2-a]pyrazine-2,8-dicarboxylic acid 8-amide 2-[4-(trifluoromethylphenyl)amide], Example 1(ar);

3-[(8-carbamoyl-7-chloro-6-phenyl-3,4-dihydro-1H-pyrrolo[1,2-a]pyrazine-2-carbonyl)amino]benzoic acid ethyl ester, Example 1(as);

7-chloro-6-phenyl-3,4-dihydro-1H-pyrrolo[1,2-a]pyrazine-2,8-dicarboxylic acid 8-amide 2-[(3-chloro-4-fluorophenyl)amide], Example 1(at);

7-Chloro-6-phenyl-3,4-dihydro-1H-pyrrolo[1,2-a]pyrazine-2,8-dicarboxylic acid 8-amide 2-pyridin-3-ylamide, Example 2(a);

7-chloro-6-phenyl-3,4-dihydro-1H-pyrrolo[1,2-a]pyrazine-2,8-dicarboxylic acid 8-amide 2-[(2,4,6-trifluorophenyl)amide], Example 2(b);

7-chloro-6-phenyl-3,4-dihydro-1H-pyrrolo[1,2-a]pyrazine-2,8-dicarboxylic acid 8-amide 2-[(3,4-difluorophenyl)amide], Example 2(c);

7-chloro-6-phenyl-3,4-dihydro-1H-pyrrolo[1,2-a]pyrazine-2,8-dicarboxylic acid 8-amide 2-pyridin-4-ylamide, Example 2(d);

7-chloro-6-phenyl-3,4-dihydro-1H-pyrrolo[1,2-a]pyrazine-2,8-dicarboxylic acid 8-amide 2-[(2,3,4-trifluorophenyl)amide], Example 2(e);

7-chloro-6-phenyl-3,4-dihydro-1H-pyrrolo[1,2-a]pyrazine-2,8-dicarboxylic acid 8-amide 2-[(4-cyanophenyl)amide], Example 2(f);

7-chloro-6-phenyl-3,4-dihydro-1H-pyrrolo[1,2-a]pyrazine-2,8-dicarboxylic acid 8-amide 2-cyclopentylamide, Example 2(g);

7-chloro-6-phenyl-3,4-dihydro-1H-pyrrolo[1,2-a]pyrazine-2,8-dicarboxylic acid 8-amide 2-thiazol-2-ylamide, Example 2(h);

7-chloro-6-phenyl-3,4-dihydro-1H-pyrrolo[1,2-a]pyrazine-2,8-dicarboxylic acid 8-amide 2-[(4-morpholin-4-ylmethylphenyl)amide], Example 2(i);

7-chloro-6-phenyl-3,4-dihydro-1H-pyrrolo[1,2-a]pyrazine-2,8-dicarboxylic acid 8-amide 2-[(3-morpholin-4-ylmethylphenyl)amide], Example 2(j);

7-chloro-6-phenyl-3,4-dihydro-1H-pyrrolo[1,2-a]pyrazine-2,8-dicarboxylic acid 8-amide 2-[(4-morpholin-4-ylphenyl)amide], Example 2(k);

7-chloro-6-phenyl-3,4-dihydro-1H-pyrrolo[1,2-a]pyrazine-2,8-dicarboxylic acid 8-amide 2-{[4-(4-methylpiperazine-1-carbonyl)phenyl]amide}, Example 2(l);

7-chloro-6-phenyl-3,4-dihydro-1H-pyrrolo[1,2-a]pyrazine-2,8-dicarboxylic acid 8-amide 2-{[3-(4-methylpiperazine-1-carbonyl)phenyl]amide}, Example 2(m);

7-chloro-6-phenyl-3,4-dihydro-1H-pyrrolo[1,2-a]pyrazine-2,8-dicarboxylic acid 8-amide 2-{[4-(4-methyl[1,4]diazepane-1-carbonyl)phenyl]amide}, Example 2(n);

7-chloro-6-phenyl-3,4-dihydro-1H-pyrrolo[1,2-a]pyrazine-2,8-dicarboxylic acid 8-amide 2-{[3-(4-methyl[1,4]diazepane-1-carbonyl)phenyl]amide, Example 2(o);

7-chloro-6-phenyl-3,4-dihydro-1H-pyrrolo[1,2-a]pyrazine-2,8-dicarboxylic acid 8-amide 2-{[4-(4-fluorophenoxy)phenyl]amide}, Example 2(p);

7-chloro-6-phenyl-3,4-dihydro-1H-pyrrolo[1,2-a]pyrazine-2,8-dicarboxylic acid 8-amide 2-{[4-(4-isopropylpiperazine-1-carbonyl)phenyl]-amide}, Example 2(q);

7-chloro-6-phenyl-3,4-dihydro-1H-pyrrolo[1,2-a]pyrazine-2,8-dicarboxylic acid 8-amide 2-{[4-(4-isopropyl[1,4]diazepane-1-carbonyl)phenyl]amide}, Example 2(r);

7-chloro-6-phenyl-3,4-dihydro-1H-pyrrolo[1,2-a]pyrazine-2,8-dicarboxylic acid 8-amide 2-{[4-(3-dimethylaminopropoxy)phenyl]amide}, Example 2(s);

7-chloro-6-phenyl-3,4-dihydro-1H-pyrrolo[1,2-a]pyrazine-2,8-dicarboxylic acid 8-amide 2-indan-2-ylamide, Example 2(t);

7-chloro-6-phenyl-3,4-dihydro-1H-pyrrolo[1,2-a]pyrazine-2,8-dicarboxylic acid 8-amide 2-quinolin-6-ylamide, Example 2(u);

7-chloro-6-phenyl-3,4-dihydro-1H-pyrrolo[1,2-a]pyrazine-2,8-dicarboxylic acid 8-amide 2-{[1-(morpholine-4-carbonyl)piperidin-4-yl]amide}, Example 2(v);

4-[(8-carbamoyl-7-chloro-6-phenyl-3,4-dihydro-1H-pyrrolo[1,2-a]pyrazine-2-carbonyl)amino]piperidine-1-carboxylic acid isopropyl ester, Example 2(w);

7-Chloro-6-(tetrahydropyran-4-yl)-3,4-dihydro-1H-pyrrolo[1,2-a]pyrazine-2,8-dicarboxylic acid 8-amide 2-[(4-fluorophenyl)amide], Example 3;

7-Chloro-6-pyridin-3-yl-3,4-dihydro-1H-pyrrolo[1,2-a]pyrazine-2,8-dicarboxylic acid 8-amide 2-[(4-methanesulfonylphenyl)amide], Example 4(a);

7-chloro-6-pyridin-3-yl-3,4-dihydro-1H-pyrrolo[1,2-a]pyrazine-2,8-dicarboxylic acid 8-amide 2-[(4-fluorophenyl)amide], Example 4(b);

7-chloro-6-pyridin-3-yl-3,4-dihydro-1H-pyrrolo[1,2-a]pyrazine-2,8-dicarboxylic acid 8-amide 2-[(tetrahydropyran-4-yl)amide], Example 4(c);

4-[(8-carbamoyl-7-chloro-6-pyridin-3-yl-3,4-dihydro-1H-pyrrolo[1,2a]pyrazine-2-carbonyl)amino]benzoic acid ethyl ester, Example 4(d);

7-chloro-6-pyridin-3-yl-3,4-dihydro-1H-pyrrolo[1,2-a]pyrazine-2,8-dicarboxylic acid 8-amide 2-[(3-cyanophenyl)amide], Example 4(e);

7-chloro-6-pyridin-3-yl-3,4-dihydro-1H-pyrrolo[1,2-a]pyrazine-2,8-dicarboxylic acid 8-amide 2-[(3-trifluoromethylphenyl)amide], Example 4(f);

7-chloro-6-pyridin-3-yl-3,4-dihydro-1H-pyrrolo[1,2-a]pyrazine-2,8-dicarboxylic acid 8-amide 2-[(4-trifluoromethylphenyl)amide], Example 4(g);

7-Chloro-6-pyridin-3-yl-3,4-dihydro-1H-pyrrolo[1,2-a]pyrazine-2,8-dicarboxylic acid 8-amide 2-[(4-cyanophenyl)amide], Example 5;

7-Chloro-6-methyl-3,4-dihydro-1H-pyrrolo[1,2-a]pyrazine-2,8-dicarboxylic acid 8-amide 2-[(3-fluorophenyl)amide], Example 6;

7-Cyano-6-phenyl-3,4-dihydro-1H-pyrrolo[1,2-a]pyrazine-2,8-dicarboxylic acid 8-amide 2-[(3-fluorophenyl)amide], Example 7(a);

7-cyano-6-phenyl-3,4-dihydro-1H-pyrrolo[1,2-a]pyrazine-2,8-dicarboxylic acid 8-amide 2-[(4-methoxyphenyl)amide], Example 7(b);

7-cyano-6-phenyl-3,4-dihydro-1H-pyrrolo[1,2-a]pyrazine-2,8-dicarboxylic acid 8-amide 2-[(4-fluorophenyl)amide], Example 7(c);

4-[(8-carbamoyl-7-cyano-6-phenyl-3,4-dihydro-1H-pyrrolo[1,2a]pyrazine-2-carbonyl)amino]benzoic acid ethyl ester, Example 7(d);

7-cyano-6-phenyl-3,4-dihydro-1H-pyrrolo[1,2-a]pyrazine-2,8-dicarboxylic acid 8-amide 2-[(4-methanesulfonylphenyl)amide], Example 7(e);

7-cyano-6-phenyl-3,4-dihydro-1H-pyrrolo[1,2-a]pyrazine-2,8-dicarboxylic acid 8-amide 2-[(tetrahydropyran-4-yl)amide], Example 7(f);

7-cyano-6-phenyl-3,4-dihydro-1H-pyrrolo[1,2-a]pyrazine-2,8-dicarboxylic acid 8-amide 2-tert-butylamide, Example 7g);

7-cyano-6-phenyl-3,4-dihydro-1H-pyrrolo[1,2-a]pyrazine-2,8-dicarboxylic acid 8-amide 2-[(3-cyanophenyl)amide], Example 7(h);

7-cyano-6-phenyl-3,4-dihydro-1H-pyrrolo[1,2-a]pyrazine-2,8-dicarboxylic acid 8-amide 2-[(4-trifluoromethylphenyl)amide], Example 7(i);

7-cyano-6-phenyl-3,4-dihydro-1H-pyrrolo[1,2-a]pyrazine-2,8-dicarboxylic acid 8-amide 2-[(3-trifluoromethylphenyl)amide], Example 7(j);

(±)-trans-7-cyano-6-phenyl-3,4-dihydro-1H-pyrrolo[1,2-a]pyrazine-2,8-dicarboxylic acid 8-amide 2-[(2-phenylcyclopropyl)amide], Example 7(k);

7-Cyano-6-phenyl-3,4-dihydro-1H-pyrrolo[1,2-a]pyrazine-2,8-dicarboxylic acid 8-amide 2-pyridin-3-ylamide, Example 8(a);

7-cyano-6-phenyl-3,4-dihydro-1H-pyrrolo[1,2-a]pyrazine-2,8-dicarboxylic acid 8-amide 2-cyclopropylamide, Example 8(b);

7-cyano-6-phenyl-3,4-dihydro-1H-pyrrolo[1,2-a]pyrazine-2,8-dicarboxylic acid 8-amide 2-cyclopentylamide, Example 8(c);

(±) 7-cyano-6-phenyl-3,4-dihydro-1H-pyrrolo[1,2-a]pyrazine-2,8-dicarboxylic acid 8-amide 2-exo-bicyclo[2.2.1.]hept-2-ylamide, Example 8(d);

(±) 7-cyano-6-phenyl-3,4-dihydro-1H-pyrrolo[1,2-a]pyrazine-2,8-dicarboxylic acid 8-amide 2-endo-bicyclo[2.2.1.]hept-2-ylamide, Example 8(e);

7-cyano-6-phenyl-3,4-dihydro-1H-pyrrolo[1,2-a]pyrazine-2,8-dicarboxylic acid 8-amide 2-[(4-morpholin-4-ylmethylphenyl)amide], Example 8(f);

7-cyano-6-phenyl-3,4-dihydro-1H-pyrrolo[1,2-a]pyrazine-2,8-dicarboxylic acid 8-amide 2-{[4-(4-methylpiperazin-1-ylmethyl)phenyl]amide}, Example 8(g);

7-cyano-6-phenyl-3,4-dihydro-1H-pyrrolo[1,2-a]pyrazine-2,8-dicarboxylic acid 8-amide 2-{[4-(2-morpholin-4-ylethoxy)phenyl]amide}, Example 8(h);

7-cyano-6-phenyl-3,4-dihydro-1H-pyrrolo[1,2-a]pyrazine-2,8-dicarboxylic acid 8-amide 2-{[4-(morpholin-4-ylacetyl)-phenyl]-amide}, Example 8(i);

7-cyano-6-phenyl-3,4-dihydro-1H-pyrrolo[1,2-a]pyrazine-2,8-dicarboxylic acid 8-amide 2-[(4-cyanophenyl)amide], Example 8(j);

7-cyano-6-phenyl-3,4-dihydro-1H-pyrrolo[1,2-a]pyrazine-2,8-dicarboxylic acid 8-amide 2-pyridin-4-ylamide, Example 8(k);

7-cyano-6-phenyl-3,4-dihydro-1H-pyrrolo[1,2-a]pyrazine-2,8-dicarboxylic acid 8-amide 2-indan-2-ylamide, Example 8(l);

7-cyano-6-phenyl-3,4-dihydro-1H-pyrrolo[1,2-a]pyrazine-2,8-dicarboxylic acid 8-amide 2-quinolin-6-ylamide, Example 8(m);

7-cyano-6-phenyl-3,4-dihydro-1H-pyrrolo[1,2-a]pyrazine-2,8-dicarboxylic acid 8-amide 2-[(4-chlorophenyl)amide]. Example 8(n);

7-cyano-6-phenyl-3,4-dihydro-1H-pyrrolo[1,2-a]pyrazine-2,8-dicarboxylic acid 8-amide 2-{[1-(morpholine-4-carbonyl)piperidin-4-yl]amide}, Example 8(o);

4-[(8-carbamoyl-7-cyano-6-phenyl-3,4-dihydro-1H-pyrrolo[1,2-a]pyrazine-2-carbonyl)amino]piperidine-1-carboxylic acid isopropyl ester, Example 8(p);

7-Cyano-6-cyclopropyl-3,4-dihydro-1H-pyrrolo[1,2-a]pyrazine-2,8-dicarboxylic acid 8-amide 2-[(4-fluorophenyl)amide], Example 9(a);

7-cyano-6-cyclopropyl-3,4-dihydro-1H-pyrrolo[1,2-a]pyrazine-2,8-dicarboxylic acid 8-amide 2-[(tetrahydropyran-4-yl)amide], Example 9(b);

4-[(8-carbamoyl-7-cyano-6-cyclopropyl-3,4-dihydro-1H-pyrrolo[1,2a]pyrazine-2-carbonyl)amino]benzoic acid ethyl ester, Example 9(c);

7-cyano-6-cyclopropyl-3,4-dihydro-1H-pyrrolo[1,2-a]pyrazine-2,8-dicarboxylic acid 8-amide 2-[(4-chlorophenyl)amide], Example 9(d);

7-cyano-6-cyclopropyl-3,4-dihydro-1H-pyrrolo[1,2-a]pyrazine-2,8-dicarboxylic acid 8-amide 2-[(4-methanesulfonylphenyl)amide], Example 9(e);

(±) trans-7-cyano-6-cyclopropyl-3,4-dihydro-1H-pyrrolo[1,2-a]pyrazine-2,8-dicarboxylic acid 8-amide 2-[(2-phenylcyclopropyl)amide], Example 9(f);

7-cyano-6-cyclopropyl-3,4-dihydro-1H-pyrrolo[1,2-a]pyrazine-2,8-dicarboxylic acid 8-amide 2-[(3-chloro-4-fluorophenyl)amide], Example 9(g);

7-cyano-6-cyclopropyl-3,4-dihydro-1H-pyrrolo[1,2-a]pyrazine-2,8-dicarboxylic acid 8-amide 2-[(4-trifluoromethylphenyl)amide], Example 9(h);

7-cyano-6-cyclopropyl-3,4-dihydro-1H-pyrrolo[1,2-a]pyrazine-2,8-dicarboxylic acid 8-amide 2-[(3-trifluoromethylphenyl)amide], Example 9(i);

7-cyano-6-cyclopropyl-3,4-dihydro-1H-pyrrolo[1,2-a]pyrazine-2,8-dicarboxylic acid 8-amide 2-cyclohexylamide, Example 9(j);

7-cyano-6-cyclopropyl-3,4-dihydro-1H-pyrrolo[1,2-a]pyrazine-2,8-dicarboxylic acid 8-amide 2-[(5-methylthiophen-2-yl)amide], Example 9(k);

7-cyano-6-cyclopropyl-3,4-dihydro-1H-pyrrolo[1,2-a]pyrazine-2,8-dicarboxylic acid 8-amide 2-{[4-(4-methylpiperazine-1-carbonyl)phenyl]amide}, Example 10(a);

7-cyano-6-cyclopropyl-3,4-dihydro-1H-pyrrolo[1,2-a]pyrazine-2,8-dicarboxylic acid 8-amide 2-[(4-morpholin-4-ylmethylphenyl)amide], Example 10(b);

7-cyano-6-cyclopropyl-3,4-dihydro-1H-pyrrolo[1,2-a]pyrazine-2,8-dicarboxylic acid 8-amide 2-{[4-(4-methylpiperazin-1-ylmethyl)phenyl]amide}, Example 10(c);

7-cyano-6-cyclopropyl-3,4-dihydro-1H-pyrrolo[1,2-a]pyrazine-2,8-dicarboxylic acid 8-amide 2-{[4-(2-morpholin-4-ylethoxy)phenyl]amide}, Example 10(d);

7-cyano-6-cyclopropyl-3,4-dihydro-1H-pyrrolo[1,2-a]pyrazine-2,8-dicarboxylic acid 8-amide 2-{[4-(morpholine-4-carbonyl)phenyl]amide}, Example 10(e);

7-cyano-6-cyclopropyl-3,4-dihydro-1H-pyrrolo[1,2-a]pyrazine-2,8-dicarboxylic acid 8-amide 2-[(4-cyanophenyl)amide], Example 10(f);

7-cyano-6-cyclopropyl-3,4-dihydro-1H-pyrrolo[1,2-a]pyrazine-2,8-dicarboxylic acid 8-amide 2-[(3,4-difluorophenyl)amide], Example 10(g);

7-cyano-6-cyclopropyl-3,4-dihydro-1H-pyrrolo[1,2-a]pyrazine-2,8-dicarboxylic acid 8-amide 2-{[4-(4-fluorophenoxy)phenyl]amide, Example, 10(h);

7-cyano-6-cyclopropyl-3,4-dihydro-1H-pyrrolo[1,2-a]pyrazine-2,8-dicarboxylic acid 8-amide 2-quinolin-6-ylamide, Example 10(i);

7-cyano-6-cyclopropyl-3,4-dihydro-1H-pyrrolo[1,2-a]pyrazine-2,8-dicarboxylic acid 8-amide 2-[(4-methylsulfanylphenyl)amide], Example 10(j);

7-cyano-6-cyclopropyl-3,4-dihydro-1H-pyrrolo[1,2-a]pyrazine-2,8-dicarboxylic acid 8-amide 2-[(3-cyanophenyl)amide], Example 10(k);

{4-[(8-carbamoyl-7-cyano-6-cyclopropyl-3,4-dihydro-1H-pyrrolo[1,2-a]pyrazine-2-carbonyl)amino]phenyl}acetic acid ethyl ester, Example 10(l);

7-cyano-6-cyclopropyl-3,4-dihydro-1H-pyrrolo[1,2-a]pyrazine-2,8-dicarboxylic acid 8-amide 2-pyridin-3-ylamide, Example 10(m);

7-cyano-6-cyclopropyl-3,4-dihydro-1H-pyrrolo[1,2-a]pyrazine-2,8-dicarboxylic acid 2-[(4-acetylphenyl)amide] 8-amide, Example 10(n);

7-cyano-6-cyclopropyl-3,4-dihydro-1H-pyrrolo[1,2-a]pyrazine-2,8-dicarboxylic acid 8-amide 2-indan-2-ylamide, Example 10(o);

7-cyano-6-cyclopropyl-3,4-dihydro-1H-pyrrolo[1,2-a]pyrazine-2,8-dicarboxylic acid 8-amide 2-[(4-trifluoromethoxyphenyl)amide], Example 10(p);

7-cyano-6-cyclopropyl-3,4-dihydro-1H-pyrrolo[1,2-a]pyrazine-2,8-dicarboxylic acid 8-amide 2-pyridin-4-ylamide, Example 10(q);

7-cyano-6-cyclopropyl-3,4-dihydro-1H-pyrrolo[1,2-a]pyrazine-2,8-dicarboxylic acid 8-amide 2-{[4-(4-isopropylpiperazine-1-carbonyl)-phenyl]amide}, Example 10(r);

4-[(8-carbamoyl-7-cyano-6-cyclopropyl-3,4-dihydro-1H-pyrrolo[1,2-a]pyrazine-2-carbonyl)amino]piperidine-1-carboxylic acid isopropyl ester, Example 10(s);

7-cyano-6-cyclopropyl-3,4-dihydro-1H-pyrrolo[1,2-a]pyrazine-2,8-dicarboxylic acid 8-amide 2-[(1-benzoylpiperidin-4-yl)amide], Example 10(t);

7-cyano-6-(2-methylpyridin-3-yl)-3,4-dihydro-1H-pyrrolo[1,2-a]pyrazine-2,8-dicarboxylic acid 8-amide 2-[(4-fluorophenyl)amide], Example 11(a);

7-cyano-6-(2-methylpyridin-3-yl)-3,4-dihydro-1H-pyrrolo[1,2-a]pyrazine-2,8-dicarboxylic acid 8-amide 2-[(tetrahydropyran-4-yl)amide], Example 11(b);

4-[(8-carbamoyl-7-cyano-6-(2-methylpyridin-3-yl)-3,4-dihydro-1H-pyrrolo[1,2a]pyrazine-2-carbonyl)amino]benzoic acid ethyl ester, Example 11(c);

7-cyano-6-pyridin-3-yl-3,4-dihydro-1H-pyrrolo[1,2-a]pyrazine-2,8-dicarboxylic acid 8- amide 2[(4-fluorophenyl)amide], Example 12(a);

7-cyano-6-pyridin-3-yl-3,4-dihydro-1H-pyrrolo[1,2-a]pyrazine-2,8-dicarboxylic acid 8- amide 2-[(4-methanesulfonylphenyl)amide], Example 12(b);

7-cyano-6-pyridin-3-yl-3,4-dihydro-1H-pyrrolo[1,2-a]pyrazine-2,8-dicarboxylic acid 8- amide 2-[(3-trifluoromethylphenyl)amide], Example 12(c);

7-cyano-6-pyridin-3-yl-3,4-dihydro-1H-pyrrolo[1,2-a]pyrazine-2,8-dicarboxylic acid 8- amide 2-[(4-trifluoromethylphenyl)amide], Example 12(d);

7-cyano-6-pyridin-3-yl-3,4-dihydro-1H-pyrrolo[1,2-a]pyrazine-2,8-dicarboxylic acid 8- amide 2-[(4-cyanophenyl)amide], Example 13;

7-cyano-6-(1-methanesulfonylpiperidin-4-yl)-3,4-dihydro-1H-pyrrolo[1,2-a]pyrazine-2,8-dicarboxylic acid 8-amide 2-[(4-fluorophenyl)amide], Example 14(a);

7-cyano-6-(1-methanesulfonylpiperidin-4-yl)-3,4-dihydro-1H-pyrrolo[1,2-a]pyrazine-2,8-dicarboxylic acid 8-amide 2-[(tetrahydropyran-4-yl)amide, Example 14(b);

4-[(8-carbamoyl-7-cyano-6-(1-methanesulfonylpiperidin-4-yl)-3,4-dihydro-1H-pyrrolo[1,2a]pyrazine-2-carbonyl)amino]benzoic acid ethyl ester, Example 14(c);

7-cyano-6-(1-methanesulfonylpiperidin-4-yl)-3,4-dihydro-1H-pyrrolo[1,2-a]pyrazine-2,8-dicarboxylic acid 8-amide 2-[(4-cyanophenyl)amide], Example 15;

7-chloro-6-cyclopropyl-3,4-dihydro-1H-pyrrolo[1,2-a]pyrazine-2,8-dicarboxylic acid 8-amide 2-[(4-fluorophenyl)amide], Example 16(a);

7-chloro-6-cyclopropyl-3,4-dihydro-1H-pyrrolo[1,2-a]pyrazine-2,8-dicarboxylic acid 8-amide 2-[(4-trifluoromethylphenyl)amide], Example 16(b);

(±)-trans-7-chloro-6-cyclopropyl-3,4-dihydro-1H-pyrrolo[1,2-a]pyrazine-2,8-dicarboxylic acid 8-amide 2-[(2-phenylcyclopropyl)amide], Example 16(c);

7-chloro-6-cyclopropyl-3,4-dihydro-1H-pyrrolo[1,2-a]pyrazine-2,8-dicarboxylic acid 8-amide 2-[(3-trifluoromethylphenyl)amide], Example 16(d);

7-chloro-6-cyclopropyl-3,4-dihydro-1H-pyrrolo[1,2-a]pyrazine-2,8-dicarboxylic acid 8-amide 2-[(4-cyanophenyl)amide], Example 17(a);

7-chloro-6-cyclopropyl-3,4-dihydro-1H-pyrrolo[1,2-a]pyrazine-2,8-dicarboxylic acid 8-amide 2-quinolin-6-ylamide, Example 17(b);

7-chloro-6-cyclopropyl-3,4-dihydro-1H-pyrrolo[1,2-a]pyrazine-2,8-dicarboxylic acid 8-amide 2-indan-2-ylamide, Example 17(c);

7-chloro-6-cyclopropyl-3,4-dihydro-1H-pyrrolo[1,2-a]pyrazine-2,8-dicarboxylic acid 8-amide 2-{[4-(4-isopropylpiperazine-1-carbonyl)-phenyl]amide}, Example 17(d);

7-chloro-3,4-dihydro-1H-pyrrolo[1,2-a]pyrazine-2,8-dicarboxylic acid 8-amide 2-[(4-fluorophenyl)amide, Example 18(a);

7-chloro-3,4-dihydro-1H-pyrrolo[1,2-a]pyrazine-2,8-dicarboxylic acid 8-amide 2-[(4-trifluoromethylphenyl)amide], Example 18(b);

7-chloro-3,4-dihydro-1H-pyrrolo[1,2-a]pyrazine-2,8-dicarboxylic acid 8-amide 2-[(3-trifluoromethylphenyl)amide], Example 18(c);

(±)-trans-7-chloro-3,4-dihydro-1H-pyrrolo[1,2-a]pyrazine-2,8-dicarboxylic acid 8-amide 2-[(2-phenylcyclopropyl)amide], Example 18(d);

7-chloro-3,4-dihydro-1H-pyrrolo[1,2-a]pyrazine-2,8-dicarboxylic acid 8-amide 2-{[4-(4-isopropylpiperazine-1-carbonyl)phenyl]amide}, Example 19(a);

7-chloro-3,4-dihydro-1H-pyrrolo[1,2-a]pyrazine-2,8-dicarboxylic acid 8-amide 2-indan-2-ylamide, Example 19(b);

7-chloro-3,4-dihydro-1H-pyrrolo[1,2-a]pyrazine-2,8-dicarboxylic acid 8-amide 2-[(4-cyanophenyl)amide], Example 19(c);

7-chloro-3,4-dihydro-1H-pyrrolo[1,2-a]pyrazine-2,8-dicarboxylic acid 8-amide 2-[(5-pyridin-2-ylthiophen-2-yl)amide], Example 20;

7-chloro-6-(4-methylpyridin-3-yl)-3,4-dihydro-1H-pyrrolo[1,2-a]pyrazine-2,8-dicarboxylic acid 8-amide 2-[(4-fluorophenyl)amide], Example 21(a);

7-chloro-6-(4-methylpyridin-3-yl)-3,4-dihydro-1H-pyrrolo[1,2-a]pyrazine-2,8-dicarboxylic acid 8-amide 2-[(3-trifluoromethylphenyl)amide], Example 21(b);

(±)-trans-7-chloro-6-(4-methylpyridin-3-yl)-3,4-dihydro-1H-pyrrolo[1,2-a]pyrazine-2,8-dicarboxylic acid 8-amide 2-[(2-phenylcyclopropyl)amide], Example 21(c);

7-chloro-6-(4-methylpyridin-3-yl)-3,4-dihydro-1H-pyrrolo[1,2-a]pyrazine-2,8-dicarboxylic acid 8-amide 2-quinolin-6-ylamide, Example 22(a);

7-chloro-6-(4-methylpyridin-3-yl)-3,4-dihydro-1H-pyrrolo[1,2-a]pyrazine-2,8-dicarboxylic acid 8-amide 2-[(4-cyanophenyl)amide, Example 22(b);

7-chloro-6-(4-methylpyridin-3-yl)-3,4-dihydro-1H-pyrrolo[1,2-a]pyrazine-2,8-dicarboxylic acid 8-amide 2-indan-2-ylamide. Example 22(c);

4-{[8-carbamoyl-7-chloro-6-(4-methylpyridin-3-yl)-3,4-dihydro-1H-pyrrolo[1,2-a]pyrazine-2-carbonyl]amino}piperidine-1-carboxylic acid isopropyl ester, Example 22(d);

7-cyano-6-(4-methylpyridin-3-yl)-3,4-dihydro-1H-pyrrolo[1,2-a]pyrazine-2,8-dicarboxylic acid 8-amide 2-[(4-trifluoromethylphenyl)amide], Example 23;

7-cyano-6-(tetrahydropyran-4-yl)-3,4-dihydro-1H-pyrrolo[1,2-a]pyrazine-2,8-dicarboxylic acid 8-amide 2-[(3-trifluoromethylphenyl)amide], Example 24(a);

7-cyano-6-(tetrahydropyran-4-yl)-3,4-dihydro-1H-pyrrolo[1,2-a]pyrazine-2,8-dicarboxylic acid 8-amide 2-[(4-trifluoromethylphenyl)amide], Example 24(b);

7-cyano-6-(tetrahydropyran-4-yl)-3,4-dihydro-1H-pyrrolo[1,2-a]pyrazine-2,8-dicarboxylic acid 8-amide 2-[(4-fluorophenyl)amide], Example 24(c);

(±)-trans-7-cyano-6-(tetrahydropyran-4-yl)-3,4-dihydro-1H-pyrrolo [1,2-a]pyrazine-2,8-dicarboxylic acid 8-amide 2-[(2-phenylcyclopropyl)amide], Example 24(d);

7-cyano-6-(tetrahydropyran-4-yl)-3,4-dihydro-1H-pyrrolo[1,2-a]pyrazine-2,8-dicarboxylic acid 8-amide 2-[(5-methylthiophen-2-yl)amide], Example 24(e);

7-cyano-6-(tetrahydropyran-4-yl)-3,4-dihydro-1H-pyrrolo[1,2-a]pyrazine-2,8-dicarboxylic acid 8-amide 2-quinolin-6-ylamide, Example 25(a);

7-cyano-6-(tetrahydropyran-4-yl)-3,4-dihydro-1H-pyrrolo[1,2-a]pyrazine-2,8-dicarboxylic acid 8-amide 2-indan-2-ylamide, Example 25(b);

7-cyano-6-(tetrahydropyran-4-yl)-3,4-dihydro-1H-pyrrolo[1,2-a]pyrazine-2,8-dicarboxylic acid 8-amide 2-[(4-cyanophenyl)amide], Example 25(c);

4-{[8-carbamoyl-7-cyano-6-(tetrahydropyran-4-yl)-3,4-dihydro-1H-pyrrolo[1,2-a]pyrazine-2-carbonyl]amino}piperidine-1-carboxylic acid isopropyl ester, Example 25(d);

7-Cyano-6-trifluoromethyl-3,4-dihydro-1H-pyrrolo[1,2-a]pyrazine-2,8-dicarboxylic acid 8-amide 2-[(4-trifluoromethylphenyl)amide], Example 26;

7-cyano-6-cyclopropyl-3,4-dihydro-1H-pyrrolo[1,2-a]pyrazine-2,8-dicarboxylic acid 8-amide 2-[(6-trifluoromethylpyridin-3-yl)amide], Example 27(a);

7-chloro-6-cyclopropyl-3,4-dihydro-1H-pyrrolo[1,2-a]pyrazine-2,8-dicarboxylic acid 8-amide 2-[(6-trifluoromethylpyridin-3-yl)amide], Example 27(b);

7-chloro-3,4-dihydro-1H-pyrrolo[1,2-a]pyrazine-2,8-dicarboxylic acid 8-amide 2-[(6-trifluoromethylpyridin-3-yl)amide], Example 27(c);

7-cyano-6-phenyl-3,4-dihydro-1H-pyrrolo[1,2-a]pyrazine-2,8-dicarboxylic acid 8-amide 2-[(6-trifluoromethylpyridin-3-yl)amide], Example 27(d);

7-cyano-6-(tetrahydropyran-4-yl)-3,4-dihydro-1H-pyrrolo[1,2-a]pyrazine-2,8-dicarboxylic acid 8-amide 2-[(6-trifluoromethylpyridin-3-yl)amide], Example 27(e);

7-chloro-6-phenyl-3,4-dihydro-1H-pyrrolo[1,2-a]pyrazine-2,8-dicarboxylic acid 8-amide 2-[(6-trifluoromethylpyridin-3-yl)amide], Example 27(f);

4-[(8-carbamoyl-7-cyano-6-phenyl-3,4-dihydro-H-pyrrolo[1,2a]pyrazine-2-carbonyl)amino]benzoic acid, Example 28(a);

4-[(8-carbamoyl-7-chloro-6-phenyl-3,4-dihydro-H-pyrrolo[1,2-a]pyrazine-2-carbonyl)amino]benzoic acid, Example 28(b);

4-[(8-carbamoyl-7-cyano-6-cyclopropyl-3,4-dihydro-1H-pyrrolo[1,2-a]pyrazine-2-carbonyl)amino]benzoic acid, Example 28(c);

4-[(8-carbamoyl-7-chloro-6-pyridin-3-yl-3,4-dihydro-1H-pyrrolo[1,2a]pyrazine-2-carbonyl)amino]benzoic acid, Example 28(d);

4-[(8-carbamoyl-7-cyano-6-(2-methylpyridin-3-yl)-3,4-dihydro-1H-pyrrolo[1,2a]pyrazine-2-carbonyl)amino]benzoic acid, Example 28(e);

4-[(8-carbamoyl-7-cyano-6-(1-methanesulfonylpiperidin-4-yl)-3,4-dihydro-1H-pyrrolo[1,2a]pyrazine-2-carbonyl)amino]benzoic acid, Example 28(f);

3-[(8-carbamoyl-7-chloro-6-phenyl-3,4-dihydro-1H-pyrrolo[1,2-a]pyrazine-2-carbonyl)amino]benzoic acid, Example 28(g);

7-chloro-6-phenyl-3,4-dihydro-1H-pyrrolo[1,2-a]pyrazine-2,8-dicarboxylic acid 8-amide 2-[(2-hydroxyphenyl)amide], Example 29(a);

7-chloro-6-phenyl-3,4-dihydro-1H-pyrrolo[1,2-a]pyrazine-2,8-dicarboxylic acid 8-amide 2-[(4-hydroxyphenyl)amide], Example 29(b);

7-chloro-2-(3-cyclohexylpropionyl)-6-phenyl-1,2,3,4-tetrahydropyrrolo[1,2-a]pyrazine-8-carboxylic acid amide, Example 30(a);

7-chloro-2-(3-cyclopentylpropionyl)-6-phenyl-1,2,3,4-tetrahydropyrrolo[1,2-a]pyrazine-8-carboxylic acid amide, Example 30(b);

7-chloro-2-phenoxyacetyl-6-phenyl-1,2,3,4-tetrahydropyrrolo[1,2-a]pyrazine-8-carboxylic acid amide, Example 30(c);

7-chloro-2-(morpholine-4-carbonyl)-6-phenyl-1,2,3,4-tetrahydropyrrolo[1,2-a]pyrazine-8-carboxylic acid amide, Example 30(d);

7-chloro-6-phenyl-2-(thiophen-2-ylacetyl)-1,2,3,4-tetrahydropyrrolo[1,2-a]pyrazine-8-carboxylic acid amide, Example 30(e);

7-chloro-2-[(4-methoxyphenyl)acetyl]-6-phenyl-1,2,3,4-tetrahydropyrrolo[1,2-a]pyrazine-8-carboxylic acid amide, Example 30(f);

7-chloro-2-(furan-2-carbonyl)-6-phenyl-1,2,3,4-tetrahydropyrrolo[1,2-a]pyrazine-8-carboxylic acid amide, Example 30(g);

7-chloro-6-phenyl-2-(thiophene-2-carbonyl)-1,2,3,4-tetrahydropyrrolo[1,2-a]pyrazine-8-carboxylic acid amide, Example 30(h);

7-chloro-6-phenyl-2-(5-pyridin-2-ylthiophene-2-carbonyl)-1,2,3,4-tetrahydropyrrolo[1,2-a]pyrazine-8-carboxylic acid amide, Example 30(i);

7-chloro-6-phenyl-2-(thiophene-2-sulfonyl)-1,2,3,4-tetrahydropyrrolo[1,2-a]pyrazine-8-carboxylic acid amide, Example 31(a);

7-chloro-6-phenyl-2-(toluene-4-sulfonyl)-1,2,3,4-tetrahydropyrrolo[1,2-a]pyrazine-8-carboxylic acid amide, Example 31(b);

2-benzenesulfonyl-7-chloro-6-phenyl-1,2,3,4-tetrahydropyrrolo[1,2-a]pyrazine-8-carboxylic acid amide, Example 31(c);

7-chloro-2-(4-chlorobenzenesulfonyl)-6-phenyl-1,2,3,4-tetrahydropyrrolo[1,2-a]pyrazine-8-carboxylic acid amide, Example 31(d);

7-chloro-2-(3-cyanobenzenesulfonyl)-6-phenyl-1,2,3,4-tetrahydropyrrolo[1,2-a]pyrazine-8-carboxylic acid amide, Example 31(e);

7-chloro-2-(4-cyanobenzenesulfonyl)-6-phenyl-1,2,3,4-tetrahydropyrrolo[1,2-a]pyrazine-8-carboxylic acid amide, Example 31(f);

7-chloro-2-(2-fluorobenzenesulfonyl)-6-phenyl-1,2,3,4-tetrahydropyrrolo[1,2-a]pyrazine-8-carboxylic acid amide, Example 31(g);

7-chloro-6-phenyl-2-(3-trifluoromethylbenzenesulfonyl)-1,2,3,4-tetrahydropyrrolo[1,2-a]pyrazine-8-carboxylic acid amide, Example 31(h);

7-chloro-2-(4-fluorobenzenesulfonyl)-6-phenyl-1,2,3,4-tetrahydropyrrolo[1,2-a]pyrazine-8-carboxylic acid amide, Example 31(i);

7-chloro-2-(4-nitrobenzenesulfonyl)-6-phenyl-1,2,3,4-tetrahydropyrrolo[1,2-a]pyrazine-8-carboxylic acid amide, Example 31(j);

7-chloro-2-(4-methanesulfonylbenzenesulfonyl)-6-phenyl-1,2,3,4-tetrahydropyrrolo[1,2-a]pyrazine-8-carboxylic acid amide, Example 31(k);

7-chloro-2-[5-(1-methyl-5-trifluoromethyl-1H-pyrazol-3-yl)thiophene-2-sulfonyl]-6-phenyl-1,2,3,4-tetrahydropyrrolo[1,2-a]pyrazine-8-carboxylic acid amide, Example 31(l);

7-chloro-2-(1-methyl-1H-imidazole-4-sulfonyl)-6-phenyl-1,2,3,4-tetrahydropyrrolo[1,2-a]pyrazine-8-carboxylic acid amide, Example 31(m);

7-chloro-2-(5-isoxazol-3-ylthiophene-2-sulfonyl)-6-phenyl-1,2,3,4-tetrahydropyrrolo[1,2-a]pyrazine-8-carboxylic acid amide, Example 31(n);

7-chloro-6-phenyl-2-(4-trifluoromethyl-benzenesulfonyl)-1,2,3,4-tetrahydropyrrolo[1,2-a]pyrazine-8-carboxylic acid amide, Example 31(o);

7-chloro-2-(3,4-dichlorobenzenesulfonyl)-6-phenyl-1,2,3,4-tetrahydropyrrolo[1,2-a]pyrazine-8-carboxylic acid amide, Example 31(p);

7-chloro-6-phenyl-2-(toluene-3-sulfonyl)-1,2,3,4-tetrahydropyrrolo[1,2-a]pyrazine-8-carboxylic acid amide, Example 31(q);

7-chloro-6-phenyl-2-(pyridine-4-sulfonyl)-1,2,3,4-tetrahydropyrrolo[1,2-a]pyrazine-8-carboxylic acid amide, Example 31(r);

7-chloro-2-(4-methoxybenzenesulfonyl)-6-phenyl-1,2,3,4-tetrahydropyrrolo[1,2-a]pyrazine-8-carboxylic acid amide, Example 31(s);

7-chloro-6-phenyl-2-(5-pyridin-2-ylthiophene-2-sulfonyl)-1,2,3,4-tetrahydropyrrolo[1,2-a]pyrazine-8-carboxylic acid amide, Example 31(t);

7-cyano-6-cyclopropyl-2-(4-trifluoromethylbenzenesulfonyl)-1,2,3,4-tetrahydropyrrolo[1,2-a]pyrazine-8-carboxylic acid amide, Example 32;

7-chloro-6-pyridin-3-yl-2-(4-trifluoromethylbenzenesulfonyl)-1,2,3,4-tetrahydropyrrolo[1,2-a]pyrazine-8-carboxylic acid amide, Example 33;

7-chloro-2-(5-pyridin-2-ylthiophene-2-sulfonyl)-1,2,3,4-tetrahydropyrrolo[1,2-a]pyrazine-8 -carboxylic acid amide, Example 34(a);

7-chloro-2-(4-trifluoromethylbenzenesulfonyl)-1,2,3,4-tetrahydro-pyrrolo[1,2-a]pyrazine-8-carboxylic acid amide, Example 34(b);

7-chloro-6-phenyl-2-phenylsulfamoyl-1,2,3,4-tetrahydropyrrolo[1,2-a]pyrazine-8-carboxylic acid amide, Example 35(a);

7-chloro-2-(4-methoxyphenylsulfamoyl)-6-phenyl-1,2,3,4-tetrahydropyrrolo[1,2-a]pyrazine-8-carboxylic acid amide, Example 35(b);

7-chloro-2-(4-trifluoromethylphenylsulfamoyl)-6-phenyl-1,2,3,4-tetrahydropyrrolo[1,2-a]pyrazine-8-carboxylic acid amide, Example 35(c);

7-chloro-2-(4-fluorophenylsulfamoyl)-6-phenyl-1,2,3,4-tetrahydropyrrolo[1,2-a]pyrazine-8-carboxylic acid amide, Example 35(d);

7-chloro-2-methylsulfamoyl-6-phenyl-1,2,3,4-tetrahydropyrrolo[1,2-a]pyrazine-8-carboxylic acid amide, Example 35(e);

8-carbamoyl-7-chloro-6-phenyl-3,4-dihydro-1H-pyrrolo[1,2-a]pyrazine-2-carboxylic acid phenyl ester, Example 37;

7-chloro-2-(4-methoxyphenylthiocarbamoyl)-6-phenyl-1,2,3,4-tetrahydropyrrolo[1,2-a]pyrazine-8-carboxylic acid amide, Example 38;

2-[(cyanoimino)(4-methoxyphenylamino)methyl]-7-chloro-6-phenyl-1,2,3,4-tetrahydropyrrolo[1,2-a]pyrazine-8-carboxylic acid amide, Example 39;

6-phenyl-3,4-dihydro-1H-pyrrolo[1,2-a]pyrazine-2,8-dicarboxylic acid 8-amide 2-[(4-methoxyphenyl)amide], Example 40;

7-chloro-6-pyridin-3-yl-8-thiocarbamoyl-3,4-dihydro-1H-pyrrolo[1,2-a]pyrazine-2-carboxylic acid (4-fluorophenyl)amide; Example 41;

7-chloro-6-phenyl-3,4-dihydro-1H-pyrrolo[1,2-a]pyrazine-2,8-dicarboxylic acid 8-amide 2-{[4-(morpholine-4-carbonyl)phenyl]amide}, Example 42;

7-cyano-6-cyclopropyl-3,4-dihydro-1H-pyrrolo[1,2-a]pyrazine-2,8-dicarboxylic acid 8-amide 2-{[4-(2-morpholin-4-ylethylcarbamoyl)phenyl]amide}, Example 43;

7-chloro-6-cyclopropyl-1,2,3,4-tetrahydropyrrolo[1,2-a]pyrazine-8-carboxylic acid amide trifluoroacetic acid salt, Example 44(a);

7-cyano-6-cyclopropyl-1,2,3,4-tetrahydropyrrolo[1,2-a]pyrazine-8-carboxylic acid amide trifluoroacetic acid salt, Example 44(b);

2-benzooxazol-2-yl-7-chloro-6-phenyl-1,2,3,4-tetrahydropyrrolo[1,2-a]-pyrazine-8-carboxylic acid amide, Example 45(a);

2-benzothiazol-2-yl-7-chloro-6-phenyl-1,2,3,4-tetrahydropyrrolo[1,2-a]pyrazine-8-carboxylic acid amide, Example 45(b);

and the corresponding N-oxides, and their prodrugs; and pharmaceutically acceptable salts and solvates (e.g. hydrates) of such compounds and their N-oxides and prodrugs.

Preferred compounds of formula (Ia) of the invention for the inhibition of JNK are:

7-chloro-6-phenyl-3,4-dihydro-1H-pyrrolo[1,2-a]pyrazine-2,8-dicarboxylic acid 8-amide 2-[(4-methoxyphenyl)amide], (compound denoted as A38-B1-C1), Example 1(a):

7-chloro-6-phenyl-3,4-dihydro-1H-pyrrolo[1,2-a]pyrazine-2,8-dicarboxylic acid 8-amide 2-p-tolylamide, (compound denoted as A16-B1-C1), Example 1(b);

7-chloro-6-phenyl-3,4-dihydro-1H-pyrrolo[1,2-a]pyrazine-2,8-dicarboxylic acid 8-amide 2-phenylamide, (compound denoted as A57-B1-C1), Example 1(c);

7-chloro-6-phenyl-3,4-dihydro-1H-pyrrolo[1,2-a]pyrazine-2,8-dicarboxylic acid 8-amide 2-[(4-trifluoromethoxyphenyl)amide], (compound denoted as A37-B1-C1), Example 1(d);

7-chloro-6-phenyl-3,4-dihydro-1H-pyrrolo[1,2-a]pyrazine-2,8-dicarboxylic acid 8-amide 2-[(3-fluorophenyl)amide], (compound denoted as A50-B1-C1), Example 1(e);

7-chloro-6-phenyl-3,4-dihydro-1H-pyrrolo[1,2-a]pyrazine-2,8-dicarboxylic acid 8-amide 2-[(3-ethylphenyl)amide], (compound denoted as A18-B1-C1), Example 1(f);

7-chloro-6-phenyl-3,4-dihydro-1H-pyrrolo[1,2-a]pyrazine-2,8-dicarboxylic acid 8-amide 2-[(3-methoxyphenyl)amide], (compound denoted as A39-B1-C1), Example 1(g);

7-chloro-6-phenyl-3,4-dihydro-1H-pyrrolo[1,2-a]pyrazine-2,8-dicarboxylic acid 8-amide 2-[(3-trifluoromethylphenyl)amide], (compound denoted as A21-B1-C1), Example 1(h);

(±) trans-7-chloro-6-phenyl-3,4-dihydro-1H-pyrrolo[1,2-a]pyrazine-2,8-dicarboxylic acid 8-amide 2-[2-phenylcyclopropyl)amide], (compound denoted as A77-B1-C1), Example 1(i);

7-chloro-6-phenyl-3,4-dihydro-1H-pyrrolo[1,2-a]pyrazine-2,8-dicarboxylic acid 8-amide 2-furan-2-ylamide, (compound denoted as A64-B1-C1), Example 1(j);

7-chloro-6-phenyl-3,4-dihydro-1H-pyrrolo[1,2-a]pyrazine-2,8-dicarboxylic acid 8-amide 2-[(4-isopropylphenyl)amide], (compound denoted as A19-B1-C1), Example 1(k);

7-chloro-6-phenyl-3,4-dihydro-1H-pyrrolo[1,2-a]pyrazine-2,8-dicarboxylic acid 2-[(4-acetylphenyl)amide] 8-amide, (compound denoted as A12-B1-C1), Example 1(n);

7-chloro-6-phenyl-3,4-dihydro-1H-pyrrolo[1,2-a]pyrazine-2,8-dicarboxylic acid 8-amide 2-[(4-fluorophenyl)amide], (compound denoted as A47-B1-C1), Example 1(o);

7-chloro-6-phenyl-3,4-dihydro-1H-pyrrolo[1,2-a]pyrazine-2,8-dicarboxylic acid 8-amide 2-[(3-chlorophenyl)amide], Example 1(q);

7-chloro-6-phenyl-3,4-dihydro-1H-pyrrolo[1,2-a]pyrazine-2,8-dicarboxylic acid 8-amide 2-cyclohexylamide, (compound denoted as A76-B1-C1), Example 1(t);

7-chloro-6-phenyl-3,4-dihydro-1H-pyrrolo[1,2-a]pyrazine-2,8-dicarboxylic acid 8-amide 2-[(3-cyanophenyl)amide], (compound denoted as A30-B1-C1), Example 1(u);

7-chloro-6-phenyl-3,4-dihydro-1H-pyrrolo[1,2-a]pyrazine-2,8-dicarboxylic acid 8-amide 2-m-tolylamide, (compound denoted as A17-B1-C1), Example 1(x);

7-chloro-6-phenyl-3,4-dihydro-1H-pyrrolo[1,2-a]pyrazine-2,8-dicarboxylic acid 8-amide 2-[(3,4-dichlorophenyl)amide], (compound denoted as A74-B1-C1), Example 1(z);

7-chloro-6-phenyl-3,4-dihydro-1H-pyrrolo[1,2-a]pyrazine-2,8-dicarboxylic acid 8-amide 2-[(4-phenoxyphenyl)amide], (compound denoted as A34-B1-C1), Example 1(ab);

7-chloro-6-phenyl-3,4-dihydro-1H-pyrrolo[1,2-a]pyrazine-2,8-dicarboxylic acid 8-amide 2-[(4-chlorophenyl)amide], (compound denoted as A48-B1-C1), Example 1(ac);

7-chloro-6-phenyl-3,4-dihydro-1H-pyrrolo[1,2-a]pyrazine-2,8-dicarboxylic acid 8-amide 2-[(4-chloro-3-trifluoromethylphenyl)amide], (compound denoted as A72-B1-C1), Example 1(ad);

7-chloro-6-phenyl-3,4-dihydro-1H-pyrrolo[1,2-a]pyrazine-2,8-dicarboxylic acid 8-amide 2-[(2,5-difluorophenyl)amide], (compound denoted as A75-B1-C1), Example 1(ai);

4-[(8-carbamoyl-7-chloro-6-phenyl-3,4-dihydro-1H-pyrrolo[1,2-a]pyrazine-2-carbonyl)amino]benzoic acid ethyl ester, Example 1(aj);

7-chloro-6-phenyl-3,4-dihydro-1H-pyrrolo[1,2-a]pyrazine-2,8-dicarboxylic acid 8-amide 2-[(4-benzyloxyphenyl)amide], (compound denoted as A43-B1-C1), Example 1(ak);

7-chloro-6-phenyl-3,4-dihydro-1H-pyrrolo[1,2-a]pyrazine-2,8-dicarboxylic acid 8-amide 2-[(4-methanesulfonylphenyl)amide], (compound denoted as A55-B1-C1), Example 1(am);

7-chloro-6-phenyl-3,4-dihydro-1H-pyrrolo[1,2-a]pyrazine-2,8-dicarboxylic acid 8-amide 2-thiophen-2-ylamide, (compound denoted as A65-B1-C1), Example 1(aq);

7-chloro-6-phenyl-3,4-dihydro-1H-pyrrolo[1,2-a]pyrazine-2,8-dicarboxylic acid 8-amide 2-[4-(trifluoromethylphenyl)amide], (compound denoted as A20-B1-C1), Example 1(ar);

3-[(8-carbamoyl-7-chloro-6-phenyl-3,4-dihydro-1H-pyrrolo[1,2-a]pyrazine-2-carbonyl)amino]benzoic acid ethyl ester, (compound denoted as A32-B1-C1), Example 1(as);

7-chloro-6-phenyl-3,4-dihydro-1H-pyrrolo[1,2-a]pyrazine-2,8-dicarboxylic acid 8-amide 2-[(3-chloro-4-fluorophenyl)amide], (compound denoted as A73-B1-C1), Example 1(at);

7-chloro-6-phenyl-3,4-dihydro-1H-pyrrolo[1,2-a]pyrazine-2,8-dicarboxylic acid 8-amide 2-pyridin-3-ylamide, (compound denoted as A62-B1-C1), Example 2(a);

7-chloro-6-phenyl-3,4-dihydro-1H-pyrrolo[1,2-a]pyrazine-2,8-dicarboxylic acid 8-amide 2-[(3,4-difluorophenyl)amide], (compound denoted as A71-B1-C1), Example 2(c);

7-chloro-6-phenyl-3,4-dihydro-1H-pyrrolo[1,2-a]pyrazine-2,8-dicarboxylic acid 8-amide 2-[(4-cyanophenyl)amide], (compound denoted as A29-B1-C1), Example 2(f);

7-chloro-6-phenyl-3,4-dihydro-1H-pyrrolo[1,2-a]pyrazine-2,8-dicarboxylic acid 8-amide 2-thiazol-2-ylamide, (compound denoted as A63-B1-C1), Example 2(h);

7-chloro-6-phenyl-3,4-dihydro-1H-pyrrolo[1,2-a]pyrazine-2,8-dicarboxylic acid 8-amide 2-[(4-morpholin-4-ylmethylphenyl)amide], (compound denoted as A22-B1-C1), Example 2(i);

7-chloro-6-phenyl-3,4-dihydro-1H-pyrrolo[1,2-a]pyrazine-2,8-dicarboxylic acid 8-amide 2-[(3-morpholin-4-ylmethylphenyl)amide], (compound denoted as A23-B1-C1), Example 2(j);

7-chloro-6-phenyl-3,4-dihydro-1H-pyrrolo[1,2-a]pyrazine-2,8-dicarboxylic acid 8-amide 2-[(4-morpholin-4-ylphenyl)amide], (compound denoted as A83-B1-C1), Example 2(k);

7-chloro-6-phenyl-3,4-dihydro-1H-pyrrolo[1,2-a]pyrazine-2,8-dicarboxylic acid 8-amide 2-{[4-(4-methylpiperazine-1-carbonyl)phenyl]amide}, (compound denoted as A1-B1-C1), Example 2(l);

7-chloro-6-phenyl-3,4-dihydro-1H-pyrrolo[1,2-a]pyrazine-2,8-dicarboxylic acid 8-amide 2-{[3-(4-methylpiperazine-1-carbonyl)phenyl]amide}, (compound denoted as A6-B1-C1), Example 2(m);

7-chloro-6-phenyl-3,4-dihydro-1H-pyrrolo[1,2-a]pyrazine-2,8-dicarboxylic acid 8-amide 2-{[4-(4-methyl[1,4]diazepane-1-carbonyl)phenyl]amide}, (compound denoted as A9-B1-C1), Example 2(n);

7-chloro-6-phenyl-3,4-dihydro-1H-pyrrolo[1,2-a]pyrazine-2,8-dicarboxylic acid 8-amide 2-{[3-(4-methyl[1,4]diazepane-1-carbonyl)phenyl]amide, (compound denoted as A8-B1-C1), Example 2(o);

7-chloro-6-phenyl-3,4-dihydro-1H-pyrrolo[1,2-a]pyrazine-2,8-dicarboxylic acid 8-amide 2-{[4-(4-fluorophenoxy)phenyl]amide}, (compound denoted as A35-B1-C1), Example 2(p);

7-chloro-6-phenyl-3,4-dihydro-1H-pyrrolo[1,2-a]pyrazine-2,8-dicarboxylic acid 8-amide 2-{[4-(4-isopropylpiperazine-1-carbonyl)phenyl]-amide}, (compound denoted as A2-B1-C1), Example 2(q);

7-chloro-6-phenyl-3,4-dihydro-1H-pyrrolo[1,2-a]pyrazine-2,8-dicarboxylic acid 8-amide 2-{[4-(4-isopropyl[1,4]diazepane-1-carbonyl)phenyl]amide}, (compound denoted as A10-B1-C1), Example 2(r);

7-chloro-6-phenyl-3,4-dihydro-1H-pyrrolo[1,2-a]pyrazine-2,8-dicarboxylic acid 8-amide 2-{[4-(3-dimethylaminopropoxy)phenyl]amide}, (compound denoted as A44-B1-C1), Example 2(s);

7-chloro-6-phenyl-3,4-dihydro-1H-pyrrolo[1,2-a]pyrazine-2,8-dicarboxylic acid 8-amide 2-indan-2-ylamide, (compound denoted as A58-B1-C1), Example 2(t);

7-chloro-6-phenyl-3,4-dihydro-1H-pyrrolo[1,2-a]pyrazine-2,8-dicarboxylic acid 8-amide 2-quinolin-6-ylamide, (compound denoted as A60-B1-C1), Example 2(u);

7-chloro-6-phenyl-3,4-dihydro-1H-pyrrolo[1,2-a]pyrazine-2,8-dicarboxylic acid 8-amide 2-{[1-(morpholine-4-carbonyl)piperidin-4-yl]amide}, (compound denoted as A79-B1-C1), Example 2(v);

4-[(8-carbamoyl-7-chloro-6-phenyl-3,4-dihydro-1H-pyrrolo[1,2-a]pyrazine-2-carbonyl)amino]piperidine-1-carboxylic acid isopropyl ester, (compound denoted as A78-B1-C1), Example 2(w);

7-chloro-6-(tetrahydropyran-4-yl)-3,4-dihydro-1H-pyrrolo[1,2-a]pyrazine-2,8-dicarboxylic acid 8-amide 2-[(4-fluorophenyl)amide, (compound denoted as A47-B1-C3), Example 3;

7-chloro-6-pyridin-3-yl-3,4-dihydro-1H-pyrrolo[1,2-a]pyrazine-2,8-dicarboxylic acid 8-amide 2-[(4-methanesulfonylphenyl)amide], (compound denoted as A55-B1-C6), Example 4(a);

4-[(8-carbamoyl-7-chloro-6-pyridin-3-yl-3,4-dihydro-1H-pyrrolo[1,2a]pyrazine-2-carbonyl)amino]benzoic acid ethyl ester, Example 4(d);

7-chloro-6-pyridin-3-yl-3,4-dihydro-1H-pyrrolo[1,2-a]pyrazine-2,8-dicarboxylic acid 8-amide 2-[(3-cyanophenyl)amide], (compound denoted as A30-B1-C6), Example 4(e);

7-chloro-6-pyridin-3-yl-3,4-dihydro-1H-pyrrolo[1,2-a]pyrazine-2,8-dicarboxylic acid 8-amide 2-[(3-trifluoromethylphenyl)amide], (compound denoted as A21-B1-C6), Example 4(f);

7-chloro-6-pyridin-3-yl-3,4-dihydro-1H-pyrrolo[1,2-a]pyrazine-2,8-dicarboxylic acid 8-amide 2-[(4-trifluoromethylphenyl)amide], (compound denoted as A20-B1-C6), Example 4(g);

7-Chloro-6-pyridin-3-yl-3,4-dihydro-1H-pyrrolo[1,2-a]pyrazine-2,8-dicarboxylic acid 8-amide 2-[(4-cyanophenyl)amide], (compound denoted as A29-B 1-C6), Example 5;

7-Chloro-6-methyl-3,4-dihydro-1H-pyrrolo[1,2-a]pyrazine-2,8-dicarboxylic acid 8-amide 2-[(3-fluorophenyl)amide], (compound denoted as A50-B1-C7), Example 6;

7-Cyano-6-phenyl-3,4-dihydro-1H-pyrrolo[1,2-a]pyrazine-2,8-dicarboxylic acid 8-amide 2-[(3-fluorophenyl)amide], (compound denoted as A50-B2-C1), Example 7(a);

7-cyano-6-phenyl-3,4-dihydro-1H-pyrrolo[1,2-a]pyrazine-2,8-dicarboxylic acid 8-amide 2-[(4-methoxyphenyl)amide], (compound denoted as A38-B2-C1), Example 7(b);

4-[(8-carbamoyl-7-cyano-6-phenyl-3,4-dihydro-1H-pyrrolo[1,2a]pyrazine-2-carbonyl)amino]benzoic acid ethyl ester, Example 7(d);

7-cyano-6-phenyl-3,4-dihydro-1H-pyrrolo[1,2-a]pyrazine-2,8-dicarboxylic acid 8-amide 2-[(4-methanesulfonylphenyl)amide], (compound denoted as A55-B2-C1), Example 7(e);

7-cyano-6-phenyl-3,4-dihydro-1H-pyrrolo[1,2-a]pyrazine-2,8-dicarboxylic acid 8-amide 2-[(3-cyanophenyl)amide], (compound denoted as A30-B2-C1), Example 7(h);

7-cyano-6-phenyl-3,4-dihydro-1H-pyrrolo[1,2-a]pyrazine-2,8-dicarboxylic acid 8-amide 2-[(4-trifluoromethylphenyl)amide], (compound denoted as A20-B2-C1), Example 7(i);

7-cyano-6-phenyl-3,4-dihydro-1H-pyrrolo[1,2-a]pyrazine-2,8-dicarboxylic acid 8-amide 2-pyridin-3-ylamide, (compound denoted as A61-B2-C1), Example 8(a);

7-cyano-6-phenyl-3,4-dihydro-1H-pyrrolo[1,2-a]pyrazine-2,8-dicarboxylic acid 8-amide 2-[(4-morpholin-4-ylmethylphenyl)amide], (compound denoted as A22-B2-C1), Example 8(f);

7-cyano-6-phenyl-3,4-dihydro-1H-pyrrolo[1,2-a]pyrazine-2,8-dicarboxylic acid 8-amide 2-{[4-(4-methylpiperazin-1-ylmethyl)phenyl]amide}, (compound denoted as A25-B2-C1), Example 8(g);

7-cyano-6-phenyl-3,4-dihydro-1H-pyrrolo[1,2-a]pyrazine-2,8-dicarboxylic acid 8-amide 2-{[4-(2-morpholin-4-ylethoxy)phenyl]-amide}, (compound denoted as A46-B2-C1), Example 8(h);

7-cyano-6-phenyl-3,4-dihydro-1H-pyrrolo[1,2-a]pyrazine-2,8-dicarboxylic acid 8-amide 2-{[4-(morpholin-4-ylacetyl)-phenyl]-amide}, (compound denoted as A15-B2-C1), Example 8(i);

7-cyano-6-phenyl-3,4-dihydro-1H-pyrrolo[1,2-a]pyrazine-2,8-dicarboxylic acid 8-amide 2-[(4-cyanophenyl)amide], (compound denoted as A29-B2-C1), Example 8(j);

7-cyano-6-phenyl-3,4-dihydro-1H-pyrrolo[1,2-a]pyrazine-2,8-dicarboxylic acid 8-amide 2-pyridin-4-ylamide, (compound denoted as A61-B2-C1), Example 8(k);

7-cyano-6-phenyl-3,4-dihydro-1H-pyrrolo[1,2-a]pyrazine-2,8-dicarboxylic acid 8-amide 2-indan-2-ylamide, (compound denoted as A58-B2-C$_1$), Example 8(l);

7-cyano-6-phenyl-3,4-dihydro-1H-pyrrolo[1,2-a]pyrazine-2,8-dicarboxylic acid 8-amide 2-quinolin-6-ylamide, (compound denoted as A60-B2-C1), Example 8(m);

7-cyano-6-phenyl-3,4-dihydro-1H-pyrrolo[1,2-a]pyrazine-2,8-dicarboxylic acid 8-amide 2-[(4-chlorophenyl)amide], (compound denoted as A48-B2-C1), Example 8(n);

4-[(8-carbamoyl-7-cyano-6-phenyl-3,4-dihydro-1H-pyrrolo[1,2-a]pyrazine-2-carbonyl)amino]piperidine-1-carboxylic acid isopropyl ester, (compound denoted as A78-B2-C1), Example 8(p);

4-[(8-carbamoyl-7-cyano-6-cyclopropyl-3,4-dihydro-1H-pyrrolo[1,2a]pyrazine-2-carbonyl)amino]benzoic acid ethyl ester, Example 9(c);

7-cyano-6-cyclopropyl-3,4-dihydro-1H-pyrrolo[1,2-a]pyrazine-2,8-dicarboxylic acid 8-amide 2-[(4-chlorophenyl)amide], (compound denoted as A48-B2-C2), Example 9(d);

(±) trans-7-cyano-6-cyclopropyl-3,4-dihydro-1H-pyrrolo[1,2-a]pyrazine-2,8-dicarboxylic acid 8-amide 2-[(2-phenylcyclopropyl)amide], (compound denoted as A77-B2-C2), Example 9(f);

7-cyano-6-cyclopropyl-3,4-dihydro-1H-pyrrolo[1,2-a]pyrazine-2,8-dicarboxylic acid 8-amide 2-[(3-chloro-4-fluorophenyl)amide], (compound denoted as A73-B2-C2), Example 9(g);

7-cyano-6-cyclopropyl-3,4-dihydro-1H-pyrrolo[1,2-a]pyrazine-2,8-dicarboxylic acid 8-amide 2-[(4-trifluoromethylphenyl)amide], (compound denoted as A20-B2-C2), Example 9(h);

7-cyano-6-cyclopropyl-3,4-dihydro-1H-pyrrolo[1,2-a]pyrazine-2,8-dicarboxylic acid 8-amide 2-[(3-trifluoromethylphenyl)amide], (compound denoted as A21-B2-C2), Example 9(i);

7-cyano-6-cyclopropyl-3,4-dihydro-1H-pyrrolo[1,2-a]pyrazine-2,8-dicarboxylic acid 8-amide 2-{[4-(4-methylpiperazine-1-carbonyl)phenyl]amide}, (compound denoted as A1-B2-C2), Example 10(a);

7-cyano-6-cyclopropyl-3,4-dihydro-1H-pyrrolo[1,2-a]pyrazine-2,8-dicarboxylic acid 8-amide 2-[(4-morpholin-4-ylmethylphenyl)amide], (compound denoted as A22-B2-C2), Example 10(b);

7-cyano-6-cyclopropyl-3,4-dihydro-1H-pyrrolo[1,2-a]pyrazine-2,8-dicarboxylic acid 8-amide 2-{[4-(4-methylpiperazin-1-ylmethyl)phenyl]amide}, (compound denoted as A25-B2-C2), Example 10(c);

7-cyano-6-cyclopropyl-3,4-dihydro-1H-pyrrolo[1,2-a]pyrazine-2,8-dicarboxylic acid 8-amide 2-{[4-(2-morpholin-4-ylethoxy)phenyl]amide}, (compound denoted as A46-B2-C2), Example 10(d);

7-cyano-6-cyclopropyl-3,4-dihydro-1H-pyrrolo[1,2-a]pyrazine-2,8-dicarboxylic acid 8-amide 2-{[4-(morpholine-4-carbonyl)phenyl]amide}, (compound denoted as A4-B2-C2), Example 10(e);

7-cyano-6-cyclopropyl-3,4-dihydro-1H-pyrrolo[1,2-a]pyrazine-2,8-dicarboxylic acid 8-amide 2-[(4-cyanophenyl)amide], (compound denoted as A29-B2-C2), Example 10(f);

7-cyano-6-cyclopropyl-3,4-dihydro-1H-pyrrolo[1,2-a]pyrazine-2,8-dicarboxylic acid 8-amide 2-[(3,4-difluorophenyl)amide], (compound denoted as A71-B2-C2), Example 10(g);

7-cyano-6-cyclopropyl-3,4-dihydro-1H-pyrrolo[1,2-a]pyrazine-2,8-dicarboxylic acid 8-amide 2-{[4-(4-fluorophenoxy)phenyl]amide, (compound denoted as A35-B2-C2), Example 10(h);

7-cyano-6-cyclopropyl-3,4-dihydro-1H-pyrrolo[1,2-a]pyrazine-2,8-dicarboxylic acid 8-amide 2-quinolin-6-ylamide, (compound denoted as A60-B2-C2), Example 10(i);

7-cyano-6-cyclopropyl-3,4-dihydro-1H-pyrrolo[1,2-a]pyrazine-2,8-dicarboxylic acid 8-amide 2-[(4-methylsulfanylphenyl)amide], (compound denoted as A56-B2-C2), Example 10(j);

7-cyano-6-cyclopropyl-3,4-dihydro-1H-pyrrolo[1,2-a]pyrazine-2,8-dicarboxylic acid 8-amide 2-[(3-cyanophenyl)amide], (compound denoted as A30-B2-C2), Example 10(k);

{4-[(8-carbamoyl-7-cyano-6-cyclopropyl-3,4-dihydro-1H-pyrrolo[1,2-a]pyrazine-2-carbonyl)amino]phenyl}acetic acid ethyl ester, Example 10(1);

7-cyano-6-cyclopropyl-3,4-dihydro-1H-pyrrolo[1,2-a]pyrazine-2,8-dicarboxylic acid 8-amide 2-pyridin-3-ylamide, (compound denoted as A62-B2-C2), Example 10(m);

7-cyano-6-cyclopropyl-3,4-dihydro-1H-pyrrolo[1,2-a]pyrazine-2,8-dicarboxylic acid 2-[(4-acetylphenyl)amide] 8-amide, (compound denoted as A12-B2-C2), Example 10(n);

7-cyano-6-cyclopropyl-3,4-dihydro-1H-pyrrolo[1,2-a]pyrazine-2,8-dicarboxylic acid 8-amide 2-indan-2-ylamide, (compound denoted as A58-B2-C2), Example 10(o);

7-cyano-6-cyclopropyl-3,4-dihydro-1H-pyrrolo[1,2-a]pyrazine-2,8-dicarboxylic acid 8-amide 2-pyridin-4-ylamide, (compound denoted as A61-B2-C2), Example 10(q);

4-[(8-carbamoyl-7-cyano-6-cyclopropyl-3,4-dihydro-1H-pyrrolo[1,2-a]pyrazine-2-carbonyl)amino]piperidine-1-carboxylic acid isopropyl ester, (compound denoted as A78-B2-C2), Example 10(s);

7-cyano-6-cyclopropyl-3,4-dihydro-1H-pyrrolo[1,2-a]pyrazine-2,8-dicarboxylic acid 8-amide 2-[(1-benzoylpiperidin-4-yl)amide], (compound denoted as A84-B2-C2), Example 10(t);

7-cyano-6-pyridin-3-yl-3,4-dihydro-1H-pyrrolo[1,2-a]pyrazine-2,8-dicarboxylic acid 8- amide 2-[(4-methanesulfonylphenyl)amide], (compound denoted as A55-B2-C6), Example 12(b);

7-cyano-6-pyridin-3-yl-3,4-dihydro-1H-pyrrolo[1,2-a]pyrazine-2,8-dicarboxylic acid 8- amide 2-[(4-trifluoromethylphenyl)amide], (compound denoted as A20-B2-C6), Example 12(d);

7-cyano-6-(1-methanesulfonylpiperidin-4-yl)-3,4-dihydro-1H-pyrrolo[1,2-a]pyrazine-2,8-dicarboxylic acid 8-amide 2-[(4-fluorophenyl)amide], (compound denoted as A47-B2-C9), Example 14(a);

7-cyano-6-(1-methanesulfonylpiperidin-4-yl)-3,4-dihydro-1H-pyrrolo[1,2-a]pyrazine-2,8-dicarboxylic acid 8-amide 2-[(4-cyanophenyl)amide], (compound denoted as A29-B2-C6), Example 15;

7-chloro-6-cyclopropyl-3,4-dihydro-1H-pyrrolo[1,2-a]pyrazine-2,8-dicarboxylic acid 8-amide 2-[(4-fluorophenyl)amide], (compound denoted as A47-B1-C2), Example 16(a);

7-chloro-6-cyclopropyl-3,4-dihydro-1H-pyrrolo[1,2-a]pyrazine-2,8-dicarboxylic acid 8-amide 2-[(4-trifluoromethylphenyl)amide], (compound denoted as A20-B1-C2), Example 16(b);

(±)-trans-7-chloro-6-cyclopropyl-3,4-dihydro-1H-pyrrolo[1,2-a]pyrazine-2,8-dicarboxylic acid 8-amide 2-[(2-phenylcyclopropyl)amide], (compound denoted as A77-B1-C2), Example 16(c);

7-chloro-6-cyclopropyl-3,4-dihydro-1H-pyrrolo[1,2-a]pyrazine-2,8-dicarboxylic acid 8-amide 2-[(4-cyanophenyl)amide], (compound denoted as A29-B1-C2), Example 17(a);

7-chloro-6-cyclopropyl-3,4-dihydro-1H-pyrrolo[1,2-a]pyrazine-2,8-dicarboxylic acid 8-amide 2-quinolin-6-ylamide, (compound denoted as A60-B1-C2), Example 17(b);

7-chloro-6-cyclopropyl-3,4-dihydro-1H-pyrrolo[1,2-a]pyrazine-2,8-dicarboxylic acid 8-amide 2-indan-2-ylamide, (compound denoted as A58-B1-C2), Example 17(c);

7-chloro-6-cyclopropyl-3,4-dihydro-1H-pyrrolo[1,2-a]pyrazine-2,8-dicarboxylic acid 8-amide 2-{[4-(4-isopropylpiperazine-1-carbonyl)-phenyl]amide}, (compound denoted as A2-B1-C2), Example 17(d);

7-chloro-3,4-dihydro-1H-pyrrolo[1,2-a]pyrazine-2,8-dicarboxylic acid 8-amide 2-[(4-trifluoromethylphenyl)amide], (compound denoted as A20-B1-C11), Example 18(b);

7-chloro-3,4-dihydro-1H-pyrrolo[1,2-a]pyrazine-2,8-dicarboxylic acid 8-amide 2-{[4-(4-isopropylpiperazine-1-carbonyl)phenyl]amide}, (compound denoted as A2-B1-C11), Example 19(a);

7-chloro-6-(4-methylpyridin-3-yl)-3,4-dihydro-1H-pyrrolo[1,2-a]pyrazine-2,8- dicarboxylic acid 8-amide 2-[(4-fluorophenyl)amide], (compound denoted as A47-B1-C4), Example 21(a);

7-chloro-6-(4-methylpyridin-3-yl)-3,4-dihydro-1H-pyrrolo[1,2-a]pyrazine-2,8- dicarboxylic acid 8-amide 2-[(3-trifluoromethylphenyl)amide], (compound denoted as A21-B1-C4), Example 21(b);

(±)-trans-7-chloro-6-(4-methylpyridin-3-yl)-3,4-dihydro-1H-pyrrolo[1,2-a]pyrazine-2,8-dicarboxylic acid 8-amide 2-[(2-phenylcyclopropyl)amide], (compound denoted as A77-B1-C4), Example 21(c);

7-Chloro-6-(4-methylpyridin-3-yl)-3,4-dihydro-1H-pyrrolo[1,2-a]pyrazine-2,8-dicarboxylic acid 8-amide 2-quinolin-6-ylamide, (compound denoted as A60-B1-C4), Example 22(a);

7-chloro-6-(4-methylpyridin-3-yl)-3,4-dihydro-1H-pyrrolo[1,2-a]pyrazine-2,8-dicarboxylic acid 8-amide 2-[(4-cyanophenyl)amide, (compound denoted as A29-B1-C4), Example 22(b);

7-chloro-6-(4-methylpyridin-3-yl)-3,4-dihydro-1H-pyrrolo[1,2-a]pyrazine-2,8-dicarboxylic acid 8-amide 2-indan-2-ylamide, (compound denoted as A58-B1-C4), Example 22(c);

7-cyano-6-(tetrahydropyran-4-yl)-3,4-dihydro-1H-pyrrolo[1,2-a]pyrazine-2,8-dicarboxylic acid 8-amide 2-[(3-trifluoromethylphenyl)amide], (compound denoted as A21-B2-C3), Example 24(a);

7-cyano-6-(tetrahydropyran-4-yl)-3,4-dihydro-1H-pyrrolo[1,2-a]pyrazine-2,8-dicarboxylic acid 8-amide 2-[(4-trifluoromethylphenyl)amide], (compound denoted as A20-B2-C3), Example 24(b);

7-cyano-6-(tetrahydropyran-4-yl)-3,4-dihydro-1H-pyrrolo[1,2-a]pyrazine-2,8-dicarboxylic acid 8-amide 2-[(4-fluorophenyl)amide], (compound denoted as A47-B2-C3), Example 24(c);

(±)-trans-7-cyano-6-(tetrahydropyran-4-yl)-3,4-dihydro-1H-pyrrolo[1,2-a]pyrazine-2,8-dicarboxylic acid 8-amide 2-[(2-phenylcyclopropyl)amide], (compound denoted as A77-B2-C3), Example 24(d);

7-cyano-6-(tetrahydropyran-4-yl)-3,4-dihydro-1H-pyrrolo[1,2-a]pyrazine-2,8-dicarboxylic acid 8-amide 2-[(5-methylthiophen-2-yl)amide], (compound denoted as A66-B2-C3), Example 24(e);

7-cyano-6-(tetrahydropyran-4-yl)-3,4-dihydro-1H-pyrrolo[1,2-a]pyrazine-2,8-dicarboxylic acid 8-amide 2-quinolin-6-ylamide, (compound denoted as A60-B2-C3), Example 25(a);

7-cyano-6-(tetrahydropyran-4-yl)-3,4-dihydro-1H-pyrrolo[1,2-a]pyrazine-2,8-dicarboxylic acid 8-amide 2-indan-2-ylamide, (compound denoted as A58-B2-C3), Example 25(b);

7-cyano-6-(tetrahydropyran-4-yl)-3,4-dihydro-1H-pyrrolo[1,2-a]pyrazine-2,8-dicarboxylic acid 8-amide 2-[(4-cyanophenyl)amide], (compound denoted as A29-B2-C3), Example 25(c);

4-{[8-carbamoyl-7-cyano-6-(tetrahydropyran-4-yl)-3,4-dihydro-1H-pyrrolo[1,2-a]pyrazine-2-carbonyl]amino}piperidine-1-carboxylic acid isopropyl ester, (compound denoted as A78-B2-C3), Example 25(d);

7-cyano-6-cyclopropyl-3,4-dihydro-1H-pyrrolo[1,2-a]pyrazine-2,8-dicarboxylic acid 8-amide 2-[(6-trifluoromethylpyridin-3-yl)amide], (compound denoted as A59-B2-C2), Example 27(a);

7-chloro-6-cyclopropyl-3,4-dihydro-1H-pyrrolo[1,2-a]pyrazine-2,8-dicarboxylic acid 8-amide 2-[(6-trifluoromethylpyridin-3-yl)amide], (compound denoted as A59-B1-C2), Example 27(b);

7-chloro-3,4-dihydro-1H-pyrrolo[1,2-a]pyrazine-2,8-dicarboxylic acid 8-amide 2-[(6-trifluoromethylpyridin-3-yl)amide], (compound denoted as A59-B1-C11), Example 27(c);

7-cyano-6-phenyl-3,4-dihydro-1H-pyrrolo[1,2-a]pyrazine-2,8-dicarboxylic acid 8-amide 2-[(6-trifluoromethylpyridin-3-yl)amide], (compound denoted as A59-B2-C1), Example 27(d);

7-cyano-6-(tetrahydropyran-4-yl)-3,4-dihydro-1H-pyrrolo[1,2-a]pyrazine-2,8-dicarboxylic acid 8-amide 2-[(6-trifluoromethylpyridin-3-yl)amide], (compound denoted as A59-B2-C4), Example 27(e);

7-chloro-6-phenyl-3,4-dihydro-1H-pyrrolo[1,2-a]pyrazine-2,8-dicarboxylic acid 8-amide 2-[(6-trifluoromethylpyridin-3-yl)amide], (compound denoted as A59-B1-C1), Example 27(f);

4-[(8-carbamoyl-7-cyano-6-phenyl-3,4-dihydro-1H-pyrrolo[1,2a]pyrazine-2-carbonyl)amino]benzoic acid, (compound denoted as A31-B2-C1), Example 28(a);

4-[(8-carbamoyl-7-chloro-6-phenyl-3,4-dihydro-1H-pyrrolo[1,2-a]pyrazine-2-carbonyl)amino]benzoic acid, (compound denoted as A31-B1-C2), Example 28(b);

4-[(8-carbamoyl-7-cyano-6-cyclopropyl-3,4-dihydro-1H-pyrrolo[1,2-a]pyrazine-2-carbonyl)amino]benzoic acid, (compound denoted as A31-B2-C2), Example 28(c);

4-[(8-carbamoyl-7-chloro-6-pyridin-3-yl-3,4-dihydro-1H-pyrrolo[1,2a]pyrazine-2-carbonyl)amino]benzoic acid, (compound denoted as A31-B1-C6), Example 28(d);

4-[(8-carbamoyl-7-cyano-6-(1-methanesulfonylpiperidin-4-yl)-3,4-dihydro-1H-pyrrolo[1,2a]pyrazine-2-carbonyl)amino]benzoic acid, (compound denoted as A31-B2-C9), Example 28(f);

3-[(8-carbamoyl-7-chloro-6-phenyl-3,4-dihydro-1H-pyrrolo[1,2-a]pyrazine-2-carbonyl)amino]benzoic acid, (compound denoted as A31-B1-C1), Example 28(g);

7-chloro-6-phenyl-3,4-dihydro-1H-pyrrolo[1,2-a]pyrazine-2,8-dicarboxylic acid 8-amide 2-[(4-hydroxyphenyl)amide], (compound denoted as A42-B1-C1), Example 29(b);

7-chloro-2-(4-methoxybenzenesulfonyl)-6-phenyl-1,2,3,4-tetrahydropyrrolo[1,2-a]pyrazine-8-carboxylic acid amide, (compound denoted as A123-B1-C1), Example 31(s);

7-chloro-6-phenyl-3,4-dihydro-1H-pyrrolo[1,2-a]pyrazine-2,8-dicarboxylic acid 8-amide 2-{[4-(morpholine-4-carbonyl)phenyl]amide}, (compound denoted as A4-B1-C1), Example 42;

7-cyano-6-cyclopropyl-3,4-dihydro-1H-pyrrolo[1,2-a]pyrazine-2,8-dicarboxylic acid 8-amide 2-{[4-(2-morpholin-4-ylethylcarbamoyl)phenyl]amide), (compound denoted as A11-B1-C1), Example 43;

7-chloro-6-cyclopropyl-1,2,3,4-tetrahydropyrrolo[1,2-a]pyrazine-8-carboxylic acid amide trifluoroacetic acid salt, (compound denoted as A129-B1-C2), Example 44(a);

7-cyano-6-cyclopropyl-1,2,3,4-tetrahydropyrrolo[1,2-a]pyrazine-8-carboxylic acid amide trifluoroacetic acid salt, (compound denoted as A129-B2-C2), Example 44(b);

and the corresponding N-oxides, and their prodrugs; and pharmaceutically acceptable salts and solvates (e.g. hydrates) of such compounds and their N-oxides and prodrugs.

Especially preferred compounds of formula (1a) of the invention for the inhibition of JNK are:

7-chloro-6-phenyl-3,4-dihydro-1H-pyrrolo[1,2-a]pyrazine-2,8-dicarboxylic acid 8-amide 2-[(4-methanesulfonylphenyl)amide], Example 1(a);

7-chloro-6-phenyl-3,4-dihydro-1H-pyrrolo[1,2-a]pyrazine-2,8-dicarboxylic acid 8-amide 2-{[4-(4-methylpiperazine-1-carbonyl)phenyl]amide}, Example 2(l);

and the corresponding N-oxides, and their prodrugs; and pharmaceutically acceptable salts and solvates (e.g. hydrates) of such compounds and their N-oxides and prodrugs.

The present invention concerns particularly the following compounds of formula (ICC):

EXAMPLE 1(aa)

7-chloro-6-phenyl-3,4-dihydro-1H-pyrrolo[1,2-a]pyrazine-2,8-dicarboxylic acid 8-amide 2-cyclopentylmethylamide

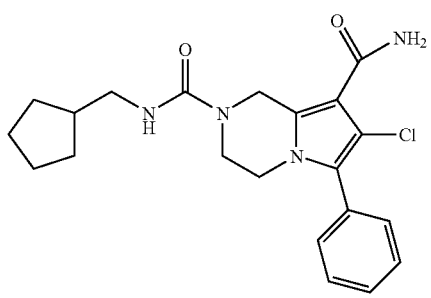

EXAMPLE 1(ah)

7-chloro-6-phenyl-3,4-dihydro-1H-pyrrolo[1,2-a]pyrazine-2,8-dicarboxylic acid 8-amide 2-[(2,4-difluorophenyl)amide]

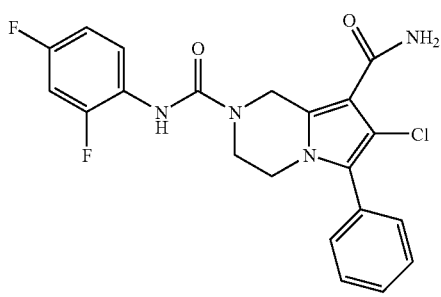

EXAMPLE 1(j)

7-chloro-6-phenyl-3,4-dihydro-1H-pyrrolo[1,2-a]pyrazine-2,8-dicarboxylic acid 8-amide 2-furan-2-ylamide

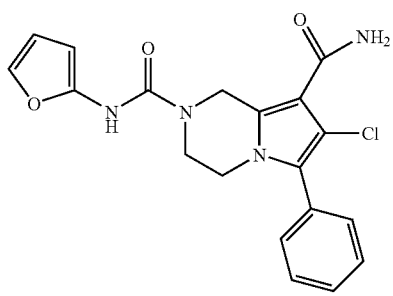

EXAMPLE 1(p)

7-chloro-6-phenyl-3,4-dihydro-1H-pyrrolo[1,2-a]pyrazine-2,8-dicarboxylic acid 8-amide 2-[(2,6-difluorophenyl)amide]

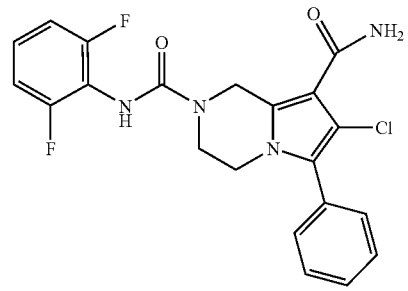

EXAMPLE 1(ao)

[(8-carbamoyl-7-chloro-6-phenyl-3,4-dihydro-1H-pyrrolo[1,2-a]pyrazine-2-carbonyl)amino]acetic acid ethyl ester

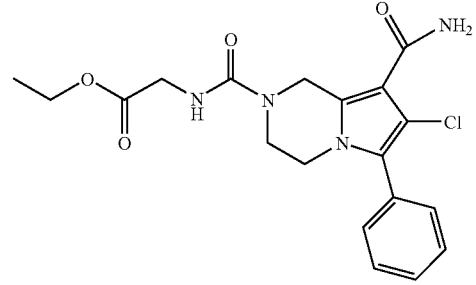

EXAMPLE 8(c)

7-cyano-6-phenyl-3,4-dihydro-1H-pyrrolo[1,2-a]pyrazine-2,8-dicarboxylic acid 8-amide 2-cyclopentylamide

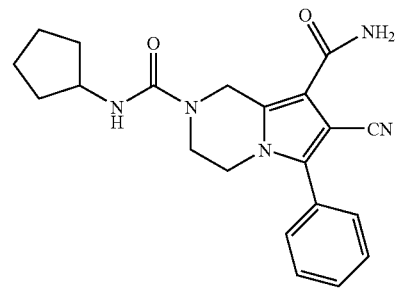

EXAMPLE 7(c)

7-cyano-6-phenyl-3,4-dihydro-1H-pyrrolo[1,2-a]pyrazine-2,8-dicarboxylic acid 8-amide 2-[(4-fluorophenyl)amide]

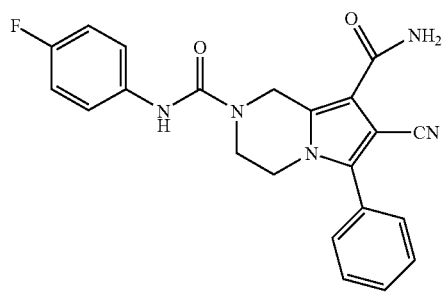

EXAMPLE 2(g)

7-chloro-6-phenyl-3,4-dihydro-1H-pyrrolo[1,2-a]pyrazine-2,8-dicarboxylic acid 8-amide 2-cyclopentylamide

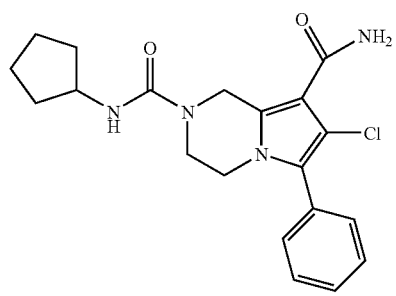

EXAMPLE 64

{4-[(8-Carbamoyl-7-chloro-6-phenyl-3,4-dihydro-1H-pyrrolo 1,2-a]pyrazine-2-carbonyl)-amino]-phenoxy}-acetic acid

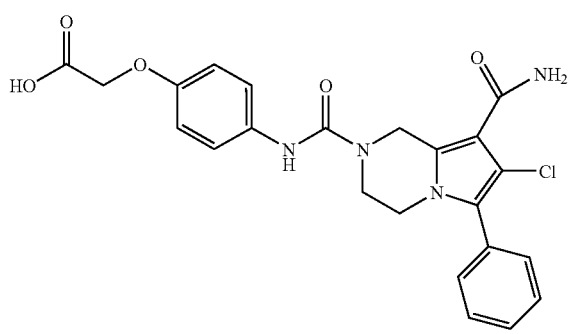

EXAMPLE 8(h)

7-cyano-6-phenyl-3,4-dihydro-1H-pyrrolo[1,2-a]pyrazine-2,8-dicarboxylic acid 8-amide 2-{[4-(2-morpholin-4-ylethoxy)phenyl]amide}

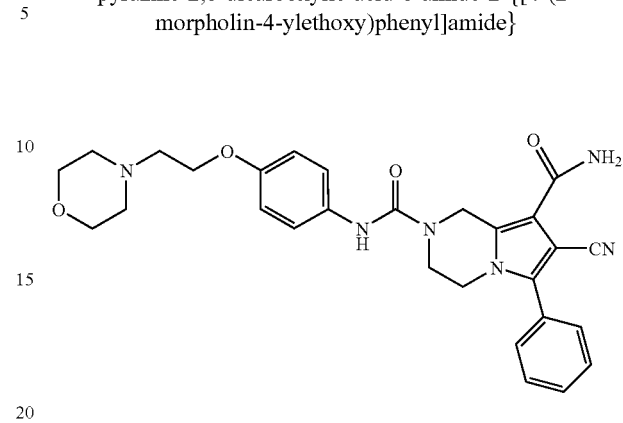

EXAMPLE 8(f)

7-cyano-6-phenyl-3,4-dihydro-1H-pyrrolo[1,2-a]pyrazine-2,8-dicarboxylic acid 8-amide 2-[(4-morpholin-4-ylmethylphenyl)amide]

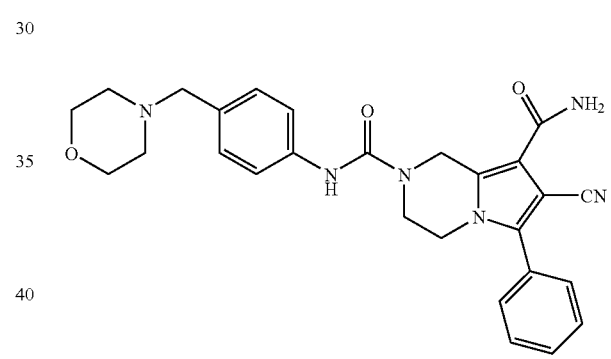

EXAMPLE 2(j)

7-chloro-6-phenyl-3,4-dihydro-1H-pyrrolo[1,2-a]pyrazine-2,8-dicarboxylic acid 8-amide 2-[(3-morpholin-4-ylmethylphenyl)amide]

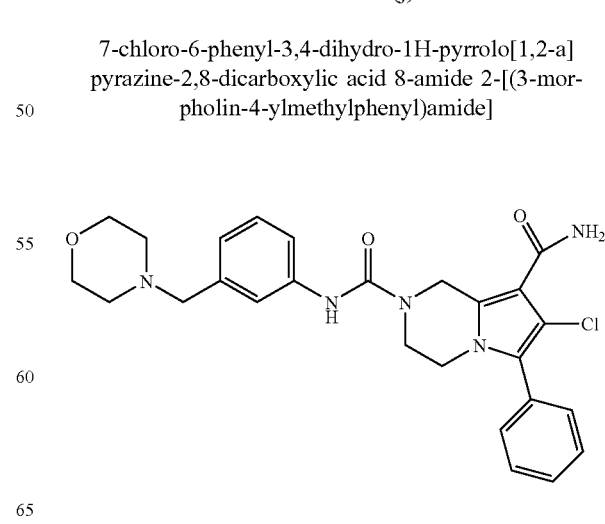

EXAMPLE 2(n)

7-chloro-6-phenyl-3,4-dihydro-1H-pyrrolo[1,2-a]pyrazine-2,8-dicarboxylic acid 8-amide 2-{[4-(4-methyl[1,4]diazepane-1-carbonyl)phenyl]amide}

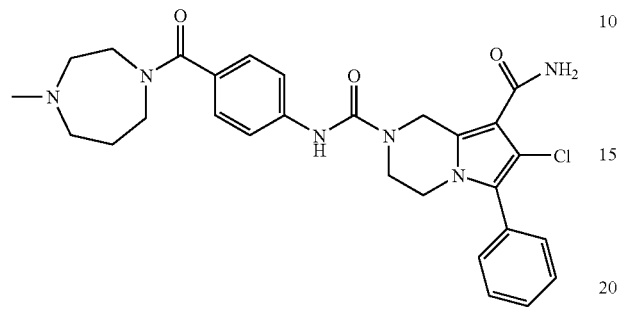

EXAMPLE 65

7-chloro-6-phenyl-3,4-dihydro-1H-pyrrolo[1,2-a]pyrazine-2,8-dicarboxylic acid 8-amide 2-{[3-(1-methyl-piperidine-4-carbonyl)-phenyl]-amide}

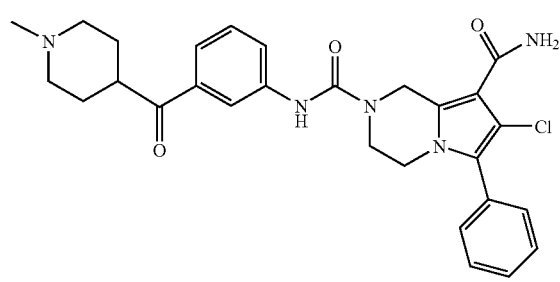

EXAMPLE 66

7-chloro-6-phenyl-3,4-dihydro-1H-pyrrolo[1,2-a]pyrazine-2,8-dicarboxylic acid 8-amide 2-{[4-(1-methyl-piperid-4-yl-methyl)-phenyl]-amide}

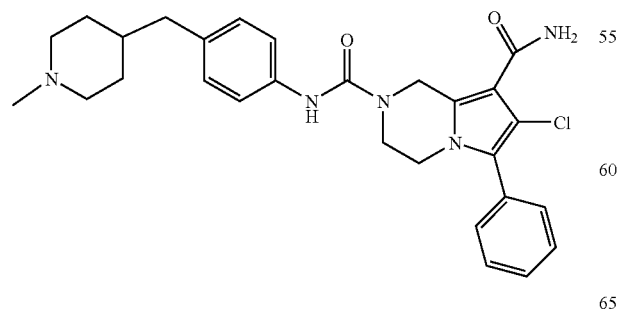

EXAMPLE 7(k)

(±)-trans-7-cyano-6-phenyl-3,4-dihydro-1H-pyrrolo[1,2-a]pyrazine-2,8-dicarboxylic acid 8-amide 2-[(2-phenylcyclopropyl)amide]

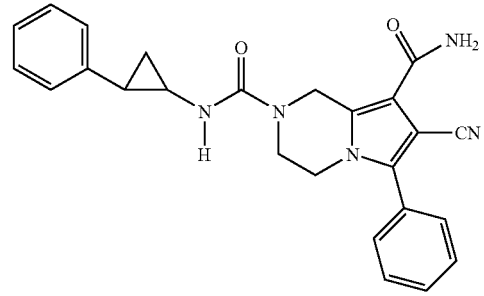

EXAMPLE 1(x)

7-chloro-6-phenyl-3,4-dihydro-1H-pyrrolo[1,2-a]pyrazine-2,8-dicarboxylic acid 8-amide 2-m-tolylamide

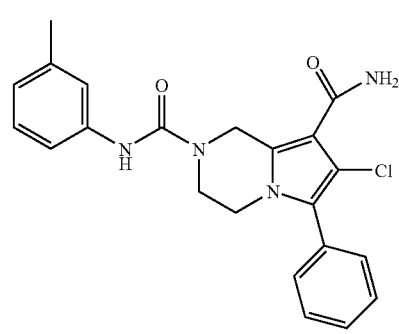

EXAMPLE 1(q)

7-chloro-6-phenyl-3,4-dihydro-1H-pyrrolo[1,2-a]pyrazine-2,8-dicarboxylic acid 8-amide 2-[(3-chlorophenyl)amide]

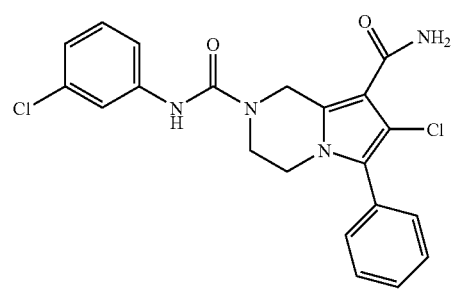

EXAMPLE 1(g)

7-chloro-6-phenyl-3,4-dihydro-1H-pyrrolo[1,2-a]pyrazine-2,8-dicarboxylic acid 8-amide 2-[(3-methoxyphenyl)amide]

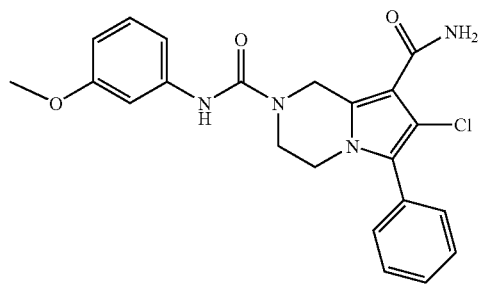

EXAMPLE 1(e)

7-chloro-6-phenyl-3,4-dihydro-1H-pyrrolo[1,2-a]pyrazine-2,8-dicarboxylic acid 8-amide 2-[(3-fluorophenyl)amide]

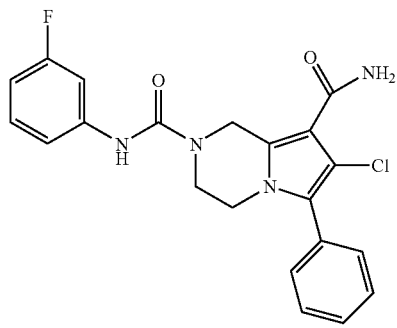

EXAMPLE 1(l) (67)

7-chloro-6-phenyl-3,4-dihydro-1H-pyrrolo[1,2-a]pyrazine-2,8-dicarboxylic acid 8-amide 2-[(2-chlorophenyl)amide]

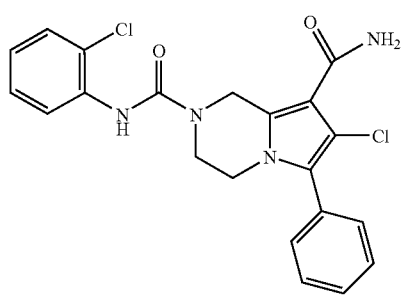

EXAMPLE 28(b)

4-[(8-carbamoyl-7-chloro-6-phenyl-3,4-dihydro-1H-pyrrolo[1,2-a]pyrazine-2-carbonyl)amino]benzoic acid

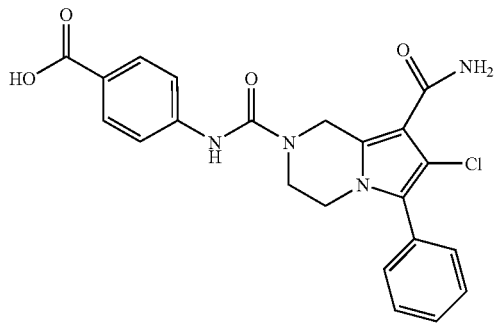

EXAMPLE 1(al)

7-chloro-6-phenyl-3,4-dihydro-1H-pyrrolo[1,2-a]pyrazine-2,8-dicarboxylic acid 8-amide 2-[(tetrahydropyran-4-yl)amide]

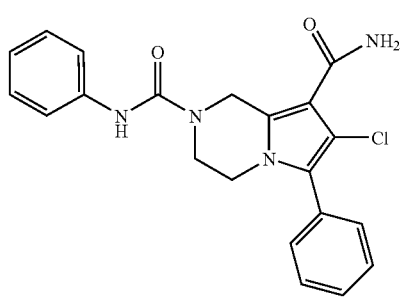

EXAMPLE 2(m)

7-chloro-6-phenyl-3,4-dihydro-1H-pyrrolo[1,2-a]pyrazine-2,8-dicarboxylic acid 8-amide 2-{[3-(4-methylpiperazine-1-carbonyl)phenyl]amide}

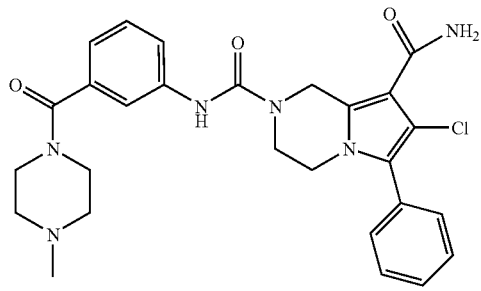

EXAMPLE 68

7-chloro-6-phenyl-3,4-dihydro-1H-pyrrolo[1,2-a]pyrazine-2,8-dicarboxylic acid 8-amide 2 2-{[2-(2-hydroxy-ethyl)-1,2,3,4-tetrahydro-isoquinolin-7-yl]-amide}

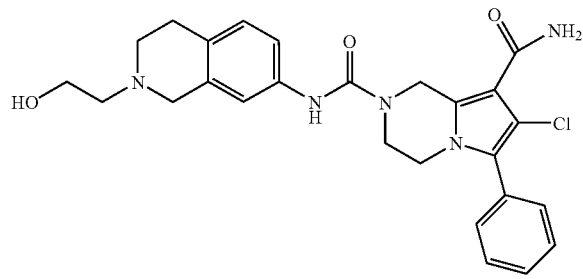

EXAMPLE 69

7-chloro-6-phenyl-3,4-dihydro-1H-pyrrolo[1,2-a]pyrazine-2,8-dicarboxylic acid 8-amide) 2-{[3-(1-morpholin-4-yl-ethyl)-phenyl]-amide}

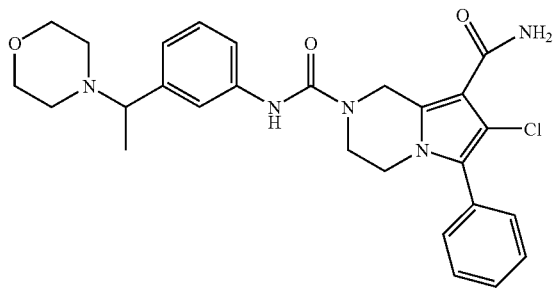

The present invention concerns then particularly the following compounds of formula (ICC):

7-chloro-6-phenyl-3,4-dihydro-1H-pyrrolo[1,2-a]pyrazine-2,8-dicarboxylic acid 8-amide 2-cyclopentylmethylamide
7-chloro-6-phenyl-3,4-dihydro-1H-pyrrolo[1,2-a]pyrazine-2,8-dicarboxylic acid 8-amide 2-[(2,4-difluorophenyl)amide]
7-chloro-6-phenyl-3,4-dihydro-1H-pyrrolo[1,2-a]pyrazine-2,8-dicarboxylic acid 8-amide 2-furan-2-ylamide
7-chloro-6-phenyl-3,4-dihydro-1H-pyrrolo[1,2-a]pyrazine-2,8-dicarboxylic acid 8-amide 2-[(2,6-difluorophenyl)amide]
[(8-carbamoyl-7-chloro-6-phenyl-3,4-dihydro-1H-pyrrolo[1,2-a]pyrazine-2-carbonyl)amino] acetic acid ethyl ester
7-cyano-6-phenyl-3,4-dihydro-1H-pyrrolo[1,2-a]pyrazine-2,8-dicarboxylic acid 8-amide 2-cyclopentylamide
7-cyano-6-phenyl-3,4-dihydro-1H-pyrrolo[1,2-a]pyrazine-2,8-dicarboxylic acid 8-amide 2-[(4-fluorophenyl)amide]
7-chloro-6-phenyl-3,4-dihydro-1H-pyrrolo[1,2-a]pyrazine-2,8-dicarboxylic acid 8-amide 2-cyclopentylamide
{4-[(8-Carbamoyl-7-chloro-6-phenyl-3,4-dihydro-1H-pyrrolo[1,2-a]pyrazine-2-carbonyl)-amino]-phenoxy}-acetic acid
7-cyano-6-phenyl-3,4-dihydro-1H-pyrrolo[1,2-a]pyrazine-2,8-dicarboxylic acid 8-amide 2-{[4-(2-morpholin-4-ylethoxy)phenyl]amide}
7-cyano-6-phenyl-3,4-dihydro-1H-pyrrolo[1,2-a]pyrazine-2,8-dicarboxylic acid 8-amide 2-[(4-morpholin-4-ylmethylphenyl)amide]
7-chloro-6-phenyl-3,4-dihydro-1H-pyrrolo[1,2-a]pyrazine-2,8-dicarboxylic acid 8-amide 2-[(3-morpholin-4-ylmethylphenyl)amide]
7-chloro-6-phenyl-3,4-dihydro-1H-pyrrolo[1,2-a]pyrazine-2,8-dicarboxylic acid 8-amide 2-{[4-(4-methyl[1,4]diazepane-1-carbonyl)phenyl]amide}
7-chloro-6-phenyl-3,4-dihydro-1H-pyrrolo[1,2-a]pyrazine-2,8-dicarboxylic acid 8-amide 2-{[3-(1-methyl-piperidine-4-carbonyl)-phenyl]-amide}
7-chloro-6-phenyl-3,4-dihydro-1H-pyrrolo[1,2-a]pyrazine-2,8-dicarboxylic acid 8-amide 2-{[4-(1-methyl-piperid-4-yl-methyl)-phenyl[-amide}
(±)-trans-7-cyano-6-phenyl-3,4-dihydro-1H-pyrrolo[1,2-a]pyrazine-2,8-dicarboxylic acid 8-amide 2-[(2-phenylcyclopropyl)amide]
7-chloro-6-phenyl-3,4-dihydro-1H-pyrrolo[1,2-a]pyrazine-2,8-dicarboxylic acid 8-amide 2-m-tolylamide
7-chloro-6-phenyl-3,4-dihydro-1H-pyrrolo[1,2-a]pyrazine-2,8-dicarboxylic acid 8-amide 2-[(3-chlorophenyl)amide]
7-chloro-6-phenyl-3,4-dihydro-1H-pyrrolo[1,2-a]pyrazine-2,8-dicarboxylic acid 8-amide 2-[(3-methoxyphenyl)amide]
7-chloro-6-phenyl-3,4-dihydro-1H-pyrrolo[1,2-a]pyrazine-2,8-dicarboxylic acid 8-amide 2-[(3-fluorophenyl)amide]
7-chloro-6-phenyl-3,4-dihydro-1H-pyrrolo[1,2-a]pyrazine-2,8-dicarboxylic acid 8-amide 2-[(2-chlorophenyl)amide]
4-[(8-carbamoyl-7-chloro-6-phenyl-3,4-dihydro-1H-pyrrolo[1,2-a]pyrazine-2-carbonyl)amino]benzoic acid
7-chloro-6-phenyl-3,4-dihydro-1H-pyrrolo[1,2-a]pyrazine-2,8-dicarboxylic acid 8-amide 2-[(tetrahydropyran-4-yl)amide]
7-chloro-6-phenyl-3,4-dihydro-1H-pyrrolo[1,2-a]pyrazine-2,8-dicarboxylic acid 8-amide 2-{[3-(4-methylpiperazine-1-carbonyl)phenyl]amide}
7-chloro-6-phenyl-3,4-dihydro-1H-pyrrolo[1,2-a]pyrazine-2,8-dicarboxylic acid 8-amide 2-{[2-(2-hydroxy-ethyl)-1,2,3,4-tetrahydro-isoquinolin-7-yl]-amide}
7-chloro-6-phenyl-3,4-dihydro-1H-pyrrolo[1,2-a]pyrazine-2,8-dicarboxylic acid 8-amide 2-{[3-(1-morpholin-4-yl-ethyl)-phenyl]-amide} and the corresponding N-oxides, and their prodrugs; and pharmaceutically acceptable salts and solvates (e.g. hydrates) of such compounds and their N-oxides and prodrugs.

Especially preferred compounds of the invention for the inhibition of GF1R are the above compounds of formula (ICC).

The compounds of the invention exhibit useful pharmacological activity and accordingly are incorporated into pharmaceutical compositions and used in the treatment of patients suffering from certain medical disorders. The present invention thus provides, according to a further aspect, compounds of the invention and compositions containing compounds of the invention for use in therapy.

Compounds within the scope of the present invention are inhibitors of the generation of tumour necrosis factor (TNF), especially TNF-alpha, according to tests described in the literature and described in vitro and in vivo procedures hereinafter, and which tests results are believed to correlate to pharmacological activity in humans and other mammals.

Thus, in a further embodiment, the present invention provides compounds of the invention and compositions containing compounds of the invention for use in the treatment of a patient suffering from, or subject to, conditions which can be ameliorated by the administration of an inhibitor of TNF, especially of TNF-alpha. For Example, compounds of the present invention are useful in the treatment of joint inflammation, including arthritis, rheumatoid arthritis and other arthritic conditions such as rheumatoid spondylitis, gouty arthritis, traumatic arthritis, rubella arthritis, psoriatic arthritis and osteoarthritis. Additionally, the compounds are useful in the treatment of acute synovitis, tuberculosis, atherosclerosis, muscle degeneration, cachexia, Reiter's syndrome, endotoxaemia, sepsis, septic shock, endotoxic shock, gram negative sepsis, gout, toxic shock syndrome, chronic pulmonary inflammatory diseases including asthma and adult respiratory distress syndrome, silicosis, pulmonary sarcoidosis, bone resorption diseases, reperfusion injury, graft vs. host reaction, allograft rejection and leprosy. Furthermore, the compounds are useful in the treatment of: infections such as viral infections, for Example HIV, cytomegalovirus (CMV), influenza, adenovirus and the Herpes group of viruses, parasitic infections, for Example malaria such as cerebral malaria, and yeast and fungal infections, for Example fungal meningitis; fever and myalgias due to infection; AIDS; AIDS related complex (ARC); cachexia secondary to infection or malignancy; cachexia secondary to acquired immune deficiency syndrome (AIDS) or to cancer; keloid and scar tissue formation; pyresis; diabetes; and inflammatory bowel diseases such as Crohn's disease and ulcerative colitis. The compounds of the invention are also useful in the treatment of diseases of or injury to the brain in which over-expression of TNFα has been implicated such as multiple sclerosis, meningitis and head trauma.

Compounds of the invention may also be useful in inhibiting diseases associated with over-production of other pro-inflammatory cytokines, IL-1, Il-2, Il-6 and IL-8 and increased expression of adhesion molecules such as E-selectin. Inhibitors of c-Jun phosphorylation may also be useful in diseases in which programmed cell death (apoptosis) results in cell loss and tissue disfunction. For Example, the JNK pathway plays an important role in neuronal degeneration induced by excitatory amino acids, growth factor deprivation, aberrant protein processing, osmotic stress and free radical injury. Therefore inhibitors are useful in the treatment of neurological disorders resulting from acute ischemia (e.g. stroke) and in chronic neurodegenerative diseases including Alzheimer's disease, Huntington's disease, AIDS dementia complex, neuropathic pain syndrome, olivopontocerebellar atrophy, Parkinsonism, amytrophic lateral sclerosis, multiple sclerosis. Furthermore, JNK inhibitors are useful in treatment of the neurological sequelae of cardiac surgery and cardiac arrest, brain and spinal injury, peripheral nerve trauma, diabetic neuropathy and neuronal damage induced by neurotoxins.

AP-1 is implicated in cell proliferation and in the mechanism by which oncogenes transform cells and, therefore, compounds of the invention are useful for the treatment of cancer and other proliferative disorders, including atherosclerosis. Indeed, the JNK pathway is highly activated in certain leukemias and colorectal cancer.

JNK by increasing c-Jun phosphorylation and AP-1 activity is important in regulating the release of metalloproteinases (MMPs) which are over produced in a wide number of inflammatory and proliferative diseases. Excessive production of MMPs plays an important role in the growth and spread of malignant tumors, including colorectal, lung, breast, cervical and prostate cancers. Increased release of MMPs contribute to the tissue destruction and remodeling that occur in diseases such arthritis, inflammatory bowel disease, periodontal disease, graft-versus-host reaction and inflammatory airway diseases such as chronic obstructive pulmonary disease (COPD). Thus, JNK inhibitors are useful for the treatment of inflammatory and proliferative diseases associated with the excessive release of MMPs.

A special embodiment of the therapeutic methods of the present invention is the treating of asthma. The JNK pathway is activated by anti-CD40 stimulation of B-lymphocytes and has been implicated in the proliferation of this cell type and in the release of antibodies, particularly IgE. The compounds of the invention inhibit anti-CD40 plus IL4-induced IgE release from human tonsillar B-lymphocytes. Thus, they are useful in the treatment of allergic disorders, including asthma, eczema (atopic dermatitis) and rhinitis.

Another special embodiment of the therapeutic methods of the present invention is the treating of joint inflammation.

According to a further feature of the invention there is provided a method for the treatment of a human or animal patient suffering from, or subject to, conditions which can be ameliorated by the administration of an inhibitor of TNF, especially TNF-alpha, for Example conditions as hereinbefore described, which comprises the administration to the patient of an effective amount of compound of the invention or a composition containing a compound of the invention. "Effective amount" is meant to describe an amount of compound of the present invention effective in inhibiting TNF and thus producing the desired therapeutic effect.

References herein to treatment should be understood to include prophylactic therapy as well as treatment of established conditions.

The products of formula (I) as defined above and also the addition salts thereof with acids have advantageous pharmacological properties, especially on account of their kinase-inhibiting properties as indicated above. It may be indicated that since certain kinase proteins have a central role in the initiation, development and completion of events of the cell cycle, molecules that inhibit such kinases are capable of limiting unwanted cell proliferations such as those observed in cancers.

The products of the present invention are especially useful for tumour therapy. The products of the invention can thus also increase the therapeutic effects of commonly-used anti-tumoral agents. These properties justify their therapeutic use, and the subject of the invention is, particularly, as medicinal products, the products of formula (I) as defined above, the said products of formula (I) being in any possible racemic, enantiomeric or diastereoisomeric isomer form, and also the addition salts with pharmaceutically acceptable mineral and organic acids or with pharmaceutically acceptable mineral and organic bases of the said products of formula (I).

One subject of the invention is thus, more particularly, as medicinal products, the products as defined by formula (Ia), (Ib), (Ic), (ICC), (Id), (Ie) or (If), the said products of formula (Ia), (Ib), (Ic), (ICC), (Id), (Ie) or (If), being in any possible racemic, enantiomeric or diastereoisomeric isomer form, and also the addition salts with pharmaceutically acceptable mineral and organic acids or with pharmaceutically acceptable mineral and organic bases of the said products of formula (Ia), (Ib), (Ic), (ICC), (Id), (Ie) or (If).

The present invention concerns more particularly, as medicinal products, the products as defined by formula (ICC), the said products of formula (ICC), being in any possible racemic, enantiomeric or diastereoisomeric isomer form, and also the addition salts with pharmaceutically acceptable mineral and organic acids or with pharmaceutically acceptable mineral and organic bases of the said products of formula (ICC).

The invention also relates to pharmaceutical compositions containing, as active principle, at least one of the products of formula (I) as defined above, or a pharmaceutically acceptable salt of this product or a prodrug of this product and, where appropriate, a pharmaceutically acceptable support.

The present invention also includes within its scope pharmaceutical compositions comprising at least one of the compounds of the invention in association with a pharmaceutically acceptable carrier or excipient.

The present invention thus covers pharmaceutical compositions containing, as active principle, at least one of the medicinal products as defined above. Such pharmaceutical compositions of the present invention can also, where appropriate, contain active principles of other antimitotic medicinal products such as, in particular, those based on taxol, cis-platin, DNA-intercalating agents and the like.

The present invention covers pharmaceutical compositions as defined above containing in more active principles of other anti-cancer chemotherapeutic medicinal products such as, in particular, those based on antimicrotubule agents like taxoids, vinka-alkaloids, on alkylating agents like cyclophosphamide, on DNA-intercalating agents like cis-platinum, on topoisomerase interactive agents like camptothecin derivatives, anthracyclins such as adriamycin, on antimetabolites like 5-fluorouracil and derivatives, and the like.

Compounds of the invention may be administered by any suitable means. In practice compounds of the present invention may generally be administered parenterally, topically, rectally, orally or by inhalation, especially by the oral route.

Compositions according to the invention may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations. The choice of vehicle and the content of active substance in the vehicle are generally determined in accordance with the solubility and chemical properties of the active compound, the particular mode of administration and the provisions to be observed in pharmaceutical practice. For Example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for Example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

For topical administration, gels (water or alcohol based), creams or ointments containing compounds of the invention may be used. Compounds of the invention may also be incorporated in a gel or matrix base for application in a patch, which would allow a controlled release of compound through the transdermal barrier.

For administration by inhalation compounds of the invention may be dissolved or suspended in a suitable carrier for use in a nebulizer or a suspension or solution aerosol, or may be absorbed or adsorbed onto a suitable solid carrier for use in a dry powder inhaler Solid compositions for rectal administration include suppositories formulated in accordance with known methods and containing at least one compound of the invention.

The percentage of active ingredient in the compositions of the invention may be varied, it being necessary that it should constitute a proportion such that a suitable dosage shall be obtained. Obviously, several unit dosage forms may be administered at about the same time.

The dose employed will be determined by the physician, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

The compounds according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for some patients, it will be necessary to prescribe not more than one or two doses per day. The subject of the present invention is then the use of the products of formula (I) as defined above, or of pharmaceutically acceptable salts of these products, for the preparation of a medicinal product intended for inhibiting the activity of a kinase protein.

A subject of the present invention is also the use of products of formula (I) as defined above for the preparation of a medicinal product for treating or preventing a disease characterized by deregulation of the activity of a kinase protein.

Such a medicinal product may especially be intended for treating or preventing a disease in a mammal.

A subject of the present invention is also the use defined above, in which the kinase protein is a tyrosine kinase protein.

A subject of the present invention is also the use defined above, in which the kinase protein is chosen from the following group:

EGFR, Fak, FLK-1, FGFR1, FGFR2, FGFR3, FGFR4, FGFR5, flt-1, IGF-1R, KDR, PDGFR, tie2, VEGFR.

A subject of the present invention is then the use defined above, in which the kinase protein is FAK.

A subject of the present invention is particularly the use defined above, in which the kinase protein is IGF-1R.

A subject of the present invention is also the use defined above, in which the kinase protein is in a cell culture.

A subject of the present invention is also the use defined above, in which the kinase protein is in a mammal.

A subject of the present invention is particularly the use of a product of formula (I) as defined above, for the preparation of a medicinal product for treating or preventing a disease chosen from the following group: disorders of the proliferation of blood vessels, fibrotic disorders, disorders of the proliferation of "mesangial" cells, metabolic disorders, allergies, asthma, thrombosis, diseases of the nervous system, retinopathy, psoriasis, rheumatoid arthritis, diabetes, muscle degeneration and cancers.

A subject of the present invention is, most particularly, the use of a product of formula (I) as defined above, for the preparation of a medicinal product for treating oncology diseases and especially intended for the treatment of cancers.

Among these cancers, the treatment of solid tumours and the treatment of cancers that are resistant to cytotoxic agents are of interest.

Among these cancers, the treatment of breast cancer, stomach cancer, cancer of the ovaries, cancer of the colon, lung cancer, brain cancer, cancer of the larynx, cancer of the lymphatic system, cancer of the genito-urinary tract including the bladder and the prostate, bone cancer and cancer of the pancreas, and most particularly treatment of breast cancer, cancer of the colon or lung cancer, are of interest.

A subject of the present invention is also the use of the products of formula (I) as defined above, for the preparation of medicinal products for cancer chemotherapy.

Such medicinal products intended for cancer chemotherapy may be used alone or in combination.

The products of the present patent application may especially be administered alone or in combination with chemotherapy or radiotherapy or alternatively in combination, for Example, with other therapeutic agents.

Such therapeutic agents may be commonly-used antitumoral agents.

As Examples of known kinase inhibitors, mention may be made of butyrolactone, flavopiridol and 2-(2-hydroxyethylamino)-6-benzylamino-9-methylpurine, also known as olomucine.

The present invention concerns then the products of formula (I) as defined above as kinases inhibitors, the said products of formula (I) being in any possible racemic, enantiomeric or diastereoisomeric isomer form, and also the addition salts with pharmaceutically acceptable mineral and organic acids or with pharmaceutically acceptable mineral and organic bases of the said products of formula (I).

The present invention concerns then products of formula (I) as defined above as FAK inhibitors.

The present invention concerns particularly products of formula (I) as defined above as IGF1R inhibitors.

The present invention concerns too products of formula (I) as defined above as FAK inhibitors.

The present invention concerns particularly the products of formula (ICC) as defined above as IGF1R inhibitors.

A preferred group of invention for the inhibition of IGF1R are the compounds of formula (ICC) and among them, are especially preferred the compounds of the present invention given in the following table.

The preparations of the compounds of the following table are described herebelow in the experimental part of the present invention and their respective corresponding numbers of exemples are indicated of the following table.

The Examples which follow, which are products of formula (I), illustrate the invention without, however, limiting it.

The compounds of the invention may be prepared by the application or adaptation of known methods, by which is meant methods used heretofore or described in the literature, for Example those described by R. C. Larock in Comprehensive Organic Transformations, VCH publishers, 1989.

In the reactions described hereinafter it may be necessary to protect reactive functional groups, for Example hydroxy, amino, imino, thio or carboxy groups, where these are desired in the final product, to avoid their unwanted participation in the reactions. Conventional protecting groups may be used in accordance with standard practice, for Examples see T. W. Greene and P. G. M. Wuts in "Protective Groups in Organic Chemistry" John Wiley and Sons, 1991.

Compounds of formula (I), wherein $R^2$, $R^3$, Z, n and m are as hereinbefore defined and $R^1$ is $R^4$—NH—C(=O)—, may be prepared by reaction of compounds of formula (I), wherein $R^2$, $R^3$, Z, n and m are as hereinbefore defined and $R^1$ is hydrogen, with isocyanates of formula (II):

$$R^4\text{—N}=\text{C}=\text{O} \qquad (II)$$

wherein $R^4$ is as hereinbefore defined. The reaction may conveniently be carried out in an inert solvent, such as dichloromethane, and at a temperature at about room temperature.

Compounds of formula (I), wherein $R^2$, $R^3$, Z, n and m are as hereinbefore defined and $R^1$ is $R^4$—NH—C(=O)—, may also be prepared by reaction of compounds of formula (III):

$$R^4\text{—NH}_2 \qquad (III)$$

wherein $R^4$ is as hereinbefore defined, with triphosgene, in dichloromethane at a temperature at about −70° C. and subsequent treatment of the reaction mixture with compounds of formula (I), wherein $R^2$, $R^3$, Z, n and m are as hereinbefore defined and $R^1$ is hydrogen.

Compounds of formula (I), wherein $R^2$, $R^3$, Z, n and m are as hereinbefore defined and $R^1$ is $R^4$—NH—C(=O)—, may be also be prepared by reaction of compounds of formula (I), wherein $R^2$, $R^3$, Z, n and m are as hereinbefore defined and $R^1$ is hydrogen, with acid azides of formula (IV):

$$R^4\text{—C}(=\text{O})\text{—N}_3 \qquad (IV)$$

wherein $R^4$ is as hereinbefore defined, in an inert solvent, such as toluene and at a temperature at about 120° C. This procedure is particularly suitable for the preparation of compounds of formula (I) in which $R^1$ is $R^4$—NH—C (=O)— wherein $R^4$ is heteroaryl.

Compounds of formula (I), wherein $R^2$, $R^3$, Z, n and m are as hereinbefore defined and $R^1$ is $R^4$—NH—C(=S)—, may be prepared by reaction of compounds of formula (I), wherein $R^2$, $R^3$, Z, n and m are as hereinbefore defined and $R^1$ is hydrogen, with isothiocyanates of formula (V):

$$R^4\text{—N}=\text{C}=\text{S} \qquad (V)$$

wherein R⁴ is as hereinbefore defined. The reaction may conveniently be carried out in an inert solvent, such as dichloromethane, and at a temperature at about room temperature.

Compounds of formula (I), wherein R², R³, Z, n and m are as hereinbefore defined and R¹ is R⁴—NH—C(=NCN)—, may be prepared by reaction of compounds of formula (I), wherein R², R³, Z, n and m are as hereinbefore defined and R¹ is hydrogen, with trimethylaluminum in an inert solvent, such as toluene and at room temperature followed by reaction with compounds of formula (VI):

R⁴—NH—C(=NCN)—OPh       (VI)

wherein R⁴ is as hereinbefore defined, at a temperature from about room temperature to about 50° C.

Compounds of formula (I), wherein R², R³, Z, n and m are as hereinbefore defined and R¹ is R⁴—C(=O)—, may be prepared by reaction of compounds of formula (I), wherein R², R³, Z, n and m are as hereinbefore defined and R¹ is hydrogen, with compounds of formula (VI):

R⁴—C(=O)—X¹       (VII)

wherein R⁴ is as hereinbefore defined and X¹ is a hydroxy group or a halogen, preferably chlorine, atom, with compounds of formula (I), wherein R², R³, Z, n and m are as hereinbefore defined and R¹ is hydrogen. When X¹ is a hydroxy group the reaction may be carried out using standard peptide coupling procedures for Example coupling in the presence of O-(7-azabenzotriazol-1-yl)-1,1,3,3-tetramethyluronium hexafluorophosphate and diisopropylethylamine (or triethylamine) in dimethylformamide (or tetrahydrofuran), at room temperature. When X¹ is a halogen atom the acylation reaction may be carried out with the aid of a base, such as triethylamine, in an inert solvent, such as dichloromethane, and at a temperature at about room temperature.

Compounds of formula (I), wherein R², R³, Z, n and m are as hereinbefore defined and R¹ is R⁴—SO₂—, may be prepared by reaction of compounds of formula (I), wherein R², R³, Z, n and m are as hereinbefore defined and R¹ is hydrogen, with compounds of formula (VIII):

R⁴—SO₂Cl       (VIII)

wherein R⁴ is as hereinbefore defined, in the presence of a suitable base, such as triethylamine, in an inert solvent, such as acetonitrile, and at a temperature from about room temperature to about 60° C.

Compounds of formula (I), wherein R², R³, Z, n and m are as hereinbefore defined and R¹ is R⁴—NH—SO₂—, may be prepared by reaction of compounds of formula (I), wherein R², R³, Z, n and m are as hereinbefore defined and R¹ is hydrogen, with sulfamoyl chlorides of formula (IX):

R⁴—NHSO₂Cl       (IX)

wherein R⁴ is as hereinbefore defined, in the presence of a suitable base, such as triethylamine, in an inert solvent, such as acetonitrile, and at a temperature at about room temperature.

Compounds of formula (I), wherein R², R³, Z, n and m are as hereinbefore defined and R¹ is R⁴, may be prepared by alkylation of compounds of formula (I), wherein R², R³, Z, n and m are as hereinbefore defined and R¹ is hydrogen, with compounds of formula R⁴—X, wherein X² is a halogen, preferably bromine or chlorine, atom. The alkylation may conveniently be carried out in the presence of a base, such as an alkali metal carbonate (e.g. potassium carbonate) or an alkali metal hydrogen carbonate (e.g. sodium bicarbonate), in an inert solvent, such as a mixture of an alcohol (e.g. isopropanol) and water, and at a temperature from about room temperature to about 80° C. This reaction is particularly suitable for the preparation of compounds where R⁴ is benzooxazol-2-yl and benzothiazol-2-yl. The alkylation of compounds of formula (I), wherein R², R³, Z, n and m are as hereinbefore defined and R¹ is hydrogen, with compounds of formula R⁴—X, wherein X² is a halogen, may also be carried out in the presence of an alkali metal hydride (e.g. sodium hydride) in an inert solvent, such as dimethyl formamide, and at a temperature from about room temperature to about 100° C.

Compounds of formula (I), wherein R², R³, Z, n and m are as hereinbefore defined and R¹ is hydrogen, may be prepared by reaction of compounds of formula (I) wherein R², R³, Z, n and m are as hereinbefore defined and R¹ is R⁴O—C(=O)— (in which R⁴ is tertiary-butyl) with trifluoroacetic acid in an inert solvent, such as dichloromethane, and at a temperature at about room temperature.

Compounds of formula (I) wherein R³, Z, n and m are as hereinbefore defined, R¹ is R⁴O—C(=O)— (in which R⁴ is tertiary-butyl) and R² is chloro may be prepared by reaction of compounds of formula (I), wherein R³, Z, n and m are as hereinbefore defined, R¹ is; R⁴O—C(=O)— (in which R⁴ is tertiary-butyl) and R² is hydrogen, with N-chlorosuccinimide in an inert solvent, such as dichloromethane, and at a temperature at about room temperature.

Compounds of formula (I) wherein R³, Z, n and m are as hereinbefore defined, R¹ is R⁴O—C(=O)— (in which R⁴ is tertiary-butyl) and R² is chloro may also be prepared by reaction of compounds of formula (X):

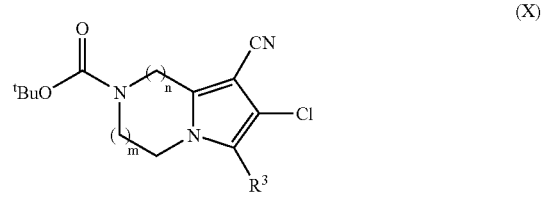

(X)

wherein R³, n and m are as hereinbefore defined, with hydrogen peroxide in the presence of sodium hydroxide, in methanol at a temperature at about 55° C.

Compounds of formula (I), wherein R³, Z, n and m are as hereinbefore defined, R¹ is R⁴O—C(=O)— (in which R⁴ is tertiary-butyl) and R² is hydrogen, may be similarly prepared by reaction of compounds of formula (XI):

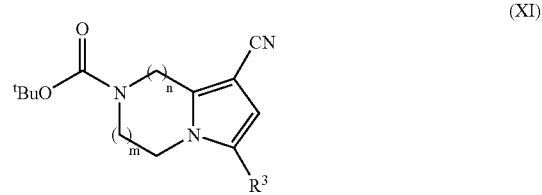

(XI)

wherein R³, n and m are as hereinbefore defined, with hydrogen peroxide.

Compounds of formula (I) wherein R³, Z, n and m are as hereinbefore defined, R¹ is R⁴O—C(=O)— (in which R⁴ is tertiary-butyl) and R² is cyano may be similarly prepared by reaction of compounds of formula (XII):

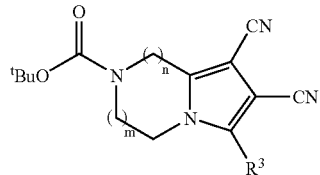

(XII)

wherein R³, n and m are as hereinbefore defined, with hydrogen peroxide in the presence of sodium hydroxide.

Compounds of formula (I) wherein R¹, R², R³, n and m are as hereinbefore defined and Z is O, may be prepared by reaction of compounds of formula (XI):

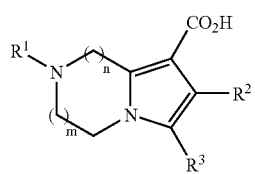

(XIII)

wherein R¹, R², R³, n and m are as hereinbefore defined, with ammonium chloride in the presence of triethylamine, 1-(3-dimethylaminopropyl)-3-ethylcarbodiimide hydrochloride, and 1-hydroxybenzotriazole hydrate. The reaction is conveniently carried out in an inert solvent, such as dimethylformamide and at a temperature at about 80° C.

Compounds of formula (I), wherein R¹ is R⁴O—C(=O)— (in which R⁴ is tertiary-butyl), R² is cyano, R³ is alkyl, aryl, cycloalkyl or heteroaryl, Z is O, and n and m are both 1, represented by formula I(f), may be prepared as shown in scheme 1.

For Example, piperazine-2-carboxylic acid dihydrochloride (XIV) may be treated, in step 1, with acid anhydrides of formula R³—C(=O)—O—C(=O)—R³ (in which R³ is alkyl, aryl, cycloalkyl or heteroaryl) in the presence of a suitable base, such as triethylamine, followed by reaction with chlorofumaronitrile. The resulting pyrrolo[1,2-a]pyrazines (XV) may then be treated, in Step 2, with potassium carbonate in methanol followed by reaction with di-tert-butylcarbonate in dimethylformamide. The resulting compounds of formula (XVI) may then be treated, in Step 3, with hydrogen peroxide in the presence of sodium hydroxide as described hereinbefore. This procedure is particularly suitable for the preparation of compounds of formula (If) in which R³ is trifluoromethyl.

Compounds of the invention may also be prepared by interconversion of other compounds of the invention.

Thus, for Example, compounds of formula (I) in which R¹ contains a carboxy group may be prepared by hydrolysis of the corresponding esters. The hydrolysis may conveniently be carried out by alkaline hydrolysis using a base, such as an alkali metal hydroxide, e.g. lithium hydroxide, or an alkali metal carbonate, e.g. potassium carbonate, in the presence of an aqueous/organic solvent mixture, using organic solvents such as dioxan, tetrahydrofuran or methanol, at a temperature from about ambient to about reflux. The hydrolysis of the esters may also be carried out by acid hydrolysis using an inorganic acid, such as hydrochloric acid, in the presence of an aqueous/inert organic solvent mixture, using organic solvents such as dioxan or tetrahydrofuran, at a temperature from about 50° C. to about 80° C.

As another Example compounds of formula (I) in which R¹ contains a carboxy group may be prepared by acid catalysed removal of the tert-butyl group of the corresponding tert-butyl esters using standard reaction conditions, for Example reaction with trifluoroacetic acid at a temperature at about room temperature.

As another Example compounds of formula (I) in which R¹ contains a carboxy group may be prepared by hydrogenation of the corresponding benzyl esters. The reaction may be carried out in the presence of ammonium formate and a

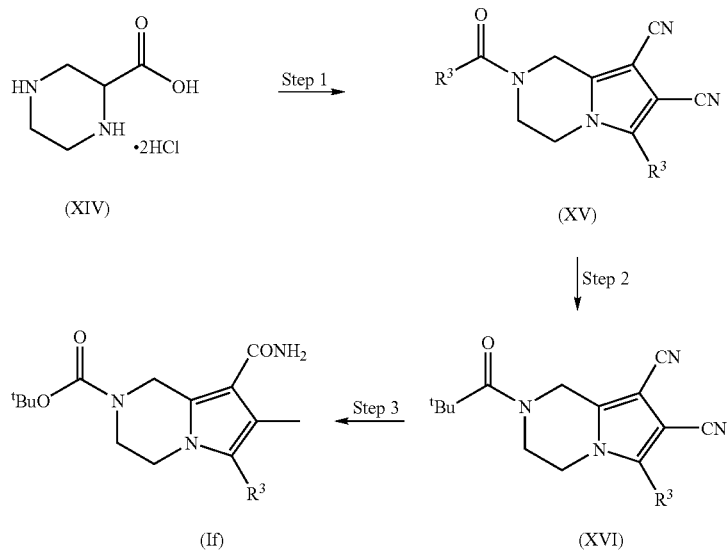

suitable metal catalyst, e.g. palladium, supported on an inert carrier such as carbon, preferably in a solvent such as methanol or ethanol and at a temperature at about reflux temperature. The reaction may alternatively be carried out in the presence of a suitable metal catalyst, e.g. platinum or palladium optionally supported on an inert carrier such as carbon, preferably in a solvent such as methanol or ethanol.

As another Example of the interconversion process, compounds of formula (I) in which Z is S may be prepared by reaction of the corresponding compounds of formula (I) in which Z is O with 4-methoxyphenylthionophosphine sulfide dimer, in an inert solvent, such as toluene and at a temperature at about 80° C.

As another Example of the interconversion process, compounds of formula (I) in which $R^1$ contains an aryl or heteroaryl group substituted by hydroxy may be prepared by reaction of the corresponding compounds of formula (I) in which $R^1$ contains an aryl or heteroaryl group substituted by methoxy with a Lewis acid, such as boron tribromide, in an inert solvent, such as dichloromethane and at a temperature from about −70° C. to about room temperature.

As another Example of the interconversion process, compounds of formula (I) in which $R^1$ contains a —C(=O)NY$^3$Y$^4$ group, may be prepared by reaction of compounds of formula (I), in which $R^1$ contains a carboxy group, with compounds of formula (XVII):

$$Y^3Y^4NH \quad (XVII)$$

wherein $Y^3$ and $Y^4$ is as hereinbefore defined. The reaction is conveniently carried out in the presence of 1-(3-dimethylaminopropyl)-3-ethylcarbodiimide hydrochloride and 1-hydroxybenzotriazole, in an inert solvent, such as dimethylformamide, and at a temperature from about room temperature to about 60° C. Alternatively the coupling reaction may be carried out in the presence of O-(7-azabenzotriazol-1-yl)-1,1,3,3-tetramethyluronium hexafluorophosphate and diisopropylethylamine (or triethylamine) in dimethylformamide (or tetrahydrofuran), at room temperature.

It will be appreciated that compounds of the present invention may contain asymmetric centres. These asymmetric centres may independently be in either the R or S configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds of formula (I) hereinabove. Such isomers can be separated from their mixtures, by the application or adaptation of known methods, for Example chromatographic techniques and recrystallisation techniques, or they are separately prepared from the appropriate isomers of their intermediates.

According to a further feature of the invention, acid addition salts of the compounds of this invention may be prepared by reaction of the free base with the appropriate acid, by the application or adaptation of known methods. For Example, the acid addition salts of the compounds of this invention may be prepared either by dissolving the free base in water or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For Example, parent compounds of the invention can be regenerated from their acid addition salts by treatment with an alkali, e.g. aqueous sodium bicarbonate solution or aqueous ammonia solution.

Compounds of this invention can be regenerated from their base addition salts by the application or adaptation of known methods. For Example, parent compounds of the invention can be regenerated from their base addition salts by treatment with an acid, e.g. hydrochloric acid.

Compounds of the present invention may be conveniently prepared, or formed during the process of the invention, as solvates (e.g. hydrates). Hydrates of compounds of the present invention may be conveniently prepared by recrystallisation from an aqueous/organic solvent mixture, using organic solvents such as dioxan, tetrahydrofuran or methanol.

According to a further feature of the invention, base addition salts of the compounds of this invention may be prepared by reaction of the free acid with the appropriate base, by the application or adaptation of known methods. For Example, the base addition salts of the compounds of this invention may be prepared either by dissolving the free acid in water or aqueous alcohol solution or other suitable solvents containing the appropriate base and isolating the salt by evaporating the solution, or by reacting the free acid and base in an organic solvent, in which case the salt separates directly or can be obtained by concentration of the solution.

The starting materials and intermediates may be prepared by the application or adaptation of known methods, for Example methods as described in the Reference Examples or their obvious chemical equivalents.

Intermediates of formula (X), wherein $R^3$, n and m are as hereinbefore defined, may be prepared by (i) reaction of compounds of formula (1):

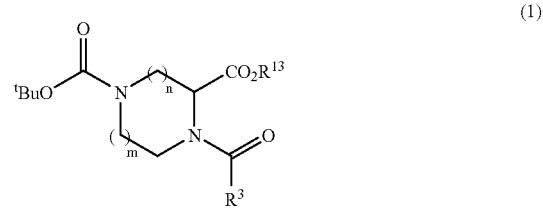

(1)

10 wherein $R^3$, n and m are as hereinbefore defined and $R^{13}$ is lower alkyl, with sodium hydroxide in ethanol at room temperature; followed by (ii) treatment of the resulting sodium salts of formula (2):

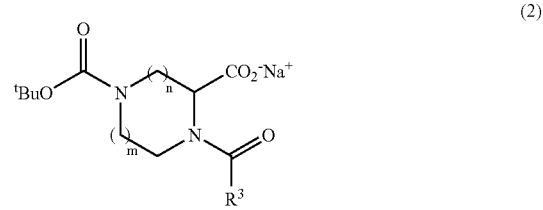

(2)

wherein $R^3$, n and m are as hereinbefore defined, with p-toluenesulphonyl chloride followed by reaction with 2,3-dichloroacrylonitrile in the presence of triethylamine, in an inert solvent, such as dichloromethane, and at a temperature at about room temperature.

Intermediates of formula (XI), wherein $R^3$, n and m are as hereinbefore defined, may be similarly prepared by reaction of sodium salts of formula (2), wherein $R^3$, n and m are as hereinbefore defined, with p-toluenesulphonyl chloride followed by reaction with 2-chloroacrylonitrile in the presence of triethylamine.

Intermediates of formula (XII), wherein $R^3$, n and m are as hereinbefore defined, may be similarly prepared by reaction of sodium salts of formula (2), wherein $R^3$, n and m are as hereinbefore defined, with p-toluenesulphonyl chloride followed by reaction with chlorofumaronitrile in the presence of triethylamine.

Compounds of formula (1), wherein n and m are as hereinbefore defined, $R^3$ is alkyl, aryl, cycloalkyl, heteroaryl or heterocycloalkyl and $R^{13}$ is lower alkyl, may be prepared by reaction of compounds of formula (3):

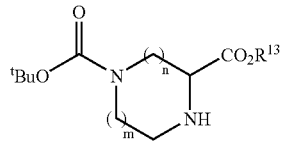

(3)

wherein n and m are as hereinbefore defined and $R^{13}$ is lower alkyl, with the compounds of formula (4):

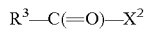

(4)

wherein $R^3$ is alkyl, aryl, cycloalkyl, heteroaryl or heterocycloalkyl and $X^2$ is a hydroxy group, or a —O—C(=O)—$R^3$ group or a halogen, preferably chlorine, atom. When $X^2$ is a hydroxy group the reaction may be carried out using standard peptide coupling procedures for Example coupling in the presence of 1-(3-dimethylaminopropyl)-3-ethylcarbodiimide and 4-dimethylaminopyridine, in an inert solvent, such as dichloromethane, and at room temperature. When $X^2$ is a halogen atom the acylation reaction may be carried out with the aid of a base, such as triethylamine, in an inert solvent, such as dichloromethane, and at a temperature at about room temperature.

Compounds of formula (5) wherein $R^{13}$, n and m are as hereinbefore defined may be prepared by reaction of compounds of formula (5):

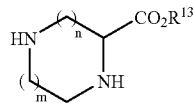

(5)

wherein $R^{13}$, n and m are as hereinbefore defined, with di-tert-butyl dicarbonate in the presence of a suitable base, such as triethylamine, in an inert solvent, such ass dimethylformamide, and at a temperature at about room temperature. The compound of formula (3), wherein $R^{13}$ is ethyl, and n and m are both 1, may be prepared as described in Step B on page 94 of International Patent Application Number WO 96/31478.

Compounds of formula (1), wherein n and m are as hereinbefore defined, $R^3$ is hydrogen and $R^{13}$ is lower alkyl, may be prepared by reaction of compounds of formula (3), wherein $R^{13}$ and n and m are as hereinbefore defined, with pentafluorophenyl formate, then with N,N-dimethylethylenediamine. The reaction is conveniently carried out in an inert solvent, such as dichloromethane, and at a temperature at about room temperature.

Intermediates of formula (XII), wherein $R^3$, n and m are as hereinbefore defined, may be prepared by reaction of a mixture of intermediates of formula (XI) wherein $R^3$, n and m are as hereinbefore defined, and the corresponding 7-cyano isomers, with chlorosulfonyl, isocyanate, in an inert solvent, such as dichloromethane, and at a temperature at about 0° C.

Intermediates of formula (XII), wherein $R^3$, n and m are as hereinbefore defined, may also be prepared by reaction of the acids of formula (6):

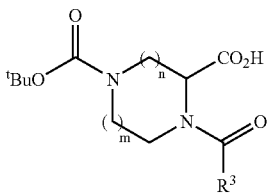

(6)

wherein $R^3$, n and m are as hereinbefore defined, with 2-chloro-but-2-enedinitrile in the presence of triethylamine and acetic anhydride, in an inert solvent, such as toluene, and at a temperature at about 60° C.

Acids of formula (6), wherein n and m are as hereinbefore defined and $R^3$ is alkyl, aryl, cycloalkyl, heteroaryl or heterocycloalkyl, may be prepared by reaction of compounds of formula (7):

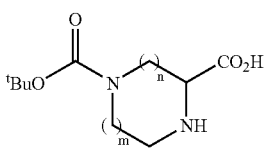

(7)

with compounds of formula (4), wherein $R^3$ is alkyl, aryl, cycloalkyl, heteroaryl or heterocycloalkyl and $X^2$ is a halogen, preferably chlorine, atom. The acylation reaction may be carried out with the aid of a base, such as triethylamine, in an inert solvent, such as dichloromethane, and at a temperature at about room temperature.

Intermediates of formula (XIII), wherein $R^1$, $R^3$, n and m are as hereinbefore defined and $R^2$ is cyano, may be prepared by reaction of compounds of formula (8):

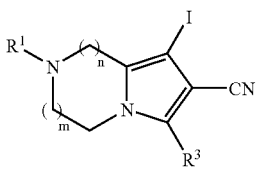

(8)

wherein $R^1$, $R^3$, n and m are as hereinbefore defined, with carbon monoxide in the presence of a catalyst, such as bis(triphenylphosphine)palladium (II) chloride, triphenylphosphine and poly(ethylene glycol) (Average $M_n$ ca 4600, 850 g). The coupling reaction is conveniently carried out in an inert solvent, such as 4-methylanisole, and at a temperature at about 80° C.

Compounds of formula (8), wherein $R^1$, $R^3$, n and m are as hereinbefore defined, may be prepared by reaction of compounds of formula (9):

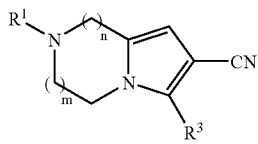

(9)

wherein $R^1$, $R^3$, n and m are as hereinbefore defined, with N-iodosuccinamide, in an inert solvent, such as dimethylformamide, and at a temperature at about room temperature.

Compounds of formula (9), wherein $R^1$, $R^3$, n and m are as hereinbefore defined, may be prepared (along with the corresponding 8-cyano isomers) by reaction of compounds of formula (10):

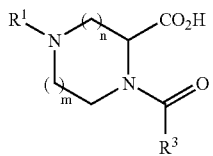

(10)

wherein $R^1$, $R^3$, n and m are as hereinbefore defined, with sodium hydroxide in ethanol at room temperature, and subsequent treatment of the resulting acids with p-toluenesulphonyl chloride followed by 2-chloroacrylonitrile and then triethylamine, in an inert solvent, such as dichloromethane, and at a temperature at about room temperature. This reaction is particularly suitable for the preparation of compounds of formula (9) in which $R^1$ is $^tBuO-C(=O)-$.

The present invention is further exemplified but not limited by the following illustrative Examples and Reference Examples.

EXAMPLE 1

(a) 7-Chloro-6-phenyl-3,4-dihydro-1H-pyrrolo[1,2-a]pyrazine-2,8-dicarboxylic acid 8-amide 2-[(4-methoxyphenyl)amide]

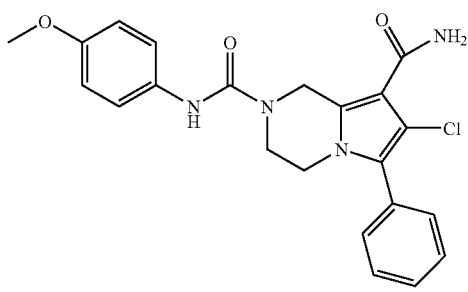

A stirred suspension of 7-chloro-6-phenyl-1,2,3,4-tetrahydropyrrolo[1,2-a]pyrazine-8-carboxylic acid amide trifluoroacetic acid salt (70 mg, Reference Example 1) in dry dichloromethane (7 mL) was treated with dry triethylamine (70 µL), then with a solution of 4-methoxyphenyl isocyanate (55 mg) in dry dichloromethane (3 mL). After stirring at room temperature for a further 4 hours the reaction mixture was treated with methanol (0.5 mL) and then evaporated. The residue was subjected to column chromatography on silica eluting initially with a mixture of dichloromethane and ethyl acetate (1:1, v/v) and then with ethyl acetate to give 7-chloro-6-phenyl-3,4-dihydro-1H-pyrrolo[1,2-a]pyrazine-2,8-dicarboxylic acid 8-amide 2-[(4-methoxyphenyl)amide] (44 mg) as a white solid, m.p. 246–248° C. [Elemental analysis: C, 59.13; H, 5.21; N, 12.43%. Calculated for $C_{22}H_{21}ClN_4O_3 \cdot 1.2H_2O$: C, 59.18; H, 5.28; N, 12.55%].

(b) 7-chloro-6-phenyl-3,4-dihydro-1H-pyrrolo[1,2-a]pyrazine-2,8-dicarboxylic acid 8-amide 2-p-tolylamide

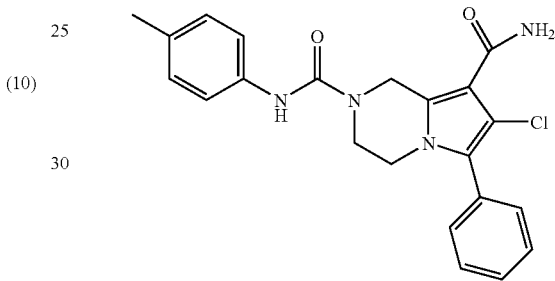

By proceeding in a similar manner to Example 1(a) above but using p-tolyl isocyanate there was prepared 7-chloro-6-phenyl-3,4-dihydro-1H-pyrrolo[1,2-a]pyrazine-2,8-dicarboxylic acid 8-amide 2-p-tolylamide as a white solid, m.p. 244–246° C. MS: 411 $[MH]^+$, 409 $[MH]^+$.

(c) 7-chloro-6-phenyl-3,4-dihydro-1H-pyrrolo[1,2-a]pyrazine-2,8-dicarboxylic acid 8-amide 2-phenylamide

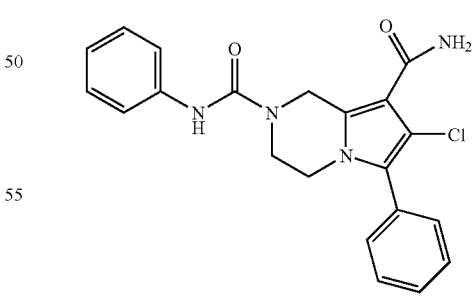

By proceeding in a similar manner to Example 1(a) above but using phenyl isocyanate there was prepared 7-chloro-6-phenyl-3,4-dihydro-1H-pyrrolo[1,2-a]pyrazine-2,8-dicarboxylic acid 8-amide 2-phenylamide as a white solid, m.p. 257–259° C. [Elemental analysis: C, 63.50; H, 4.45; N, 13.79%. Calculated for $C_{21}H_{19}ClN_4O_2$: C, 63.88; H, 4.85; N, 14.19%].

(d) 7-chloro-6-phenyl-3,4-dihydro-1H-pyrrolo[1,2-a]pyrazine-2,8-dicarboxylic acid 8-amide 2-[(4-trifluoromethoxyphenyl)amide]

(f) 7-chloro-6-phenyl-3,4-dihydro-1H-pyrrolo[1,2-a]pyrazine-2,8-dicarboxylic acid 8-amide 2-[(3-ethylphenyl)amide]

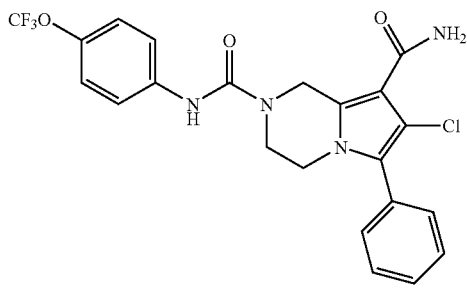

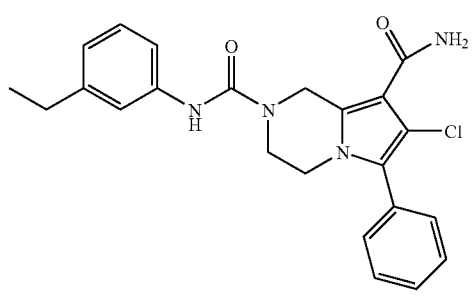

By proceeding in a similar manner to Example 1(a) above but using 4-(trifluoromethoxy)phenyl isocyanate there was prepared 7-chloro-6-phenyl-3,4-dihydro-1H-pyrrolo[1,2-a]pyrazine-2,8-dicarboxylic acid 8-amide 2-[(4-trifluoromethoxyphenyl) amide] as a white solid, m.p. 244–246° C. [Elemental analysis: C, 55.27; H, 3.86; N, 11.35%. Calculated for $C_{22}H_{18}ClF_3N_4O_3$: C, 55.18; H, 3.79; N, 11.70%].

By proceeding in a similar manner to Example 1(a) above but using 3-ethylphenyl isocyanate there was prepared 7-chloro-6-phenyl-3,4-dihydro-1H-pyrrolo[1,2-a]pyrazine-2,8-dicarboxylic acid 8-amide 2-[(3-ethylphenyl)amide] as a white solid, m.p. 256–258° C. [Elemental analysis: C, 65.02; H, 5.50; N, 13.05%. Calculated for $C_{23}H_{23}ClN_4O_2$: C, 65.32; H, 5.48; N, 13.25%].

(e) 7-chloro-6-phenyl-3,4-dihydro-1H-pyrrolo[1,2-a]pyrazine-2,8-dicarboxylic acid 8-amide 2-[(3-fluorophenyl)amide]

(g) 7-chloro-6-phenyl-3,4-dihydro-1H-pyrrolo[1,2-a]pyrazine-2,8-dicarboxylic acid 8-amide 2-[(3-methoxyphenyl)amide]

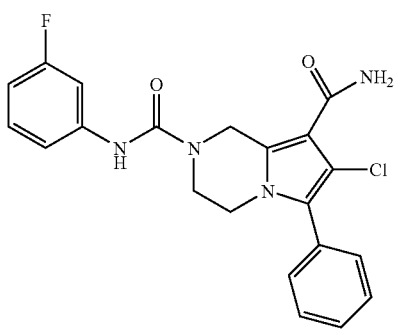

By proceeding in a similar manner to Example 1(a) above but using 3-fluorophenyl isocyanate there was prepared 7-chloro-6-phenyl-3,4-dihydro-1H-pyrrolo[1,2-a]pyrazine-2,8-dicarboxylic acid 8-amide 2-[(3-fluorophenyl)amide] as a white solid, m.p. 248–250° C. [Elemental analysis: C, 60.91; H, 3.97; N, 13.59%. Calculated for $C_{21}H_{18}ClFN_4O_2$: C, 61.10; H, 4.39; N, 13.57%].

By proceeding in a similar manner to Example 1(a) above but using 3-methoxyphenyl isocyanate there was prepared 7-chloro-6-phenyl-3,4-dihydro-1H-pyrrolo[1,2-a]pyrazine-2,8-dicarboxylic acid 8-amide 2-[(3-methoxyphenyl)amide] as a white solid, m.p. 217–219° C. [Elemental analysis: C, 61.22; H, 5.01; N, 12.75%. Calculated for $C_{22}H_{21}ClN_4O_3 \cdot 0.5H_2O$: C, 60.90; H, 5.11; N, 12.91%].

(h) 7-chloro-6-phenyl-3,4-dihydro-1H-pyrrolo[1,2-a]pyrazine-2,8-dicarboxylic acid 8-amide 2-[(3-trifluoromethylphenyl)amide]

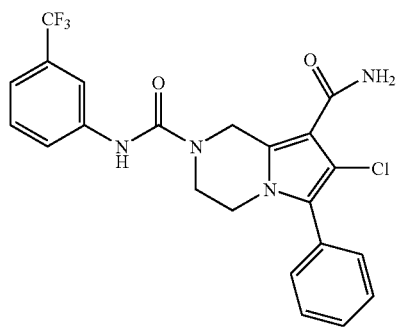

By proceeding in a similar manner to Example 1(a) above but using 3-trifluoromethylphenyl isocyanate there was prepared 7-chloro-6-phenyl-3,4-dihydro-1H-pyrrolo[1,2-a]pyrazine-2,8-dicarboxylic acid 8-amide 2-[(3-trifluoromethylphenyl)amide] as a white solid, m.p. 245–246° C. [Elemental analysis: C, 54.80; H, 3.98; N, 11.39%. Calculated for $C_{22}H_{18}ClF_3N_4O_2 \cdot H_2O$: C, 54.95; H, 4.19; N, 11.65%].

(i) (±)-trans-7-chloro-6-phenyl-3,4-dihydro-1H-pyrrolo[1,2-a]pyrazine-2,8-dicarboxylic acid 8-amide 2-[2-phenylcyclopropyl)amide]

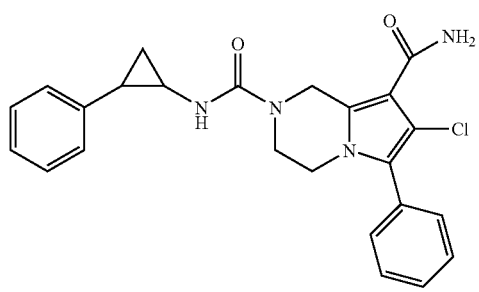

By proceeding in a similar manner to Example 1(a) above but using (±)-trans-2-phenylcyclopropyl isocyanate there was prepared (±)-trans-7-chloro-6-phenyl-3,4-dihydro-1H-pyrrolo[1,2-a]pyrazine-2,8-dicarboxylic acid 8-amide 2-[2-phenylcyclopropyl)amide] as a white solid, m.p. 219–221° C. [Elemental analysis: C, 65.94; H, 5.12; N, 12.62; Calculated for $C_{24}H_{23}ClN_4O_2$: C, 66.28; H, 5.33; N, 12.88%].

(j) 7-chloro-6-phenyl-3,4-dihydro-1H-pyrrolo[1,2-a]pyrazine-2,8-dicarboxylic acid 8-amide 2-furan-2-ylamide

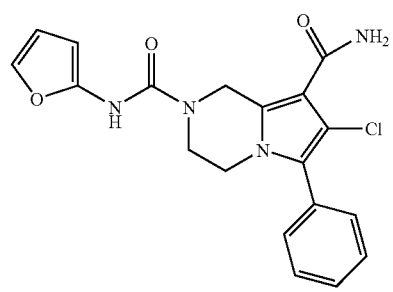

By proceeding in a similar manner to Example 1(a) above but using 2-furyl isocyanate (prepared according to the procedure of Singleton and Edwards, JACS, 1938, 60, 540) there was prepared 7-chloro-6-phenyl-3,4-dihydro-1H-pyrrolo[1,2-a]pyrazine-2,8-dicarboxylic acid 8-amide 2-furan-2-ylamide as a white solid, m.p. 237–238° C. [Elemental analysis: C, 57.70; H, 4.45; N, 13.87%. Calculated for $C_{19}H_{17}ClN_4O_3 \cdot 0.5H_2O$: C, 57.95; H, 4.61; N, 14.23%].

(k) 7-chloro-6-phenyl-3,4-dihydro-1H-pyrrolo[1,2-a]pyrazine-2,8-dicarboxylic acid 8-amide 2-[(4-isopropylphenyl)amide]

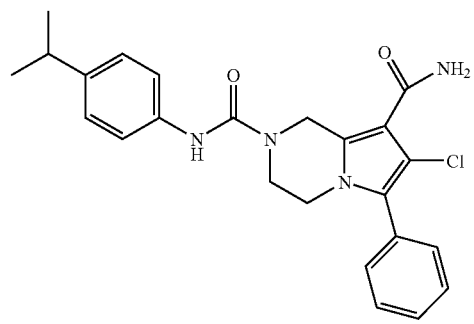

By proceeding in a similar manner to Example 1(a) above but using 4-isopropylphenyl isocyanate there was prepared 7-chloro-6-phenyl-3,4-dihydro-1H-pyrrolo[1,2-a]pyrazine-2,8-dicarboxylic acid 8-amide 2-[(4-isopropylphenyl)amide] as a white solid, m.p. >250° C. MS: 439 [MH]$^+$, 437 [MH]$^+$.

(l) 7-chloro-6-phenyl-3,4-dihydro-1H-pyrrolo[1,2-a]pyrazine-2,8-dicarboxylic acid 8-amide 2-[(2-fluorophenyl)amide]

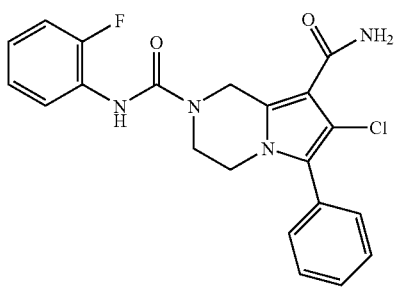

By proceeding in a similar manner to Example 1(a) above but using 2-fluorophenyl isocyanate there was prepared 7-chloro-6-phenyl-3,4-dihydro-1H-pyrrolo[1,2-a]pyrazine-2,8-dicarboxylic acid 8-amide 2-[(2-fluorophenyl)amide] as a white solid, m.p. 199–200° C. [Elemental analysis: C, 60.99; H, 4.00; N, 13.21%. Calculated for $C_{21}H_{18}ClFN_4O_2$: C, 61.10; H, 4.39; N, 13.57%].

(m) 7-chloro-6-phenyl-3,4-dihydro-1H-pyrrolo[1,2-a]pyrazine-2,8-dicarboxylic acid 8-amide 2-[(2-chlorophenyl)amide]

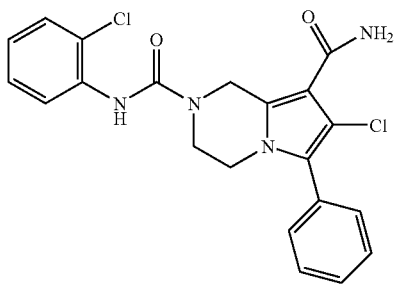

By proceeding in a similar manner to Example 1(a) above but using 2-chlorophenyl isocyanate there was prepared 7-chloro-6-phenyl-3,4-dihydro-1H-pyrrolo[1,2-a]pyrazine-2,8-dicarboxylic acid 8-amide 2-[(2-chlorophenyl)amide] as a white solid, m.p. 223–224° C. [Elemental analysis: C, 58.96; H, 4.13; N, 12.85%. Calculated for $C_{21}H_{18}Cl_2N_4O_2$: C, 58.75; H, 4.23; N, 13.05%].

(n) 7-chloro-6-phenyl-3,4-dihydro-1H-pyrrolo[1,2-a]pyrazine-2,8-dicarboxylic acid 2-[(4-acetylphenyl)amide] 8-amide

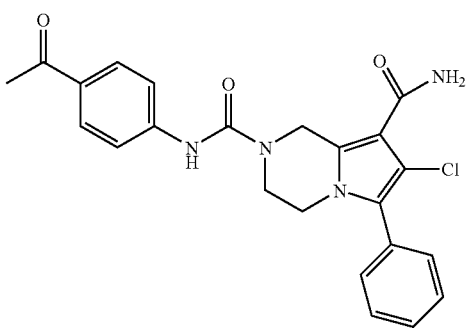

By proceeding in a similar manner to Example 1(a) above but using 4-acetylphenyl isocyanate there was prepared 7-chloro-6-phenyl-3,4-dihydro-1H-pyrrolo[1,2-a]pyrazine-2,8-dicarboxylic acid 2-[(4-acetylphenyl)amide] 8-amide as a white solid, m.p. 250–252° C. [Elemental analysis: C, 62.92; H, 5.14; N, 12.55%. Calculated for $C_{23}H_{21}ClN_4O_3$: C, 63.23; H, 4.84; N, 12.82%].

(o) 7-chloro-6-phenyl-3,4-dihydro-1H-pyrrolo[1,2-a]pyrazine-2,8-dicarboxylic acid 8-amide 2-[(4-fluorophenyl)amide]

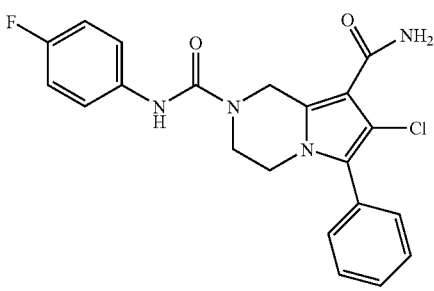

By proceeding in a similar manner to Example 1(a) above but using 4-fluorophenyl isocyanate there was prepared 7-chloro-6-phenyl-3,4-dihydro-1H-pyrrolo[1,2-a]pyrazine-2,8-dicarboxylic acid 8-amide 2-[(4-fluorophenyl)amide] as a white solid, m.p. 258–262° C. MS: 415 [MH]$^+$, 413 [MH]$^+$.

(p) 7-chloro-6-phenyl-3,4-dihydro-1H-pyrrolo[1,2-a]pyrazine-2,8-dicarboxylic acid 8-amide 2-[(2,6-difluorophenyl)amide]

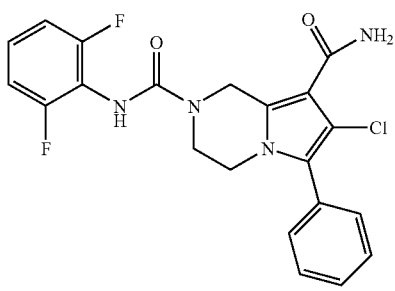

By proceeding in a similar manner to Example 1(a) above but using 2,6-difluorophenyl isocyanate there was prepared 7-chloro-6-phenyl-3,4-dihydro-1H-pyrrolo[1,2-a]pyrazine-2,8-dicarboxylic acid 8-amide 2-[(2,6-difluorophenyl)amide] as a white solid, m.p. 196–198° C. MS: 433 [MH]$^+$, 431 [MH]$^+$.

(q) 7-chloro-6-phenyl-3,4-dihydro-1H-pyrrolo[1,2-a]pyrazine-2,8-dicarboxylic acid 8-amide 2-[(3-chlorophenyl)amide]

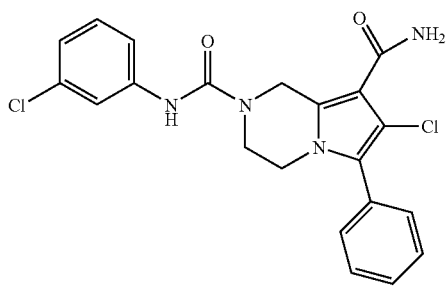

By proceeding in a similar manner to Example 1(a) above but using 3-chlorophenyl isocyanate there was prepared 7-chloro-6-phenyl-3,4-dihydro-1H-pyrrolo[1,2-a]pyrazine-2,8-dicarboxylic acid 8-amide 2-[(3-chlorophenyl)amide] as a white solid, m.p. 208–212° C. [Elemental analysis: C, 58.43; H, 3.84; N, 12.75%. Calculated for $C_{21}H_{18}Cl_2N_4O_2$: C, 58.75; H, 4.23; N, 13.05%].

(r) 7-chloro-6-phenyl-3,4-dihydro-1H-pyrrolo[1,2-a]pyrazine-2,8-dicarboxylic acid 8-amide 2-benzylamide

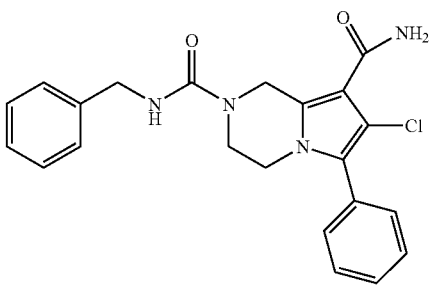

By proceeding in a similar manner to Example 1(a) above but using benzyl isocyanate there was prepared 7-chloro-6-phenyl-3,4-dihydro-1H-pyrrolo[1,2-a]pyrazine-2,8-dicarboxylic acid 8-amide 2-benzylamide as a white solid, m.p. 191–192° C. [Elemental analysis: C, 64.86; H, 4.91; N, 13.55%. Calculated for $C_{22}H_{21}ClN_4O_2$: C, 64.62; H, 5.18; N, 13.70%].

(s) 7-chloro-6-phenyl-3,4-dihydro-1H-pyrrolo[1,2-a]pyrazine-2,8-dicarboxylic acid 2-[(3-acetylphenyl)amide] 8-amide

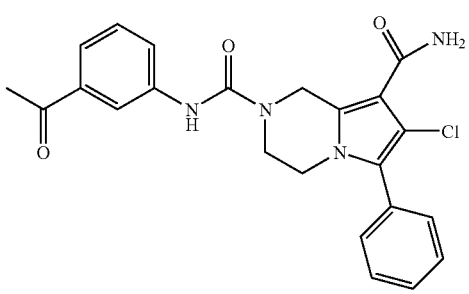

By proceeding in a similar manner to Example 1(a) above but using 3-acetylphenyl isocyanate there was prepared 7-chloro-6-phenyl-3,4-dihydro-1H-pyrrolo[1,2-a]pyrazine-2,8-dicarboxylic acid 2-[(3-acetylphenyl)amide] 8-amide as a white solid, m.p. 215–217° C. MS: 439 [MH]$^+$, 437 [MH]$^+$.

(t) 7-chloro-6-phenyl-3,4-dihydro-1H-pyrrolo[1,2-a]pyrazine-2,8-dicarboxylic acid 8-amide 2-cyclohexylamide

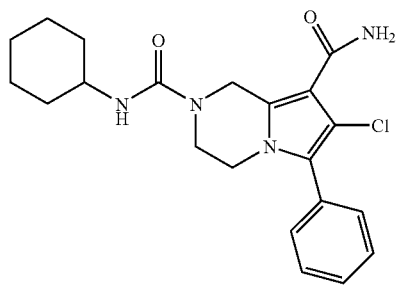

By proceeding in a similar manner to Example 1(a) above but using cyclohexyl isocyanate there was prepared 7-chloro-6-phenyl-3,4-dihydro-1H-pyrrolo[1,2-a]pyrazine-2,8-dicarboxylic acid 8-amide 2-cyclohexylamide as a white solid, m.p. 121–125° C. [Elemental analysis: C, 60.72; H, 6.22; N, 13.13%. Calculated for $C_{21}H_{25}ClN_4O_2 \cdot 0.75H_2O$: C, 60.86; H, 6.45; N, 13.52%].

(u) 7-chloro-6-phenyl-3,4-dihydro-1H-pyrrolo[1,2-a]pyrazine-2,8-dicarboxylic acid 8-amide 2-[(3-cyanophenyl)amide]

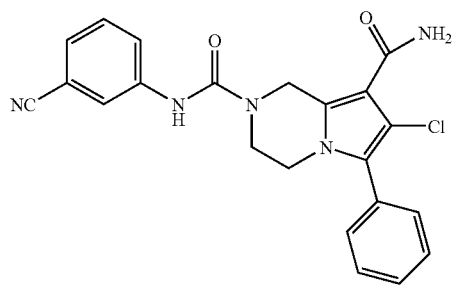

By proceeding in a similar manner to Example 1(a) above but using 3-cyanophenyl isocyanate there was prepared 7-chloro-6-phenyl-3,4-dihydro-1H-pyrrolo[1,2-a]pyrazine-2,8-dicarboxylic acid 8-amide 2-[(3-cyanophenyl)amide] as a white solid, m.p. 246–248° C. MS: 422 [MH]$^+$, 420 [MH]$^+$.

(v) 3-[(8-carbamoyl-7-chloro-6-phenyl-3,4-dihydro-1H-pyrrolo[1,2-a]pyrazine-2-carbonyl)amino]propionic acid ethyl ester By proceeding in a similar manner to Example 1(a) above but using ethyl 3-isocyanatopropionate there was prepared 3-[(8-carbamoyl-7-chloro-6-phenyl-3,4-dihydro-1H-pyrrolo[1,2-a]pyrazine-2-carbonyl)amino]propionic acid ethyl ester as white solid, m.p. 50–60° C. $^1$H NMR [(CD$_3$)$_2$SO)]: δ 7.53–7.35 (m, 5H), 7.32–7.18 (bs, 1H), 6.82 (t, 1H), 6.79–6.69 (bs, 1H), 4.73 (s, 2H), 4.01 (q, 2H), 3.72 (t, 2H), 3.58 (t, 2H), 3.24 (q, 2H), 2.42 (t, 2H) and 1.13 (t, 3H).

(w) 7-chloro-6-phenyl-3,4-dihydro-1H-pyrrolo[1,2-a]pyrazine-2,8-dicarboxylic acid 8-amide 2-ethylamide

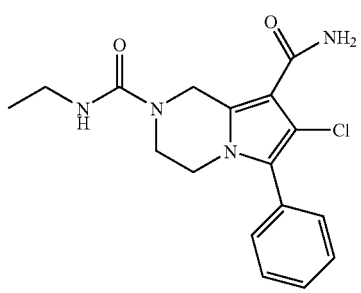

By proceeding in a similar manner to Example 1(a) above but using ethyl isocyanate there was prepared 7-chloro-6-phenyl-3,4-dihydro-1H-pyrrolo[1,2-a]pyrazine-2,8-dicarboxylic acid 8-amide 2-ethylamide as a white solid, m.p. 115–120° C. MS: 349 [MH]$^+$, 347 [MH]$^+$.

(x) 7-chloro-6-phenyl-3,4-dihydro-1H-pyrrolo[1,2-a]pyrazine-2,8-dicarboxylic acid 8-amide 2-m-tolylamide

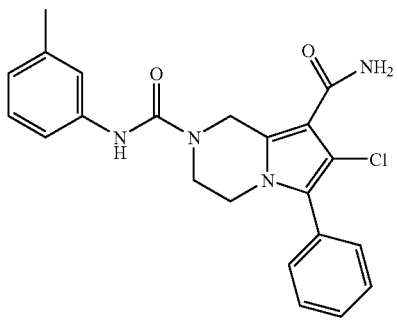

By proceeding in a similar manner to Example 1(a) above but using m-tolyl isocyanate there was prepared 7-chloro-6-phenyl-3,4-dihydro-1H-pyrrolo[1,2-a]pyrazine-2,8-dicarboxylic acid 8-amide 2-m-tolylamide as a white solid, m.p. 216–219° C. [Elemental analysis: C, 64.30; H, 5.18; N, 13.56%. Calculated for $C_{22}H_{21}ClN_4O_2$: C, 64.62; H, 5.18; N, 13.70%].

(y) 7-chloro-6-phenyl-3,4-dihydro-1H-pyrrolo[1,2-a]pyrazine-2,8-dicarboxylic acid 8-amide 2-isopropylamide

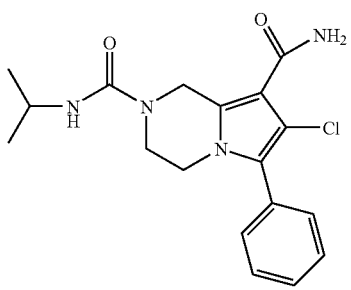

By proceeding in a similar manner to Example 1(a) above but using isopropyl isocyanate there was prepared 7-chloro-6-phenyl-3,4-dihydro-1H-pyrrolo[1,2-a]pyrazine-2,8-dicarboxylic acid 8-amide 2-isopropylamide as a white solid, m.p. 214–217° C. [Elemental analysis: C, 59.77; H, 5.94; N, 15.15%. Calculated for $C_{18}H_{21}ClN_4O_2$: C, 59.91; H, 5.87; N, 15.53%].

(z) 7-chloro-6-phenyl-3,4-dihydro-1H-pyrrolo[1,2-a]pyrazine-2,8-dicarboxylic acid 8-amide 2-[(3,4-dichlorophenyl)amide]

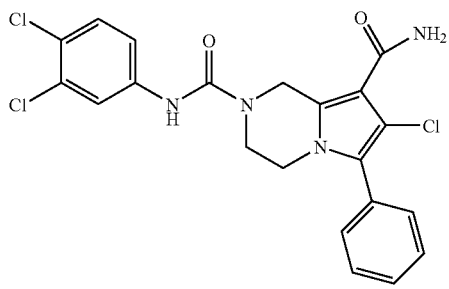

By proceeding in a similar manner to Example 1(a) above but using 3,4-dichlorophenyl isocyanate there was prepared 7-chloro-6-phenyl-3,4-dihydro-1H-pyrrolo[1,2-a]pyrazine-2,8-dicarboxylic acid 8-amide 2-[(3,4-dichlorophenyl)amide] as a white solid, m.p. 233–234° C. [Elemental analysis: C, 54.58; H, 3.46; N, 11.83%. Calculated for $C_{21}H_{17}Cl_3N_4O_2$: C, 54.39; H, 3.69; N, 12.08%].

(aa) 7-chloro-6-phenyl-3,4-dihydro-1H-pyrrolo[1,2-a]pyrazine-2,8-dicarboxylic acid 8-amide 2-cyclopentylmethylamide

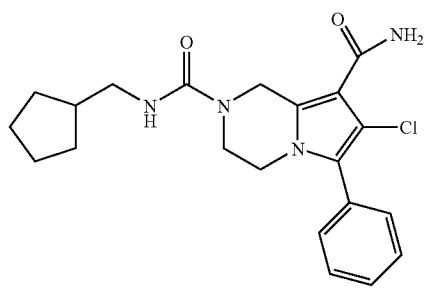

By proceeding in a similar manner to Example 1(a) above but using cyclopentylmethyl isocyanate (Reference Example 42) there was prepared 7-chloro-6-phenyl-3,4-dihydro-1H-pyrrolo[1,2-a]pyrazine-2,8-dicarboxylic acid 8-amide 2-cyclopentylmethylamide as a white solid, m.p. 151–153° C. MS: 403 $[MH]^+$, 401 $[MH]^+$.

(ab) 7-chloro-6-phenyl-3,4-dihydro-1H-pyrrolo[1,2-a]pyrazine-2,8-dicarboxylic acid 8-amide 2-[(4-phenoxyphenyl)amide]

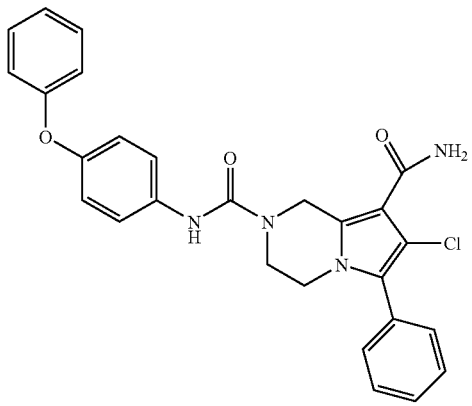

By proceeding in a similar manner to Example 1(a) above but using 4-phenoxyphenyl isocyanate there was prepared 7-chloro-6-phenyl-3,4-dihydro-1H-pyrrolo[1,2-a]pyrazine-2,8-dicarboxylic acid 8-amide 2-[(4-phenoxyphenyl)amide] as a white solid, m.p. 221–222° C. MS: 489 [MH]$^+$, 487 [MH]$^+$.

(ac) 7-chloro-6-phenyl-3,4-dihydro-1H-pyrrolo[1,2-a]pyrazine-2,8-dicarboxylic acid 8-amide 2-[(4-chlorophenyl)amide]

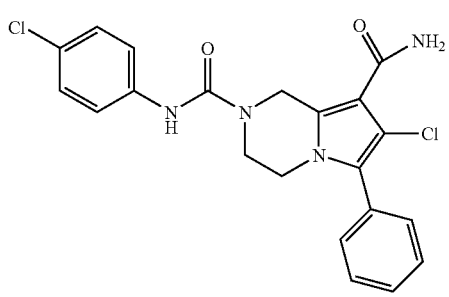

By proceeding in a similar manner to Example 1(a) above but using 4-chlorophenyl isocyanate there was prepared 7-chloro-6-phenyl-3,4-dihydro-1H-pyrrolo[1,2-a]pyrazine-2,8-dicarboxylic acid 8-amide 2-[(4-chlorophenyl)amide] as a white solid, m.p. 234–238° C. MS: 431 [MH]$^+$, 429 [MH]$^+$.

(ad) 7-chloro-6-phenyl-3,4-dihydro-1H-pyrrolo[1,2-a]pyrazine-2,8-dicarboxylic acid 8-amide 2-[(4-chloro-3-trifluoromethylphenyl)amide]

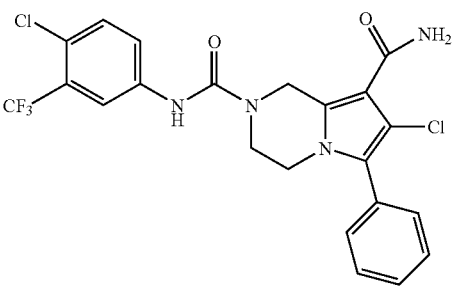

By proceeding in a similar manner to Example 1(a) above but using 4-chloro-3-(trifluoromethyl)phenyl isocyanate there was prepared 7-chloro-6-phenyl-3,4-dihydro-1H-pyrrolo[1,2-a]pyrazine-2,8-dicarboxylic acid 8-amide 2-[(4-chloro-3-trifluoromethylphenyl) amide] as a white solid, m.p. 237–238° C. [Elemental analysis: C, 53.12; H, 3.66; N, 11.25%. Calculated for $C_{22}H_{17}Cl_2F_3N_4O_2$: C, 53.14; H, 3.45; N, 11.27%].

(ae) 7-chloro-6-phenyl-3,4-dihydro-1H-pyrrolo[1,2-a]pyrazine-2,8-dicarboxylic acid 8-amide 2-[(2-thiophen-2-ylethyl)amide]

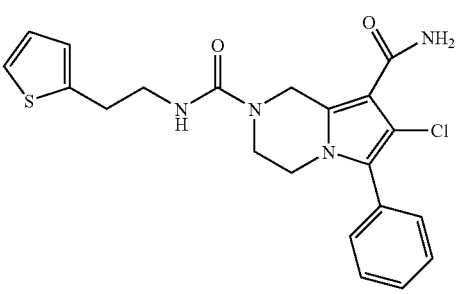

By proceeding in a similar manner to Example 1(a) above but using 2-(thien-2-yl)ethyl isocyanate there was prepared 7-chloro-6-phenyl-3,4-dihydro-1H-pyrrolo[1,2-a]pyrazine-2,8-dicarboxylic acid 8-amide 2-[(2-thiophen-2-ylethyl)amide] as a white solid, m.p. 165–168° C.

$^1$H NMR [(CD$_3$)$_2$SO]: δ 7.53–7.20 (m, 7H), 6.92 (t, 1H), 6.89 (dd, 1H), 6.82 (d, 1H), 6.80–6.67 (bs, 1H), 4.75 (s, 2H), 3.72 (t, 2H), 3.61 (t, 2H), 3.24 (q, 2H) and 2.91 (t, 2H).

(af) 7-chloro-6-phenyl-3,4-dihydro-1H-pyrrolo[1,2-a]pyrazine-2,8-dicarboxylic acid 8-amide 2-[(2-methoxyphenyl)amide]

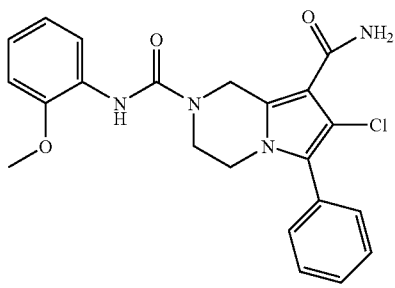

By proceeding in a similar manner to Example 1(a) above but using 2-methoxyphenyl isocyanate there was prepared 7-chloro-6-phenyl-3,4-dihydro-1H-pyrrolo[1,2-a]pyrazine-2,8-dicarboxylic acid 8-amide 2-[(2-methoxyphenyl)amide] as a white solid, m.p. 203–204° C. [Elemental analysis: C, −62.50; H, 5.03; N, 13.13%. Calculated for $C_{22}H_{21}ClN_4O_3$: C, 62.19; H, 4.98; N, 13.19%].

(ag) 7-chloro-6-phenyl-3,4-dihydro-1H-pyrrolo[1,2-a]pyrazine-2,8-dicarboxylic acid 8-amide 2-[(3,5-bistrifluoromethylphenyl)amide]

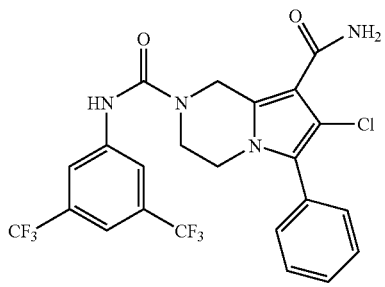

By proceeding in a similar manner to Example 1(a) above but using 3,5-bis(trifluoromethyl)phenyl isocyanate there was prepared 7-chloro-6-phenyl-3,4-dihydro-1H-pyrrolo[1,2-a]pyrazine-2,8-dicarboxylic acid 8-amide 2-[(3,5-bistrifluoromethylphenyl) amide] as a white solid, m.p. 256–257° C. [Elemental analysis: C, 51.76; H, 3.07; N, 10.61%. Calculated for $C_{23}H_{17}ClF_6N_4O_2$: C, 52.04; H, 3.23; N, 10.55%].

(ah) 7-chloro-6-phenyl-3,4-dihydro-1H-pyrrolo[1,2-a]pyrazine-2,8-dicarboxylic acid 8-amide 2-[(2,4-difluorophenyl)amide]

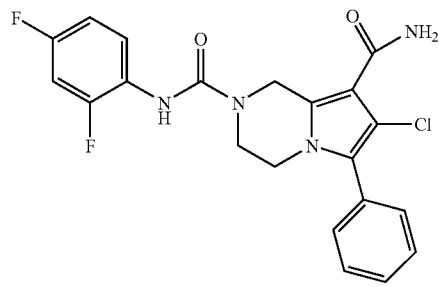

By proceeding in a similar manner to Example 1(a) above but using 2,4-difluorophenyl isocyanate there was prepared 7-chloro-6-phenyl-3,4-dihydro-1H-pyrrolo[1,2-a]pyrazine-2,8-dicarboxylic acid 8-amide 2-[(2,4-difluorophenyl) amide] as a white solid, m.p. 208–210° C. [Elemental analysis: C, 58.58; H, 3.63; N, 12.57%. Calculated for $C_{21}H_{17}ClF_2N_4O_2$: C, 58.54; H, 3.98; N, 13.00%].

(ai) 7-chloro-6-phenyl-3,4-dihydro-1H-pyrrolo[1,2-a]pyrazine-2,8-dicarboxylic acid 8-amide 2-[(2,5-difluorophenyl)amide]

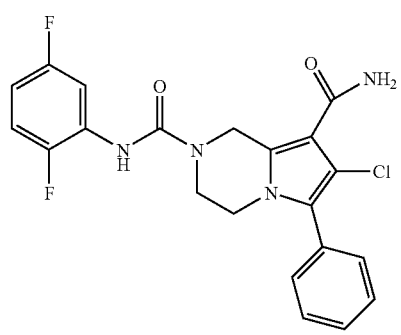

By proceeding in a similar manner to Example 1(a) above but using 2,5-difluorophenyl isocyanate there was prepared 7-chloro-6-phenyl-3,4-dihydro-1H-pyrrolo[1,2-a]pyrazine-2,8-dicarboxylic acid 8-amide 2-[(2,5-difluorophenyl) amide] as a white solid, m.p. 204–205° C. MS: 433 [MH]$^+$, 431 [MH]$^+$.

(aj) 4-[(8-carbamoyl-7-chloro-6-phenyl-3,4-dihydro-1H-pyrrolo[1,2-a]pyrazine-2-carbonyl)amino]benzoic acid ethyl ester

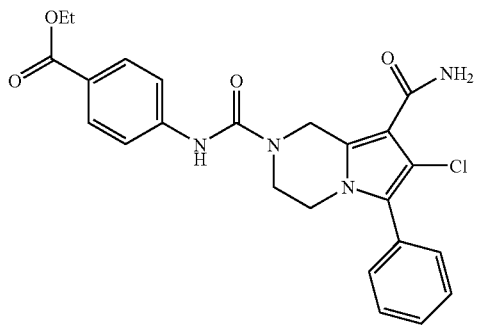

By proceeding in a similar manner to Example 1(a) above but using ethyl-4-isocyanatobenzoate there was prepared 4-[(8-carbamoyl-7-chloro-6-phenyl-3,4-dihydro-1H-pyrrolo[1,2-a]pyrazine-2-carbonyl)amino]benzoic acid ethyl ester as a white solid, m.p. 260–262° C. [Elemental analysis: C, 61.58; H, 4.74; N, 11.68%. Calculated for $C_{24}H_{23}ClN_4O_4$: C, 61.74; H, 4.97; N, 12.00%].

(ak) 7-chloro-6-phenyl-3,4-dihydro-1H-pyrrolo[1,2-a]pyrazine-2,8-dicarboxylic acid 8-amide 2-[(4-benzyloxyphenyl)amide]

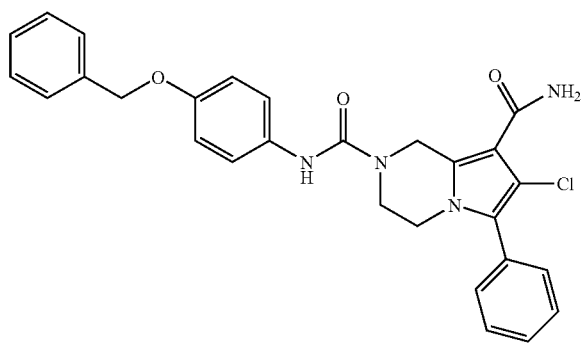

By proceeding in a similar manner to Example 1(a) above but using 4-benzyloxyphenyl isocyanate there was prepared 7-chloro-6-phenyl-3,4-dihydro-1H-pyrrolo[1,2-a]pyrazine-2,8-dicarboxylic acid 8-amide 2-[(4-benzyloxyphenyl)amide] as a white solid, m.p. 224–226° C. [Elemental analysis: C, 67.55; H, 5.03; N, 11.15%. Calculated for $C_{28}H_{25}ClN_4O_3$: C, 67.13; H, 5.03; N, 11.18%].

(al) 7-chloro-6-phenyl-3,4-dihydro-1H-pyrrolo[1,2-a]pyrazine-2,8-dicarboxylic acid 8-amide 2-[(tetrahydropyran-4-yl)amide]

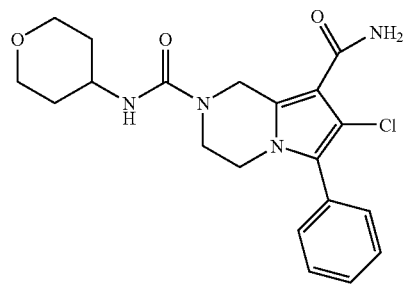

By proceeding in a similar manner to Example 1(a) above but using 4-tetrahydropyranyl isocyanate (prepared according to the procedure described in WO 96/27588, Intermediate 26) there was prepared 7-chloro-6-phenyl-3,4-dihydro-1H-pyrrolo[1,2-a]pyrazine-2,8-dicarboxylic acid 8-amide 2-[(tetrahydropyran-4-yl)amide] as a white solid, m.p. 184–186° C. [Elemental analysis: C, 58.91; H, 6.10; N, 13.62%. Calculated for $C_{20}H_{23}ClN_4O_3 \cdot 0.3H_2O$: C, 58.84; H, 5.83; N, 13.72%].

(am) 7-chloro-6-phenyl-3,4-dihydro-1H-pyrrolo[1,2-a]pyrazine-2,8-dicarboxylic acid 8-amide 2-[(4-methanesulfonylphenyl)amide]

By proceeding in a similar manner to Example 1(a) above but using 4-methanesulfonylphenyl isocyanate (prepared according to the procedure of Rasmussen et. al, J. Med. Chem. 1978, 21, 1044) 7-chloro-6-phenyl-3,4-dihydro-1H-pyrrolo[1,2-a]pyrazine-2,8-dicarboxylic acid 8-amide 2-[(4-methanesulfonylphenyl)amide] was prepared as a white solid, m.p. 270–272° C. $^1$H NMR [$(CD_3)_2SO$]: δ 9.32 (s, 1H), 7.80 (d, 2H), 7.72 (d, 2H), 7.56–7.40 (m, 5H), 7.40–7.30 (bs, 1H), 6.92–6.76 (bs, 1H), 4.98 (s, 2H), 3.88 (t, 2H), 3.82 (t, 2H) and 3.16 (s, 3H).

115

(an) 7-chloro-6-phenyl-3,4-dihydro-1H-pyrrolo[1,2-a]pyrazine-2,8-dicarboxylic acid 8-amide 2-naphthalen-1-ylamide

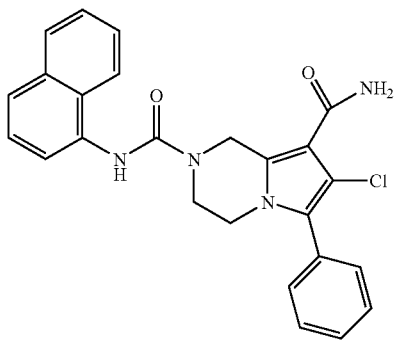

By proceeding in a similar manner to Example 1(a) above but using 1-naphthyl isocyanate there was prepared 7-chloro-6-phenyl-3,4-dihydro-1H-pyrrolo[1,2-a]pyrazine-2,8-dicarboxylic acid 8-amide 2-naphthalen-1-ylamide as a white solid, m.p. 237–238° C. [Elemental analysis: C, 67.18; H, 4.41; N, 12.56%. Calculated for $C_{25}H_{21}ClN_4O_2$: C, 67.49; H, 4.76; N, 12.59%].

(ao) [(8-carbamoyl-7-chloro-6-phenyl-3,4-dihydro-1H-pyrrolo[1,2-a]pyrazine-2-carbonyl)amino]acetic acid ethyl ester

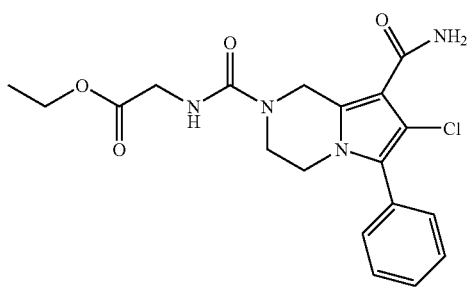

By proceeding in a similar manner to Example 1(a) above but using ethyl isocyanatoacetate there was prepared [(8-carbamoyl-7-chloro-6-phenyl-3,4-dihydro-1H-pyrrolo[1,2-a]pyrazine-2-carbonyl)amino] acetic acid ethyl ester as a white solid, m.p. 94–97° C. $^1$H NMR [$(CD_3)_2SO$]: δ 7.56–7.39 (m, 5H), 7.38–7.27 (bs, 1H), 7.26 (t, 1H), 6.88–6.73 (bs, 1H), 4.81 (s, 2H), 4.08 (q, 2H), 3.80 (t, 2H), 3.76 (d, 2H), 3.68 (t, 2H) and 1.18 (t, 3H).

116

(ap) 7-chloro-6-phenyl-3,4-dihydro-1H-pyrrolo[1,2-a]pyrazine-2,8-dicarboxylic acid 8-amide 2-{[4-(6-methylbenzothiazol-2-yl)phenyl]amide}

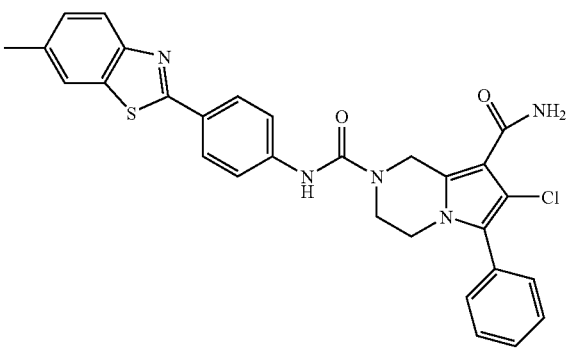

By proceeding in a similar manner to Example 1(a) above but using 4-(6-methyl-2-benzothiazolyl)phenyl isocyanate there was prepared 7-chloro-6-phenyl-3,4-dihydro-1H-pyrrolo[1,2-a]pyrazine-2,8-dicarboxylic acid 8-amide 2-{[4-(6-methylbenzothiazol-2-yl)phenyl]amide} as a white solid, m.p. 272–273° C.; MS: 544 [MH]$^+$, 542 [MH]$^+$.

(aq) 7-chloro-6-phenyl-3,4-dihydro-1H-pyrrolo[1,2-a]pyrazine-2,8-dicarboxylic acid 8-amide 2-thiophen-2-ylamide

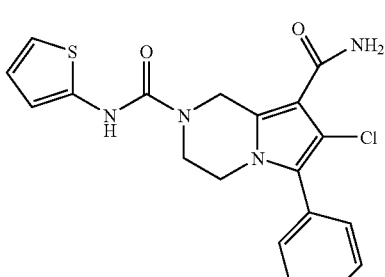

By proceeding in a similar manner to Example 1(a) above but using 2-thienyl isocyanate (prepared according to the procedure described in WO 95/18143, Preparation JJ) there was prepared 7-chloro-6-phenyl-3,4-dihydro-1H-pyrrolo[1,2-a]pyrazine-2,8-dicarboxylic acid 8-amide 2-thiophen-2-ylamide as a white solid, m.p. 257–259° C. MS: 403 [MH]$^+$, 401 [MH]$^+$.

(ar) 7-chloro-6-phenyl-3,4-dihydro-1H-pyrrolo[1,2-a]pyrazine-2,8-dicarboxylic acid 8-amide 2-[4-(trifluoromethylphenyl)amide]

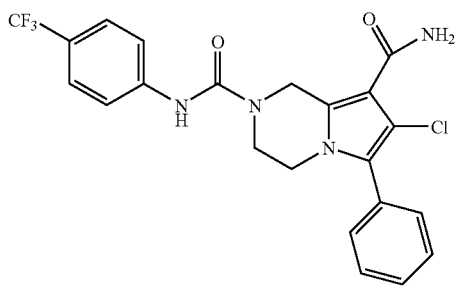

By proceeding in a similar manner to Example 1(a) above but using 4-trifluoromethylphenyl isocyanate there was prepared 7-chloro-6-phenyl-3,4-dihydro-1H-pyrrolo[1,2-a]pyrazine-2.8-dicarboxylic acid 8-amide 2-[4-(trifluoromethylphenyl)amide] as a white solid, m.p. 249–252° C. MS: 465 [MH]$^+$, 463 [MH]$^+$.

(as) 3-[(8-carbamoyl-7-chloro-6-phenyl-3,4-dihydro-1H-pyrrolo[1,2-a]pyrazine-2-carbonyl)amino]benzoic acid ethyl ester

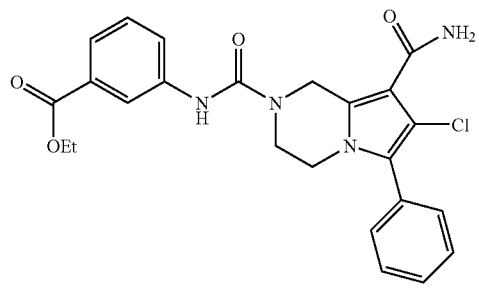

By proceeding in a similar manner to Example 1(a) above but using ethyl-3-isocyanatobenzoate there was prepared 3-[(8-carbamoyl-7-chloro-6-phenyl-3,4-dihydro-1H-pyrrolo[1,2-a]pyrazine-2-carbonyl)amino]benzoic acid ethyl ester as a white solid, m.p. 126–128° C. [Elemental analysis: C, 60.19; H, 5.02; N, 11.41%. Calculated for $C_{24}H_{23}ClN_4O_4 \cdot 0.70H_2O$: C, 60.11; H, 5.13; N, 11.68%].

(at) 7-chloro-6-phenyl-3,4-dihydro-1H-pyrrolo[1,2-a]pyrazine-2,8-dicarboxylic acid 8-amide 2-[(3-chloro-4-fluorophenyl)amide]

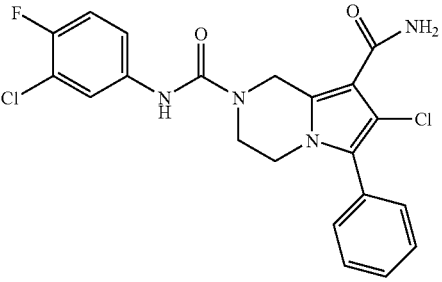

By proceeding in a similar manner to Example 1(a) above but using 3-chloro-4-fluorophenyl isocyanate there was prepared 7-chloro-6-phenyl-3,4-dihydro-1H-pyrrolo[1,2-a]pyrazine-2,8-dicarboxylic acid 8-amide 2-[(3-chloro-4-fluorophenyl)amide] as a white solid, m.p. 238–240° C. MS: 449 [MH]$^+$, 447 [MH]$^+$.

EXAMPLE 2

(a) 7-Chloro-6-phenyl-3,4-dihydro-1H-pyrrolo[1,2-a]pyrazine-2,8-dicarboxylic acid 8-amide 2-pyridin-3-ylamide

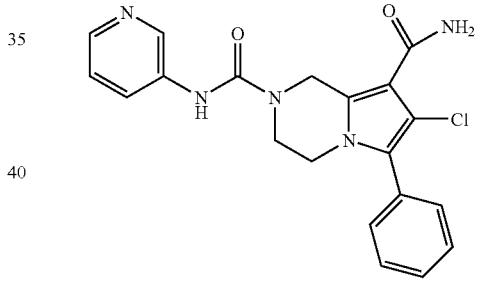

A stirred solution of triphosgene (40 mg) in dry dichloromethane (3 mL), under a blanket of nitrogen and at −70° C., was treated dropwise with a solution of 3-aminopyridine (34 mg) and triethylamine (25 μL) in dry dichloromethane (3 mL) over 1 hour whilst maintaining the temperature below −65° C. The resulting reaction mixture was stirred at −70° C. for a further 45 minutes, then treated dropwise with a solution of 7-chloro-6-phenyl-1,2,3,4-tetrahydropyrrolo[1,2-a]pyrazine-8-carboxylic acid amide trifluoroacetic acid salt (100 mg, Reference Example 1) and triethylamine (72 μL) in dry dichloromethane (3 mL) whilst maintaining the temperature below −65° C. The resulting reaction mixture was allowed to warm to room temperature over 2 hours and then treated with water. The organic phase was separated, then dried over magnesium sulfate, and then evaporated. The resulting residue was subjected to column chromatography on silica eluting with a mixture of methanol and dichloromethane (1:19, v/v) to give 7-chloro-6-phenyl-3,4-dihydro-1H-pyrrolo[1,2-a]pyrazine-2,8-dicarboxylic acid 8-amide 2-pyridin-3-ylamide (45 mg) as a white solid, m.p. 261–263° C. [Elemental analysis: C, 60.39; H, 4.58; N, 17.32; Calculated for $C_{20}H_{18}ClN_5O_2$: C, 60.69; H, 4.58; N, 17.69%].

(b) 7-chloro-6-phenyl-3,4-dihydro-1H-pyrrolo[1,2-a]pyrazine-2,8-dicarboxylic acid 8-amide 2-[(2,4,6-trifluorophenyl)amide]

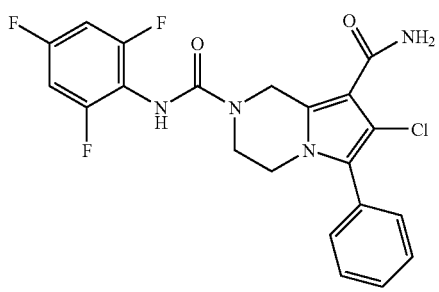

By proceeding in a similar manner to Example 2(a) above but using 2,4,6-trifluoroaniline there was prepared 7-chloro-6-phenyl-3,4-dihydro-1H-pyrrolo[1,2-a]pyrazine-2,8-dicarboxylic acid 8-amide 2-[(2,4,6-trifluorophenyl)amide] as a white solid, m.p. 225–226° C.; MS: 451 [MH]$^+$, 449 [MH]$^+$.

(c) 7-chloro-6-phenyl-3,4-dihydro-1H-pyrrolo[1,2-a]pyrazine-2,8-dicarboxylic acid 8-amide 2-[(3,4-difluorophenyl)amide]

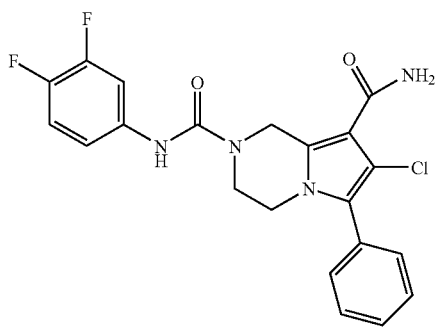

By proceeding in a similar manner to Example 2(a) above but using 3,4-difluoroaniline there was prepared 7-chloro-6-phenyl-3,4-dihydro-1H-pyrrolo[1,2-a]pyrazine-2,8-dicarboxylic acid 8-amide 2-[(3,4-difluorophenyl)amide] as a white solid, m.p. 255–257° C. [Elemental analysis: C, 58.57; H, 3.78; N, 12.76; Calculated for $C_{21}H_{17}ClF_2N_4O_2$: C, 58.54; H, 3.98; N, 13.00%].

(d) 7-chloro-6-phenyl-3,4-dihydro-1H-pyrrolo[1,2-a]pyrazine-2,8-dicarboxylic acid 8-amide 2-pyridin-4-ylamide

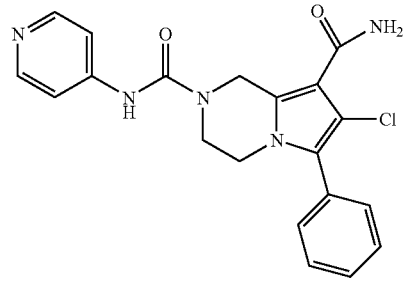

By proceeding in a similar manner to Example 2(a) above but using 4-aminopyridine there was prepared 7-chloro-6-phenyl-3,4-dihydro-1H-pyrrolo[1,2-a]pyrazine-2,8-dicarboxylic acid 8-amide 2-pyridin-4-ylamide as a white solid, m.p. 145–150° C. MS: 398 [MH]$^+$, 396 [MH]$^+$.

(e) 7-chloro-6-phenyl-3,4-dihydro-1H-pyrrolo[1,2-a]pyrazine-2,8-dicarboxylic acid 8-amide 2-[(2,3,4-trifluorophenyl)amide]

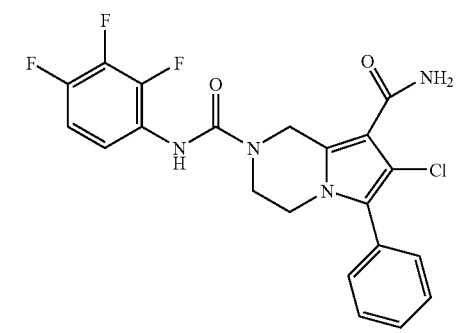

By proceeding in a similar manner to Example 2(a) above but using 2,3,4-trifluoroaniline there was prepared 7-chloro-6-phenyl-3,4-dihydro-1H-pyrrolo[1,2-a]pyrazine-2,8-dicarboxylic acid 8-amide 2-[(2,3,4-trifluorophenyl)amide] as a white solid, m.p. 235–236° C. [Elemental analysis: C, 56.25; H, 3.26; N, 12.17%. Calculated for $C_{21}H_{16}ClF_3N_4O_2$: C, 56.20; H, 3.59; N, 12.48%].

(f) 7-chloro-6-phenyl-3,4-dihydro-1H-pyrrolo[1,2-a]pyrazine-2,8-dicarboxylic acid 8-amide 2-[(4-cyanophenyl)amide]

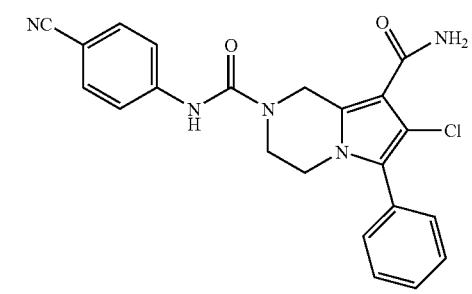

By proceeding in a similar manner to Example 2(a) above but using 4-cyanoaniline there was prepared 7-chloro-6-phenyl-3,4-dihydro-1H-pyrrolo[1,2-a]pyrazine-2,8-dicarboxylic acid 8-amide 2-[(4-cyanophenyl)amide] as a white solid, m.p. 241–243° C. [Elemental analysis: C, 58.78; H, 4.70; N, 15.82%. Calculated for $C_{22}H_{18}ClN_5O_2 \cdot 1.6H_2O$: C, 58.89; H, 4.76; N, 15.60%].

(g) 7-chloro-6-phenyl-3,4-dihydro-1H-pyrrolo[1,2-a]pyrazine-2,8-dicarboxylic acid 8-amide 2-cyclopentylamide

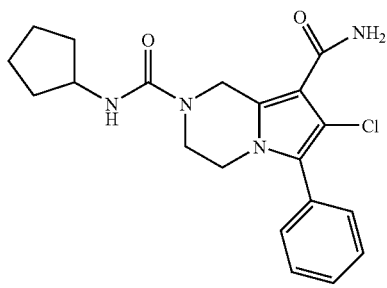

By proceeding in a similar manner to Example 2(a) above but using cyclopentylamine there was prepared 7-chloro-6-phenyl-3,4-dihydro-1H-pyrrolo[1,2-a]pyrazine-2,8-dicarboxylic acid 8-amide 2-cyclopentylamide as a white solid, m.p. 207–209° C. [Elemental analysis: C, 60.80; H, 5.99; N, 13.89%. Calculated for $C_{20}H_{23}ClN_4O_2 \cdot 0.5H_2O$: C, 60.68; H, 6.11; N, 14.15%].

(h) 7-chloro-6-phenyl-3,4-dihydro-1H-pyrrolo[1,2-a]pyrazine-2,8-dicarboxylic acid 8-amide 2-thiazol-2-ylamide

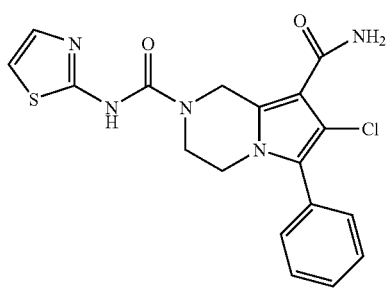

By proceeding in a similar manner to Example 2(a) above but using 2-aminothiazole there was prepared 7-chloro-6-phenyl-3,4-dihydro-1H-pyrrolo[1,2-a]pyrazine-2,8-dicarboxylic acid 8-amide 2-thiazol-2-ylamide as a white solid, m.p. 188–190° C.; MS: 404 [MH]$^+$, 402 [MH]$^+$.

(i) 7-chloro-6-phenyl-3,4-dihydro-1H-pyrrolo[1,2-a]pyrazine-2,8-dicarboxylic acid 8-amide 2-[(4-morpholin-4-ylmethylphenyl)amide]

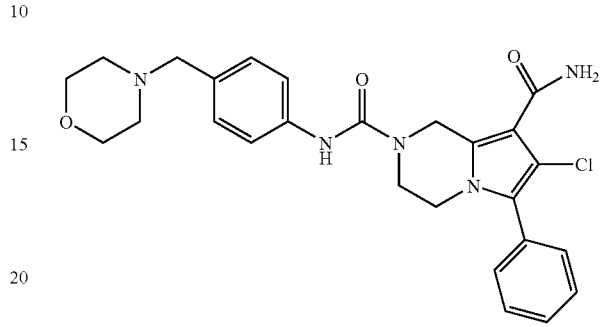

By proceeding in a similar manner to Example 2(a) above but using 4-morpholin-4-ylmethylphenylamine (Reference Example 47), conducting the reaction at 0° C. and quenching the reaction with a 0.5 M aqueous solution of sodium carbonate to pH 9, there was prepared 7-chloro-6-phenyl-3,4-dihydro-1H-pyrrolo[1,2-a]pyrazine-2,8-dicarboxylic acid 8-amide 2-[(4-morpholin-4-ylmethylphenyl)amide] as a white solid, m.p. 208–210° C.; $^1$H NMR [$(CD_3)_2SO$]: δ 8.81 (s, 1H), 7.55–7.37 (m, 7H), 7.36–7.28 (bs, 1H), 7.17 (d, 2H), 6.90–6.75 (bs, 1H), 4.94 (s, 2H), 3.87 (t, 2H), 3.79 (t, 2H), 3.56 (t, 4H), 3.37 (s, 2H) and 2.40–2.24 (brs, 4H).

(j) 7-chloro-6-phenyl-3,4-dihydro-1H-pyrrolo[1,2-a]pyrazine-2,8-dicarboxylic acid 8-amide 2-[(3-morpholin-4-ylmethylphenyl)amide]

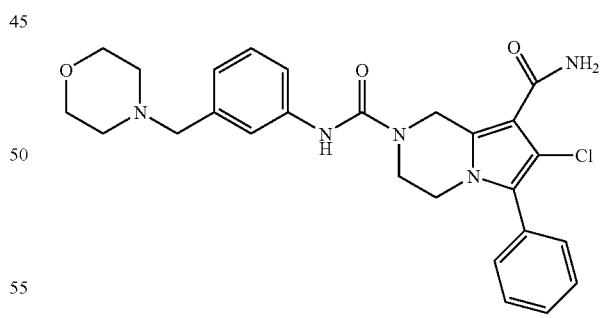

By proceeding in a similar manner to Example 2(a) above but using 3-morpholin-4-ylmethylphenylamine (Reference Example 52), and quenching the reaction with a 0.5 M aqueous solution of sodium carbonate to pH 9, there was prepared 7-chloro-6-phenyl-3,4-dihydro-1H-pyrrolo[1,2-a]pyrazine-2,8-dicarboxylic acid 8-amide 2-[(3-morpholin-4-ylmethylphenyl)amide] as a white solid, m.p. 126–128° C. [Elemental analysis: C, 62.11; H, 5.58; N, 13.81%. Calculated for $C_{26}H_{28}ClN_5O_3 \cdot 0.5H_2O$: C, 62.08; H, 5.81; N, 13.92%].

(k) 7-chloro-6-phenyl-3,4-dihydro-1H-pyrrolo[1,2-a]pyrazine-2,8-dicarboxylic acid 8-amide 2-[(4-morpholin-4-ylphenyl)amide]

(m) 7-chloro-6-phenyl-3,4-dihydro-1H-pyrrolo[1,2-a]pyrazine-2,8-dicarboxylic acid 8-amide 2-{[3-(4-methylpiperazine-1-carbonyl)phenyl]amide}

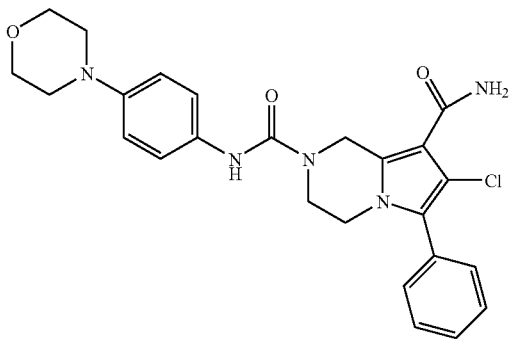

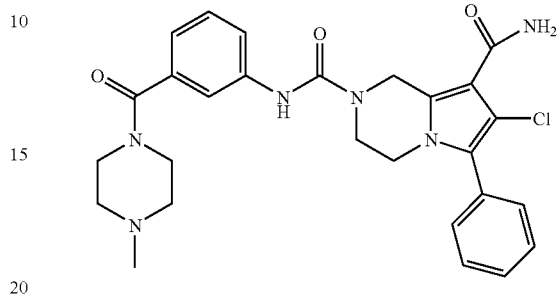

By proceeding in a similar manner to Example 2(a) above but using 4-morpholinoaniline there was prepared 7-chloro-6-phenyl-3,4-dihydro-1H-pyrrolo[1,2-a]pyrazine-2,8-dicarboxylic acid 8-amide 2-[(4-morpholin-4-ylphenyl)amide] as a white solid, m.p. 248–250° C. [Elemental analysis: C, 60.10; H, 5.45; N, 13.95%. Calculated for $C_{25}H_{26}ClN_5O_3 \cdot H_2O$: C, 60.30; H, 5.67; N, 14.06%].

(l) 7-chloro-6-phenyl-3,4-dihydro-1H-pyrrolo[1,2-a]pyrazine-2,8-dicarboxylic acid 8-amide 2-{[4-(4-methylpiperazine-1-carbonyl)phenyl]amide}

By proceeding in a similar manner to Example 2(a) above but using 1-(3-aminobenzoyl)-4-methylpiperazine (Reference Example 52c) and quenching the reaction with a saturated aqueous solution of sodium hydrogen carbonate, there was prepared 7-chloro-6-phenyl-3,4-dihydro-1H-pyrrolo[1,2-a]pyrazine-2,8-dicarboxylic acid 8-amide 2-{[3-(4-methylpiperazine-1-carbonyl)phenyl]amide} as a white solid, m.p. 250–252° C. $^1$H NMR [$(CD_3)_2SO$]: δ 8.96 (s, 1H), 7.56–7.39 (m, 7H), 7.38–7.28 (bs and t overlapping, 2H), 6.95 (d, 1H), 6.89–6.77 (bs, 1H), 4.95 (s, 2H), 3.88 (t, 2H), 3.80 (t, 2H), 3.69–3.25 (2bs overlapping, 4H) and 2.44–2.15 (2bs and s overlapping, 7H).

(n) 7-chloro-6-phenyl-3,4-dihydro-1H-pyrrolo[1,2-a]pyrazine-2,8-dicarboxylic acid 8-amide 2-{[4-(4-methyl[1,4]diazepane-1-carbonyl)phenyl]amide}

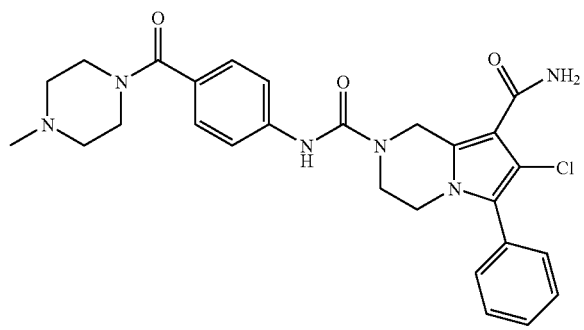

By proceeding in a similar manner to Example 2(a) above but using 1-(4-aminobenzoyl)-4-methylpiperazine (Reference Example 48), and quenching the reaction with a saturated aqueous solution of sodium hydrogen carbonate, there was prepared 7-chloro-6-phenyl-3,4-dihydro-1H-pyrrolo[1,2-a]pyrazine-2,8-dicarboxylic acid 8-amide 2-{[4-(4-methylpiperazine-1-carbonyl)phenyl]amide} as a white solid, m.p. 218–220° C. [Elemental analysis: C, 59.28; H, 5.58; N, 14.98%. Calculated for $C_{27}H_{29}ClN_6O_3 \cdot 1.5H_2O$: C, 59.17; H, 5.89; N, 15.33%].

By proceeding in a similar manner to Example 2(a) above but using 1-(4-aminobenzoyl)-4-methyl-[1,4]diazepane (Reference Example 52d), conducting the reaction at 0° C. and quenching the reaction with a saturated aqueous solution of sodium hydrogen carbonate there was prepared 7-chloro-6-phenyl-3,4-dihydro-1H-pyrrolo[1,2-a]pyrazine-2,8-dicarboxylic acid 8-amide 2-{[4-(4-methyl[1,4]diazepane-1-carbonyl)phenyl]amide} as a white solid, m.p. 145–155° C. MS: 535 [MH]$^+$, 537 [MH]$^+$.

(o) 7-chloro-6-phenyl-3,4-dihydro-1H-pyrrolo[1,2-a]pyrazine-2,8-dicarboxylic acid 8-amide 2-{[3-(4-methyl[1,4]diazepane-1-carbonyl)phenyl]amide}

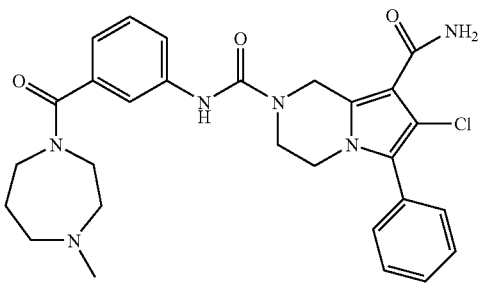

By proceeding in a similar manner to Example 2(a) above but using 1-(3-aminobenzoyl)-4-methyl-[1,4]diazepane (Reference Example 52e), conducting the reaction at 0° C. and quenching the reaction with a saturated aqueous solution of sodium hydrogen carbonate, there was prepared 7-chloro-6-phenyl-3,4-dihydro-1H-pyrrolo[1,2-a]pyrazine-2,8-dicarboxylic acid 8-amide 2-{[3-(4-methyl[1,4]diazepane-1-carbonyl)phenyl]amide} as a white solid, m.p. 145–150° C. [Elemental analysis: C, 62.36; H, 6.00; N, 15.22%. Calculated for $C_{28}H_{31}ClN_6O_3.0.2H_2O$: C, 62.44; H, 5.88; N, 15.60%].

(p) 7-chloro-6-phenyl-3,4-dihydro-1H-pyrrolo[1,2-a]pyrazine-2,8-dicarboxylic acid 8-amide 2-{[4-(4-fluorophenoxy)phenyl]amide}

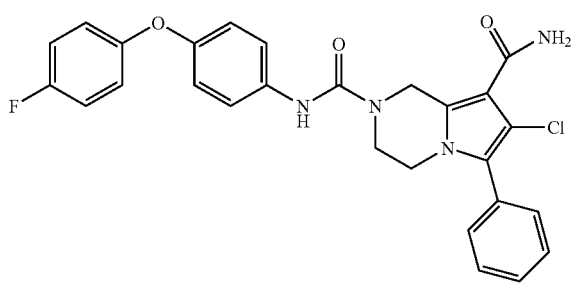

By proceeding in a similar manner to Example 2(a) above but using 4-(4-fluorophenoxy)phenylamine (Reference Example 52 g) there was prepared 7-chloro-6-phenyl-3,4-dihydro-1H-pyrrolo[1,2-a]pyrazine-2,8-dicarboxylic acid 8-amide 2-{[4-(4-fluorophenoxy)phenyl]amide} as a white solid, m.p. 194° C. $^1$H NMR [$(CD_3)_2SO$]: δ 8.84 (s, 1H), 7.55–7.41 (m, 7H), 7.39–7.27 (bs, 1H), 7.20 (t, 2H), 7.00 (dd, 2H), 6.93 (d, 2H), 6.89–6.77 (bs, 1H), 4.95 (s, 2H), 3.87 (t, 2H) and 3.80 (t, 2H).

(q) 7-chloro-6-phenyl-3,4-dihydro-1H-pyrrolo[1,2-a]pyrazine-2,8-dicarboxylic acid 8-amide 2-{[4-(4-isopropylpiperazine-1-carbonyl)phenyl]-amide}

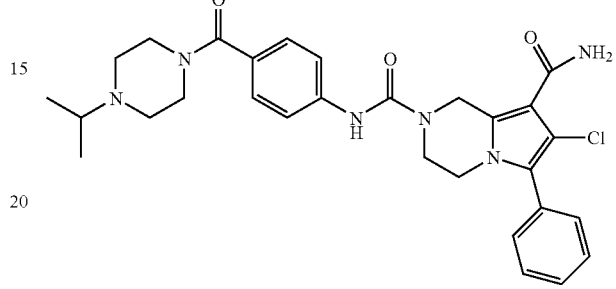

By proceeding in a similar manner to Example 2(a) above but using 1-(4-aminobenzoyl)-4-isopropylpiperazine (Reference Example 52h) there was prepared 7-chloro-6-phenyl-3,4-dihydro-1H-pyrrolo[1,2-a]pyrazine-2,8-dicarboxylic acid 8-amide 2-{[4-(4-isopropylpiperazine-1-carbonyl)phenyl]-amide} as an off white solid, m.p. 206–207° C. MS: 551 [MH]$^+$, 449 [MH]$^+$.

(r) 7-chloro-6-phenyl-3,4-dihydro-1H-pyrrolo[1,2-a]pyrazine-2,8-dicarboxylic acid 8-amide 2-{[4-(4-isopropyl[1,4]diazepane-1-carbonyl)phenyl]amide}

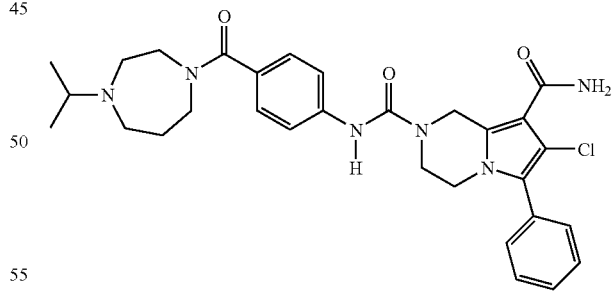

By proceeding in a similar manner to Example 2(a) above but using 1-(4-aminobenzoyl)-4-isopropyl[1,4]diazepane (Reference Example 52i) there was prepared 7-chloro-6-phenyl-3,4-dihydro-1H-pyrrolo[1,2-a]pyrazine-2,8-dicarboxylic acid 8-amide 2-{[4-(4-isopropyl[1,4] diazepane-1-carbonyl)phenyl]amide} as an off white solid, m.p. 136–138° C. MS: 565 [MH]$^+$, 563 [MH]$^+$.

(s) 7-chloro-6-phenyl-3,4-dihydro-1H-pyrrolo[1,2-a]pyrazine-2,8-dicarboxylic acid 8-amide 2-{[4-(3-dimethylaminopropoxy)phenyl]amide}

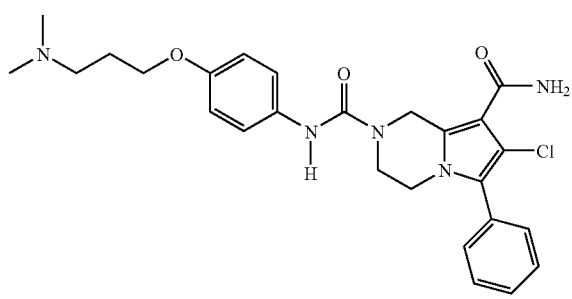

By proceeding in a similar manner to Example 2(a) above but using 4-(3-dimethylaminopropoxy)-phenylamine (prepared according to the procedure of Wyatt et. al, J. Med. Chem. 1995 38, 1657) there was prepared 7-chloro-6-phenyl-3,4-dihydro-1H-pyrrolo[1,2-a]pyrazine-2,8-dicarboxylic acid 8-amide 2-{[4-(3-dimethylaminopropoxy) phenyl]amide} as an off white solid, m.p. 143–145° C. MS: 498 [MH]$^+$, 496 [MH]$^+$.

(t) 7-chloro-6-phenyl-3,4-dihydro-1H-pyrrolo[1,2-a]pyrazine-2,8-dicarboxylic acid 8-amide 2-indan-2-ylamide

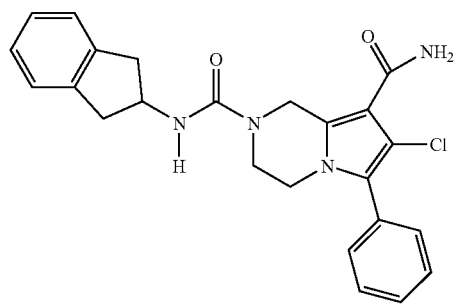

By proceeding in a similar manner to Example 2(a) above but using 2-indanamine hydrochloride there was prepared 7-chloro-6-phenyl-3,4-dihydro-1H-pyrrolo[1,2-a]pyrazine-2,8-dicarboxylic acid 8-amide 2-indan-2-ylamide as a white solid, m.p. 241–243° C. $^1$H NMR [(CD$_3$)$_2$SO]: δ 7.54–7.40 (m, 5H), 7.35–7.23 (bs, 1H), 7.22–7.08 (m, 4H), 6.94 (d, 1H), 6.86–6.70 (bs, 1H), 4.80 (s, 2H), 4.50–4.37 (m, 1H), 3.78 (t, 2H), 3.65 (t, 2H), 3.13 (dd, 2H) and 2.84 (dd, 2H).

(u) 7-chloro-6-phenyl-3,4-dihydro-1H-pyrrolo[1,2-a]pyrazine-2,8-dicarboxylic acid 8-amide 2-quinolin-6-ylamide

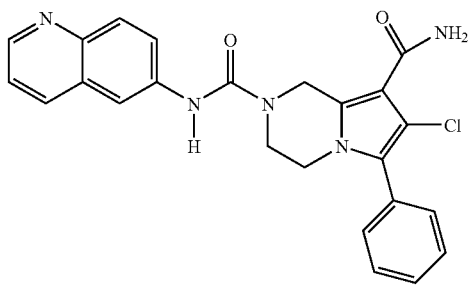

By proceeding in a similar manner to Example 2(a) above but using 6-aminoquinoline there was prepared 7-chloro-6-phenyl-3,4-dihydro-1H-pyrrolo[1,2-a]pyrazine-2,8-dicarboxylic acid 8-amide 2-quinolin-6-ylamide as an off white solid, m.p. 236–238° C. $^1$H NMR [(CD$_3$)$_2$SO]: δ 9.20 (s, 1H), 8.74 (dd, 1H), 8.22 (d, 1H), 8.08 (d, 1H), 7.92 (d, 1H), 7.85 (dd, 1H), 7.56–7.27 (m and bs overlapping, 7H), 6.93–6.76 (bs, 1H), 5.01 (s, 2H), 3.92 (t, 2H) and 3.87 (t, 2H).

(v) 7-chloro-6-phenyl-3,4-dihydro-1H-pyrrolo[1,2-a]pyrazine-2,8-dicarboxylic acid 8-amide 2-{[1-(morpholine-4-carbonyl)piperidin-4-yl]amide}

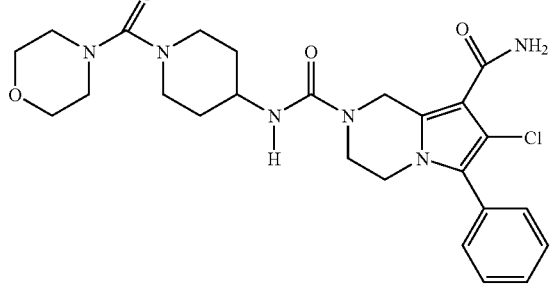

By proceeding in a similar manner to Example 2(a) above but using (4-amino-piperidin-1-yl)-morpholin-4-yl-methanone, trifluoroacetic acid salt (Reference Example 59) there was prepared 7-chloro-6-phenyl-3,4-dihydro-1H-pyrrolo[1,2-a]pyrazine-2,8-dicarboxylic acid 8-amide 2-{[1-(morpholine-4-carbonyl)piperidin-4-yl]amide} as a white solid, m.p. 135–138° C. (dec). MS: 539 [MNa]$^+$, 537 [MNa]$^+$.

(w) 4-[(8-carbamoyl-7-chloro-6-phenyl-3,4-dihydro-1H-pyrrolo[1,2-a]pyrazine-2-carbonyl)amino]piperidine-1-carboxylic acid isopropyl ester

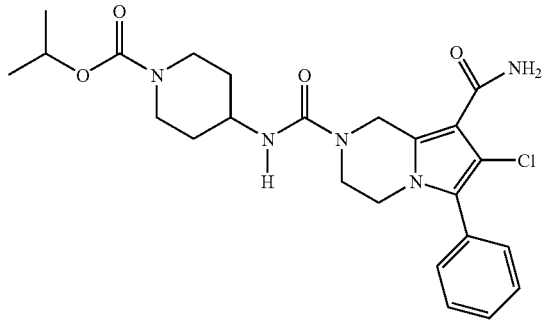

By proceeding in a similar manner to Example 2(a) above but using 4-amino-piperidine-1-carboxylic acid isopropyl ester, trifluoroacetic acid salt (Reference Example 60) there was prepared 4-[(8-carbamoyl-7-chloro-6-phenyl-3,4-dihydro-1H-pyrrolo [1,2-a]pyrazine-2-carbonyl)amino]piperidine-1-carboxylic acid isopropyl ester as a white solid, m.p. 166–167° C. MS: 512 [MNa]$^+$, 510 [MNa]$^+$.

EXAMPLE 3

7-Chloro-6-(tetrahydropyran-4-yl)-3,4-dihydro-1H-pyrrolo[1,2-a]pyrazine-2,8-dicarboxylic acid 8-amide 2-[(4-fluorophenyl)amide]

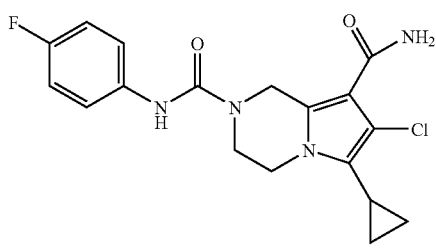

A stirred suspension of 7-chloro-6-(tetrahydropyran-4-yl)-1,2,3,4-tetrahydropyrrolo[1,2-a]pyrazine-8-carboxylic acid amide trifluoroacetic acid salt (36 mg, Reference Example 1a) in dry dichloromethane (3 mL) was treated with dry triethylamine (40 μL), then with a solution of 4-fluorophenyl isocyanate (14 mg) in dry dichloromethane (1 mL). After stirring at room temperature for a further 4 hours the reaction mixture was treated with methanol (0.5 mL), then the solvent removed under reduced pressure. The residue was triturated with diethyl ether and methanol to give 7-chloro-6-(tetrahydropyran-4-yl)-3,4-dihydro-1H-pyrrolo[1,2-a]pyrazine-2,8-dicarboxylic acid 8-amide 2-[(4-fluorophenyl)amide] (23 mg) as a white solid, m.p. 266–267° C. $^1$H NMR[(CD$_3$)$_2$SO]: δ 8.87 (s, 1H), 7.44 (dd, 2H), 7.30–7.16 (bs, 1H), 7.09 (t, 2H), 6.79–6.68 (bs, 1H), 4.82 (s, 2H), 4.00 (t, 2H), 3.93 (dd, 2H), 3.84 (t, 2H), 3.39 (t, 2H), 3.07–2.97 (m, 1H), 2.19–2.05 (m, 2H) and 1.56 (d, 2H).

EXAMPLE 4

(a) 7-Chloro-6-pyridin-3-yl-3,4-dihydro-1H-pyrrolo[1,2-a]pyrazine-2,8-dicarboxylic acid 8-amide 2-[(4-methanesulfonylphenyl)amide]

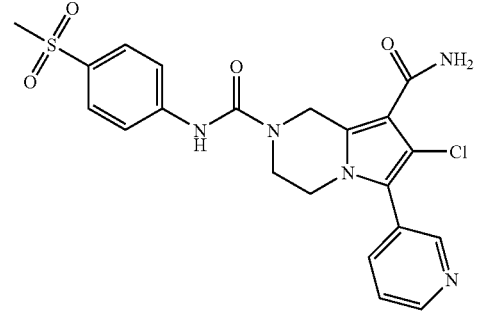

A stirred suspension of 7-chloro-6-pyridin-3-yl-1,2,3,4-tetrahydropyrrolo[1,2-a]pyrazine-8-carboxylic acid amide bis trifluoroacetic acid salt (110 mg, Reference Example 1b) in dry dichloromethane (1 mL) was treated with dry triethylamine (0.89 mL), then with a solution of 4-methanesulfonylphenyl isocyanate (43 mg, prepared according to the procedure of Rasmussen et. al, J. Med. Chem. 1978, 21, 1044) in dry dichloromethane (1 mL). After stirring at room temperature for a further 1 hour the reaction mixture was then filtered. The solid collected was washed with dichloromethane to give 7-chloro-6-pyridin-3-yl-3,4-dihydro-1H-pyrrolo[1,2-a]pyrazine-2,8-dicarboxylic acid 8-amide 2-[(4-methanesulfonylphenyl)amide] as a white solid, m.p. 268–270° C. $^1$H NMR [(CD$_3$)$_2$SO]: δ 9.30 (s, 1H), 8.66 (s, 1H), 8.60 (d, 1H), 7.90 (d, 1H), 7.76 (d, 2H), 7.68 (d, 2H), 7.50 (dd, 1H), 7.42–7.28 (bs, 1H), 6.92–6.74 (bs, 1H), 4.96 (s, 2H), 3.90 (t, 2H), 3.80 (t, 2H) and 3.12 (s, 3H).

(b) 7-chloro-6-pyridin-3-yl-3,4-dihydro-1H-pyrrolo[1,2-a]pyrazine-2,8-dicarboxylic acid 8-amide 2-[(4-fluorophenyl)amide]

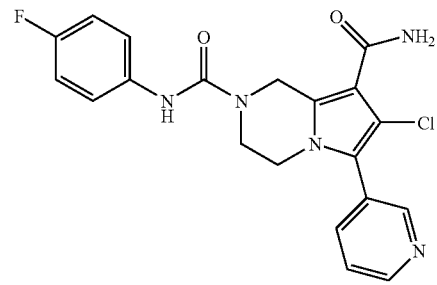

By proceeding in a similar manner to Example 4(a) above but using 4-fluorophenyl isocyanate there was prepared 7-chloro-6-pyridin-3-yl-3,4-dihydro-1H-pyrrolo[1,2-a]pyrazine-2,8-dicarboxylic acid 8-amide 2-[(4-fluorophenyl)amide] as a white solid, m.p. 253–255° C. [Elemental analysis: C, 57.90; H, 3.85; N, 16.90%. Calculated for C$_{20}$H$_{17}$ClFN$_5$O$_2$: C, 58.05; H, 4.14; N, 16.92%].

(c) 7-chloro-6-pyridin-3-yl-3,4-dihydro-1H-pyrrolo[1,2-a]pyrazine-2,8-dicarboxylic acid 8-amide 2-[(tetrahydropyran-4-yl)amide]

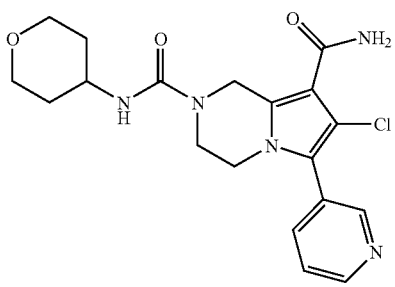

By proceeding in a similar manner to Example 4(a) above but using 4-tetrahydropyranyl isocyanate (prepared according to the procedure described in WO 96/27588, Intermediate 26) there was prepared 7-chloro-6-pyridin-3-yl-3,4-dihydro-1H-pyrrolo[1,2-a]pyrazine-2,8-dicarboxylic acid 8-amide 2-[(tetrahydropyran-4-yl)amide] as a white solid, m.p. 253–255° C. [Elemental analysis: C, 56.04; H, 5.54; N, 16.98%. Calculated for $C_{19}H_{22}ClN_5O_3$: C, 56.51; H, 5.49; N, 17.34%].

(d) 4-[(8-carbamoyl-7-chloro-6-pyridin-3-yl-3,4-dihydro-1H-pyrrolo[1,2a]pyrazine-2-carbonyl)amino]benzoic acid ethyl ester

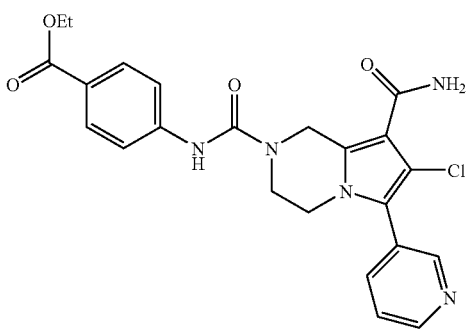

By proceeding in a similar manner to Example 4(a) above but using ethyl-4-isocyanatobenzoate there was prepared 4-[(8-carbamoyl-7-chloro-6-pyridin-3-yl-3,4-dihydro-1H-pyrrolo[1,2a]pyrazine-2-carbonyl)amino]benzoic acid ethyl ester as a white solid, m.p. 252–256° C. $^1$H NMR [$(CD_3)_2SO$]: δ 9.23 (s, 1H), 8.69 (s, 1H), 8.63 (d, 1H), 7.94 (d, 1H), 7.87 (d, 2H), 7.62 (d, 2H), 7.54 (dd, 1H), 7.44–7.31 (bs, 1H), 6.93–6.79 (bs, 1H), 4.99 (s, 2H), 4.27 (q, 2H), 3.93 (t, 2H), 3.84 (t, 2H) and 1.31 (t, 3H).

(e) 7-chloro-6-pyridin-3-yl-3,4-dihydro-1H-pyrrolo[1,2-a]pyrazine-2,8-dicarboxylic acid 8-amide 2-[(3-cyanophenyl)amide]

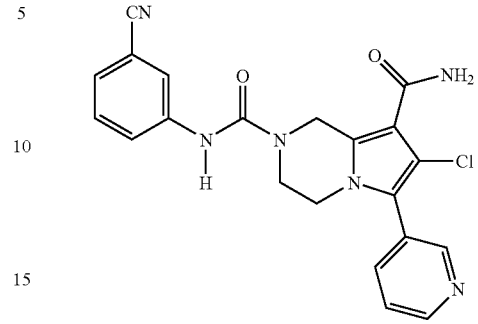

By proceeding in a similar manner to Example 4(a) above but using 3-cyanophenyl isocyanate there was prepared 7-chloro-6-pyridin-3-yl-3,4-dihydro-1H-pyrrolo[1,2-a]pyrazine-2,8-dicarboxylic acid 8-amide 2-[(3-cyanophenyl)amide] as a white solid, m.p. 242–246° C. [Elemental analysis: C, 57.34; H, 4.21; N, 18.70%. Calculated for $C_{21}H_{17}ClN_6O_2 \cdot 1.1H_2O$: C, 57.24; H, 4.39; N, 19.07%].

(f) 7-chloro-6-pyridin-3-yl-3,4-dihydro-1H-pyrrolo[1,2-a]pyrazine-2,8-dicarboxylic acid 8-amide 2-[(3-trifluoromethylphenyl)amide]

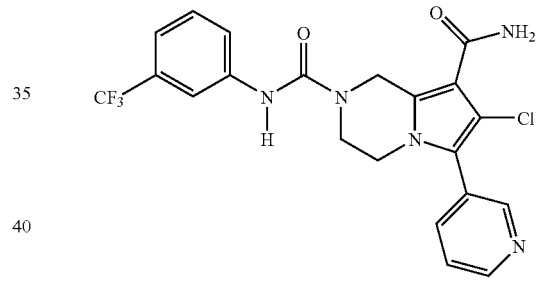

By proceeding in a similar manner to Example 4(a) above but using 3-trifluoromethylphenyl isocyanate there was prepared 7-chloro-6-pyridin-3-yl-3,4-dihydro-1H-pyrrolo[1,2-a]pyrazine-2,8-dicarboxylic acid 8-amide 2-[(3-trifluoromethylphenyl)amide] as a white solid, m.p. 207–209° C. MS: 466 [MH]$^+$, 464 [MH]$^+$.

(g) 7-chloro-6-pyridin-3-yl-3,4-dihydro-1H-pyrrolo[1,2-a]pyrazine-2,8-dicarboxylic acid 8-amide 2-[(4-trifluoromethylphenyl)amide]

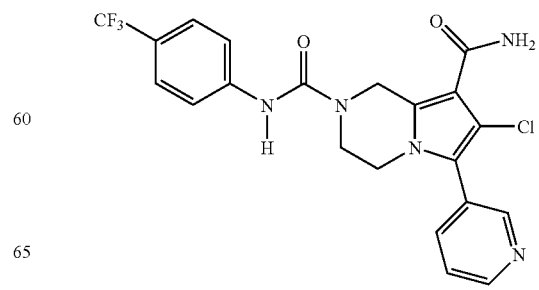

By proceeding in a similar manner to Example 4(a) above but using 4-trifluoromethylphenyl isocyanate there was prepared 7-chloro-6-pyridin-3-yl-3,4-dihydro-1H-pyrrolo[1,2-a]pyrazine-2,8-dicarboxylic acid 8-amide 2-[(4-trifluoromethylphenyl)amide] as a white solid, m.p. 273–274° C. MS: 466 [MH]$^+$, 464 [MH]$^+$.

EXAMPLE 5

7-Chloro-6-pyridin-3-yl-3,4-dihydro-1H-pyrrolo[1,2-a]pyrazine-2,8-dicarboxylic acid 8-amide 2-[(4-cyanophenyl)amide]

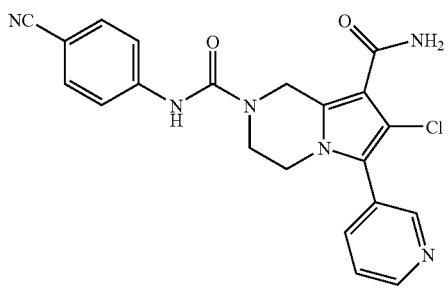

A stirred solution of triphosgene (90 mg) in dry dichloromethane (5mL), under a blanket of nitrogen at −70° C., was treated dropwise with a solution of 4-cyanoaniline (107 mg) and triethylamine (0.14 mL) in dry dichloromethane (10 mL) over 1 hour whilst maintaining the temperature below −65° C. After stirring at −70° C. for a further 3 hours the reaction mixture was treated with a suspension of 7-chloro-6-pyridin-3-yl-1,2,3,4-tetrahydropyrrolo[1,2-a]pyrazine-8-carboxylic acid amide bis trifluoroacetic acid salt (355 mg, Reference Example 1b) and triethylamine (0.28 mL) in dry dichloromethane (20mL) whilst maintaining the temperature below −65° C. The reaction mixture was then allowed to warm to room temperature and stand overnight. The reaction mixture was filtered and the solid collected was washed with water and diethyl ether to give 7-chloro-6-pyridin-3-yl-3,4-dihydro-1H-pyrrolo[1,2-a]pyrazine-2,8-dicarboxylic acid 8-amide 2-[(4-cyanophenyl)amide] as a white solid (103 mg); m.p. 271–274° C. [Elemental analysis: C, 59.24; H, 4.04; N, 19.60%. Calculated for $C_{21}H_{17}ClN_6O_2 \cdot 0.25H_2O$: C, 59.30; H, 4.15; N, 19.76%].

EXAMPLE 6

7-Chloro-6-methyl-3,4-dihydro-1H-pyrrolo[1,2-a]pyrazine-2,8-dicarboxylic acid 8-amide 2-[(3-fluorophenyl)amide]

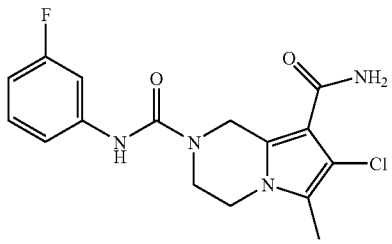

A suspension of 7-chloro-6-methyl-1,2,3,4-tetrahydropyrrolo[1,2-a]pyrazine-8-carboxylic acid amide trifluoroacetic acid salt (87 mg, Reference Example 1c) in dry dichloromethane (5 mL) was treated with dry triethylamine (0.10 mL). After stirring at room temperature for a further 10 minutes the reaction mixture was treated with a solution of 3-fluorophenyl isocyanate (34 mg) in dry dichloromethane (1 mL) and stirring continued for a further 2 hours. The reaction mixture was filtered, the solid collected washed with dichloromethane, then triturated with water and washed with water to give 7-chloro-6-methyl-3,4-dihydro-1H-pyrrolo[1,2-a]pyrazine-2,8-dicarboxylic acid 8-amide 2-[(3-fluorophenyl)amide] as a white solid, m.p. 229–231° C. [Elemental analysis: C, 52.09; H, 4.41; N, 14.96%. Calculated for $C_{16}H_{16}ClFN_4O_2 \cdot H_2O$: C, 52.11; H, 4.92; N, 15.19%].

EXAMPLE 7

(a) 7-Cyano-6-phenyl-3,4-dihydro-1H-pyrrolo[1,2-a]pyrazine-2,8-dicarboxylic acid 8-amide 2-[(3-fluorophenyl)amide]

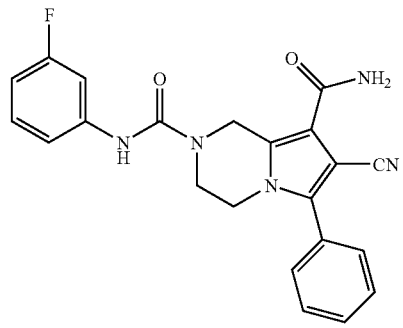

A suspension of 7-cyano-6-phenyl-1,2,3,4-tetrahydropyrrolo[1,2-a]pyrazine-8-carboxylic acid amide trifluoroacetic acid salt (217 mg, Reference Example 17) in dry dichloromethane (15 mL) was treated with dry triethylamine (0.24 mL). After stirring at room temperature for a further 10 minutes the reaction mixture was treated with a solution of 3-fluorophenyl isocyanate (78 mg) in dry dichloromethane (2 mL) and stirring continued for a further 2 hours. The reaction mixture was evaporated and the residue then treated with water. The insoluble material was collected and washed with diethyl ether and ethyl acetate, then recrystallised from industrial methylated spirits to give 7-cyano-6-phenyl-3,4-dihydro-1H-pyrrolo[1,2-a]pyrazine-2,8-dicarboxylic acid 8-amide 2-[(3-fluorophenyl)amide] (180 mg) as a white solid, m.p. 219–220° C. [Elemental analysis: C, 64.86; H, 4.32; N, 17.07; F, 4.61%. Calculated for $C_{22}H_{18}FN_5O_2 \cdot 0.25$ MeOH: C, 64.94; H, 4.66; N, 17.01; F, 4.62%].

(b) 7-cyano-6-phenyl-3,4-dihydro-1H-pyrrolo[1,2-a]pyrazine-2,8-dicarboxylic acid 8-amide 2-[(4-methoxyphenyl)amide]

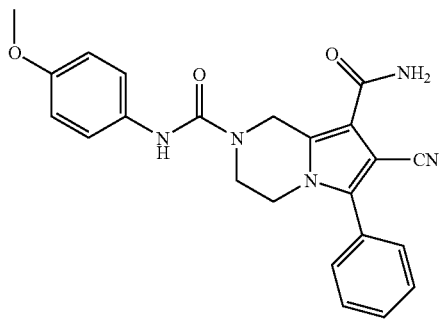

By proceeding in a similar manner to Example 7(a) above but using 4-methoxyphenyl isocyanate there was prepared 7-cyano-6-phenyl-3,4-dihydro-1H-pyrrolo[1,2-a]pyrazine-2,8-dicarboxylic acid 8-amide 2-[(4-methoxyphenyl)amide] as a white solid, m.p. 229–231° C. $^1$H NMR [(CD$_3$)$_2$SO]: δ 8.66 (s, 1H), 7.62–7.50 (m, 5H), 7.50–7.40 (bs, 1H), 7.34 (d, 2H), 7.10–6.92 (bs, 1H), 6.84 (d, 2H), 4.94 (s, 2H), 4.00 (t, 2H), 3.80 (t, 2H) and 3.71 (s, 3H).

(c) 7-cyano-6-phenyl-3,4-dihydro-1H-pyrrolo[1,2-a]pyrazine-2,8-dicarboxylic acid 8-amide 2-[(4-fluorophenyl)amide]

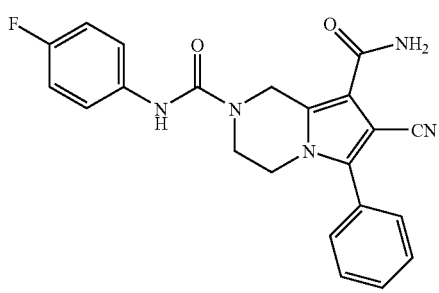

By proceeding in a similar manner to Example 7(a) above but using 4-fluorophenyl isocyanate there was prepared 7-cyano-6-phenyl-3,4-dihydro-1H-pyrrolo[1,2-a]pyrazine-2,8-dicarboxylic acid 8-amide 2-[(4-fluorophenyl)amide] as a white solid, m.p. 222–223° C. [Elemental analysis: C, 65.10; H, 4.46; N, 17.38%. Calculated for C$_{22}$H$_{18}$FN$_5$O$_2$: C, 65.50; H, 4.50; N, 17.36%].

(d) 4-[(8-carbamoyl-7-cyano-6-phenyl-3,4-dihydro-1H-pyrrolo[1,2a]pyrazine-2-carbonyl)amino]benzoic acid ethyl ester

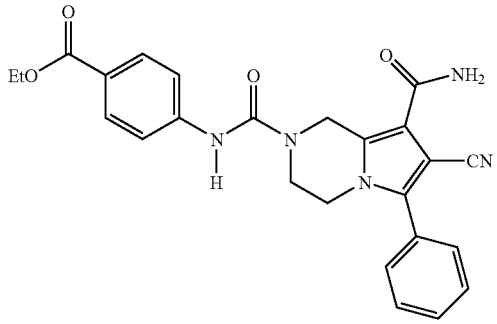

By proceeding in a similar manner to Example 7(a) above but using ethyl-4-isocyanatobenzoate there was prepared 4-[(8-carbamoyl-7-cyano-6-phenyl-3,4-dihydro-1H-pyrrolo[1,2a]pyrazine-2-carbonyl)amino]benzoic acid ethyl ester as a white solid, m.p. 265–267° C. $^1$H NMR [(CD$_3$)$_2$SO]: δ 9.21 (s, 1H), 7.87 (d, 2H), 7.70–7.37 (m, 8H), 7.17–6.95 (bs, 1H), 5.00 (s, 2H), 4.27 (q, 2H), 4.04 (t, 2H), 3.85 (t, 2H) and 1.31 (t, 3H).

(e) 7-cyano-6-phenyl-3,4-dihydro-1H-pyrrolo[1,2-a]pyrazine-2,8-dicarboxylic acid 8-amide 2-[(4-methanesulfonylphenyl)amide]

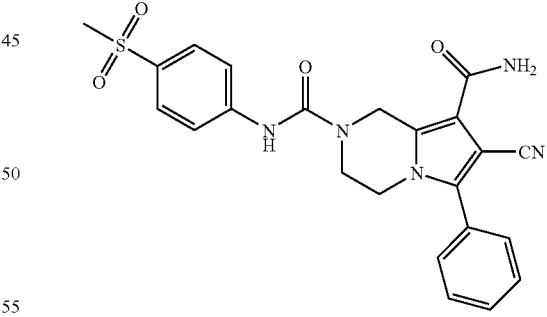

By proceeding in a similar manner to Example 7(a) above but using 4-methanesulfonylphenyl isocyanate (prepared according to the procedure of Rasmussen et. al, J. Med. Chem. 1978, 21, 1044] there was prepared 7-cyano-6-phenyl-3,4-dihydro-1H-pyrrolo[1,2-a]pyrazine-2,8-dicarboxylic acid 8-amide 2-[(4-methanesulfonylphenyl)amide] as a white solid, m.p. 260–262° C. $^1$H NMR [(CD$_3$)$_2$SO]: δ 9.31 (s, 1H), 7.81 (d, 2H), 7.72 (d, 2H), 7.62–7.50 (m, 5H), 7.42–7.50 (bs, 1H), 7.15–6.96 (bs, 1H), 5.00 (s, 2H), 4.05 (t, 2H), 3.84 (t, 2H) and 3.14 (s, 3H).

(f) 7-cyano-6-phenyl-3,4-dihydro-1H-pyrrolo[1,2-a]pyrazine-2,8-dicarboxylic acid 8-amide 2-[(tetrahydropyran-4-yl)amide]

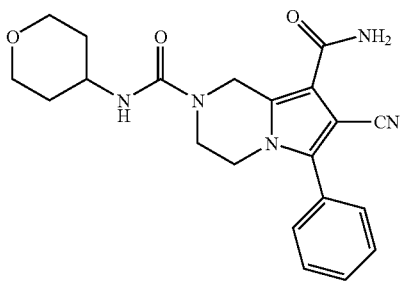

By proceeding in a similar manner to Example 7(a) above but using 4-tetrahydropyranyl isocyanate (prepared according to the procedure described in International Patent Application Number WO 96/27588, Intermediate 26) there was prepared 7-cyano-6-phenyl-3,4-dihydro-1H-pyrrolo[1,2-a]pyrazine-2,8-dicarboxylic acid 8-amide 2-[(tetrahydropyran-4-yl)amide] as a white solid, m.p. 219–221° C. [Elemental analysis: C, 62.40; H, 6.12; N, 17.41%. Calculated for $C_{21}H_{23}N_5O_3 \cdot 0.5H_2O$: C, 62.67; H, 6.01; N, 17.40%].

(g) 7-cyano-6-phenyl-3,4-dihydro-1H-pyrrolo[1l2-a]pyrazine-2,8-dicarboxylic acid 8-amide 2-tert-butylamide

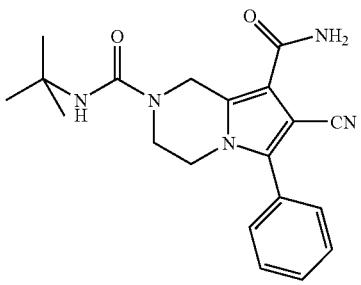

By proceeding in a similar manner to Example 7(a) above but using tert-butyl isocyanate there was prepared 7-cyano-6-phenyl-3,4-dihydro-1H-pyrrolo[1,2-a]pyrazine-2,8-dicarboxylic acid 8-amide 2-tert-butylamide as a white solid, m.p. 204–206° C. $^1$H NMR [(CD$_3$)$_2$SO]: δ 7.56–7.42 (m, 5H), 7.42–7.26 (bs, 1H), 7.06–6.86 (bs, 1H), 6.06 (s, 1H), 4.72 (s, 2H), 3.86 (t, 2H), 3.60 (t, 2H) and 1.24 (s, 9H).

(h) 7-cyano-6-phenyl-3,4-dihydro-1H-pyrrolo[1,2-a]pyrazine-2,8-dicarboxylic acid 8-amide 2-[(3-cyanophenyl)amide]

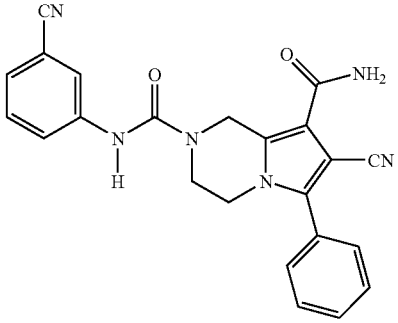

By proceeding in a similar manner to Example 7(a) above but using 3-cyanophenyl isocyanate there was prepared 7-cyano-6-phenyl-3,4-dihydro-1H-pyrrolo[1,2-a]pyrazine-2,8-dicarboxylic acid 8-amide 2-[(3-cyanophenyl)amide] as a white solid, m.p. 253–255° C. [Elemental analysis: C, 66.57; H, 4.60; N, 19.96%. Calculated for $C_{23}H_{18}N_6O_2 \cdot 0.3H_2O$: C, 66.43; H, 4.51; N, 20.21%].

(i) 7-cyano-6-phenyl-3,4-dihydro-1H-pyrrolo[1,2-a]pyrazine-2,8-dicarboxylic acid 8-amide 2-[(4-trifluoromethylphenyl)amide]

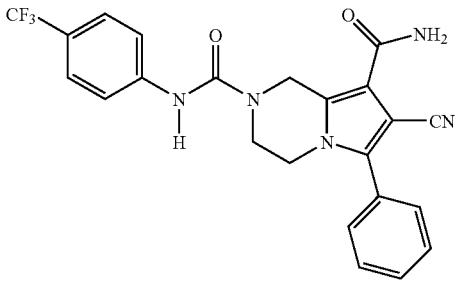

By proceeding in a similar manner to Example 7(a) above but using 4-trifluoromethylphenyl isocyanate there was prepared 7-cyano-6-phenyl-3,4-dihydro-1H-pyrrolo[1,2-a]pyrazine-2,8-dicarboxylic acid 8-amide 2-[(4-trifluoromethylphenyl)amide] as a white solid, m.p. 254–256° C. $^1$H NMR [(CD$_3$)$_2$SO]: δ 9.21 (s, 1H), 7.70 (d, 2H), 7.67–7.34 (m, 8H), 7.19–6.98 (bs, 1H), 4.99 (s, 2H), 4.04 (t, 2H) and 3.84 (t, 2H).

(j) 7-cyano-6-phenyl-3,4-dihydro-1H-pyrrolo[1,2-a]pyrazine-2,8-dicarboxylic acid 8-amide 2-[(3-trifluoromethylphenyl)amide]

By proceeding in a similar manner to Example 7(a) above but using 3-trifluoromethylphenyl isocyanate there was prepared 7-cyano-6-phenyl-3,4-dihydro-1H-pyrrolo[1,2-a]pyrazine-2,8-dicarboxylic acid 8-amide 2-[(3-trifluoromethylphenyl)amide] as a white solid, m.p. 216–218° C. $^1$H NMR [(CD$_3$)$_2$SO]: δ 9.16 (s, 1H), 7.92 (s, 1H), 7.76 (d, 1H), 7.62–7.37 (m, 7H), 7.31 (d, 1H), 7.23–6.95 (bs, 1H), 4.99 (s, 2H), 4.04 (t, 2H) and 3.84 (t, 2H).

(k) (±)-trans-7-cyano-6-phenyl-3,4-dihydro-1H-pyrrolo[1,2-a]pyrazine-2,8-dicarboxylic acid 8-amide 2-[(2-phenylcyclopropyl)amide]

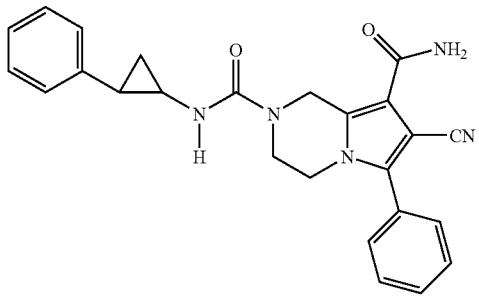

By proceeding in a similar manner to Example 7(a) above but using (±)-trans-2-phenylcyclopropyl isocyanate there was prepared (±)-trans-7-cyano-6-phenyl-3,4-dihydro-1H-pyrrolo[1,2-a]pyrazine-2,8-dicarboxylic acid 8-amide 2-[(2-phenylcyclopropyl)amide] as a white solid, m.p. 168–170° C. MS: 448 [MNa]+.

EXAMPLE 8

(a) 7-Cyano-6-phenyl-3,4-dihydro-1H-pyrrolo[1,2-a]pyrazine-2,8-dicarboxylic acid 8-amide 2-pyridin-3-ylamide

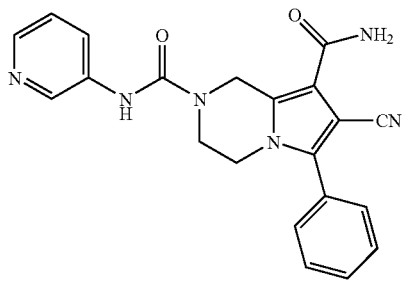

A stirred solution of triphosgene (60 mg) in dry dichloromethane (4 mL), under a blanket of nitrogen at −70° C., was treated dropwise with a solution of 3-aminopyridine (51 mg) and triethylamine (38 µL) in dry dichloromethane (4 mL) over 1 hour whilst maintaining the temperature below −65° C. After stirring at −70° C. for a further 1 hour the reaction mixture was treated portionwise with a suspension of 7-cyano-6-phenyl-1,2,3,4-tetrahydropyrrolo[1,2-a]pyrazine-8-carboxylic acid amide trifluoroacetic acid salt (147 mg, Reference Example 17) and triethylamine (0.11 mL) in dry dichloromethane (4 mL) whilst maintaining the temperature below −65° C. The reaction mixture was allowed to warm to room temperature over 3 hours and then left to stand overnight. The reaction mixture was treated with methanol (3 mL) and then evaporated. The residue was subjected to column chromatography on silica eluting with a mixture of methanol and dichloromethane (1:19, v/v). The resulting waxy solid was recrystallised from aqueous methanol to give 7-cyano-6-phenyl-3,4-dihydro-1H-pyrrolo[1,2-a]pyrazine-2,8-dicarboxylic acid 8-amide 2-pyridin-3-ylamide (72 mg) as a white solid, m.p. 264–266° C. [Elemental analysis: C, 60.70; H, 5.15; N, 20.19%. Calculated for $C_{21}H_{18}N_6O_2 \cdot 1.7H_2O$: C, 60.48; H, 5.17; N, 20.15%].

(b) 7-cyano-6-phenyl-3,4-dihydro-1H-pyrrolo[1,2-a]pyrazine-2,8-dicarboxylic acid 8-amide 2-cyclopropylamide

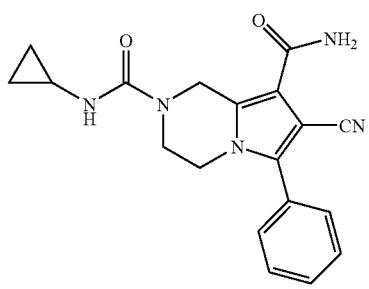

By proceeding in a similar manner to Example 8(a) above but using cyclopropylamine, and conducting the reaction at 0° C., there was prepared 7-cyano-6-phenyl-3,4-dihydro-1H-pyrrolo[1,2-a]pyrazine-2,8-dicarboxylic acid 8-amide 2-cyclopropylamide as a white solid, m.p. 144–146° C. [Elemental analysis: C, 61.00; H, 5.90; N, 18.48%. Calculated for $C_{19}H_{19}N_5O_2 \cdot 1.3H_2O$: C, 61.21; H, 5.84; N, 18.78%].

(c) 7-cyano-6-phenyl-3,4-dihydro-1H-pyrrolo[1,2-a]pyrazine-2,8-dicarboxylic acid 8-amide 2-cyclopentylamide

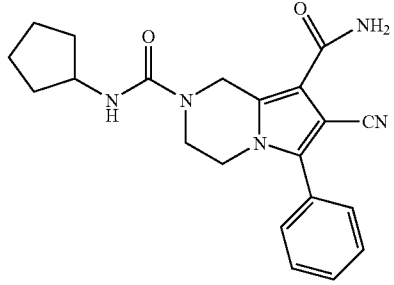

By proceeding in a similar manner to Example 8(a) above but using cyclopentylamine, and conducting the reaction at 0° C., there was prepared 7-cyano-6-phenyl-3,4-dihydro-1H-pyrrolo[1,2-a]pyrazine-2,8-dicarboxylic acid 8-amide 2-cyclopentylamide as a white solid, m.p. 158–160° C. $^1$H NMR [(CD$_3$)$_2$SO]: δ 7.55–7.45 (m, 5H), 7.45–7.28 (bs, 1H), 7.10–6.80 (bs, 1H), 6.53 (d, 1H), 4.79 (s, 2H), 3.99–3.87 (m, 3H), 3.66 (t, 2H), 1.87–1.75 (m, 2H), 1.71–1.58 (m, 2H) and 1.54–1.35 (m, 4H).

(d) (±) 7-cyano-6-phenyl-3,4-dihydro-1H-pyrrolo[1,2-a]pyrazine-2,8-dicarboxylic acid 8-amide 2-exo-bicyclo[2.2.1.]hept-2-ylamide

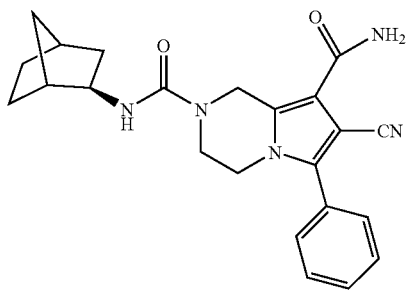

By proceeding in a similar manner to Example 8(a) above but using (±)-exo-2-aminonorbornane, and conducting the reaction at 0° C., there was prepared (±)-7-cyano-6-phenyl-3,4-dihydro-1H-pyrrolo[1,2-a]pyrazine-2,8-dicarboxylic acid 8-amide 2-exo-bicyclo[2.2.1.]hept-2-ylamide as a white solid, m.p. 158–160° C. $^1$H NMR [(CD$_3$)$_2$SO]: δ 7.55–7.45 (m, 5H), 7.30–7.43 (bs, 1H), 7.00–6.90 (bs, 1H), 6.30 (d, 1H), 4.74 (q, 2H), 3.86 (t, 2H), 3.64–3.58 (m, 2H), 3.43–3.36 (m, 1H), 2.14 (m, 1H), 2.05 (m, 1H) and 1.55–0.97 (m, 8H).

(e) (±) 7-cyano-6-phenyl-3,4-dihydro-1H-pyrrolo[1,2-a]pyrazine-2,8-dicarboxylic acid 8-amide 2-endo-bicyclo[2.2.1.]hept-2-ylamide

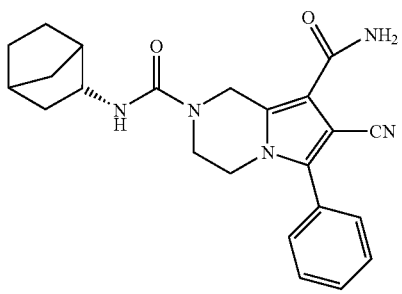

By proceeding in a similar manner to Example 8(a) above but using (_)-endo-2-aminonorbornane, and conducting the reaction at 0° C., there was prepared (±) 7-cyano-6-phenyl-3,4-dihydro-1H-pyrrolo[1,2-a]pyrazine-2,8-dicarboxylic acid 8-amide 2-endo-bicyclo[2.2.1.]hept-2-ylamide as a white solid, m.p. 191–192° C. $^1$H NMR [(CD$_3$)$_2$SO]: δ 7.56–7.43 (m, 5H), 7.43–7.27 (bs, 1H), 7.05–6.86 (bs, 1H), 6.45 (d, 1H), 4.76 (s, 2H), 3.87 (t, 2H), 3.79 (m, 1H), 3.64 (t, 2H), 2.23 (m, 1H), 2.08 (m, 1H) and 1.83–1.73 (m, 1H), 1.59–1.50 (m, 1H), 1.46–1.15 (m, 5H) and 0.990.91 (m, 1H).

(f) 7-cyano-6-phenyl-3,4-dihydro-1H-pyrrolo[1,2-a]pyrazine-2,8-dicarboxylic acid 8-amide 2-[(4-morpholin-4-ylmethylphenyl)amide]

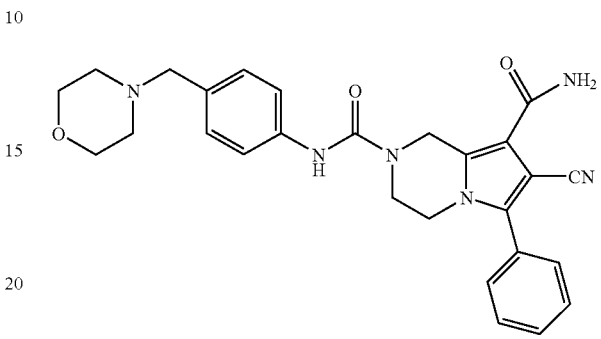

By proceeding in a similar manner to Example 8(a) above but using 4-morpholin-4-ylmethylphenylamine (Reference Example 47), conducting the reaction at 0° C. and quenching the reaction with a 0.5 M aqueous solution of sodium carbonate to pH 9, there was prepared 7-cyano-6-phenyl-3,4-dihydro-1H-pyrrolo[1,2-a]pyrazine-2,8-dicarboxylic acid 8-amide 2-[(4-morpholin-4-ylmethylphenyl)amide] as a white solid, m.p. 145–160° C. $^1$H NMR [(CD$_3$)$_2$SO]: δ 8.78 (s, 1H), 7.62–7.30 (m, 8H), 7.23–7.10 (bd, 2H), 7.09–6.94 (bs, 1H), 4.92 (s, 2H), 3.98 (t, 2H), 3.77 (t, 2H), 3.61–3.52 (bs, 4H), 3.34 (s, 2H) and 2.39–2.18 (bs, 4H).

(g) 7-cyano-6-phenyl-3,4-dihydro-1H-pyrrolo[1,2-a]pyrazine-2,8-dicarboxylic acid 8-amide 2-{[4-(4-methylpiperazin-1-ylmethyl)phenyl]amide}

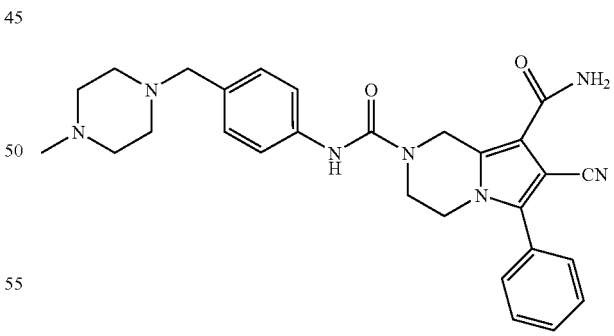

By proceeding in a similar manner to Example 8(a) above but using 4-(4-methylpiperazin-1-ylmethyl)phenylamine (Reference Example 50), conducting the reaction at 0° C. and quenching the reaction with a 0.5 M aqueous solution of sodium carbonate to pH 9, there was prepared 7-cyano-6-phenyl-3,4-dihydro-1H-pyrrolo[1,2-a]pyrazine-2,8-dicarboxylic acid 8-amide 2-{[4-(4-methylpiperazin-1-ylmethyl)phenyl]amide} as a white solid, m.p. >200° C. (dec). MS: 498 [MH]$^+$.

(h) 7-cyano-6-2henyl-3,4-dihydro-1H-pyrrolo[112-a]pyrazine-2,8-dicarboxylic acid 8-amide 2-{[4-(2-morpholin-4-ylethoxy)phenyl]amide}

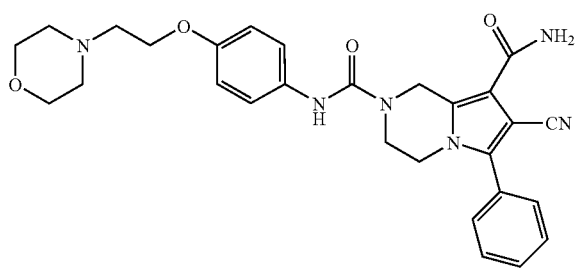

By proceeding in a similar manner to Example 8(a) above but using 4-(2-morpholin-4-ylethoxy)phenylamine (Reference Example 52a), conducting the reaction at 0° C. and quenching the reaction with a 1 M aqueous solution of sodium carbonate to pH 9, there was prepared 7-cyano-6-phenyl-3,4-dihydro-1H-pyrrolo[1,2-a]pyrazine-2,8-dicarboxylic acid 8-amide 2-{[4-(2-morpholin-4-ylethoxy)phenyl]amide} as a white solid, m.p. 169–171° C. MS: 515 [MH]$^+$.

(i) 7-cyano-6-phenyl-3,4-dihydro-1H-pyrrolo[1,2-a]pyrazine-2,8-dicarboxylic acid 8-amide 2-{[4-(morpholin-4-yl-acetyl)-phenyl]-amide}

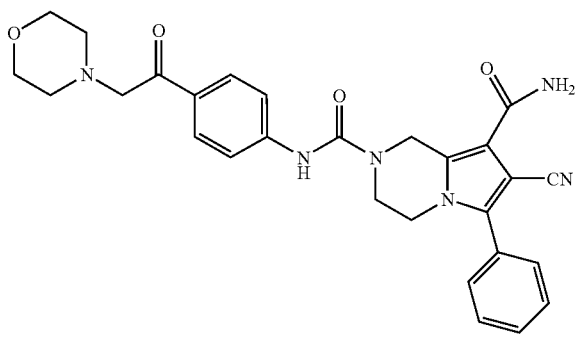

By proceeding in a similar manner to Example 8(a) above but using 1-(4-aminophenyl)-2-morpholin-4-ylethanone (Reference Example 52f), conducting the reaction at 0° C. and quenching the reaction with a 0.5 M aqueous solution of sodium carbonate to pH 9, there was prepared 7-cyano-6-phenyl-3,4-dihydro-1H-pyrrolo[1,2-a]pyrazine-2,8-dicarboxylic acid 8-amide 2-{[4-(morpholin-4-yl-acetyl)-phenyl]-amide} as a yellow solid, m.p. softens 150–170° C. [Elemental analysis: C, 63.80; H, 5.89; N, 16.30%. Calculated for $C_{28}H_{28}N_6O_4 \cdot 0.7H_2O$: C, 64.04; H, 5.64; N, 16.00%].

(j) 7-cyano-6-phenyl-3,4-dihydro-1H-pyrrolo[1,2-a]pyrazine-2,8-dicarboxylic acid 8-amide 2-[(4-cyanophenyl)amide]

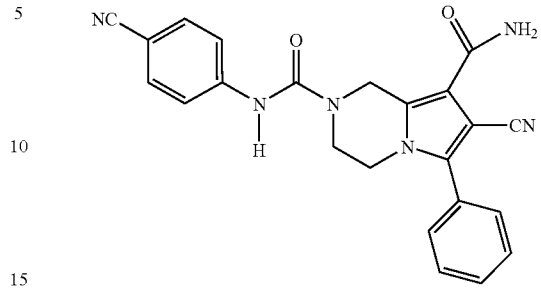

By proceeding in a similar manner to Example 8(a) above but using 4-cyanoaniline there was prepared 7-cyano-6-phenyl-3,4-dihydro-1H-pyrrolo[1,2-a]pyrazine-2,8-dicarboxylic acid 8-amide 2-[(4-cyanophenyl)amide] as a white solid, m.p. 168–170° C. $^1$H NMR [(CD$_3$)$_2$SO]: δ 9.31 (s, 1H), 7.72 (d, 2H), 7.68 (d, 2H), 7.62–7.41 (m, 6H), 7.18–6.96 (bs, 1H), 4.98 (s, 2H), 4.04 (t, 2H) and 3.84 (t, 2H).

(k) 7-cyano-6-phenyl-3,4-dihydro-1H-pyrrolo[1,2-a]pyrazine-2,8-dicarboxylic acid 8-amide 2-pyridin-4-ylamide

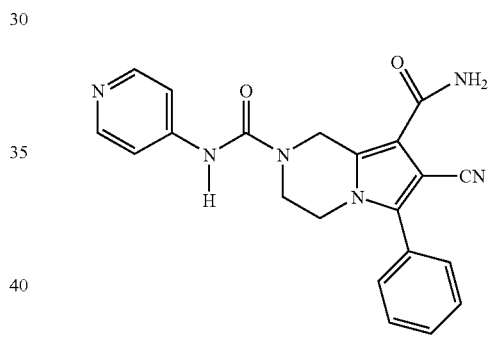

By proceeding in a similar manner to Example 8(a) above but using 4-aminopyridine there was prepared 7-cyano-6-phenyl-3,4-dihydro-1H-pyrrolo[1,2-a]pyrazine-2,8-dicarboxylic acid 8-amide 2-pyridin-4-ylamide as a white solid, m.p. 245–247° C. MS: 387 [MH]$^+$.

(l) 7-cyano-6-phenyl-3,4-dihydro-1H-pyrrolo[1,2-a]pyrazine-2,8-dicarboxylic acid 8-amide 2-indan-2-ylamide

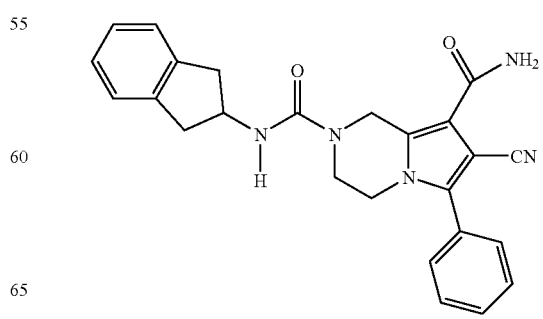

By proceeding in a similar manner to Example 8(a) above but using 2-indanamine hydrochloride there was prepared 7-cyano-6-phenyl-3,4-dihydro-1H-pyrrolo[1,2-a]pyrazine-2,8-dicarboxylic acid 8-amide 2-indan-2-ylamide as a white solid, m.p. 273–275° C. [Elemental analysis: C, 69.34; H, 5.36; N, 16.29%. Calculated for $C_{25}H_{23}N_5O_4 \cdot 0.5H_2O$: C, 69.11; H, 5.57; N, 16.12%].

(m) 7-cyano-6-phenyl-3,4-dihydro-1H-pyrrolo[1,2-a]pyrazine-2,8-dicarboxylic acid 8-amide 2-quinolin-6-ylamide

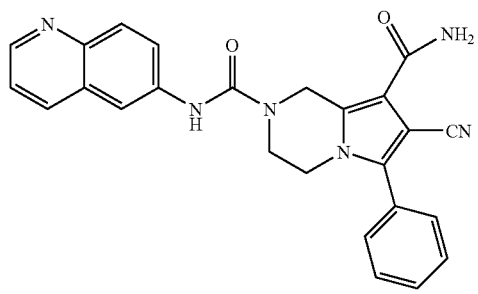

By proceeding in a similar manner to Example 8(a) above but using 6-aminoquinoline there was prepared 7-cyano-6-phenyl-3,4-dihydro-1H-pyrrolo[1,2-a]pyrazine-2,8-dicarboxylic acid 8-amide 2-quinolin-6-ylamide as a white solid, m.p. 269–270° C. MS: 437 [MH]$^+$.

(n) 7-cyano-6-phenyl-3,4-dihydro-1H-pyrrolo[1,2-a]pyrazine-2,8-dicarboxylic acid 8-amide 2-[(4-chlorophenyl)amide]

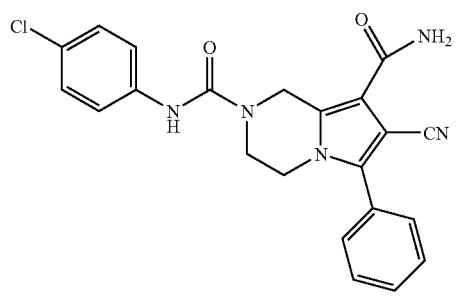

By proceeding in a similar manner to Example 8(a) above but using 4-chloroaniline there was prepared 7-cyano-6-phenyl-3,4-dihydro-1H-pyrrolo[1,2-a]pyrazine-2,8-dicarboxylic acid 8-amide 2-[(4-chlorophenyl)amide] as a white solid, m.p. 252–254° C. $^1$H NMR [(CD$_3$)$_2$SO]: δ 8.95 (s, 1H), 7.62–7.39 (m, 8H), 7.31 (d, 2H), 7.17–6.96 (bs, 1H), 4.96 (s, 2H), 4.01 (t, 2H) and 3.81 (t, 2H).

(o) 7-cyano-6-phenyl-3,4-dihydro-1H-pyrrolo[1,2-a]pyrazine-2,8-dicarboxylic acid 8-amide 2-{[1-(morholine-4-carbonyl)piperidin-4-yl]amide}

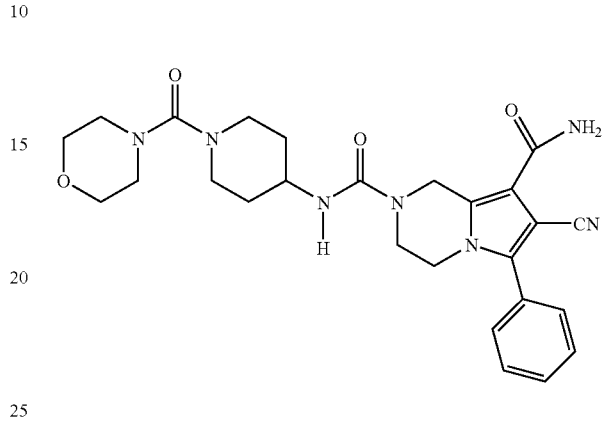

By proceeding in a similar manner to Example 8(a) above but using (4-amino-piperidin-1-yl)-morpholin-4-yl-methanone, trifluoroacetic acid salt (Reference Example 59) there was prepared 7-cyano-6-phenyl-3,4-dihydro-1H-pyrrolo[1,2-a]pyrazine-2,8-dicarboxylic acid 8-amide 2-{[1-(morpholine-4-carbonyl)piperidin-4-yl]amide} as a white solid, m.p. 170° C. (dec). MS: 528 [MNa]$^+$.

(p) 4-[(8-carbamoyl-7-cyano-6-phenyl-3,4-dihydro-1H-pyrrolo[1,2-a]pyrazine-2-carbonyl)amino]piperidine-1-carboxylic acid isopropyl ester

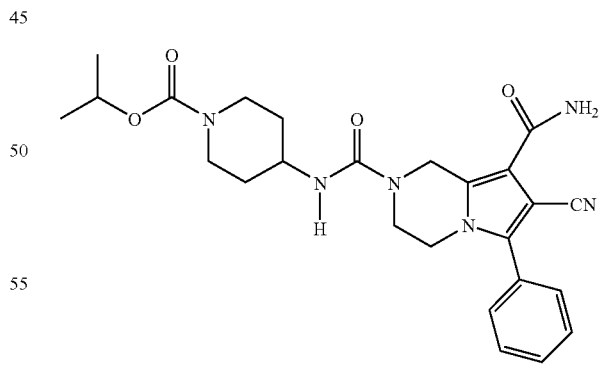

By proceeding in a similar manner to Example 8(a) above but using 4-amino-piperidine-1-carboxylic acid isopropyl ester, trifluoroacetic acid salt (Reference Example 60) there was prepared 4-[(8-carbamoyl-7-cyano-6-phenyl-3,4-dihydro-1H-pyrrolo[1,2-a]pyrazine-2-carbonyl)amino]piperidine-1-carboxylic acid isopropyl ester as a white solid, m.p. 172–174° C. MS: 479 [MH]$^+$.

EXAMPLE 9

(a) 7-Cyano-6-cyclopropyl-3,4-dihydro-1H-pyrrolo[1,2-a]pyrazine-2,8-dicarboxylic acid 8-amide 2-[(4-fluorophenyl)amide]

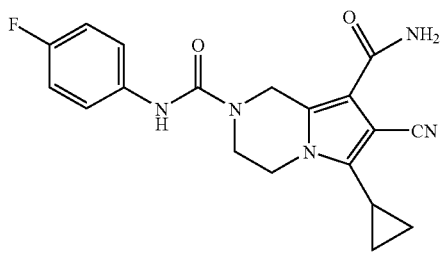

A suspension of 7-cyano-6-cyclopropyl-1,2,3,4-tetrahydropyrrolo[1,2-a]pyrazine-8-carboxylic acid amide trifluoroacetic acid salt [200 mg, Example 44(b)] in dry dichloromethane (15 mL) was treated with dry triethylamine (0.24 mL), then with a solution of 4-fluorophenyl isocyanate (80 mg) in dry dichloromethane (2 mL). After stirring at room temperature for a further 5 hours the reaction mixture was left to stand overnight and then evaporated. The residue was subjected to column chromatography on silica eluting with a mixture of dichloromethane and methanol (9:1, v/v) to give 7-cyano-6-cyclopropyl-3,4-dihydro-1H-pyrrolo[1,2-a]pyrazine-2,8-dicarboxylic acid 8-amide 2-[(4-fluorophenyl)amide] (130 mg) as a white solid, m.p. 232–234° C. [Elemental analysis: C, 61.85; H, 4.61; N, 18.87%. Calculated for $C_{19}H_{18}FN_5O_2$: C, 62.11; H, 4.94; N, 19.07%].

(b) 7-cyano-6-cyclopropyl-3,4-dihydro-1H-pyrrolo[1,2-a]pyrazine-2,8-dicarboxylic acid 8-amide 2-[(tetrahydropyran-4-yl)amide]

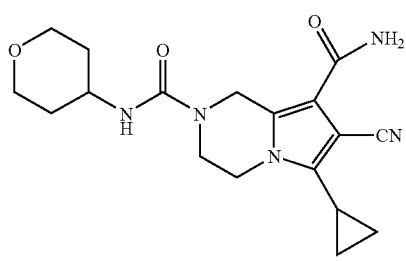

By proceeding in a similar manner to Example 9(a) above but using 4-tetrahydropyranyl isocyanate (prepared according to the procedure described in International Patent Application Number WO 96/27588, Intermediate 26) there was prepared 7-cyano-6-cyclopropyl-3,4-dihydro-1H-pyrrolo[1,2-a]pyrazine-2,8-dicarboxylic acid 8-amide 2-[(tetrahydropyran-4-yl)amide] as a white solid, m.p. 151–153° C. MS: 358 [MH]$^+$.

(c) 4-[(8-carbamoyl-7-cyano-6-cyclopropyl-3,4-dihydro-1H-pyrrolo[1,2a]pyrazine-2-carbonyl)amino]benzoic acid ethyl ester

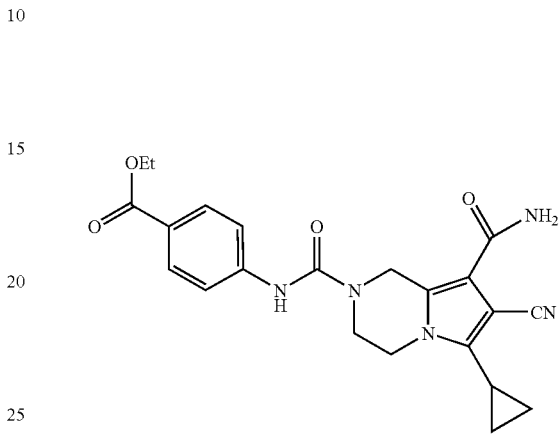

By proceeding in a similar manner to Example 9(a) above but using ethyl-4-isocyanatobenzoate there was prepared 4-[(8-carbamoyl-7-cyano-6-cyclopropyl-3,4-dihydro-1H-pyrrolo[1,2a]pyrazine-2-carbonyl)amino]benzoic acid ethyl ester as a white solid, m.p. 262–264° C. [Elemental analysis: C, 62.91; H, 5.90; N, 16.75%; Calculated for $C_{22}H_{23}N_5O_4$: C, 62.70; H, 5.50; N, 16.62%].

(d) 7-cyano-6-cyclopropyl-3,4-dihydro-1H-pyrrolo[1,2-a]pyrazine-2,8-dicarboxylic acid 8-amide 2-[(4-chlorophenyl)amide]

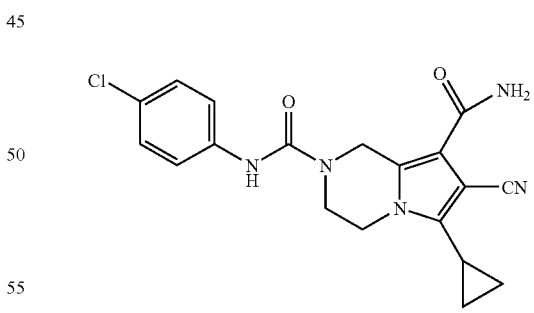

By proceeding in a similar manner to Example 9(a) above but using 4-chlorophenyl isocyanate there was prepared 7-cyano-6-cyclopropyl-3,4-dihydro-1H-pyrrolo[1,2-a]pyrazine-2,8-dicarboxylic acid 8-amide 2-[(4-chlorophenyl)amide] as a white solid, m.p. 254–257° C. $^1$H NMR [(CD$_3$)$_2$SO]: δ 8.97 (s, 1H), 7.49 (d, 2H), 7.40–7.20 (d and bs overlapping, 3H), 6.90–6.72 (bs, 1H), 4.83 (s, 2H), 4.08 (t, 2H), 3.89 (t, 2H), 1.93–1.84 (m, 1H), 1.03–0.96 (m, 2H) and 0.88–0.78 (m, 2H).

(e) 7-cyano-6-cyclopropyl-3,4-dihydro-1H-pyrrolo[1,2-a]pyrazine-2,8-dicarboxylic acid 8-amide 2-[(4-methanesulfonylphenyl)amide]

(g) 7-cyano-6-cyclopropyl-3,4-dihydro-1H-pyrrolo[1,2-a]pyrazine-2,8-dicarboxylic acid 8-amide 2-[(3-chloro-4-fluorophenyl)amide]

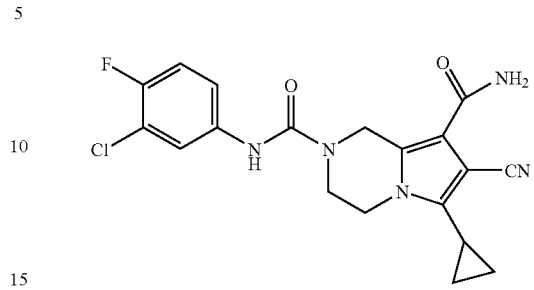

By proceeding in a similar manner to Example 9(a) above but using 3-chloro-4-fluorophenyl isocyanate there was prepared 7-cyano-6-cyclopropyl-3,4-dihydro-1H-pyrrolo[1,2-a]pyrazine-2,8-dicarboxylic acid 8-amide 2-[(3-chloro-4-fluorophenyl)amide] as a white solid, m.p. 210–211° C. $^1$H NMR [(CD$_3$)$_2$SO]: δ 9.03 (s, 1H), 7.72 (dd, 1H), 7.44–7.37 (m, 1H), 7.36–7.16 (bs and t overlapping, 2H), 6.99–6.70 (bs, 1H), 4.83 (s, 2H), 4.09 (t, 2H), 3.89 (t, 2H), 1.93–1.84 (m, 1H), 1.05–0.93 (m, 2H) and 0.91–0.79 (m, 2H).

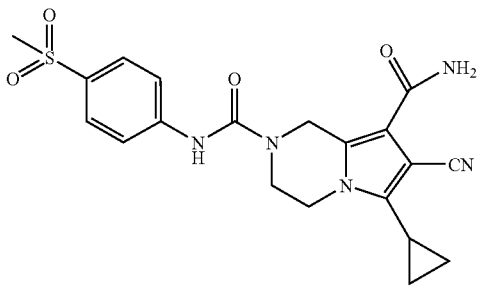

By proceeding in a similar manner to Example 9(a) above but using 4-methanesulfonylphenyl isocyanate (prepared according to the procedure of Rasmussen et. al, J. Med. Chem. 1978, 21, 1044) there was prepared 7-cyano-6-cyclopropyl-3,4-dihydro-1H-pyrrolo[1,2-a]pyrazine-2,8-dicarboxylic acid 8-amide 2-[(4-methanesulfonylphenyl)amide] as a white solid, m.p. 272–274° C. $^1$H NMR [(CD$_3$)$_2$SO]: δ 9.33 (s, 1H), 7.80 (d, 2H), 7.70 (d, 2H), 7.45–7.15 (bs, 1H), 7.02–6.71 (bs, 1H), 4.86 (s, 2H), 4.10 (t, 2H), 3.92 (t, 2H), 3.15 (s, 3H), 1.94–1.84 (m, 1H), 1.05–0.92 (m, 2H) and 0.91–0.77 (m, 2H).

(f) (±)-trans-7-cyano-6-cyclopropyl-3,4-dihydro-1H-pyrrolo[1,2-a]pyrazine-2,8-dicarboxylic acid 8-amide 2-[(2-phenylcyclopropyl)amide]

(h) 7-cyano-6-cyclopropyl-3,4-dihydro-1H-pyrrolo[1,2-a]pyrazine-2,8-dicarboxylic acid 8-amide 2-[(4-trifluoromethylphenyl)amide]

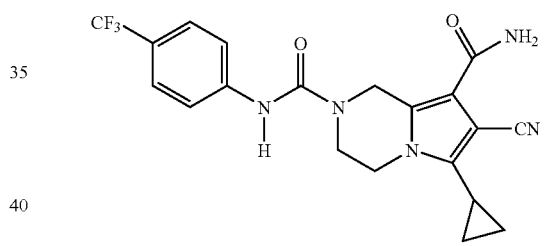

By proceeding in a similar manner to Example 9(a) above but using 4-trifluoromethylphenyl isocyanate there was prepared 7-cyano-6-cyclopropyl-3,4-dihydro-1H-pyrrolo[1,2-a]pyrazine-2,8-dicarboxylic acid 8-amide 2-[(4-trifluoromethylphenyl)amide] as a white solid, m.p. 247–248° C. [Elemental analysis: C, 57.98; H, 4.17; N, 16.96%; Calculated for C$_{20}$H$_{18}$F$_3$N$_5$O$_2$: C, 57.55; H, 4.35; N, 16.78%].

(i) 7-cyano-6-cyclopropyl-3,4-dihydro-1H-pyrrolo[1,2-a]pyrazine-2,8-dicarboxylic acid 8-amide 2-[(3-trifluoromethylphenyl)amide]

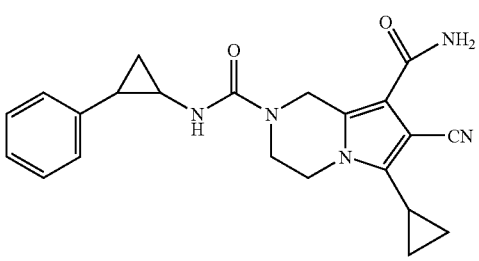

By proceeding in a similar manner to Example 9(a) above but using (i)-trans-2-phenylcyclopropyl isocyanate there was prepared (±)-trans-7-cyano-6-cyclopropyl-3,4-dihydro-1H-pyrrolo[1,2-a]pyrazine-2,8-dicarboxylic acid 8-amide 2-[(2-phenylcyclopropyl) amide] as a white solid, m.p. 136–138° C. MS: 390 [MH]$^+$.

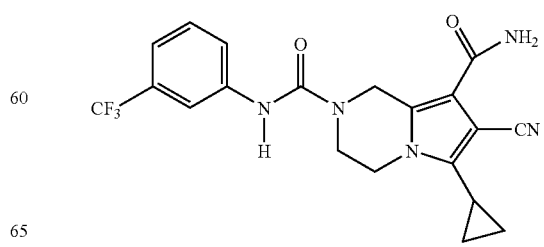

By proceeding in a similar manner to Example 9(a) above but using 3-trifluoromethylphenyl isocyanate there was prepared 7-cyano-6-cyclopropyl-3,4-dihydro-1H-pyrrolo[1,2-a]pyrazine-2,8-dicarboxylic acid 8-amide 2-[(3-trifluoromethylphenyl)amide] as a white solid, m.p. 244–246° C. [Elemental analysis: C, 57.46; H, 4.44; N, 16.76%; Calculated for $C_{20}H_{18}F_3N_5O_2$: C, 57.55; H, 4.35; N, 16.78%].

(j) 7-cyano-6-cyclopropyl-3,4-dihydro-1H-pyrrolo[1,2-a]pyrazine-2,8-dicarboxylic acid 8-amide 2-cyclohexylamide

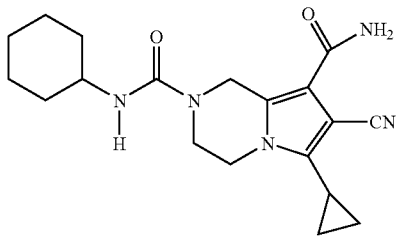

By proceeding in a similar manner to Example 9(a) above but using cyclohexyl isocyanate there was prepared 7-cyano-6-cyclopropyl-3,4-dihydro-1H-pyrrolo[1,2-a]pyrazine-2,8-dicarboxylic acid 8-amide 2-cyclohexylamide as a white solid, m.p. 215–217° C. MS: 356 [MH]$^+$.

(k) 7-cyano-6-cyclopropyl-3,4-dihydro-1H-pyrrolo[1,2-a]pyrazine-2,8-dicarboxylic acid 8-amide 2-[(5-methylthiophen-2-yl)amide]

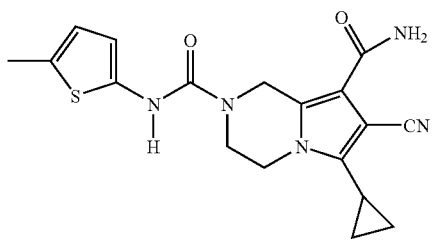

By proceeding in a similar manner to Example 9(a) above but using a 0.3M solution of 2-isocyanoto-5-methylthiophene in toluene (Reference Example 57) there was prepared 7-cyano-6-cyclopropyl-3,4-dihydro-1H-pyrrolo[1,2-a]pyrazine-2,8-dicarboxylic acid 8-amide 2-[(5-methylthiophen-2-yl)amide] as a white solid, m.p. 238–244° C. (dec). MS: 392 [MNa]$^+$.

EXAMPLE 10

(a) 7-Cyano-6-cyclopropyl-3,4-dihydro-1H-pyrrolo[1,2-a]pyrazine-2,8-dicarboxylic acid 8-amide 2-{[4-(4-methylpiperazine-1-carbonyl)phenyl]amide}

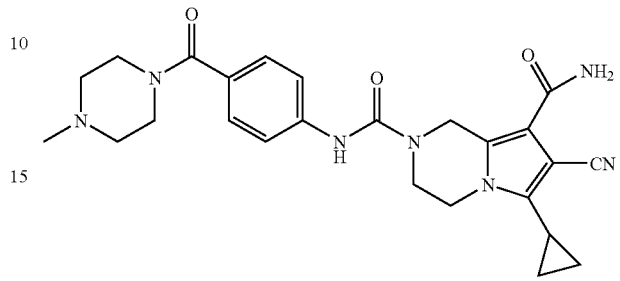

A stirred solution of triphosgene (59 mg) in dry dichloromethane (10 mL), under a blanket of nitrogen at 0° C., was treated dropwise with a solution of 1-(4-aminobenzoyl)-4-methylpiperazine (121 mg, Reference Example 48) and triethylamine (0.29 mL) in dichloromethane (12 mL) over 5 minutes whilst maintaining the temperature below 5° C.

After stirring at 0° C. for a further 5 minutes the mixture was treated portionwise with 7-cyano-6-cyclopropyl-1,2,3,4-tetrahydropyrrolo[1,2-a]pyrazine-8-carboxylic acid amide trifluoroacetic acid salt [172 mg, Example 44(b)] whilst maintaining the temperature below 5° C. The resulting reaction mixture was allowed to warm to room temperature over 3 hours and then stand overnight. The reaction mixture was treated with saturated aqueous sodium hydrogen carbonate solution (20 mL), then the layers separated and the aqueous further extracted twice with dichloromethane (25 mL). The combined organic extracts were dried over magnesium sulfate, then evaporated. The residue was subjected to column chromatography on silica eluting with dichloromethane then with a mixture of methanol and dichloromethane (1:19, v/v) and then with a mixture of methanol and dichloromethane (1:9, v/v) to give 7-cyano-6-cyclopropyl-3,4-dihydro-1H-pyrrolo[1,2-a]pyrazine-2,8-dicarboxylic acid 8-amide 2-{[4-(4-methylpiperazine-1-carbonyl)-phenyl]amide} (170 mg) as a white solid, m.p. 150–156° C. $^1$H NMR [$(CD_3)_2SO$]: δ 9.05 (s, 1H), 7.51 (d, 2H), 7.39–7.23 (d and bs overlapping, 3H), 6.92–6.72 (bs, 1H), 4.85 (s, 2H), 4.10 (t, 2H), 3.90 (t, 2H), 3.64–3.28 (bs, 4H), 2.38–2.20 (bs, 4H), 2.19 (s, 3H), 1.92–1.85 (m, 1H), 1.03–0.97 (m, 2H) and 0.88–0.82 (m, 2H).

(b) 7-cyano-6-cyclopropyl-3,4-dihydro-1H-pyrrolo[1,2-a]pyrazine-2,8-dicarboxylic acid 8-amide 2-[(4-morpholin-4-ylmethylphenyl)amide]

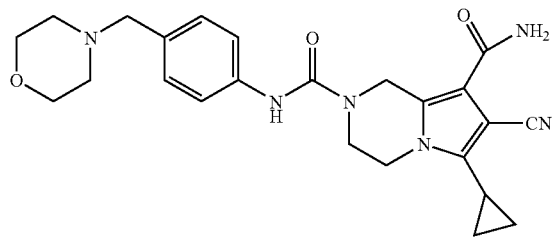

By proceeding in a similar manner to Example 10(a) above but using 4-morpholin-4-ylmethylphenylamine (Reference Example 47) there was prepared 7-cyano-6-cyclopropyl-3,4-dihydro-1H-pyrrolo[1,2-a]pyrazine-2,8-dicarboxylic acid 8-amide 2-[(4-morpholin-4-ylmethylphenyl) amide] as a white solid, m.p. 195–197° C. [Elemental analysis: C, 63.54; H, 6.32; N, 18.20%. Calculated for $C_{24}H_{28}N_6O_3 \cdot 0.4H_2O$: C, 63.25; H, 6.37; N, 18.44%].

(c) 7-cyano-6-cyclopropyl-3,4-dihydro-1H-pyrrolo[1,2-a]pyrazine-2,8-dicarboxylic acid 8-amide 2-{[4-(4-methylpiperazin-1-ylmethyl)phenyl]amide}

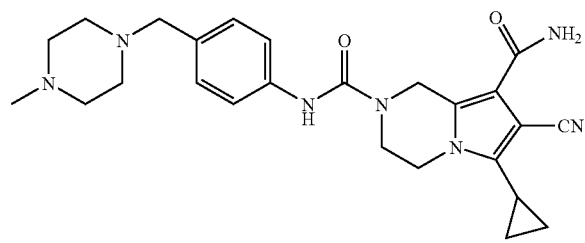

By proceeding in a similar manner to Example 10(a) above but using 4-(4-methylpiperazin-1-ylmethyl)phenylamine (Reference Example 50) there was prepared 7-cyano-6-cyclopropyl-3,4-dihydro-1H-pyrrolo[1,2-a]pyrazine-2,8-dicarboxylic acid 8-amide 2-{[4-(4-methylpiperazin-1-ylmethyl)phenyl]amide} as a white solid, m.p. >200° C. (dec). MS: 462 $[MH]^+$.

(d) 7-cyano-6-cyclopropyl-3,4-dihydro-1H-pyrrolo[1,2-a]pyrazine-2,8-dicarboxylic acid 8-amide 2-{[4-(2-morpholin-4-ylethoxy)phenyl]amide}

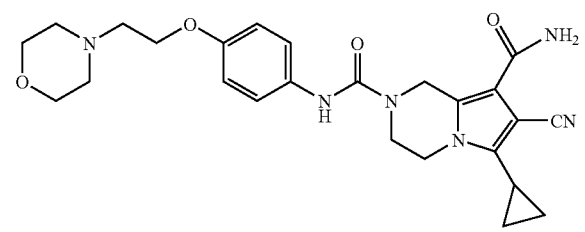

By proceeding in a similar manner to Example 10(a) above but using 4-(2-morpholin-4-ylethoxy)phenylamine (Reference Example 52a) there was prepared 7-cyano-6-cyclopropyl-3,4-dihydro-1H-pyrrolo[1,2-a]pyrazine-2,8-dicarboxylic acid 8-amide 2-{[4-(2-morpholin-4-ylethoxy)phenyl]amide} as a white solid, m.p. 186–187° C. [Elemental analysis: C, 61.80; H, 6.25; N, 17.20%. Calculated for $C_{25}H_{30}N_6O_4 \cdot 0.5H_2O$: C, 61.59; H, 6.41; N, 17.24%].

(e) 7-cyano-6-cyclopropyl-3,4-dihydro-1H-pyrrolo[1,2-a]pyrazine-2,8-dicarboxylic acid 8-amide 2-{[4-(morpholine-4-carbonyl)phenyl]amide}

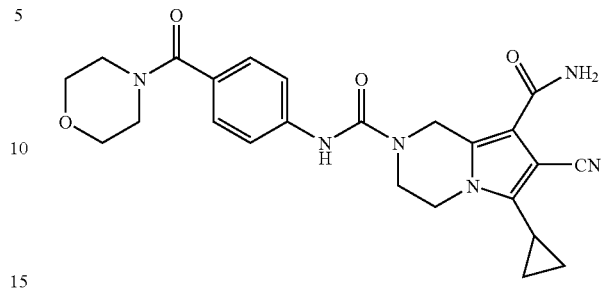

By proceeding in a similar manner to Example 10(a) above but using (4-aminophenyl)morpholin-4-ylmethanone (Reference Example 52b) there was prepared 7-cyano-6-cyclopropyl-3,4-dihydro-1H-pyrrolo[1,2-a]pyrazine-2,8-dicarboxylic acid 8-amide 2-{[4-(morpholine-4-carbonyl)phenyl]amide} as a white solid, m.p. 230–232° C. $^1$H NMR [$(CD_3)_2SO$]: δ 9.01 (s, 1H), 7.48 (d, 2H), 7.38–7.12 (d and bs overlapping, 3H), 6.86–6.68 (bs, 1H), 4.82 (s, 2H), 4.06 (t, 2H), 3.87 (t, 2H), 3.69–3.30 (2×bs overlapping, 8H), 1.90–1.80 (m, 1H), 1.01–0.93 (m, 2H) and 0.86–0.78 (m, 2H).

(f) 7-cyano-6-cyclopropyl-3,4-dihydro-1H-pyrrolo[1,2-a]pyrazine-2,8-dicarboxylic acid 8-amide 2-[(4-cyanophenyl)amide]

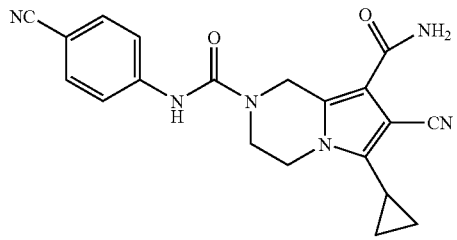

By proceeding in a similar manner to Example 10(a) above but using 4-cyanoaniline there was prepared 7-cyano-6-cyclopropyl-3,4-dihydro-1H-pyrrolo[1,2-a]pyrazine-2,8-dicarboxylic acid 8-amide 2-[(4-cyanophenyl)amide] as a white solid, m.p. 262–263° C. [Elemental analysis: C, 63.30; H, 4.91; N, 22.05%; Calculated for $C_{20}H_{18}N_6O_2 \cdot 0.2H_2O$: C, 63.55; H, 4.91; N, 22.23%].

(g) 7-cyano-6-cyclopropyl-3,4-dihydro-1H-pyrrolo[1,2-a]pyrazine-2,8-dicarboxylic acid 8-amide 2-[(3,4-difluorophenyl)amide]

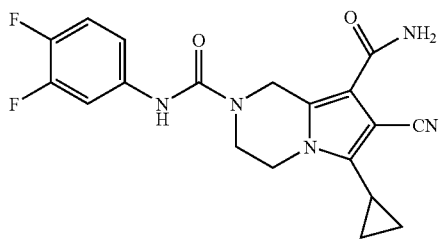

By proceeding in a similar manner to Example 10(a) above but using 3,4-difluoroaniline there was prepared 7-cyano-6-cyclopropyl-3,4-dihydro-1H-pyrrolo[1,2-a]pyrazine-2,8-dicarboxylic acid 8-amide 2-[(3,4-difluorophenyl)amide] as an off white solid, 208–210° C.

$^1$H NMR [(CD$_3$)$_2$SO]: δ 9.05 (s, 1H), 7.63–7.17 (m, 4H), 6.99–6.71 (bs, 1H), 4.84 (s, 2H), 4.09 (t, 2H), 3.89 (t, 2H), 1.92–1.84 (m, 1H), 1.04–0.92 (m, 2H) and 0.90–0.79 (m, 2H).

(h) 7-cyano-6-cyclopropyl-3,4-dihydro-1H-pyrrolo[1,2-a]pyrazine-2,8-dicarboxylic acid 8-amide 2-{[4-(4-fluorophenoxy)phenyl]amide

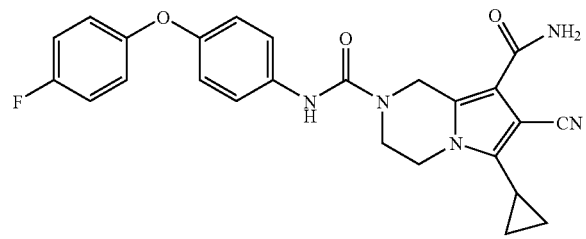

By proceeding in a similar manner to Example 10(a) above but using 4-(4-fluorophenoxy)phenylamine (Reference Example 52g) there was prepared 7-cyano-6-cyclopropyl-3,4-dihydro-1H-pyrrolo[1,2-a]pyrazine-2,8-dicarboxylic acid 8-amide 2-{[4-(4-fluorophenoxy)phenyl]amide} as a white solid, m.p. 191–193° C. $^1$H NMR [(CD$_3$)$_2$SO]: δ 8.87 (s, 1H), 7.45 (d, 2H), 7.38–7.24 (bs, 1H), 7.20 (t, 2H), 7.00 (dd, 2H), 6.94 (d, 2H), 6.90–6.73 (bs, 1H), 4.83 (s, 2H), 4.08 (t, 2H), 3.89 (t, 2H), 1.94–1.84 (m, 1H), 1.04–0.95 (m, 2H) and 0.89–0.81 (m, 2H).

(i) 7-cyano-6-cyclopropyl-3,4-dihydro-1H-pyrrolo[1,2-a]pyrazine-2,8-dicarboxylic acid 8-amide 2-quinolin-6-ylamide

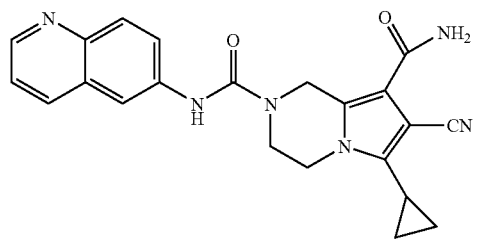

By proceeding in a similar manner to Example 10(a) above but using 6-aminoquinoline there was prepared 7-cyano-6-cyclopropyl-3,4-dihydro-1H-pyrrolo[1,2-a]pyrazine-2,8-dicarboxylic acid 8-amide 2-quinolin-6-ylamide as an off white solid, m.p. 269–279° C. $^1$H NMR [(CD$_3$)$_2$SO]: δ 9.23 (s, 1H), 8.75 (dd, 1H), 8.22 (d, 1H), 8.07 (d, 1H), 7.92 (d, 1H), 7.85 (dd, 1H), 7.45 (dd, 1H), 7.41–7.15 (bs, 1H), 6.95–6.75 (bs, 1H), 4.90 (s, 2H), 4.13 (t, 2H), 3.95 (t, 2H), 1.95–1.85 (m, 1H), 1.06–0.96 (m, 2H) and 0.92–0.78 (m, 2H).

(j) 7-cyano-6-cyclopropyl-3,4-dihydro-1H-pyrrolo[1,2-a]pyrazine-2,8-dicarboxylic acid 8-amide 2-[(4-methylsulfanylphenyl)amide]

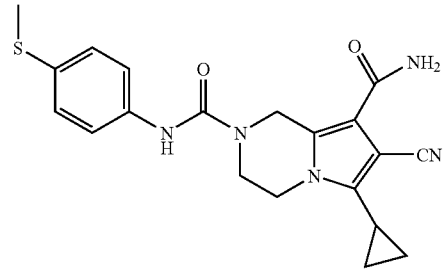

By proceeding in a similar manner to Example 10(a) above but using 4-(methylmercapto)aniline there was prepared 7-cyano-6-cyclopropyl-3,4-dihydro-1H-pyrrolo[1,2-a]pyrazine-2,8-dicarboxylic acid 8-amide 2-[(4-methylsulfanylphenyl)amide] as a white solid, m.p. 215–217° C. MS: 396 [MH]$^+$.

(k) 7-cyano-6-cyclopropyl-3,4-dihydro-1H-pyrrolo[1,2-a]pyrazine-2,8-dicarboxylic acid 8-amide 2-[(3-cyanophenyl)amide]

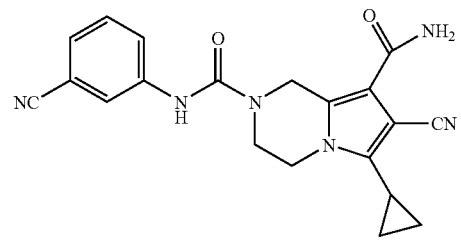

By proceeding in a similar manner to Example 10(a) above but using 3-cyanoaniline there was prepared 7-cyano-6-cyclopropyl-3,4-dihydro-1H-pyrrolo[1,2-a]pyrazine-2,8-dicarboxylic acid 8-amide 2-[(3-cyanophenyl)amide] as a white solid, m.p. 285–287° C. MS: 375 [MH]$^+$.

(l) {4-[(8-carbamoyl-7-cyano-6-cyclopropyl-3,4-dihydro-1H-pyrrolo[1,2-a]pyrazine-2-carbonyl)amino]phenyl}acetic acid ethyl ester

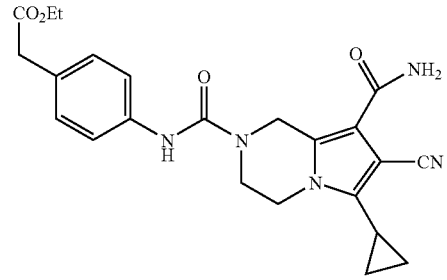

By proceeding in a similar manner to Example 10(a) above but using 4-aminophenylacetic acid ethyl ester there was prepared {4-[(8-carbamoyl-7-cyano-6-cyclopropyl-3,4- dihydro-1H-pyrrolo[1,2-a]pyrazine-2-carbonyl)amino]phenyl)}acetic acid ethyl ester as a white solid, m.p. 263–264° C. MS: 436 [MH]⁺.

(m) 7-cyano-6-cyclopropyl-3,4-dihydro-1H-pyrrolo[1,2-a]pyrazine-2,8-dicarboxylic acid 8-amide 2-pyridin-3-ylamide

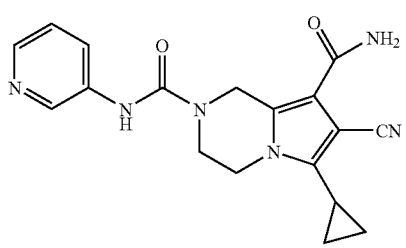

By proceeding in a similar manner to Example 10(a) above but using 3-aminopyridine there was prepared 7-cyano-6-cyclopropyl-3,4-dihydro-1H-pyrrolo[1,2-a]pyrazine-2,8-dicarboxylic acid 8-amide 2-pyridin-3-ylamide as a white solid, m.p. 256–260° C. MS: 351 [MH]⁺.

(n) 7-cyano-6-cyclopropyl-3,4-dihydro-1H-pyrrolo[1,2-a]pyrazine-2,8-dicarboxylic acid 2-[(4-acetylphenyl)amide] 8-amide

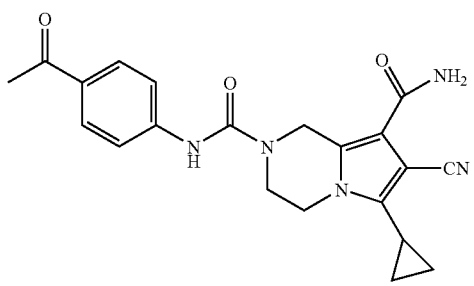

By proceeding in a similar manner to Example 10(a) above but using 4-aminoacetophenone there was prepared 7-cyano-6-cyclopropyl-3,4-dihydro-1H-pyrrolo[1,2-a]pyrazine-2,8-dicarboxylic acid 2-[(4-acetylphenyl)amide] 8-amide as a white solid, m.p. 266–268° C. ¹H NMR [(CD₃)₂SO]: δ 9.23 (s, 1H), 7.88 (d, 2H), 7.60 (d, 2H), 7.47–7.12 (bs, 1H), 6.99–6.69 (bs, 1H), 4.86 (s, 2H), 4.10 (t, 2H), 3.91 (t, 2H), 2.50 (s, 3H), 1.93–1.84 (m, 1H), 1.05–0.93 (m, 2H) and 0.91–0.79 (m, 2H).

(o) 7-cyano-6-cyclopropyl-3,4-dihydro-1H-pyrrolo[1,2-a]pyrazine-2,8-dicarboxylic acid 8-amide 2-indan-2-ylamide

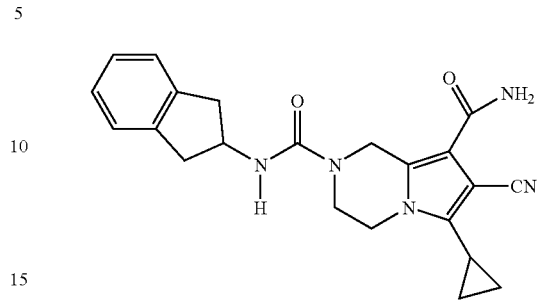

By proceeding in a similar manner to Example 10(a) above but using 2-indanamine hydrochloride there was prepared 7-cyano-6-cyclopropyl-3,4-dihydro-1H-pyrrolo[1,2-a]pyrazine-2,8-dicarboxylic acid 8-amide 2-indan-2-ylamide as a white solid, m.p. 219–221° C. [Elemental analysis: C, 67.50; H, 5.94; N, 17.92%. Calculated for C₂₂H₂₃N₅O₂: C, 67.85; H, 5.95; N, 17.98%].

(p) 7-cyano-6-cyclopropyl-3,4-dihydro-1H-pyrrolo[1,12-a]pyrazine-2,8-dicarboxylic acid 8-amide 2-[(4-trifluoromethoxyphenyl)amide]

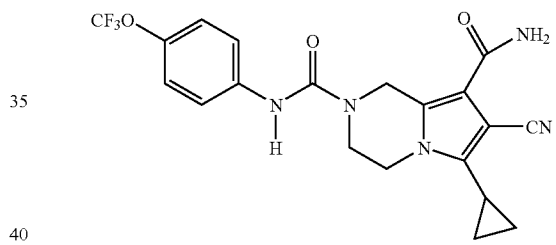

By proceeding in a similar manner to Example 10(a) above but using 4-(trifluoromethoxy)aniline there was prepared 7-cyano-6-cyclopropyl-3,4-dihydro-1H-pyrrolo[1,2-a]pyrazine-2,8-dicarboxylic acid 8-amide 2-[(4-trifluoromethoxyphenyl)amide] as a white solid, m.p. 234–236° C. MS: 434 [MH]⁺.

(q) 7-cyano-6-cyclopropyl-3,4-dihydro-1H-pyrrolo[1,2-a]pyrazine-2,8-dicarboxylic acid 8-amide 2-pyridin-4-ylamide

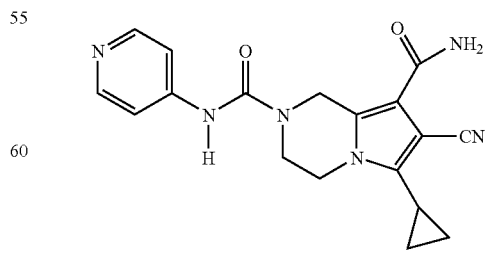

By proceeding in a similar manner to Example 10(a) above but using 4-aminopyridine there was prepared 7-cyano-6-cyclopropyl-3,4-dihydro-1H-pyrrolo[1,2-a]pyrazine-2,8-dicarboxylic acid 8-amide 2-pyridin-4-ylaride as an off white solid. MS: 351 [MH]+.

(r) 7-cyano-6-cyclopropyl-3,4-dihydro-1H-pyrrolo[1,2-a]pyrazine-2,8-dicarboxylic acid 8-amide 2-{[4-(4-isoipropylpiperazine-1-carbonyl)-phenyl]amide}

By proceeding in a similar manner to Example 10(a) above but using 1-(4-aminobenzoyl)-4-isopropylpiperazine (Reference Example 52h) there was 7-cyano-6-cyclopropyl-3,4-dihydro-1H-pyrrolo[1,2-a]pyrazine-2,8-dicarboxylic acid 8-amide 2-{[4-(4-isopropylpiperazine-1-carbonyl)-phenyl]amide} as a white solid, m.p. 174–179° C. (dec). MS: 504 [MH]+.

(s) 4-[(8-carbamoyl-7-cyano-6-cyclopropyl-3,4-dihydro-1H-pyrrolo[1,2-a]pyrazine-2-carbonyl)amino]piperidine-1-carboxylic acid isopropyl ester

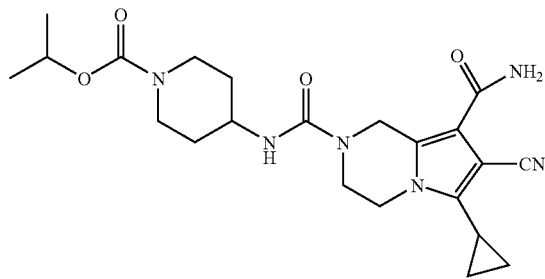

By proceeding in a similar manner to Example 10(a) above but using 4-amino-piperidine-1-carboxylic acid isopropyl ester, trifluoroacetic acid salt (Reference Example 60) there was prepared 4-[(8-carbamoyl-7-cyano-6-cyclopropyl-3,4-dihydro-1H-pyrrolo[1,2-a]pyrazine-2-carbonyl)amino]piperidine-1-carboxylic acid isopropyl ester as a white solid, m.p. 181–182° C. MS: 465 [MNa]+

(t) 7-cyano-6-cyclopropyl-3,4-dihydro-1H-pyrrolo[1,2-a]pyrazine-2,8-dicarboxylic acid 8-amide 2-[(1-benzoylpiperidin-4-yl)amide]

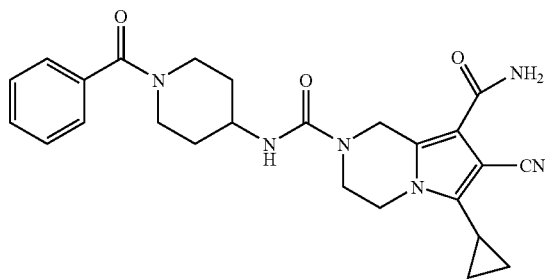

By proceeding in a similar manner to Example 10(a) above but using (4-amino-piperidin-1-yl)-phenyl-methanone, trifluoroacetic acid salt (Reference Example 61) there was prepared 7-cyano-6-cyclopropyl-3,4-dihydro-1H-pyrrolo[1,2-a]pyrazine-2,8-dicarboxylic acid 8-amide 2-[(1-benzoylpiperidin-4-yl)amide] as a white solid, m.p. 227–228° C. MS: 461 [MH]+.

EXAMPLE 11

(a) 7-Cyano-6-(2-methylpyridin-3-yl)-3,4-dihydro-1H-pyrrolo[1,2-a]pyrazine-2,8-dicarboxylic acid 8-amide 2-[(4-fluorophenyl)amide]

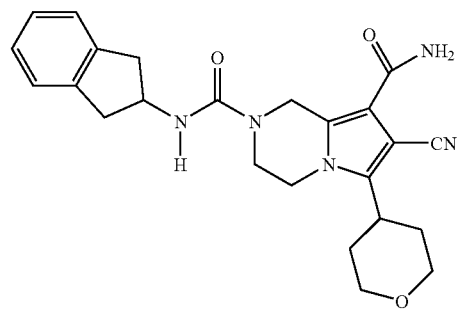

A suspension of 7-cyano-6-(2-methylpyridin-3-yl)-1,2,3,4-tetrahydropyrrolo[1,2-a]pyrazine-8-carboxylic acid amide bistrifluoroacetic acid salt (200 mg, Reference Example 6a) in dry dichloromethane (10 mL) was treated with dry triethylamine (0.22 mL), then with a solution of 4-fluorophenyl isocyanate (44 mg) in dry dichloromethane (10 mL). After stirring at room temperature overnight the reaction mixture was evaporated. The residue was subjected to column chromatography on silica eluting with a mixture of ethyl acetate and methanol (99:1, v/v) to give after trituration with diethyl ether 7-cyano-6-(2-methylpyridin-3-yl)-3,4-dihydro-1H-pyrrolo[1,2-a]pyrazine-2,8-dicarboxylic acid 8-amide 2-[(4-fluorophenyl)amide] (78 mg) as a white solid, m.p. 210–214° C. MS: 419 [MH]+.

(b) 7-cyano-6-(2-methylpyridin-3-yl)-3,4-dihydro-1H-pyrrolo[1,2-a]pyrazine-2,8-dicarboxylic acid 8-amide 2-[(tetrahydropyran-4-yl)amide]

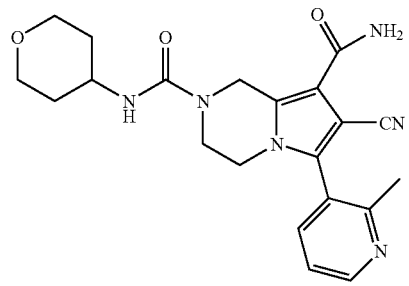

By proceeding in a similar manner to Example 11(a) above but using 4-tetrahydropyranyl isocyanate (prepared according to the procedure described in WO 96/27588, Intermediate 26) there was prepared 7-cyano-6-(2-methylpyridin-3-yl)-3,4-dihydro-1H-pyrrolo[1,2-a]pyrazine-2,8-dicarboxylic acid 8-amide 2-[(tetrahydropyran-4-yl)amide] as a white solid, m.p. 136–146° C. MS: 409 [MH]+.

(c) 4-[(8-carbamoyl-7-cyano-6-(2-methylpyridin-3-yl)-3,4-dihydro-1H-pyrrolo[1,2a]pyrazine-2-carbonyl)amino]benzoic acid ethyl ester By proceeding in a similar manner to Example 11(a) above but using ethyl-4-isocyanatobenzoate there was prepared 4-[(8-carbamoyl-7-cyano-6-(2-methylpyridin-3-yl)-3,4-dihydro-1H-pyrrolo[1,2a]pyrazine-2-carbonyl)amino]benzoic acid ethyl ester as a white solid, m.p. 265–266° C. MS: 473 [MH]+.

EXAMPLE 12

(a) 7-Cyano-6-pyridin-3-yl-3,4-dihydro-1H-pyrrolo[1,2-a]pyrazine-2,8-dicarboxylic acid 8-amide 2[(4-fluorophenyl)amide]

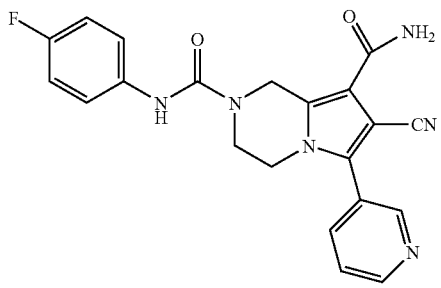

A suspension of 7-cyano-6-pyridin-3-yl-1,2,3,4-tetrahydropyrrolo[1,2-a]pyrazine-8-carboxylic acid amide bistrifluoroacetic acid salt (244 mg, Reference Example 6b) in dry dichloromethane (30 mL) was treated with dry triethylamine (0.34 mL), then with a solution of 4-fluorophenyl isocyanate (92 mg) in dry dichloromethane (2 mL). After stirring at room temperature for a further 5 hours the reaction mixture was filtered. The solid collected was washed with methanol, then with diethyl ether, then with water and then with diethyl ether to give 7-Cyano-6-pyridin-3-yl-3,4-dihydro-1H-pyrrolo[1,2-a]pyrazine-2,8-dicarboxylic acid 8-amide 2[(4-fluorophenyl)amide] (105 mg) as a white solid, m.p. 275–279° C. [Elemental analysis: C, 61.03; H, 4.20; N, 20.01%; Calculated for $C_{21}H_{17}FN_6O_2 \cdot 0.5H_2O$: C, 61.01; H, 4.39; N, 20.33%].

(b) 7-cyano-6-pyridin-3-yl-3,4-dihydro-1H-pyrrolo[2-a]pyrazine-2,8-dicarboxylic acid 8-amide 2-[(4-methanesulfonylphenyl)amide]

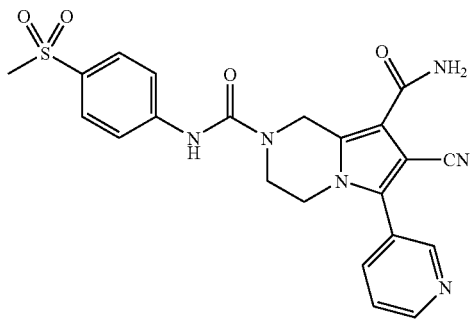

By proceeding in a similar manner to Example 12(a) above but using 4-methanesulfonylphenyl isocyanate (pre-pared according to the procedure of Rasmussen et. al, J. Med. Chem. 1978, 21, 1044) 7-cyano-6-pyridin-3-yl-3,4-dihydro-1H-pyrrolo[1,2-a]pyrazine-2,8-dicarboxylic acid 8-amide 2-[(4-methanesulfonylphenyl)amide] as a white solid, m.p. 289–294° C. [Elemental analysis: C, 55.00; H, 4.15; N, 17.42%; Calculated for $C_{22}H_{20}N_6O_4S \cdot 0.75H_2O$: C, 55.28; H, 4.53; N, 17.58%].

(c) 7-cyano-6-pyridin-3-yl-3,4-dihydro-1H-pyrrolo[1,2-a]pyrazine-2,8-dicarboxylic acid 8-amide 2-[(3-trifluoromethylphenyl)amide]

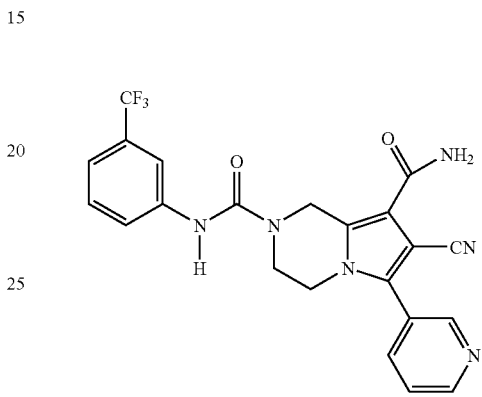

By proceeding in a similar manner to Example 12(a) above but using 3-trifluoromethylphenyl isocyanate there was prepared 7-cyano-6-pyridin-3-yl-3,4-dihydro-1H-pyrrolo[1,2-a]pyrazine-2,8-dicarboxylic acid 8-amide 2-[(3-trifluoromethylphenyl)amide] as a white solid, m.p. 233–235° C. MS: 455 [MH]+.

(d) 7-cyano-6-pyridin-3-yl-3,4-dihydro-1H-pyrrolo[1,2-a]pyrazine-2,8-dicarboxylic acid 8-amide 2-[(4-trifluoromethylphenyl)amide]

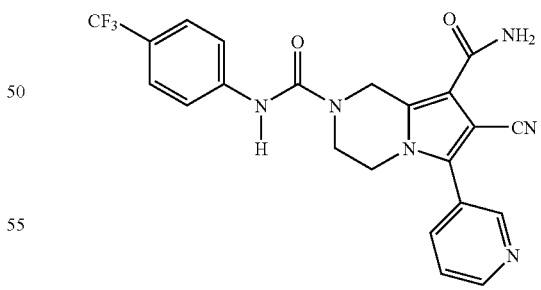

By proceeding in a similar manner to Example 12(a) above but using 4-trifluoromethylphenyl isocyanate there was prepared 7-cyano-6-pyridin-3-yl-3,4-dihydro-1H-pyrrolo[1,2-a]pyrazine-2,8-dicarboxylic acid 8-amide 2-[(4-trifluoromethylphenyl)amide] as a white solid, m.p. 290–292° C. [Elemental analysis: C, 57.01; H, 3.86; N, 18.06%; Calculated for $C_{22}H_{17}F_3N_6O_2 \cdot 0.50H_2O$: C, 57.02; H, 3.91; N, 18.13%].

EXAMPLE 13

7-Cyano-6-pyridin-3-yl-3,4-dihydro-1H-pyrrolo[1,2-a]pyrazine-2,8-dicarboxylic acid 8-amide 2-[(4-cyanophenyl)amide]

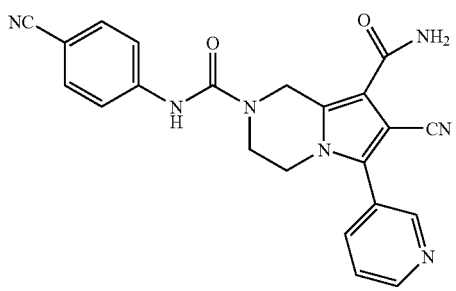

A stirred solution of triphosgene (92 mg) in dry dichloromethane (5 mL), under a blanket of nitrogen at −70° C., was treated dropwise with a solution of 4-cyanoaniline (110 mg) and triethylamine (0.14 mL) in dry dichloromethane (10 mL) over 1 hour whilst maintaining the temperature below −65° C. After stirring at −70° C. for a further 3.5 hours the mixture was treated with a suspension of 7-cyano-6-pyridin-3-yl-1,2,3,4-tetrahydropyrrolo[1,2-a]pyrazine-8-carboxylic acid amide bistrifluoroacetic acid salt (355 mg, Reference Example 6b) and triethylamine (0.28 mL) in dry dichloromethane (20 mL) whilst maintaining the temperature below −65° C. The reaction mixture was then allowed to warm to room temperature and stand overnight. The reaction mixture was filtered and the solid collected was washed with water and then diethyl ether to give 7-cyano-6-pyridin-3-yl-3,4-dihydro-1H-pyrrolo[1,2-a]pyrazine-2,8-dicarboxylic acid 8-amide 2-[(4-cyanophenyl)amide] as a white solid (83 mg); m.p. 291–296° C. $^1$H NMR [(CD$_3$)$_2$SO]: δ 9.28 (s, 1H), 8.75 (s, 1H), 8.69 (d, 1H), 8.01 (d, 1H), 7.70–7.62 (m, 4H), 7.58 (dd, 1H), 7.54–7.32 (bs, 1H), 7.15–7.00 (bs, 1H), 4.97 (s, 2H), 4.03 (t, 2H) and 3.82 (t, 2H).

EXAMPLE 14

(a) 7-Cyano-6-(1-methanesulfonylpiperidin-4-yl)-3,4-dihydro-1H-pyrrolo[1,2-a]pyrazine-2,8-dicarboxylic acid 8-amide 2-[(4-fluorophenyl)amide]

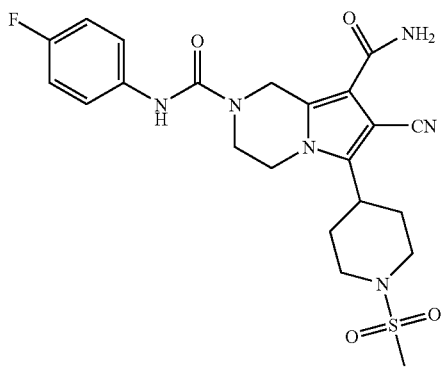

A suspension of 7-cyano-6-(1-methanesulfonylpiperidin-4-yl)-1,2,3,4-tetrahydropyrrolo[1,2-a]pyrazine-8-carboxylic acid amide trifluoroacetic acid salt (130 mg, Reference Example 11) in dry dichloromethane (10 mL) was treated with dry triethylamine (0.11 mL), then with a solution of 4-fluorophenyl isocyanate (35 mg) in dry dichloromethane (1 mL). After stirring at room temperature for a further 3 hours the reaction mixture was filtered. The solid collected was washed with diisopropyl ether and then dried at 50° C. to give 7-cyano-6-(1-methanesulfonylpiperidin-4-yl)-3,4-dihydro-1H-pyrrolo[1,2-a]pyrazine-2,8-dicarboxylic acid 8-amide 2-[(4-fluorophenyl)amide] (109 mg) as a white solid, m.p. 177–180° C. $^1$H NMR [(CD$_3$)$_2$SO]: δ 8.88 (s, 1H), 7.44 (q, 2H), 7.42–7.25 (bs, 1H), 7.09 (t, 2H), 7.03–6.83 (bs, 1H), 4.84 (s, 2H), 4.06 (t, 2H), 3.87 (t, 2H), 3.69 (d, 2H), 3.03–2.94 (m, 1H), 2.91 (s, 3H), 2.87–2.76 (m, 2H) and 2.02–1.89 (m, 4H).

(b) 7-cyano-6-(1-methanesulfonylpiperidin-4-yl)-3,4-dihydro-1H-pyrrolo[1,2-a]pyrazine-2,8-dicarboxylic acid 8-amide 2-[(tetrahydropyran-4-yl)amide

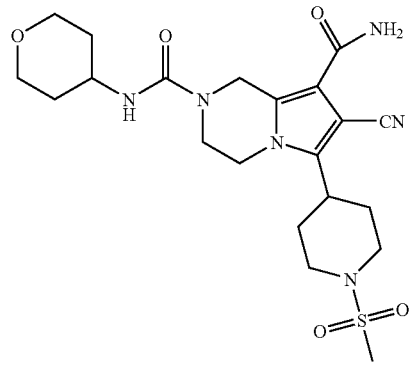

By proceeding in a similar manner to Example 14(a) above but using 4-tetrahydropyranyl isocyanate (prepared according to the procedure described in WO 96/27588, Intermediate 26) there was prepared 7-cyano-6-(1-methanesulfonylpiperidin-4-yl)-3,4-dihydro-1H-pyrrolo[1,2-a]pyrazine-2,8-dicarboxylic acid 8-amide 2-[(tetrahydropyran-4-yl)amide] as a white solid, m.p. 183–185° C. MS: 479 [MH]$^+$.

(c) 4-[(8-carbamoyl-7-cyano-6-(1-methanesulfonylpiperidin-4-yl)-3,4-dihydro-1H-pyrrolo[1,2a]pyrazine-2-carbonyl)amino]benzoic acid ethyl ester

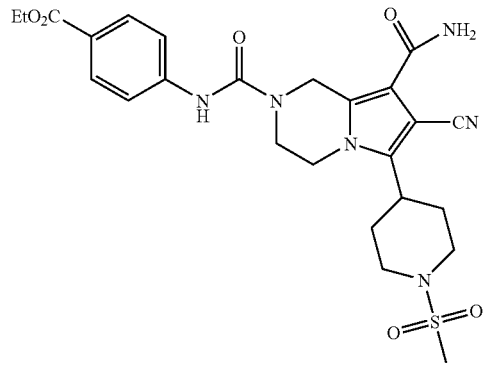

By proceeding in a similar manner to Example 14(a) above but using ethyl-4-isocyanatobenzoate there was prepared 4-[(8-carbamoyl-7-cyano-6-(1-methanesulfonylpiperidin-4-yl)-3,4-dihydro-1H-pyrrolo[1,2a]pyrazine-2-carbonyl)amino]benzoic acid ethyl ester as a white solid, m.p. 227–240° C. $^1$H NMR [(CD$_3$)$_2$SO]: δ 9.23 (s, 1H), 7.87 (d, 2H), 7.60 (d, 2H), 7.46–7.21 (bs, 1H), 7.07–6.82 (bs, 1H), 4.87 (s, 2H), 4.27 (q, 2H), 4.08 (t, 2H), 3.90 (t, 2H), 3.69 (d, 2H), 3.03–2.94 (m, 1H), 2.91 (s, 3H), 2.85–2.75 (m, 2H), 2.02–1.88 (m, 4H) and 1.31 (t, 3H).

EXAMPLE 15

7-Cyano-6-(1-methanesulfonylpiperidin-4-yl)-3,4-dihydro-1H-pyrrolo[1,2-a]pyrazine-2,8-dicarboxylic acid 8-amide 2-[(4-cyanophenyl)amide]

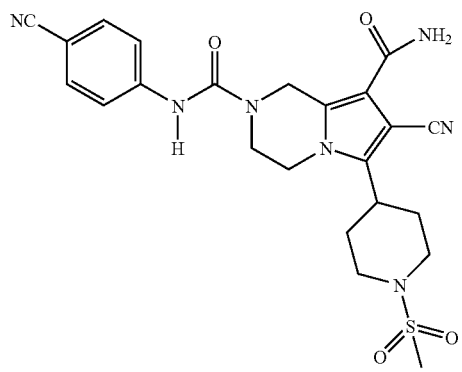

A stirred solution of triphosgene (350 mg) in dry dichloromethane (30 mL), under a blanket of nitrogen at −70° C., was treated dropwise with a solution of 4-cyanoaniline (367 mg) and triethylamine (0.5 mL) in dry dichloromethane (30 mL) over 1 hour whilst maintaining the temperature below −65° C. After stirring at −70° C. for a further 2 hours the reaction mixture was treated with a suspension of 7-cyano-6-(1-methanesulfonylpiperidin-4-yl)-1,2,3,4-tetrahydropyrrolo[1,2-a]pyrazine-8-carboxylic acid amide trifluoroacetic acid salt (1.00 g, Reference Example 11) and triethylamine (0.75 mL) in dry dichloromethane (30 mL) whilst maintaining the temperature below −65° C. After stirring at −70° C. for a further 5 hours the reaction mixture was allowed to warm to room temperature and then left to stand overnight. The reaction mixture was filtered and the solid collected to give 7-cyano-6-(1-methanesulfonylpiperidin-4-yl)-3,4-dihydro-1H-pyrrolo[1,2-a]pyrazine-2,8-dicarboxylic acid 8-amide 2-[(4-cyanophenyl)amide] (150 mg) as a white solid, m.p. 218–221° C. MS: 518 [MNa]$^+$.

EXAMPLE 16

(a) 7-Chloro-6-cyclopropyl-3,4-dihydro-1H-pyrrolo[1,2-a]pyrazine-2,8-dicarboxylic acid 8-amide 2-[(4-fluorophenyl)amide]

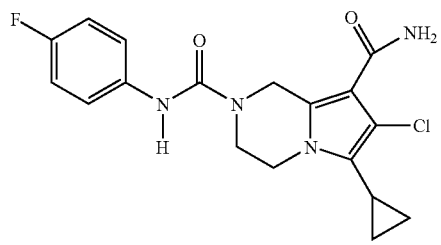

A suspension of 7-chloro-6-cyclopropyl-1,2,3,4-tetrahydropyrrolo[1,2-a]pyrazine-8-carboxylic acid amide trifluoroacetic acid salt [54 mg, Example 44(a)] in dry dichloromethane (8 mL) was treated with dry triethylamine (64 μL), then with a solution of 4-fluorophenyl isocyanate (21 mg) in dry dichloromethane (4 mL). After stirring at room temperature for a further 7 hours the reaction mixture was allowed to stand overnight. The reaction mixture was then filtered and the solid collected washed with dichloromethane to give 7-chloro-6-cyclopropyl-3,4-dihydro-1H-pyrrolo[1,2-a]pyrazine-2,8-dicarboxylic acid 8-amide 2-[(4-fluorophenyl)amide] (43 mg) as an off white solid, m.p. 230–231° C. $^1$H NMR [(CD$_3$)$_2$SO]: δ 8.85(s, 1H), 7.44 (dd, 2H), 7.27–7.12 (bs, 1H), 7.08 (t, 2H), 6.76–6.55 (bs, 1H), 4.82 (s, 2H), 4.02 (t, 2H), 3.86 (t, 2H), 1.67–1.58 (m, 1H), 0.98–0.84 (m, 2H) and 0.78–0.63 (m, 2H).

(b) 7-chloro-6-cyclopropyl-3,4-dihydro-1H-pyrrolo[1,2-a]pyrazine-2,8-dicarboxylic acid 8-amide 2-[(4-trifluoromethylphenyl)amide]

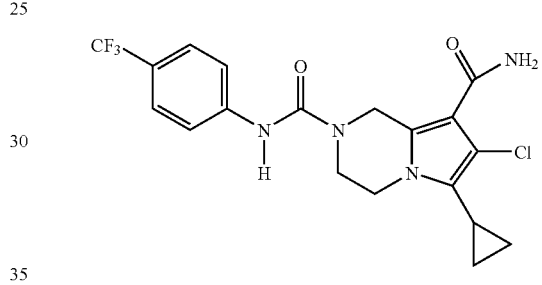

By proceeding in a similar manner to Example 16(a) above but using 4-trifluoromethylphenyl isocyanate there was prepared 7-chloro-6-cyclopropyl-3,4-dihydro-1H-pyrrolo[1,2-a]pyrazine-2,8-dicarboxylic acid 8-amide 2-[(4-trifluoromethylphenyl)amide] as a white solid, m.p. 247–250° C. MS: 429 [MH]$^+$, 427 [MH]$^+$.

(c) (±)-trans-7-chloro-6-cyclopropyl-3,4-dihydro-1H-pyrrolo[1,2-a]pyrazine-2,8-dicarboxylic acid 8-amide 2-[(2-phenylcyclopropyl)amide]

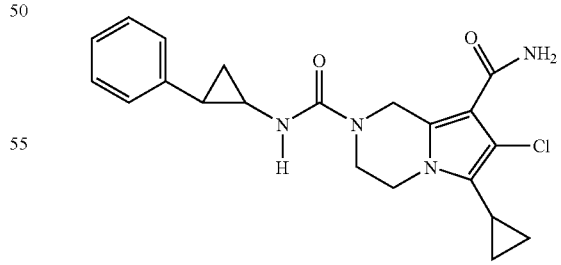

By proceeding in a similar manner to Example 16(a) above but using (±)-trans-2-phenylcyclopropyl isocyanate there was prepared (±)-trans-7-chloro-6-cyclopropyl-3,4-dihydro-1H-pyrrolo[1,2-a]pyrazine-2,8-dicarboxylic acid 8-amide 2-[(2-phenylcyclopropyl) amide] as white solid, m.p. 230–232° C. MS: 401 [MH]$^+$, 399 [MH]$^+$.

(d) 7-chloro-6-cyclopropyl-3,4-dihydro-1H-pyrrolo[1,2-a]pyrazine-2,8-dicarboxylic acid 8-amide 2-[(3-trifluoromethylphenyl)amide]

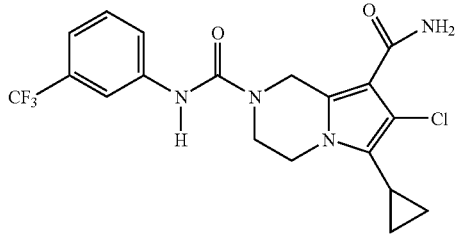

By proceeding in a similar manner to Example 16(a) above but using 3-trifluoromethylphenyl isocyanate there was prepared 7-chloro-6-cyclopropyl-3,4-dihydro-1H-pyrrolo[1,2-a]pyrazine-2,8-dicarboxylic acid 8-amide 2-[(3-trifluoromethylphenyl)amide] as a white solid, m.p. 245° C. (dec). MS: 429 [MH]$^+$, 427 [MH]$^+$.

EXAMPLE 17

(a) 7-Chloro-6-cyclopropyl-3,4-dihydro-1H-pyrrolo[1,2-a]pyrazine-2,8-dicarboxylic acid 8-amide 2-[(4-cyanophenyl)amide]

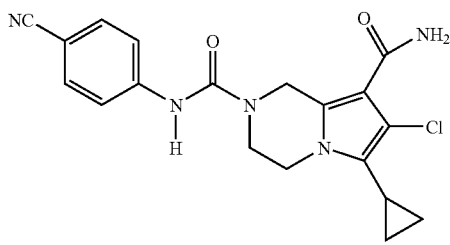

A stirred solution of triphosgene (92 mg) in dry dichloromethane (2 mL), under a blanket of nitrogen at −70° C., was treated dropwise with a solution of 4-cyanoaniline (103 mg) and triethylamine (0.13 mL) in dry dichloromethane (3 mL) over 30 minutes whilst maintaining the temperature below −65° C. After stirring at −70° C. for a further 20 minutes the mixture was treated with a suspension of 7-chloro-6-cyclopropyl-1,2,3,4-tetrahydropyrrolo[1,2-a]pyrazine-8-carboxylic acid amide trifluoroacetic acid salt [220 mg, Example 44(a)] and triethylamine (0.17 mL) in dry dichloromethane (5 mL) whilst maintaining the temperature below −65° C. The reaction mixture was then allowed to warm to room temperature and stand overnight. The reaction mixture was filtered and the solid collected washed twice with dichloromethane (10 mL), then water (3 mL) and then pentane (5 mL) to give 7-chloro-6-cyclopropyl-3,4-dihydro-1H-pyrrolo[1,2-a]pyrazine-2,8-dicarboxylic acid 8-amide 2-[(4-cyanophenyl)amide] (110 mg) as a white solid, m.p. 196–198° C. $^1$H NMR [(CD$_3$)$_2$SO]: δ 9.31 (s, 1H), 7.70 (d, 2H), 7.65 (d, 2H), 7.29–7.13 (bs, 1H), 6.74–6.59 (bs, 1H), 4.85 (s, 2H), 4.04 (t, 2H), 3.89 (t, 2H), 1.67–1.58 (m, 1H), 0.97–0.85 (m, 2H) and 0.76–0.64 (m, 2H).

(b) 7-chloro-6-cyclopropyl-3,4-dihydro-1H-pyrrolo[1,2-a]pyrazine-2,8-dicarboxylic acid 8-amide 2-quinolin-6-ylamide

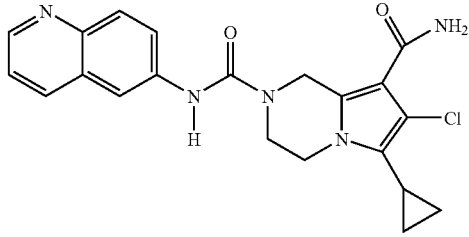

By proceeding in a similar manner to Example 17(a) above but using 6-aminoquinoline there was prepared 7-chloro-6-cyclopropyl-3,4-dihydro-1H-pyrrolo[1,2-a]pyrazine-2,8-dicarboxylic acid 8-amide 2-quinolin-6-ylamide as a white solid, m.p. 248° C. (dec). MS: 412 [MH]$^+$, 410 [MH]$^+$.

(c) 7-chloro-6-cyclopropyl-3,4-dihydro-1H-pyrrolo[1,2-a]pyrazine-2,8-dicarboxylic acid 8-amide 2-indan-2-ylamide

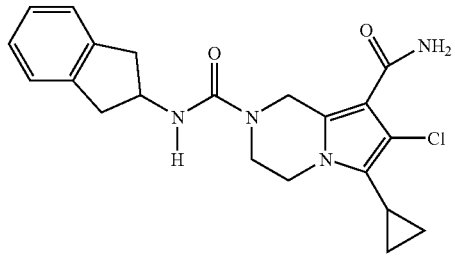

By proceeding in a similar manner to Example 17(a) above but using 2-indanamine hydrochloride there was prepared 7-chloro-6-cyclopropyl-3,4-dihydro-1H-pyrrolo[1,2-a]pyrazine-2,8-dicarboxylic acid 8-amide 2-indan-2-ylamide as a white solid, m.p. 246–248° C. MS: 399 [MH]$^+$, 401 [MH]$^+$.

(d) 7-chloro-6-cyclopropyl-3,4-dihydro-1H-pyrrolo[1,2-a]pyrazine-2,8-dicarboxylic acid 8-amide 2-{[4-(4-isopropylpiperazine-1-carbonyl)-phenyl]amide}

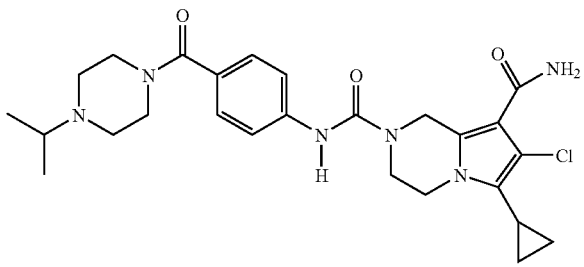

By proceeding in a similar manner but using 1-(4-aminobenzoyl)4-isopropylpiperazine (158 mg, Reference Example 52h) there was prepared 7-chloro-6-cyclopropyl- 3,4-dihydro-1H-pyrrolo[1,2-a]pyrazine-2,8-dicarboxylic acid 8-amide 2-{[4-(4-isopropylpiperazine-1-carbonyl)-phenyl]amide} as a white solid, m.p. 245–247° C. (dec). MS: 515 [MH]+, 513 [MH]+.

EXAMPLE 18

(a) 7-Chloro-3,4-dihydro-1H-pyrrolo[1,2-a]pyrazine-2,8-dicarboxylic acid 8-amide 2-[(4-fluorophenyl)amide]

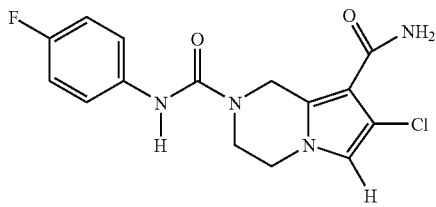

A suspension of 7-chloro-1,2,3,4-tetrahydropyrrolo[1,2-a]pyrazine-8-carboxylic acid amide trifluoroacetic acid salt (100 mg, Reference Example 24) in dry dichloromethane (10 mL) was treated with dry triethylamine (92 µL), then with a solution of 4-fluorophenyl isocyanate (42 mg) in dry dichloromethane (1 mL). After stirring at room temperature for a further 4 hours the reaction mixture was allowed to stand overnight. The reaction mixture was then filtered and the solid collected washed with diisopropyl ether to give 7-chloro-3,4-dihydro-1H-pyrrolo[1,2-a]pyrazine-2,8-dicarboxylic acid 8-amide 2-[(4-fluorophenyl)amide] (64 mg) as a white solid, m.p. 229–231° C. $^1$H NMR [(CD$_3$)$_2$SO]: δ 8.86 (s, 1H), 7.44 (dd, 2H), 7.33–7.18 (bs, 1H), 7.08 (t, 2H), 6.97 (s, 1H), 6.75–6.58 (bs, 1H), 4.83 (s, 2H), 3.98 (t, 2H) and 3.82 (t, 2H).

(b) 7-chloro-3,4-dihydro-1H-pyrrolo[1,2-a]pyrazine-2,8-dicarboxylic acid 8-amide 2-[(4-trifluoromethylphenyl)amide]

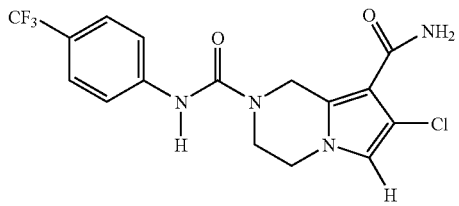

By proceeding in a similar manner to Example 18(a) above but using 4-trifluoromethylphenyl isocyanate there was prepared 7-chloro-3,4-dihydro-1H-pyrrolo[1,2-a]pyrazine-2,8-dicarboxylic acid 8-amide 2-[(4-trifluoromethylphenyl)amide] as a white solid, m.p. 247° C. MS: 389 [MH]+, 387 [MH]+.

(c) 7-chloro-3,4-dihydro-1H-pyrrolo[1,2-a]pyrazine-2,8-dicarboxylic acid 8-amide 2-[(3-trifluoromethylphenyl)amide]

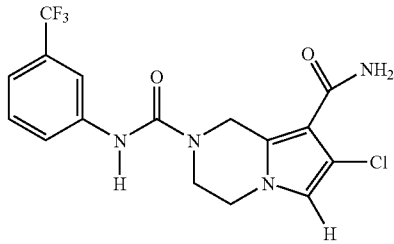

By proceeding in a similar manner to Example 18(a) above but using 3-trifluoromethylphenyl isocyanate there was prepared 7-chloro-3,4-dihydro-1H-pyrrolo[1,2-a]pyrazine-2,8-dicarboxylic acid 8-amide 2-[(3-trifluoromethylphenyl)amide] as a white solid, m.p. 228–230° C. MS: 389 [MH]+, 387 [MH]+.

(d) (±)-trans-7-chloro-3,4-dihydro-1H-pyrrolo[1,2-a]pyrazine-2,8-dicarboxylic acid 8-amide 2-[(2-phenylcyclopropyl)amide]

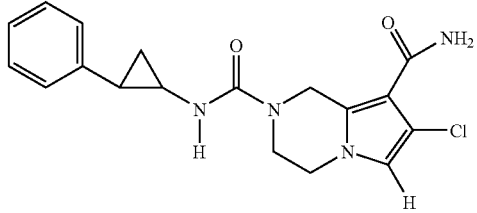

By proceeding in a similar manner to Example 18(a) above but using (±)-trans-2-phenylcyclopropyl isocyanate there was prepared (±)-trans-7-chloro-3,4-dihydro-1H-pyrrolo[1,2-a]pyrazine-2,8-dicarboxylic acid 8-amide 2-[(2-phenylcyclopropyl)amide] as a yellow solid, m.p. 141° C. (dec). MS: 361 [MH]+, 359 [MH]+.

EXAMPLE 19

(a) 7-Chloro-3,4-dihydro-1H-pyrrolo[1,2-a]pyrazine-2,8-dicarboxylic acid 8-amide 2-{[4-(4-isopropylpiperazine-1-carbonyl)phenyl]amide}

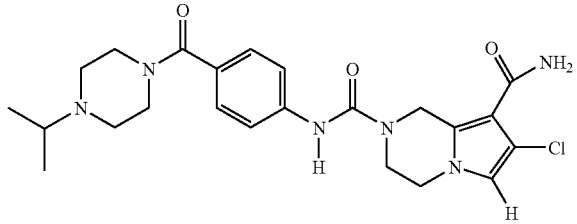

A stirred solution of triphosgene (65 mg) in dry dichloromethane (2 mL), under a blanket of nitrogen at −70° C., was treated dropwise with a solution of 1-(4-aminobenzoyl)-

4-isopropylpiperazine (158 mg, Reference Example 52h) and triethylamine (0.18 mL) in dry dichloromethane (2 mL) over 1 hour whilst maintaining the temperature below −65° C. After stirring at −70° C. for a further 45 minutes the mixture was treated with a suspension of 7-chloro-1,2,3,4-tetrahydropyrrolo[1,2-a]pyrazine-8-carboxylic acid amide trifluoroacetic acid salt (200 mg, Reference Example 24) and triethylamine (0.27 mL) in dry dichloromethane (10 mL) whilst maintaining the temperature below −65° C. After stirring at −70° C. for a further 2 hours the reaction mixture was then allowed to warm to room temperature and stand overnight. The reaction mixture was filtered and the solid collected to give 7-chloro-3,4-dihydro-1H-pyrrolo[1,2-a]pyrazine-2,8-dicarboxylic acid 8-amide 2-{[4-(4-isopropyl-piperazine-1-carbonyl)phenyl]amide} (171 mg) as a white solid, m.p. 249–256° C. MS: 475 [MH]$^+$, 473 [MH]$^+$.

(b) 7-chloro-3,4-dihydro-1H-pyrrolo[1,2-a]pyrazine-2,8-dicarboxylic acid 8-amide 2-indan-2-ylamide

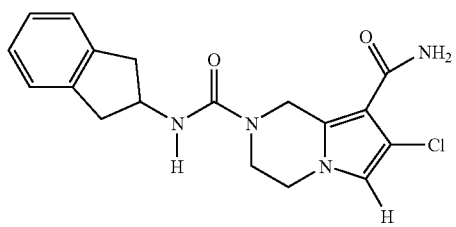

By proceeding in a similar manner to Example 19(a) above but using 2-indanamine hydrochloride there was prepared 7-chloro-3,4-dihydro-1H-pyrrolo[1,2-a]pyrazine-2,8-dicarboxylic acid 8-amide 2-indan-2-ylamide as a white solid, m.p. 223–224° C. $^1$H NMR [(CD$_3$)$_2$SO]: δ 7.30–7.08 (m, 5H), 6.94 (d, 1H), 6.92 (s, 1H), 6.75–6.52 (brs, 1H), 4.70 (s, 2H), 4.454.34 (m, 1H), 3.88 (t, 2H), 3.65 (t, 2H), 3.12 (dd, 2H) and 2.82 (dd, 2H).

(c) 7-chloro-3,4-dihydro-1H-pyrrolo[1,2-a]pyrazine-2,8-dicarboxylic acid 8-amide 2-[(4-cyanophenyl)amide]

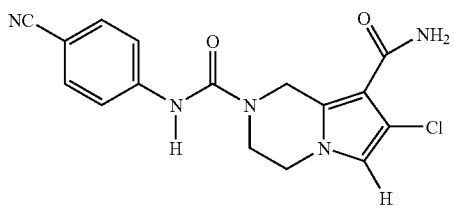

By proceeding in a similar manner to Example 19(a) above but using 4-cyanoaniline there was prepared 7-chloro-3,4-dihydro-1H-pyrrolo[1,2-a]pyrazine-2,8-dicarboxylic acid 8-amide 2-[(4-cyanophenyl)amide] as a white solid, m.p. 256–258° C. $^1$H NMR [(CD$_3$)$_2$SO]: δ 9.31 (s, 1H), 7.70 (d, 2H), 7.64 (d, 2H), 7.34–7.17 (bs, 1H), 6.98 (s, 1H), 6.75–6.57 (bs, 1H), 4.85 (s, 2H), 4.00 (t, 2H) and 3.85 (t, 2H).

EXAMPLE 20

7-Chloro-3,4-dihydro-1H-pyrrolo[1,2-a]pyrazine-2,8-dicarboxylic acid 8-amide 2-[(5-pyridin-2-ylthiophen-2-yl)amide]

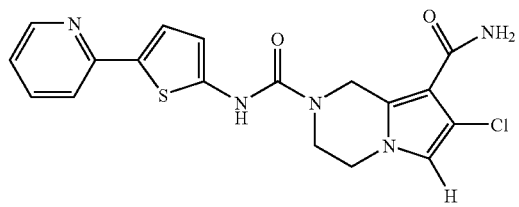

A suspension of 7-chloro-1,2,3,4-tetrahydropyrrolo[1,2-a]pyrazine-8-carboxylic acid amide trifluoroacetic acid salt (275 mg, Reference Example 24) in toluene (10 mL) was treated with triethylamine (0.26 mL), then 5-(pyrid-2-yl)thiophene-2-carbonyl azide (201 mg, Reference Example 58). After stirring for 1.5 hours at 120° C. the reaction mixture was allowed to cool to room temperature and left to stand 48 hours. The solvent was removed under reduced pressure and the residue then treated with water and ethyl acetate. The organic phase was separated, then dried over sodium sulfate and evaporated. The residue was subjected to column chromatography on silica eluting with ethyl acetate, then a mixture of ethyl acetate and methanol (9:1, v/v) to give a brown solid. The brown solid was triturated with diethyl ether to give 7-chloro-3,4-dihydro-1H-pyrrolo[1,2-a]pyrazine-2,8-dicarboxylic acid 8-amide 2-[(5-pyridin-2-ylthiophen-2-yl)amide] (80 mg) as a yellow-brown solid, m.p. 249–250° C. MS: 426 [MNa]$^+$, 424 [MNa]$^+$.

EXAMPLE 21

(a) 7-Chloro-6-(4-methylpyridin-3-yl)-3,4-dihydro-1H-pyrrolo[1,2-a]pyrazine-2,8-dicarboxylic acid 8-amide 2-[(4-fluorophenyl)amide]

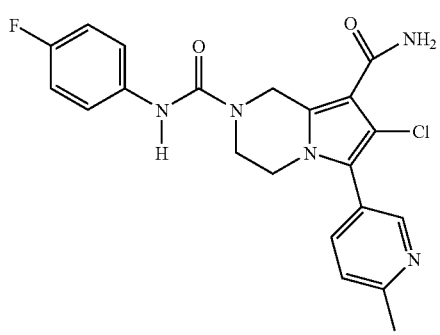

A suspension of 7-chloro-6-(4-methylpyridin-3-yl)-1,2,3,4-tetrahydropyrrolo[1,2-a]pyrazine-8-carboxylic acid amide bistrifluoroacetic acid salt (239 mg, Reference Example 28) in dry dichloromethane (5 mL) was treated with dry triethylamine (0.52 mL), then with a solution of 4-fluorophenyl isocyanate (71 mg) in dry dichloromethane (1 mL). After stirring at room temperature for a further 3 hours the reaction mixture was allowed to stand overnight. The reaction mixture was then filtered and the solid collected washed with dichloromethane to give 7-chloro-6-(4-methylpyridin-3-yl)-

3,4-dihydro-1H-pyrrolo[1,2-a]pyrazine-2,8-dicarboxylic acid 8-amide 2-[(4-fluorophenyl)amide] (114 mg) as a white solid, m.p. 235–238° C. (dec). MS: 430 [MH]$^+$, 428 [MH]$^+$.

(b) 7-chloro-6-(4-methylpyridin-3-yl)-3,4-dihydro-1H-pyrrolo[1,2-a]pyrazine-2,8-dicarboxylic acid 8-amide 2-[(3-trifluoromethylphenyl)amide]

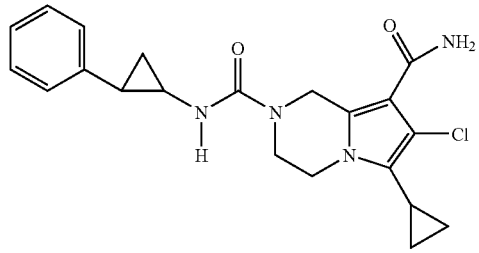

By proceeding in a similar manner to Example 21(a) above but using 3-trifluoromethylphenyl isocyanate there was prepared 7-chloro-6-(4-methylpyridin-3-yl)-3,4-dihydro-1H-pyrrolo[1,2-a]pyrazine-2,8-dicarboxylic acid 8-amide 2-[(3-trifluoromethylphenyl)amide] as a white solid, m.p. 227–230° C. (dec). MS: 480 [MH]$^+$, 478 [MH]$^+$.

(c) (±)-trans-7-chloro-6-(4-methylpyridin-3-yl)-3,4-dihydro-1H-pyrrolo[1,2-a]pyrazine-2,8-dicarboxylic acid 8-amide 2-[(2-phenylcyclopropyl)amide]

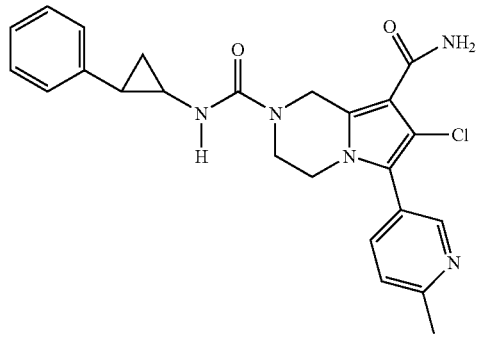

By proceeding in a similar manner to Example 21(a) above but using (±)-trans-2-phenylcyclopropyl isocyanate there was prepared (±)-trans-7-chloro-6-(4-methylpyridin-3-yl)-3,4-dihydro-1H-pyrrolo[1,2-a]pyrazine-2,8-dicarboxylic acid 8-amide 2-[(2-phenylcyclopropyl)amide] as a white solid, m.p. 188° C. (dec). MS: 452 [MH]$^+$, 450 [MH]$^+$.

EXAMPLE 22

(a) 7-Chloro-6-(4-methylpyridin-3-yl)-3,4-dihydro-1H-pyrrolo[1,2-a]pyrazine-2,8-dicarboxylic acid 8-amide 2-quinolin-6-ylamide

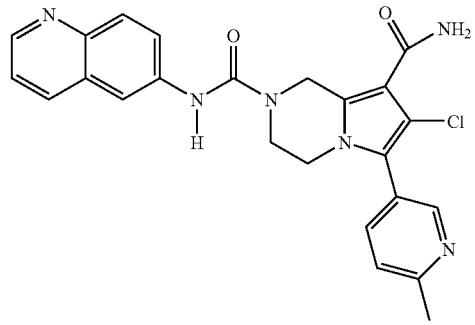

A stirred solution of triphosgene (78 mg) in dry dichloromethane (2 mL), under a blanket of nitrogen at –70° C., was treated dropwise with a solution of 6-aminoquinoline (83 mg) and triethylamine (0.10 mL) in dry dichloromethane (2 mL) over 30 minutes whilst maintaining the temperature below –65° C. After stirring at –70° C. for a further 15 minutes the mixture was treated with a suspension of 7-chloro-6-(4-methylpyridin-3-yl)-1,2,3,4-tetrahydropyrrolo[1,2-a]pyrazine-8-carboxylic acid amide bistrifluoroacetic acid salt (210 mg, Reference Example 28) and triethylamine (0.35 mL) in dry dichloromethane (4 mL) whilst maintaining the temperature below –65° C. The reaction mixture was then allowed to warm to room temperature and stand overnight. The reaction mixture was filtered and the solid collected washed with dichloromethane then pentane to give 7-chloro-6-(4-methylpyridin-3-yl)-3,4-dihydro-1H-pyrrolo[1,2-a]pyrazine-2,8-dicarboxylic acid 8-amide 2-quinolin-6-ylamide (23 mg) as a yellow solid, m.p. 221–222° C. MS: 463 [MH]$^+$, 461 [MH]$^+$.

(b) 7-chloro-6-(4-methylpyridin-3-yl)-3,4-dihydro-1H-pyrrolo[1,2-a]pyrazine-2,8-dicarboxylic acid 8-amide 2-[(4-cyanophenyl)amide]

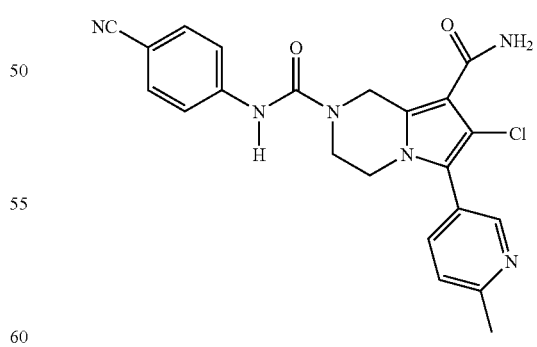

By proceeding in a similar manner to Example 22(a) above but using 4-cyanoaniline there was prepared 7-chloro-6-(4-methylpyridin-3-yl)-3,4-dihydro-1H-pyrrolo[1,2-a]pyrazine-2,8-dicarboxylic acid 8-amide 2-[(4-cyanophenyl)amide] as a white solid, m.p. 253–254° C. (dec). MS: 437 [MH]$^+$, 435 [MH]$^+$.

(c) 7-chloro-6-(4-methylpyridin-3-yl)-3,4-dihydro-1H-pyrrolo[1,2-a]pyrazine-2,8-dicarboxylic acid 8-amide 2-indan-2-ylamide

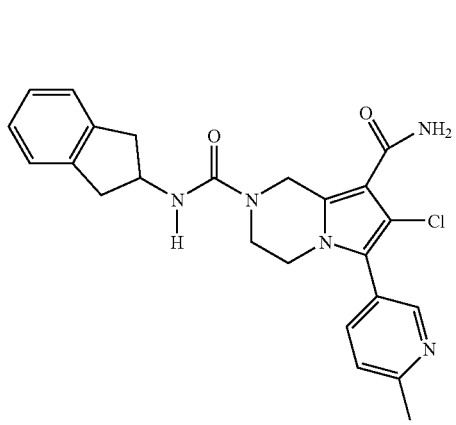

By proceeding in a similar manner to Example 22(a) above but using 2-indanamine hydrochloride there was prepared 7-chloro-6-(4-methylpyridin-3-yl)-3,4-dihydro-1H-pyrrolo[1,2-a]pyrazine-2,8-dicarboxylic acid 8-amide 2-indan-2-ylamide as white solid, m.p. 150–153° C. (dec.) MS: 452 [MH]+, 450 [MH]+.

(d) 4-{[8-carbamoyl-7-chloro-6-(4-methylpyridin-3-yl)-3,4-dihydro-1H-pyrrolo[1,2-a]pyrazine-2-carbonyl]amino}piperidine-1-carboxylic acid isopropyl ester

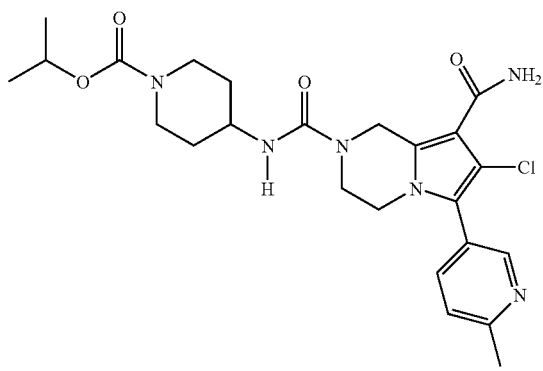

By proceeding in a similar manner to Example 22(a) above but using 4-amino-piperidine-1-carboxylic acid isopropyl ester, trifluoroacetic acid salt (Reference Example 60) there was prepared 4-{[8-carbamoyl-7-chloro-6-(4-methylpyridin-3-yl)-3,4-dihydro-1H-pyrrolo[1,2-a]pyrazine-2-carbonyl]amino}piperidine-1-carboxylic acid isopropyl ester as a white solid, 222–233° C. MS: 505 [MH]+, 503 [MH]+.

EXAMPLE 23

7-Cyano-6-(4-methylpyridin-3-yl)-3,4-dihydro-1H-pyrrolo[1,2-a]pyrazine-2,8-dicarboxylic acid 8-amide 2-[(4-trifluoromethylphenyl)amide]

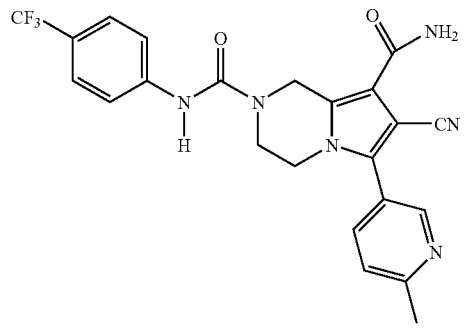

A suspension of 7-cyano-6-(4-methylpyridin-3-yl)-1,2,3,4-tetrahydropyrrolo[1,2-a]pyrazine-8-carboxylic acid amide bistrifluoroacetic acid salt (340 mg, Reference Example 33) in dry dichloromethane (90 mL) was treated with dry triethylamine (0.3 mL), then with a solution of 4-trifluoromethylphenyl isocyanate (124 mg) in dry dichloromethane. After stirring at room temperature for a further 2 hours the reaction mixture was allowed to stand overnight. The reaction mixture was then evaporated, the residue treated with dichloromethane (200 mL) and washed three times with water (5 mL). The organic phase was then dried over magnesium sulfate and evaporated. The residue was subjected to column chromatography on silica eluting with a mixture of ethyl acetate and methanol (9:1, v/v) to give 7-cyano-6-(4-methylpyridin-3-yl)-3,4-dihydro-1H-pyrrolo[1,2-a]pyrazine-2,8-dicarboxylic acid 8-amide. 2-[(4-trifluoromethylphenyl)amide] (40 mg) as an off white solid, m.p. 285–286° C. $^1$H NMR [(CD$_3$)$_2$SO]: δ 9.30 (s, 1H), 8.71 (s, 1H), 8.00 (d, 1H), 7.79 (d, 2H), 7.70 (d, 2H), 7.65–7.00 (2 bs and d overlapping, 3H), 5.04 (s, 2H), 4.11 (t, 2H), 3.92 (t, 2H) and 2.63 (s, 3H).

EXAMPLE 24

(a) 7-Cyano-6-(tetrahydropyran-4-yl)-3,4-dihydro-1H-pyrrolo[1,2-a]pyrazine-2,8-dicarboxylic acid 8-amide 2-[(3-trifluoromethylphenyl)amide]

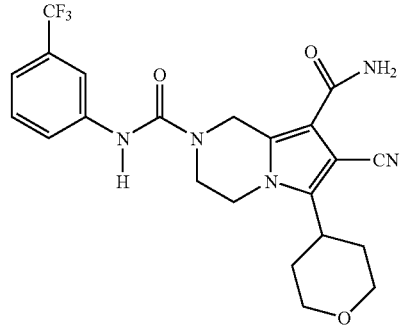

A suspension of 7-cyano-6-(tetrahydropyran-4-yl)-1,2,3,4-tetrahydropyrrolo[1,2-a]pyrazine-8-carboxylic acid amide trifluoroacetic acid salt (180 mg, Reference Example 36) in dry dichloromethane (5 mL) was treated with dry triethylamine (0.19 mL), then with a solution of 3-trifluoromethylphenyl isocyanate (90 mg) in dry dichloromethane (1 mL). After stirring at room temperature for a further 1 hour the reaction mixture was allowed to stand for 48 hours. The reaction mixture was then further treated with a solution of 3-trifluoromethylphenyl isocyanate (90 mg) in dry dichloromethane (1 mL). After stirring at room temperature for a further 15 minutes the reaction mixture was evaporated. The residue was subjected to column chromatography on silica eluting with a mixture of dichloromethane and methanol (19:1, v/v) to give 7-cyano-6-(tetrahydropyran-4-yl)-3,4-dihydro-1H-pyrrolo[1,2-a]pyrazine-2,8-dicarboxylic acid 8-amide 2-[(3-trifluoromethylphenyl)amide] (172 mg) as a white solid, m.p. 200–202° C. (dec). MS: 462 [MH]+. (b) 7-cyano-6-(tetrahydropyran-4-yl)-3,4-dihydro-1H-pyrrolo[1,2-a]pyrazine-2,8-dicarboxylic acid 8-amide 2-[(4-trifluoromethylphenyl)amide]

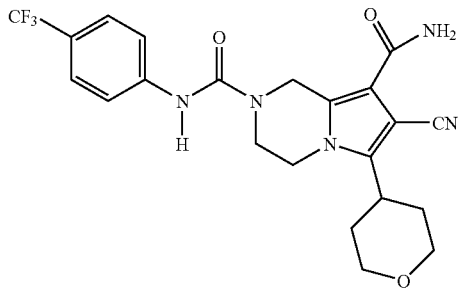

By proceeding in a similar manner to Example 24(a) above but using 4-trifluoromethylphenyl isocyanate there was prepared 7-cyano-6-(tetrahydropyran-4-yl)-3,4-dihydro-1H-pyrrolo[1,2-a]pyrazine-2,8-dicarboxylic acid 8-amide 2-[(4-trifluoromethylphenyl)amide] as a white solid, m.p. 287–291° C. (dec). MS: 462 [MH]+.

(c) 7-cyano-6-(tetrahydropyran-4-yl)-3,4-dihydro-1H-pyrrolo[1,2-a]pyrazine-2,8-dicarboxylic acid 8-amide 2-[(4-fluorophenyl)amide]

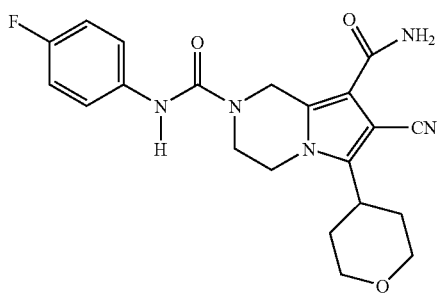

By proceeding in a similar manner to Example 24(a) above but using 4-fluorophenyl isocyanate there was prepared 7-cyano-6-(tetrahydropyran-4-yl)-3,4-dihydro-1H-pyrrolo[1,2-a]pyrazine-2,8-dicarboxylic acid 8-amide 2-[(4-fluorophenyl)amide] as a white solid, m.p. 267–268° C. (dec). 1H NMR [(CD3)2SO]: δ 8.87 (s, 1H), 7.51–7.20 (bs and dd overlapping, 3H), 7.09 (t, 2H), 7.04–6.80 (bs, 1H), 4.83 (s, 2H), 4.07 (t, 2H), 3.96 (dd, 2H), 3.86 (t, 2H), 3.40 (t, 2H), 3.16–3.04 (m, 1H), 2.05–1.90 (m, 2H) and 1.80–1.65 (d, 2H).

(d) (±)-trans-7-cyano-6-(tetrahydropyran-4-yl)-3,4-dihydro-1H-pyrrolo[1,2-a]pyrazine-2,8-dicarboxylic acid 8-amide 2-[(2-phenylcyclopropyl)amide]

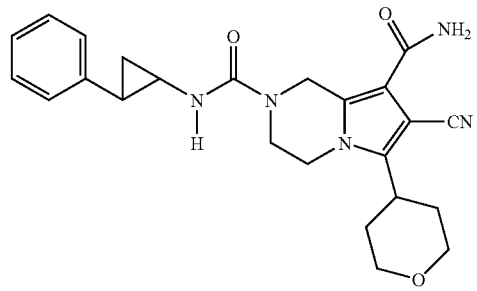

By proceeding in a similar manner to Example 24(a) above but using (±)-trans-2-phenylcyclopropyl isocyanate there was prepared (±)-trans-7-cyano-6-(tetrahydropyran-4-yl)-3,4-dihydro-1H-pyrrolo[1,2-a]pyrazine-2,8-dicarboxylic acid 8-amide 2-[(2-phenylcyclopropyl)amide] as a white solid, m.p. 150° C. (dec). MS: 456 [MNa]+.

(e) 7-cyano-6-(tetrahydropyran-4-yl)-3,4-dihydro-1H-pyrrolo[1,2-a]pyrazine-2,8-dicarboxylic acid 8-amide 2-[(5-methylthiophen-2-yl)amide]

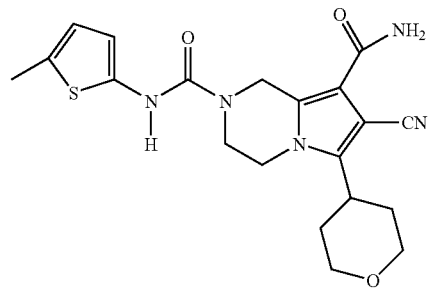

By proceeding in a similar manner to Example 24(a) above but using a 0.3M solution of 2-isocyanoto-5-methylthiophene in toluene (Reference Example 57) there was prepared 7-cyano-6-(tetrahydropyran-4-yl)-3,4-dihydro-1H-pyrrolo[1,2-a]pyrazine-2,8-dicarboxylic acid 8-amide 2-[(5-methylthiophen-2-yl)amide] as a white solid, m.p. 159–161° C. MS: 414 [MH]+.

EXAMPLE 25

(a) 7-cyano-6-(tetrahydropyran-4-yl)-3,4-dihydro-1H-pyrrolo[1,2-a]pyrazine-2,8-dicarboxylic acid 8-amide 2:quinolin-6-ylamide

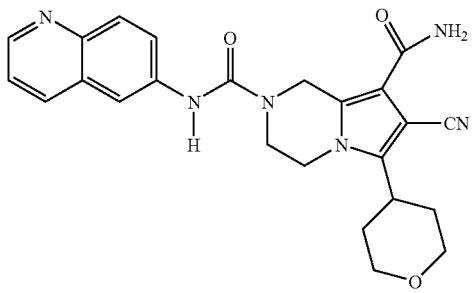

A stirred solution of triphosgene (80 mg) in dry dichloromethane (11 mL), under a blanket of nitrogen at −70° C., was treated dropwise with a solution of 6-aminoquinoline (100 mg) and triethylamine (0.5 mL) in dry dichloromethane (1 mL) over 1½ hour whilst maintaining the temperature below −65° C. After stirring at −70° C. for a further 1 hour the mixture was treated with a suspension of 7-cyano-6-(tetrahydropyran-4-yl)-1,2,3,4-tetrahydropyrrolo[1,2-a]pyrazine-8-carboxylic acid amide trifluoroacetic acid salt (200 mg, Reference Example 36) and triethylamine (0.16 mL) in dry dichloromethane (11 mL) whilst maintaining the temperature below −65° C. The reaction mixture was then allowed to warm to room temperature and stand overnight. The reaction mixture was filtered and the solid collected washed with dichloromethane. The solid was subjected to column chromatography on silica eluting with a mixture of dichloromethane and methanol (9:1, v/v) to give 7-cyano-6-(tetrahydropyran-4-yl)-3,4-dihydro-1H-pyrrolo[1,2-a]pyrazine-2,8-dicarboxylic acid 8-amide 2-quinolin-6-ylamide (161 mg) as an off white solid, m.p. 296–298° C. (dec). MS: 445 [MH]$^+$.

(b) 7-cyano-6-(tetrahydropyran-4-yl)-3,4-dihydro-1H-pyrrolo[1,2-a]pyrazine-2,8-dicarboxylic acid 8-amide 2-indan-2-ylamide

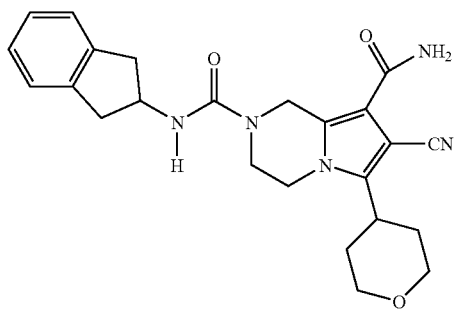

By proceeding in a similar manner to Example 25(a) above but using 2-indanamine hydrochloride there was prepared 7-cyano-6-(tetrahydropyran-4-yl)-3,4-dihydro-1H-pyrrolo[1,2-a]pyrazine-2,8-dicarboxylic acid 8-amide 2-indan-2-ylamide as white solid, m.p. 262–264° C. (dec). MS: 434 [MH]$^+$.

(c) 7-cyano-6-(tetrahydropyran-4-yl)-3,4-dihydro-1H-pyrrolo[1,2-a]pyrazine-2,8-dicarboxylic acid 8-amide 2-[(4-cyanophenyl)amide]

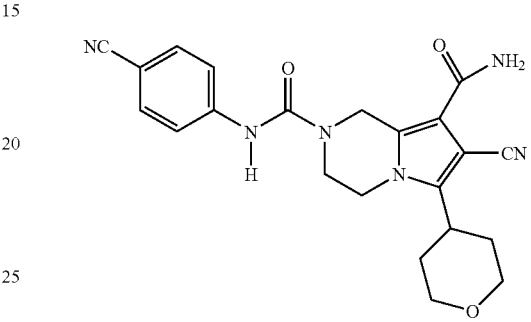

By proceeding in a similar manner to Example 25(a) above but using 4-cyanoaniline there was prepared 7-cyano-6-(tetrahydropyran-4-yl)-3,4-dihydro-1H-pyrrolo[1,2-a]pyrazine-2,8-dicarboxylic acid 8-amide 2-[(4-cyanophenyl)amide] as a white solid, m.p. 289–293° C. (dec).

$^1$H NMR [(CD$_3$)$_2$SO]: δ 9.30 (s, 1H), 7.71 (d, 2H), 7.67(d, 2H), 7.50–7.20 (bs, 1H), 7.10–6.80 (bs, 1H), 4.87 (s, 2H), 4.10 (t, 2H), 3.95 (dd, 2H), 3.90 (t, 2H), 3.40 (t, 2H), 3.16–3.03 (m, 1H), 2.04–1.90 (m, 2H) and 1.80–1.65 (d, 2H).

(d) 4-{[8-carbamoyl-7-cyano-6-(tetrahydropyran-4-yl)-3,4-dihydro-1H-pyrrolo[1,2-a]pyrazine-2-carbonyl]amino}piperidine-1-carboxylic acid isopropyl ester

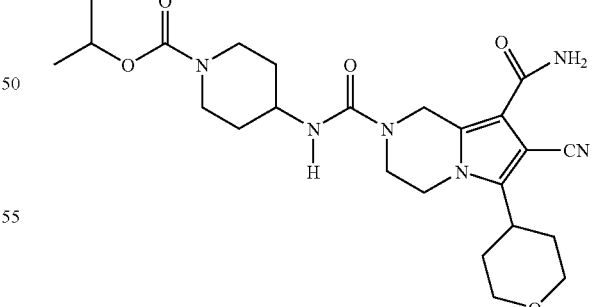

By proceeding in a similar manner to Example 25(a) above but using 4-amino-piperidine-1-carboxylic acid isopropyl ester, trifluoroacetic acid salt (Reference Example 60) there was prepared 4-{[8-carbamoyl-7-cyano-6-(tetrahydropyran-4-yl)-3,4-dihydro-1H-pyrrolo[1,2-a]pyrazine-2-carbonyl]amino}piperidine-1-carboxylic acid isopropyl-ester as a white solid, m.p. 124–126° C. MS: 509 [MNa]$^+$,

EXAMPLE 26

7-Cyano-6-trifluoromethyl-3,4-dihydro-1H-pyrrolo[1,2-a]pyrazine-2,8-dicarboxylic acid 8-amide 2-[(4-trifluoromethylphenyl)amide]

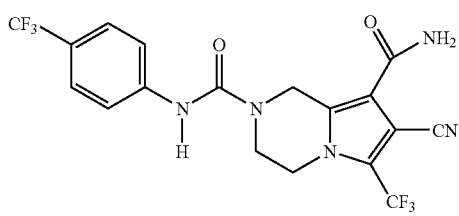

A suspension of 7-cyano-6-trifluoromethyl-1,2,3,4-tetrahydropyrrolo[1,2-a]pyrazine-8-carboxylic acid amide trifluoroacetic acid salt (289 mg, Reference Example 39) in dry dichloromethane (5 mL) was treated with dry triethylamine (0.47 mL), then with a solution of 4-trifluoromethylphenyl isocyanate (138 mg) in dry dichloromethane (1 mL). After stirring at room temperature for a further 5 hours the reaction mixture was filtered. The solid collected was washed with dichloromethane to give 7-cyano-6-trifluoromethyl-3,4-dihydro-1H-pyrrolo[1,2-a]pyrazine-2,8-dicarboxylic acid 8-amide 2-[(4-trifluoromethylphenyl)amide] (196 mg) as a white solid, m.p. 243–246° C. (dec). MS: 446 [MH]$^+$.

EXAMPLE 27

(a) 7-Cyano-6-cyclopropyl-3,4-dihydro-1H-pyrrolo[1,2-a]pyrazine-2,8-dicarboxylic acid 8-amide 2-[(6-trifluoromethylpyridin-3-yl)amide]

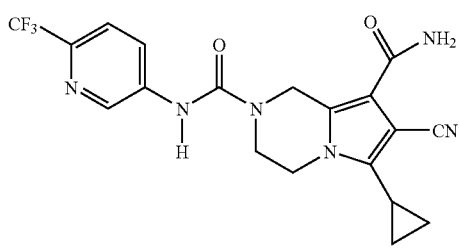

A suspension of 7-cyano-6-cyclopropyl-1,2,3,4-tetrahydropyrrolo[1,2-a]pyrazine-8-carboxylic acid amide trifluoroacetic acid salt [224 mg, Example 44(b)] in toluene (15 mL) was treated with triethylamine (0.20 mL), then a 0.3M solution of 2-trifluoromethylpyridine-4-carbonyl azide in toluene (7.00 mL, Reference Example 56). After stirring for 4.5 hours at 120° C. the reaction mixture was allowed to cool to room temperature and evaporated. The residue was treated with water and ethyl acetate. The organic phase was separated, dried over magnesium sulfate and evaporated. The residue was subjected to column chromatography on silica eluting with a mixture of ethyl acetate and pentane (2:1, v/v), then ethyl acetate to give 7-cyano-6-cyclopropyl-3,4-dihydro-1H-pyrrolo[1,2-a]pyrazine-2,8-dicarboxylic acid 8-amide 2-[(6-trifluoromethylpyridin-3-yl)amide] (164 mg) as a white solid, m.p. 149–153° C. MS: 419 [MH]$^+$ (b) 7-chloro-6-cyclopropyl-3,4-dihydro-1H-pyrrolo[1,2-a]pyrazine-2,8-dicarboxylic acid 8-amide 2-[(6-trifluoromethylpyridin-3-yl)amide]

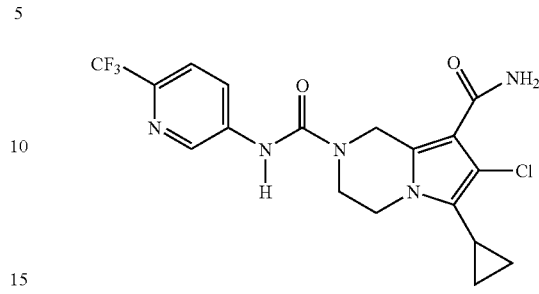

By proceeding in a similar manner to Example 27(a) above but using 7-chloro-6-cyclopropyl-1,2,3,4-tetrahydropyrrolo[1,2-a]pyrazine-8-carboxylic acid amide trifluoroacetic acid salt [Example 44(a)] there was prepared 7-chloro-6-cyclopropyl-3,4-dihydro-1H-pyrrolo[1,2-a]pyrazine-2,8-dicarboxylic acid 8-amide 2-[(6-trifluoromethylpyridin-3-yl)amide] as a white solid, m.p. 265–267° C. MS: 430 [MH]$^+$, 428 [MH]$^+$.

(c) 7-chloro-3,4-dihydro-1H-pyrrolo[1,2-a]pyrazine-2,8-dicarboxylic acid 8-amide 2-[(6-trifluoromethylpyridin-3-yl)amide]

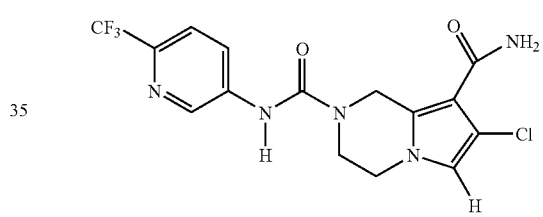

By proceeding in a similar manner to Example 27(a) above but using 7-chloro-1,2,3,4-tetrahydropyrrolo[1,2-a]pyrazine-8-carboxylic acid amide trifluoroacetic acid salt (Reference Example 24) there was prepared 7-chloro-3,4-dihydro-1H-pyrrolo[1,2-a]pyrazine-2,8-dicarboxylic acid 8-amide 2-[(6-trifluoromethylpyridin-3-yl)amide] (62 mg) as an off white solid, m.p. 279–281° C. MS: 390 [MH]$^+$, 388 [MH]$^+$.

(d) 7-cyano-6-phenyl-3,4-dihydro-1H-pyrrolo[1,2-a]pyrazine-2,8-dicarboxylic acid 8-amide 2-[(6-trifluoromethylpyridin-3-yl)amide]

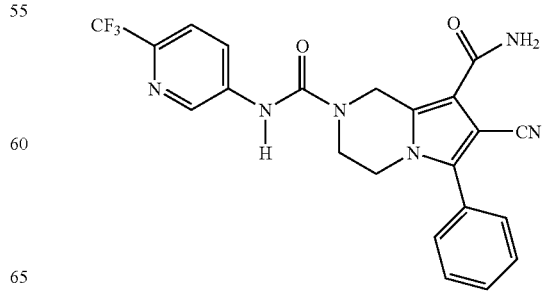

By proceeding in a similar manner to Example 27(a) above but using 7-cyano-6-phenyl-1,2,3,4-tetrahydropyrrolo[1,2-a]pyrazine-8-carboxylic acid amide trifluoroacetic acid salt (Reference Example 17) there was prepared 7-cyano-6-phenyl-3,4-dihydro-1H-pyrrolo[1,2-a]pyrazine-2,8-dicarboxylic acid 8-amide 2-[(6-trifluoromethylpyridin-3-yl)amide] as a white solid, m.p. 162–165° C. MS: 455 [MH]⁺

(e) 7-cyano-6-(tetrahydropyran-4-yl)-3,4-dihydro-1H-pyrrolo[1,2-a]pyrazine-2,8-dicarboxylic acid 8-amide 2-[(6-trifluoromethylpyridin-3-yl)amide]

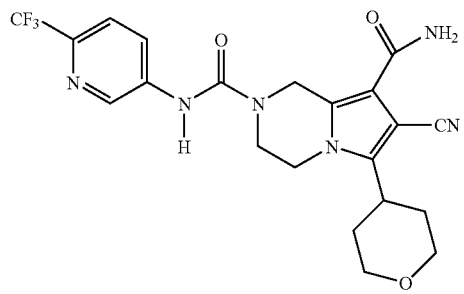

By proceeding in a similar manner to Example 27(a) above but using 7-cyano-6-(tetrahydropyran-4-yl)-1,2,3,4-tetrahydropyrrolo[1,2-a]pyrazine-8-carboxylic acid amide trifluoroacetic acid salt (Reference Example 36) there was prepared 7-cyano-6-(tetrahydropyran-4-yl)-3,4-dihydro-1H-pyrrolo[1,2-a]pyrazine-2,8-dicarboxylic acid 8-amide 2-[(6-trifluoromethylpyridin-3-yl)amide] as a white solid, m.p. 277–279° C. MS: 463 [MH]⁺

(f) 7-chloro-6-phenyl-3,4-dihydro-1H-pyrrolo[1,2-a]pyrazine-2,8-dicarboxylic acid 8-amide 2-[(6-trifluoromethylpyridin-3-yl)amide]

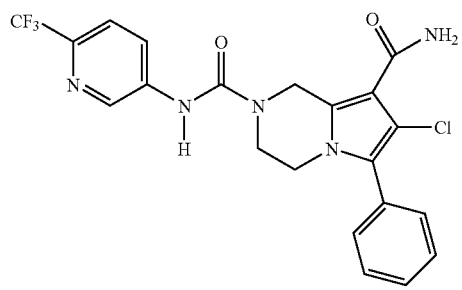

By proceeding in a similar manner to Example 27(a) above but using 7-chloro-6-phenyl-1,2,3,4-tetrahydropyrrolo[1,2-a]pyrazine-8-carboxylic acid amide trifluoroacetic acid salt (Reference Example 1) there was prepared 7-chloro-6-phenyl-3,4-dihydro-1H-pyrrolo[1,2-a]pyrazine-2,8-dicarboxylic acid 8-amide 2-[(6-trifluoromethylpyridin-3-yl)amide] as a white solid, m.p. 263–265° C. [Elemental analysis: C, 53.99; H, 3.61; N, 14.77%; Calculated for $C_{21}H_{17}ClF_3N_5O_2$: C, 54.38; H, 3.69; N, 15.10%].

EXAMPLE 28

(a) 4-[(8-Carbamoyl-7-cyano-6-phenyl-3,4-dihydro-1H-pyrrolo[1,2a]pyrazine-2-carbonyl)amino]benzoic acid

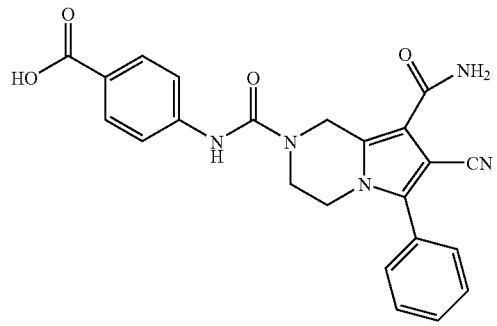

A stirred solution of 4-[(8-carbamoyl-7-cyano-6-phenyl-3,4-dihydro-1H-pyrrolo [1,2a]pyrazine-2-carbonyl)amino] benzoic acid ethyl ester (202 mg, Example 7(d)) in ethanol (14 mL) was treated with a 1M aqueous solution of sodium hydroxide (14 mL). After stirring for 4 hours at 60° C. the reaction mixture was allowed to cool to room temperature and then the bulk of ethanol removed under reduced pressure. The water residue was washed with ethyl acetate, then acidified to pH2 by treatment with concentrated hydrochloric acid and filtered. The solid collected was washed with water to give 4-[(8-carbamoyl-7-cyano-6-phenyl-3,4-dihydro-1H-pyrrolo[1,2a]pyrazine-2-carbonyl)amino]benzoic acid (148 mg) as a white solid, m.p. 286–288° C. [Elemental analysis: C, 63.09; H, 4.29; N, 15.54%; Calculated for $C_{23}H_{19}N_5O_4.0.5H_2O$: C, 63.00; H, 4.60; N, 15.98%].

(b) 4-[(8-carbamoyl-7-chloro-6-phenyl-3,4-dihydro-1H-pyrrolo[1,2-a]pyrazine-2-carbonyl)amino]benzoic acid

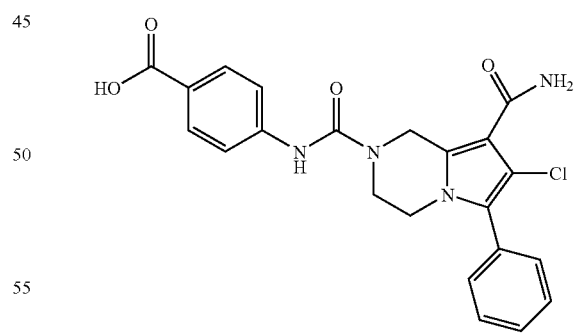

By proceeding in a similar manner to Example 28(a) above but using 4-[(8-carbamoyl-7-chloro-6-phenyl-3,4-dihydro-1H-pyrrolo[1,2-a]pyrazine-2-carbonyl)amino]benzoic acid ethyl ester (Example 1(aj)) there was prepared 4-[(8-carbamoyl-7-chloro-6-phenyl-3,4-dihydro-1H-pyrrolo[1,2-a]pyrazine-2-carbonyl)amino]benzoic acid as a white solid, m.p. 281–283° C. [Elemental analysis: C, 60.00; H, 4.41; N, 12.55%; Calculated for $C_{22}H_{19}ClN_4O_4$: C, 60.21; H, 4.36; N, 12.77%].

(c) 4-[(8-carbamoyl-7-cyano-6-cyclopropyl-3,4-dihydro-1H-pyrrolo[1,2-a]pyrazine-2-carbonyl)amino]benzoic acid

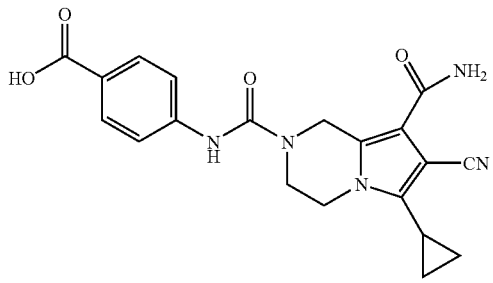

By proceeding in a similar manner to Example 28(a) above but using 4-[(8-carbamoyl-7-cyano-6-cyclopropyl-3,4-dihydro-1H-pyrrolo[1,2a]pyrazine-2-carbonyl)amino]benzoic acid ethyl ester (Example 9(c)) there was prepared 4-[(8-carbamoyl-7-cyano-6-cyclopropyl-3,4-dihydro-1H-pyrrolo[1,2-a]pyrazine-2-carbonyl)amino]benzoic acid as a white solid, m.p. 279–280° C. [Elemental analysis: C, 59.05; H, 4.87; N, 16.80%; Calculated for $C_{20}H_{19}N_5O_4 \cdot 0.75H_2O$: C, 58.99; H, 5.14; N, 17.20%].

(d) 4-[(8-carbamoyl-7-chloro-6-pyridin-3-yl-3,4-dihydro-1H-pyrrolo[1,2a]pyrazine-2-carbonyl)amino]benzoic acid

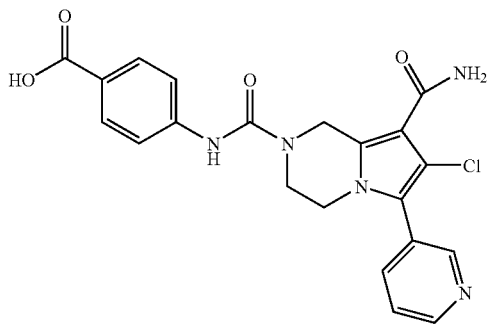

By proceeding in a similar manner to Example 28(a) above but using 4-[(8-carbamoyl-7-chloro-6-pyridin-3-yl-3,4-dihydro-1H-pyrrolo[1,2a]pyrazine-2-carbonyl)amino]benzoic acid ethyl ester (Example 4(d)) and acidifying with a saturated aqueous solution of sodium dihydrogen phosphate there was prepared 4-[(8-carbamoyl-6-chloro-6-pyridin-3-yl-3,4-dihydro-1H-pyrrolo[1,2a]pyrazine-2-carbonyl)amino]benzoic acid-as a white solid, m.p. 222–223° C. $^1$H NMR [$(CD_3)_2SO$]: δ 9.18 (s, 1H), 8.75 (s, 1H), 8.67 (d, 1H), 8.10 (d, 1H), 7.80 (d, 2H), 7.66 (dd, 1H), 7.55 (d, 2H), 7.43–7.26 (bs, 1H), 6.93–6.74 (bs, 1H), 4.94 (s, 2H), 3.91 (t, 2H) and 3.80 (t, 2H).

(e) 4-[(8-carbamoyl-7-cyano-6-(2-methylpyridin-3-yl)-3,4-dihydro-1H-pyrrolo[1,2a]pyrazine-2-arbonyl)amino]benzoic acid

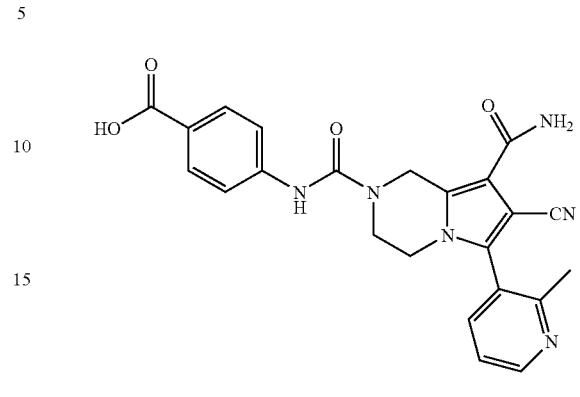

By proceeding in a similar manner to Example 28(a) above but using 4-[(8-carbamoyl-7-cyano-6-(2-methylpyridin-3-yl)-3,4-dihydro-1H-pyrrolo[1,2a]pyrazine-2-arbonyl)amino]benzoic acid ethyl ester (Example 11(c)) and acidifying with a saturated aqueous solution of sodium dihydrogen phosphate there was prepared 4-[(8-carbamoyl-7-cyano-6-(2-methylpyridin-3-yl)-3,4-dihydro-1H-pyrrolo[1,2a]pyrazine-2-carbonyl)amino] benzoic acid as a white solid, m.p. 295–298° C. $^1$H NMR [$(CD_3)_2SO$]: δ 9.12 (s, 1H), 8.59 (d, 1H), 7.80 (d and d overlapping, 3H), 7.54 (d, 2H), 7.49–7.30 (bs and dd overlapping, 2H), 7.21–6.95 (bs, 1H), 5.02 (d, 1H), 4.85 (d, 1H), 3.94–3.58 (m, 4H) and 2.35 (s, 3H).

(f) 4-[(8-carbamoyl-7-cyano-6-(1-methanesulfonylpiperidin-4-yl)-3,4-dihydro-1H-pyrrolo[1,2a]pyrazine-2-carbonyl)amino]benzoic acid

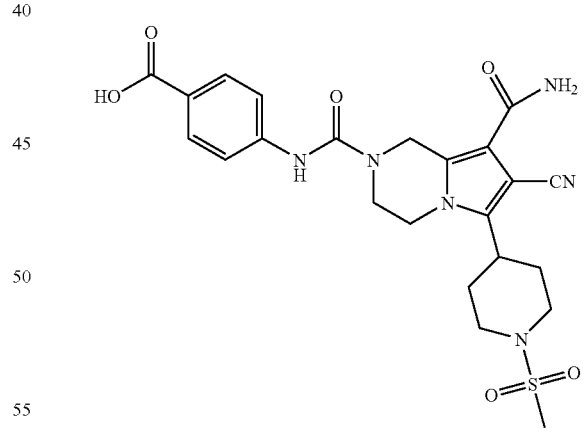

By proceeding in a similar manner to Example 28(a) above but using 4-[(8-carbamoyl-7-cyano-6-(1-methanesulfonylpiperidin-4-yl)-3,4-dihydro-1H-pyrrolo[1,2a]pyrazine-2-carbonyl)amino]benzoic acid ethyl ester (Example (14c)) there was prepared 4-[(8-carbamoyl-7-cyano-6-(1-methanesulfonylpiperidin-4-yl)-3,4-dihydro-1H-pyrrolo[1,2a]pyrazine-2-carbonyl)amino]benzoic acid as a white solid, m.p. 285° C. [Elemental analysis: C, 53.37; H, 5.14; N, 15.90%; Calculated for $C_{23}H_{26}N_6O_6S$: C, 53.69; H, 5.09; N, 16.33%].

(g) 3-[(8-carbamoyl-7-chloro-6-phenyl-3,4-dihydro-1H-pyrrolo[1,2-a]pyrazine-2-carbonyl)amino]benzoic acid

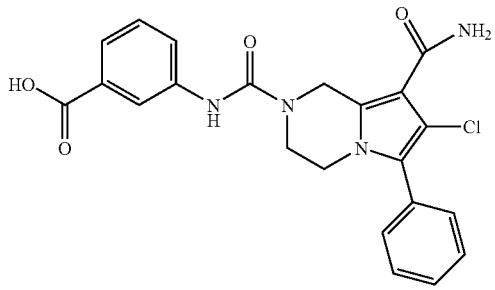

By proceeding in a similar manner to Example 28(a) above but using 3-[(8-carbamoyl-7-chloro-6-phenyl-3,4-dihydro-1H-pyrrolo[1,2-a]pyrazine-2-carbonyl)amino]benzoic acid ethyl ester (Example 1(as)) there was prepared 3-[(8-carbamoyl-7-chloro-6-phenyl-3,4-dihydro-1H-pyrrolo[1,2-a]pyrazine-2-carbonyl)amino]benzoic acid as a white solid, m.p. 263–265° C. $^1$H NMR [(CD$_3$)$_2$SO]: δ 9.03 (s, 1H), 8.09 (t, 1H), 7.76 (d, 1H), 7.56–7.41 (m, 6H), 7.39–7.27 (t and bs overlapping, 2H), 6.89–6.75 (bs, 1H), 4.97 (s, 2H), 3.88 (t, 2H) and 3.82 (t, 2H).

EXAMPLE 29

(a) 7-Chloro-6-phenyl-3,4-dihydro-1H-pyrrolo[1,2-a]pyrazine-2,8-dicarboxylic acid 8-amide 2-[(2-hydroxyphenyl)amide]

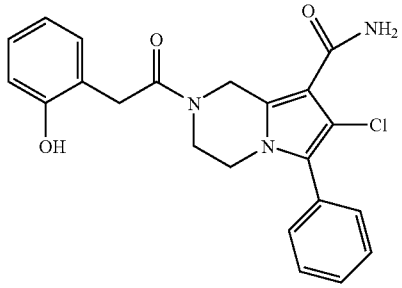

A stirred solution of 7-chloro-6-phenyl-3,4-dihydro-1H-pyrrolo[1,2-a]pyrazine-2,8-dicarboxylic acid 8-amide 2-[(2-methoxyphenyl)amide] (21 mg, Example 1(af)) in dry dichloromethane (1 mL), under a blanket of nitrogen at −70° C., was treated dropwise with a 1M solution of boron tribromide in dichloromethane (0.17 mL). The reaction mixture was allowed to warm to room temperature over 1.5 hours, then treated with water (5 mL) and 1M hydrochloric acid (2 mL), and then ethyl acetate (15 mL). The organic phase was separated and the aqueous phase further extracted twice with ethyl acetate (15 mL). The combined organic extracts were dried over magnesium sulfate, then evaporated to give 7-Chloro-6-phenyl-3,4-dihydro-1H-pyrrolo[1,2-a]pyrazine-2,8-dicarboxylic acid 8-amide 2-[(2-hydroxyphenyl)amide] (20 mg) as a white solid, m.p. 176–180° C. $^1$H NMR [(CD$_3$)$_2$SO]: δ 9.54 (s, 1H), 8.08 (s, 1H), 7.50–7.36 (m, 6H), 7.31–7.24 (bs, 1H), 6.87 (t, 1H), 6.82–6.75 (d and bs overlapping, 2H), 6.72 (t, 1H), 4.91 (s, 2H), 3.85 (t, 2H) and 3.77 (t, 2H).

(b) 7-chloro-6-phenyl-3,4-dihydro-1H-pyrrolo[1,2-a]pyrazine-2,8-dicarboxylic acid 8-amide 2-[(4-hydroxyphenyl)amide]

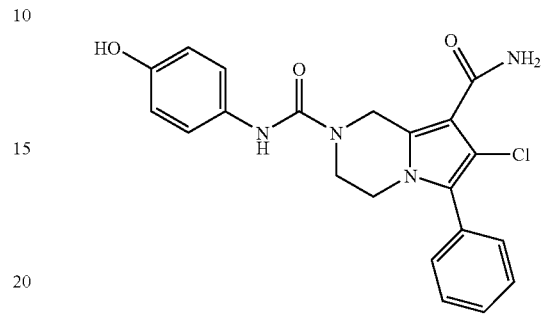

By proceeding in a similar manner to Example 29(a) above but using 7-chloro-6-phenyl-3,4-dihydro-1H-pyrrolo[1,2-a]pyrazine-2,8-dicarboxylic acid 8-amide 2-[(4-methoxyphenyl) amide] (Example 1(a)) there was prepared 7-chloro-6-phenyl-3,4-dihydro-1H-pyrrolo[1,2-a]pyrazine-2,8-dicarboxylic acid 8-amide 2-[(4-hydroxyphenyl)amide] as a white solid, m.p. 193–195° C. MS: 413 [MH]$^+$, 411 [MH]$^+$.

EXAMPLE 30

(a) 7-Chloro-2-(3-cyclohexylpropionyl)-6-phenyl-1,2,3,4-tetrahydropyrrolo[1,2-a]pyrazine-8-carboxylic acid amide

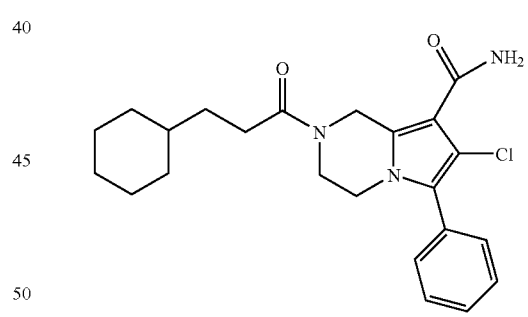

A suspension of 7-chloro-6-phenyl-1,2,3,4-tetrahydropyrrolo[1,2-a]pyrazine-8-carboxylic acid amide trifluoroacetic acid salt (100 mg, Reference Example 1) in dry dichloromethane (10 mL) was treated with dry triethylamine (0.11 mL), then with a solution of 3-cyclohexylpropionyl chloride (45 mg) in dry dichloromethane (5 mL). After stirring at room temperature overnight the reaction mixture was washed with water, then the organic phase was dried over magnesium sulfate and evaporated. The residue was subjected to column chromatography on silica eluting with a mixture of methanol and dichloromethane (1:19, v/v) to give 7-chloro-2-(3-cyclohexylpropionyl)-6-phenyl-1,2,3,4-tetrahydropyrrolo[1,2-a]pyrazine-8-carboxylic acid amide (80 mg) as a white solid, m.p. 181–182° C. MS: 416 [MH]$^+$, 414 [MH]$^+$.

(b) 7-chloro-2-(3-cyclopentylpropionyl)-6-phenyl-12,3,4-tetrahydropyrrolo[1,2-a]pyrazine-8-carboxylic acid amide

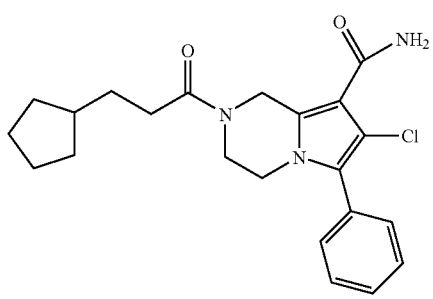

By proceeding in a similar manner to Example 30(a) above but using cyclopentylpropionyl chloride there was prepared 7-chloro-2-(3-cyclopentylpropionyl)-6-phenyl-1,2,3,4-tetrahydropyrrolo[1,2-a]pyrazine-8-carboxylic acid amide as a white solid, m.p. 172–174° C. [Elemental analysis: C, 66.11; H, 6.69; N, 10.47%; Calculated for $C_{22}H_{26}ClN_3O_2$: C, 66.07; H, 6.55; N, 10.51%].

(c) 7-chloro-2-phenoxyacetyl-6-phenyl-1,2,3,4-tetrahydropyrrolo[1,2-a]pyrazine-8-carboxylic acid amide

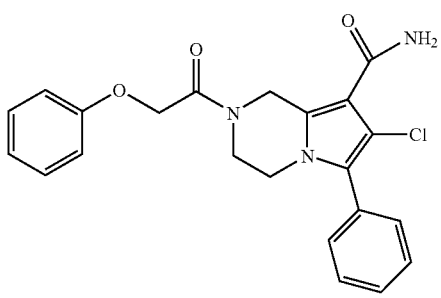

By proceeding in a similar manner to Example 30(a) above but using phenoxyacetyl chloride there was prepared 7-chloro-2-phenoxyacetyl-6-phenyl-1,2,3,4-tetrahydropyrrolo[1,2-a]pyrazine-8-carboxylic acid amide as a white solid, m.p. 169–170° C. MS: 412 [MH]$^+$, 410 [MH]$^+$.

(d) 7-chloro-2-(morpholine-4-carbonyl)-6-phenyl-1,2,3,4-tetrahydropyrrolo[1,2-a]pyrazine-8-carboxylic acid amide

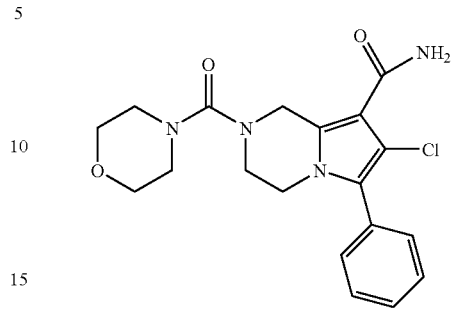

By proceeding in a similar manner to Example 30(a) above but using 4-morpholinecarbonyl chloride there was prepared 7-chloro-2-(morpholine-4-carbonyl)-6-phenyl-1,2,3,4-tetrahydropyrrolo[1,2-a]pyrazine-8-carboxylic acid amide as a white solid, m.p. 219–220° C. MS:391 [MH]$^+$, 389 [MH]$^+$.

(e) 7-chloro-6-phenyl-2-(thiophen-2-ylacetyl)-1,2,3,4-tetrahydropyrrolo[1,2-a]pyrazine-8-carboxylic acid amide

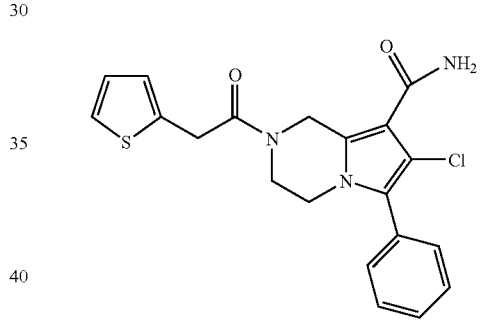

By proceeding in a similar manner to Example 30(a) above but using 2-thiophenylacetyl chloride there was prepared 7-chloro-6-phenyl-2-(thiophen-2-ylacetyl)-1,2,3,4-tetrahydropyrrolo[1,2-a]pyrazine-8-carboxylic acid amide as a white solid, m.p. 225–229° C. MS: 402 [MH]$^+$, 400 [MH]$^+$.

(f) 7-chloro-2-[(4-methoxyphenyl)acetyl]-6-phenyl-1,2,3,4-tetrahydropyrrolo[1,2-a]pyrazine-8-carboxylic acid amide

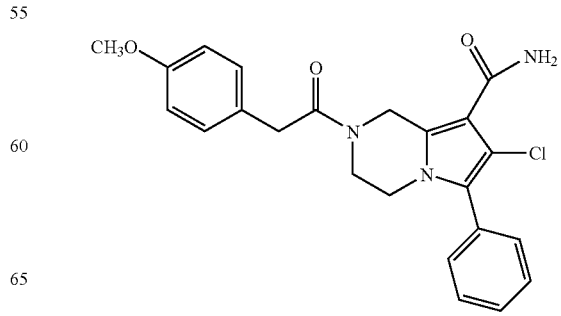

By proceeding in a similar manner to Example 30(a) above but using 4-methoxyphenylacetyl chloride there was prepared 7-chloro-2-[(4-methoxyphenyl)acetyl]-6-phenyl-1,2,3,4-tetrahydropyrrolo[1,2-a]pyrazine-8-carboxylic acid amide as a white solid, m.p. 146–148° C. MS: 426 [MH]$^+$, 424 [MH]$^+$.

(g) 7-chloro-2-(furan-2-carbonyl)-6-phenyl-1.2,3,4-tetrahydropyrrolo[1,2-a]pyrazine-8-carboxylic acid amide

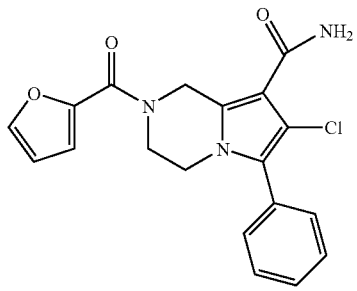

By proceeding in a similar manner to Example 30(a) above but using 2-furoyl chloride there was prepared 7-chloro-2-(furan-2-carbonyl)-6-phenyl-1,2,3,4-tetrahydropyrrolo[1,2-a]pyrazine-8-carboxylic acid amide as a white solid, m.p. 238–239° C. MS: 372 [MH]$^+$, 370 [MH]$^+$.

(h) 7-chloro-6-phenyl-2-(thiophene-2-carbonyl)-1,2,3,4-tetrahydropyrrolo[1,2-a]pyrazine-8-carboxylic acid amide

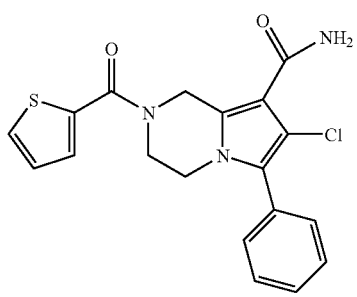

By proceeding in a similar manner to Example 30(a) above but using 2-thiophenecarbonyl chloride there was prepared 7-chloro-6-phenyl-2-(thiophene-2-carbonyl)-1,2,3,4-tetrahydropyrrolo[1,2-a]pyrazine-8-carboxylic acid amide as a white solid, m.p. 236–238° C. [Elemental analysis: C, 59.18; H, 3.82; N, 10.61%; Calculated for $C_{19}H_{16}ClN_3O_2S$: C, 59.14; H, 4.18; N, 10.89%].

(i) 7-chloro-6-phenyl-2-(5-pyridin-2-ylthiophene-2-carbonyl)-1,2,3,4-tetrahydropyrrolo[1,2-a]pyrazine-8-carboxylic acid amide

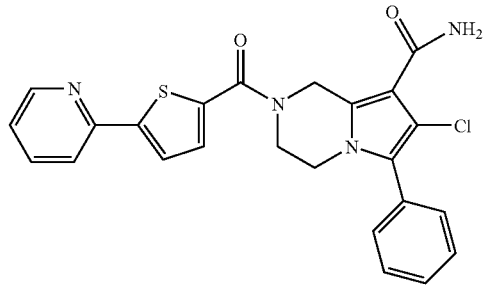

By proceeding in a similar manner to Example 30(a) above but using 5-(pyrid-2-yl)thiophene-2-carbonyl chloride (Reference Example 43) there was prepared 7-chloro-6-phenyl-2-(5-pyridin-2-ylthiophene-2-carbonyl)-1,2,3,4-tetrahydropyrrolo[1,2-a]pyrazine-8-carboxylic acid amide as a white solid, m.p. 232° C. MS: 465 [MH]$^+$, 463 [MH]$^+$.

EXAMPLE 31

(a) 7-Chloro-6-phenyl-2-(thiophene-2-sulfonyl)-1,2,3,4-tetrahydropyrrolo[1,2-a]pyrazine-8-carboxylic acid amide

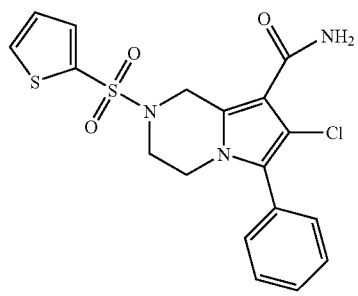

A suspension of 7-chloro-6-phenyl-1,2,3,4-tetrahydropyrrolo[1,2-a]pyrazine-8-carboxylic acid amide trifluoroacetic acid salt (100 mg, Reference Example 1) in dry acetonitrile (15 mL) was treated with dry triethylamine (0.11 mL), then with 2-thiophenesulfonyl chloride (52 mg). After stirring at 60° C. for 7 hours the reaction mixture was allowed to cool to room temperature and then stand overnight. The solvent was removed under reduced pressure and the residue then treated with water and dichloromethane. The organic phase was separated, then dried over magnesium sulfate and evaporated. The residue was subjected to column chromatography on silica eluting with a mixture of methanol and dichloromethane (1:19, v/v) to give 7-chloro-6-phenyl-2-(thiophene-2-sulfonyl)-1,2,3,4-tetrahydropyrrolo[1,2-a]pyrazine-8-carboxylic acid amide (100 mg) as a white solid, m.p. 240–242° C. [Elemental analysis: C, 50.95; H, 4.06; N, 9.98%; Calculated for $C_{18}H_{16}ClN_3O_3S_2$: C, 51.24; H, 3.82; N, 9.96%].

(b) 7-chloro-6-phenyl-2-(toluene-4-sulfonyl)-1,23,4-tetrahydropyrrolo[1,2-a]pyrazine-8-carboxylic acid amide

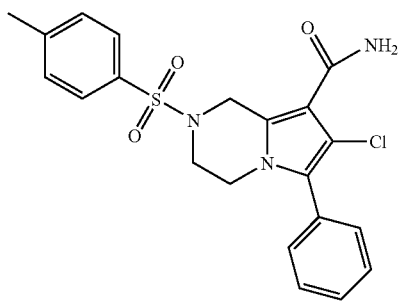

By proceeding in a similar manner to Example 31(a) above but using 4-toluenesulfonyl chloride there was prepared 7-chloro-6-phenyl-2-(toluene-4-sulfonyl)-1,2,3,4-tetrahydropyrrolo[1,2-a]pyrazine-8-carboxylic acid amide as a white solid, m.p. 188–190° C. MS: 432 [MH]$^+$, 430 [MH]$^+$.

(c) 2-benzenesulfonyl-7-chloro-6-phenyl-1,2,3,4-tetrahydropyrrolo[1,2-a]pyrazine-8-carboxylic acid amide

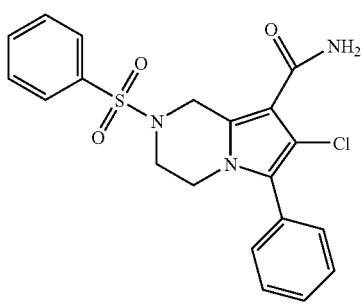

By proceeding in a similar manner to Example 31(a) above but using benzenesulfonyl chloride there was prepared 2-benzenesulfonyl-7-chloro-6-phenyl-1,2,3,4-tetrahydropyrrolo[1,2-a]pyrazine-8-carboxylic acid amide as a white solid, m.p. 250–252° C. [Elemental analysis: C, 57.37; H, 4.22; N, 9.93%; Calculated for $C_{20}H_{18}ClN_3O_3S$: C, 57.76; H, 4.36; N, 10.10%].

(d) 7-chloro-2-(4-chlorobenzenesulfonyl)-6-phenyl-1,2,3,4-tetrahydropyrrolo[1,2-a]pyrazine-8-carboxylic acid amide

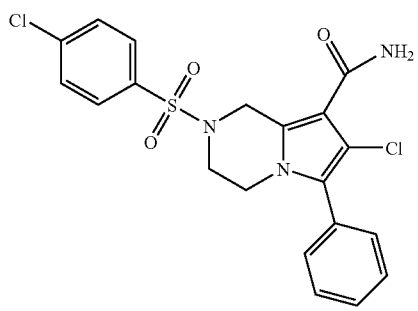

By proceeding in a similar manner to Example 31(a) above but using 4-chlorobenzenesulfonyl chloride there was prepared 7-chloro-2-(4-chlorobenzenesulfonyl)-6-phenyl-1,2,3,4-tetrahydropyrrolo[1,2-a]pyrazine-8-carboxylic acid amide as a white solid, m.p. 123–125° C. [Elemental analysis: C, 53.17; H, 3.57; N, 8.91%; Calculated for $C_{20}H_{17}Cl_2N_3O_3S$: C, 53.34; H, 3.80; N, 9.33%].

(e) 7-chloro-2-(3-cyanobenzenesulfonyl)-6-phenyl-1,2,3,4-tetrahydropyrrolo[1,2-a]pyrazine-8-carboxylic acid amide

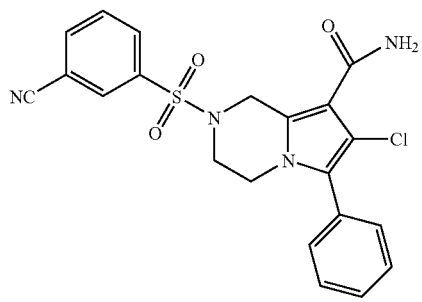

By proceeding in a similar manner to Example 31(a) above but using 3-cyanobenzenesulfonyl chloride there was prepared 7-chloro-2-(3-cyanobenzenesulfonyl)-6-phenyl-1,2,3,4-tetrahydropyrrolo[1,2-a]pyrazine-8-carboxylic acid amide as a white solid, m.p. 243–245° C. MS: 443 [MH]$^+$, 441 [MH]$^+$.

(f) 7-chloro-2-(4-cyanobenzenesulfonyl)-6-phenyl-1,2,3,4-tetrahydropyrrolo[1,2-a]pyrazine-8-carboxylic acid amide

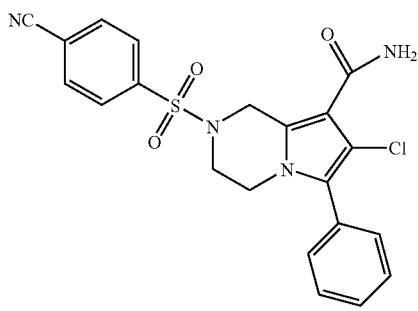

By proceeding in a similar manner to Example 31(a) above but using 4-cyanobenzenesulfonyl chloride there was prepared 7-chloro-2-(4-cyanobenzenesulfonyl)-6-phenyl-1,2,3,4-tetrahydropyrrolo[1,2-a]pyrazine-8-carboxylic acid amide as a white solid, m.p. 205–206° C. MS: 443 [MH]$^+$, 441 [MH]$^+$.

(g) 7-chloro-2-(2-fluorobenzenesulfonyl)-6-phenyl-1,2,3,4-tetrahydropyrrolo[1,2-a]pyrazine-8-carboxylic acid amide

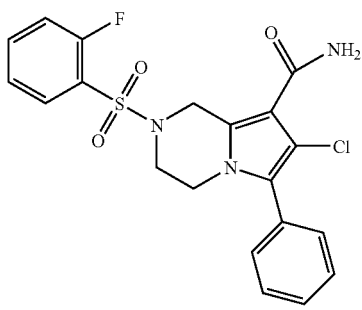

By proceeding in a similar manner to Example 31(a) above but using 2-fluorobenzenesulfonyl chloride there was prepared 7-chloro-2-(2-fluorobenzenesulfonyl)-6-phenyl-1,2,3,4-tetrahydropyrrolo[1,2-a]pyrazine-8-carboxylic acid amide as a white solid, m.p. 239–240° C. MS: 436 [MH]$^+$, 434 [MH]$^+$.

(h) 7-chloro-6-phenyl-2-(3-trifluoromethylbenzenesulfonyl)-1,2,3,4-tetrahydropyrrolo[1,2-a]pyrazine-8-carboxylic acid amide

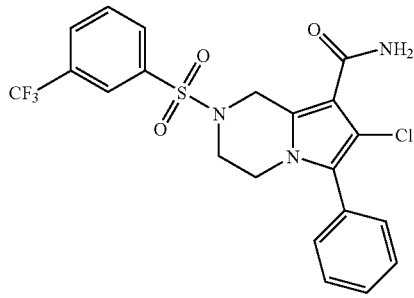

By proceeding in a similar manner but using 3-trifluoromethylbenzenesulfonyl chloride there was prepared 7-chloro-6-phenyl-2-(3-trifluoromethylbenzenesulfonyl)-1,2,3,4-tetrahydropyrrolo[1,2-a]pyrazine-8-carboxylic acid amide as a white solid, m.p. 158–159° C. [Elemental analysis: C, 50.58; H, 3.70; N, 8.38%; Calculated for $C_{21}H_{17}ClF_3N_3O_3S \cdot 0.75H_2O$: C, 50.71; H, 3.75; N, 8.45%].

(i) 7-chloro-2-(4-fluorobenzenesulfonyl)-6-phenyl-1,2,3,4-tetrahydropyrrolo[1,2-a]pyrazine-8-carboxylic acid amide

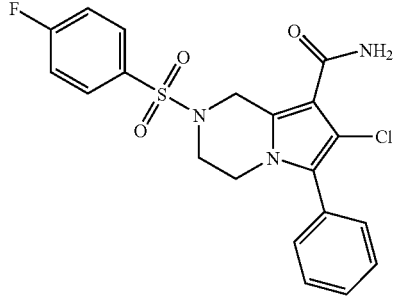

By proceeding in a similar manner to Example 31(a) above but using 4-fluorobenzenesulfonyl chloride there was prepared 7-chloro-2-(4-fluorobenzenesulfonyl)-6-phenyl-1,2,3,4-tetrahydropyrrolo[1,2-a]pyrazine-8-carboxylic acid amide as a white solid, m.p. 177–178° C. MS: 436 [MH]$^+$, 434 [MH]$^+$.

(j) 7-chloro-2-(4-nitrobenzenesulfonyl)-6-phenyl-1,2,3,4-tetrahydropyrrolo[1,2-a]pyrazine-8-carboxylic acid amide

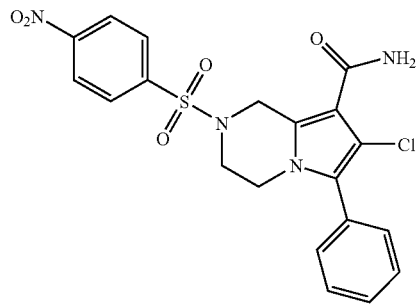

By proceeding in a similar manner to Example 31(a) above but using 4-nitrobenzenesulfonyl chloride there was prepared 7-chloro-2-(4-nitrobenzenesulfonyl)-6-phenyl-1,2,3,4-tetrahydropyrrolo[1,2-a]pyrazine-8-carboxylic acid amide as a white solid, m.p. 203–205° C. [Elemental analysis: C, 51.97; H, 3.66; N, 11.84%; Calculated for $C_{20}H_{17}ClN_4O_5S$: C, 52.12; H, 3.72; N, 12.16%].

(k) 7-chloro-2-(4-methanesulfonylbenzenesulfonyl)-6-phenyl-1,2,3,4-tetrahydropyrrolo[1,2-a]pyrazine-8-arboxylic acid amide

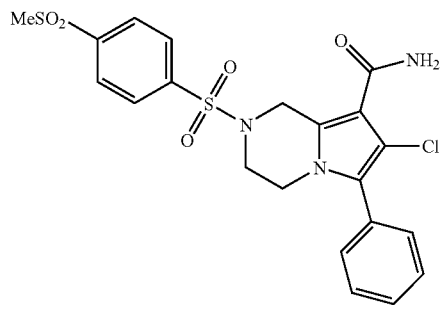

By proceeding in a similar manner to Example 31(a) above but using 4-methylsulfonylbenzenesulfonyl chloride there was prepared 7-chloro-2-(4-methanesulfonylbenzenesulfonyl)-6-phenyl-1,2,3,4-tetrahydropyrrolo[1,2-a]pyrazine-8-carboxylic acid amide as a white solid, m.p. 258–259° C. MS: 496 [MH]$^+$, 494 [MH]$^+$.

(l) 7-chloro-2-[5-(1-methyl-5-trifluoromethyl-1H-pyrazol-3-yl)thiophene-2-sulfonyl]-6-phenyl-1,2,3,4-tetrahydropyrrolo[1,2-a]pyrazine-8-carboxylic acid amide

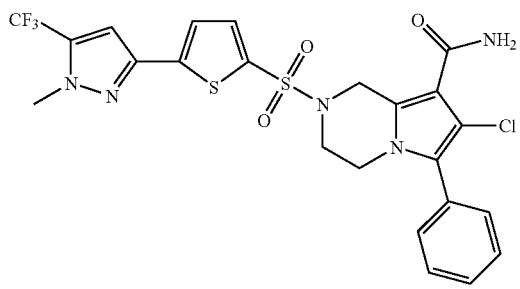

By proceeding in a similar manner to Example 31(a) above but using 2-[1-methyl-5-(trifluoromethyl)pyrazol-3-yl]thiophene-5-sulfonyl chloride there was prepared 7-chloro-2-[5-(1-methyl-5-trifluoromethyl-1H-pyrazol-3-yl)thiophene-2-sulfonyl]-6-phenyl-1,2,3,4-tetrahydropyrrolo[1,2-a]pyrazine-8-carboxylic acid amide as a white solid, m.p. 159–161° C. [Elemental analysis: C, 47.57; H, 3.83; N, 11.52%; Calculated for $C_{23}H_{19}ClF_3N_5O_3S_2 \cdot 0.75H_2O$: C, 47.34; H, 3.54; N, 12.00%].

(m) 7-chloro-2-(1-methyl-1H-imidazole-4-sulfonyl)-6-phenyl-1,2,3,4-tetrahydropyrrolo[1,2-a]pyrazine-8-carboxylic acid amide

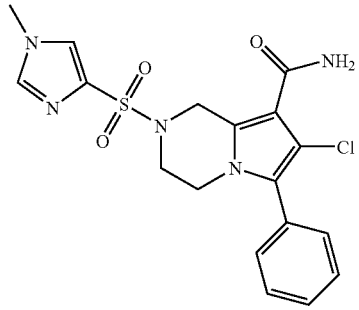

By proceeding in a similar manner to Example 31(a) above but using 1-methylimidazole-4-sulfonyl chloride there was prepared 7-chloro-2-(1-methyl-1H-imidazole-4-sulfonyl)-6-phenyl-1,2,3,4-tetrahydropyrrolo[1,2-a]pyrazine-8-carboxylic acid amide as a white solid, m.p. 260–263° C. MS: 422 [MH]$^+$, 420 [MH]$^+$.

(n) 7-chloro-2-(5-isoxazol-3-ylthiophene-2-sulfonyl)-6-phenyl-1,2,3,4-tetrahydropyrrolo [1,2-a]pyrazine-8-carboxylic acid amide

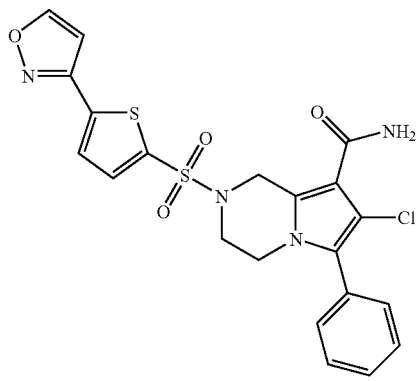

By proceeding in a similar manner to Example 31(a) above but using 5-(isoxazol-3-yl)thiophene-2-sulfonyl chloride there was prepared 7-chloro-2-(5-isoxazol-3-ylthiophene-2-sulfonyl)-6-phenyl-1,2,3,4-tetrahydropyrrolo[1,2-a]pyrazine-8-carboxylic acid amide as a white solid, m.p. 186–190° C. MS: 491[MH]+, 489[MH]+.

(o) 7-chloro-6-phenyl-2-(4-trifluoromethyl-benzenesulfonyl)-1,2,3,4-tetrahydropyrrolo[1,2-a]pyrazine-8-carboxylic acid amide

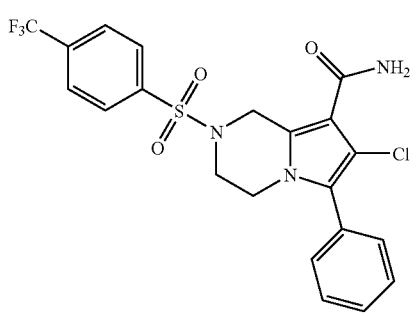

By proceeding in a similar manner to Example 31(a) above but using 4-trifluoromethyl-benzenesulfonyl chloride there was prepared 7-chloro-6-phenyl-2-(4-trifluoromethyl-benzenesulfonyl)-1,2,3,4-tetrahydropyrrolo[1,2-a]pyrazine-8-carboxylic acid amide as a white solid, 202–203° C. MS: 486 [MH]+, 484 [MH]+.

(p) 7-chloro-2-(3,4-dichlorobenzenesulfonyl)-6-phenyl-12,3,4-tetrahydropyrrolo[1,2-a]pyrazine-8-carboxylic acid amide

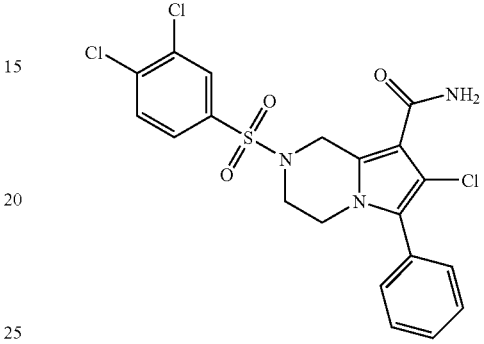

By proceeding in a similar manner to Example 31(a) above but using 3,4-dichlorobenzenesulfonyl chloride there was prepared 7-chloro-2-(3,4-dichlorobenzenesulfonyl)-6-phenyl-1,2,3,4-tetrahydropyrrolo[1,2-a]pyrazine-8-carboxylic acid amide as a white solid, m.p. 192–193° C. [Elemental analysis: C, 49.37; H, 3.31; N, 8.49%; Calculated for $C_{20}H_{16}Cl_3N_3O_3S$: C, 49.55; H, 3.33; N, 8.67%].

(q) 7-chloro-6-phenyl-2-(toluene-3-sulfonyl)-1.2,3,4-tetrahydropyrrolo[1,2-a]pyrazine-8-carboxylic acid amide

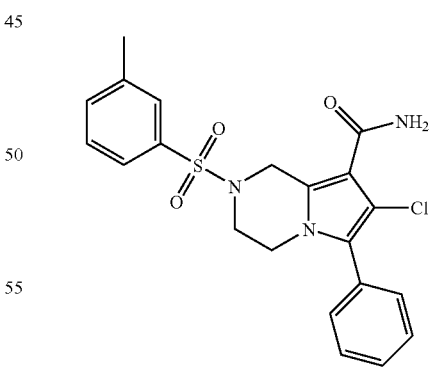

By proceeding in a similar to Example 31(a) above manner but using 3-toluenesulfonyl chloride there was prepared 7-chloro-6-phenyl-2-(toluene-3-sulfonyl)-1,2,3,4-tetrahydropyrrolo[1,2-a]pyrazine-8-carboxylic acid amide as a white solid, m.p. 165–167° C.
$^1$H NMR [(CD$_3$)$_2$SO]: δ 7.57–7.26 (m, 10H), 6.82–6.72 (bs, 1H), 4.53 (s, 2H), 3.71 (t, 2H), 3.47 (t, 2H) and 2.35 (s, 3H).

(r) 7-chloro-6-phenyl-2-(pyridine-4-sulfonyl)-1,2,3,4-tetrahydropyrrolo[1,2-a]pyrazine-8-carboxylic acid amide

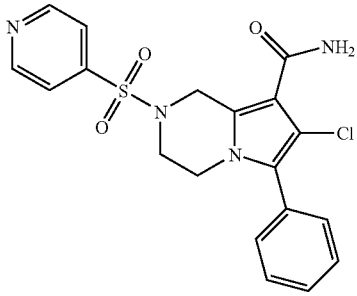

By proceeding in a similar manner to Example 31(a) above but using 4-pyridylsulfonyl chloride (prepared according to the procedure of Talik and Plazek, Acta. Pol. Pharm., 1955, 12, 5) there was prepared 7-chloro-6-phenyl-2-(pyridine-4-sulfonyl)-1,2,3,4-tetrahydropyrrolo[1,2-a]pyrazine-8-carboxylic acid amide as a white solid, m.p. 202–204° C. [Elemental analysis: C, 53.19; H, 3.84; N, 12.90%; Calculated for $C_{19}H_{17}ClN_4O_3S.0.5H_2O$: C, 53.58; H, 4.23; N, 13.16%].

(s) 7-chloro-2-(4-methoxybenzenesulfonyl)-6-phenyl-1.2,3,4-tetrahydropyrrolo[1,2-a]pyrazine-8-carboxylic acid amide

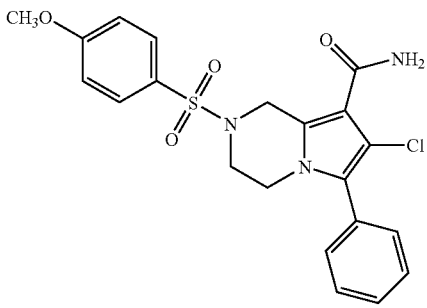

By proceeding in a similar manner to Example 31(a) above but using 4-methoxybenzenesulfonyl chloride there was prepared 7-chloro-2-(4-methoxybenzenesulfonyl)-6-phenyl-1,2,3,4-tetrahydropyrrolo[1,2-a]pyrazine-8-carboxylic acid amide as a white solid, m.p. 194–195° C. MS: 448 [MH]+, 446 [MH]+.

(t) 7-chloro-6-phenyl-2-(5-pyridin-2-ylthiophene-2-sulfonyl)-1,2,3,4-tetrahydropyrrolo[12-a]pyrazine-8-carboxylic acid amide

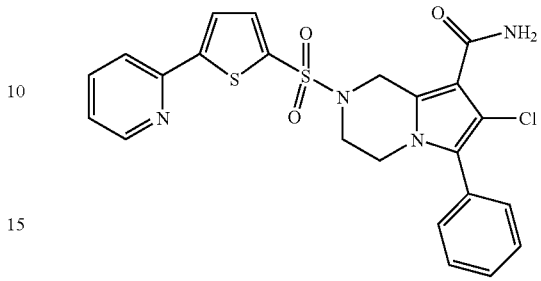

By proceeding in a similar manner to Example 31(a) above but using 5-(pyrid-2-yl)thiophene-2-sulfonyl chloride there was prepared 7-chloro-6-phenyl-2-(5-pyridin-2-ylthiophene-2-sulfonyl)-1,2,3,4-tetrahydropyrrolo[1,2-a]pyrazine-8-carboxylic acid amide as a white solid, m.p. 222–224° C. [Elemental analysis: C, 54.47; H, 3.64; N, 10.85%; Calculated for $C_{23}H_{19}ClN_4O_3S_2.0.5H_2O$: C, 54.38; H, 3.97; N, 11.03%].

EXAMPLE 32

7-Cyano-6-cyclopropyl-2-(4-trifluoromethylbenzenesulfonyl)-1,2,3,4-tetrahydropyrrolo[1,2-a]pyrazine-8-carboxylic acid amide

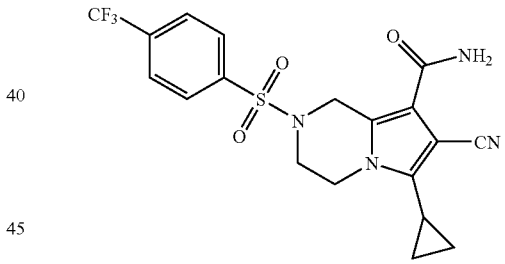

A suspension of 7-cyano-6-cyclopropyl-1,2,3,4-tetrahydropyrrolo[1,2-a]pyrazine-8-carboxylic acid amide trifluoroacetic acid salt [200 mg, Example 44(b)] in dry acetonitrile (50 mL) was treated with dry triethylamine (0.16 mL), then with 4-(trifluoromethyl)benzenesulfonyl chloride (142 mg). After stirring at 60° C. for 2.5 hours the reaction mixture was allowed to cool to room temperature and evaporated. The residue was treated with ethyl acetate (40 mL) and water (40 ml). The organic phase was separated, dried over sodium sulfate and evaporated. The residue was subjected to column chromatography on silica eluting with a mixture of ethyl acetate and pentane (1:1, v/v) to give 7-Cyano-6-cyclopropyl-2-(4-trifluoromethylbenzenesulfonyl)-1,2,3,4-tetrahydropyrrolo[1,2-a]pyrazine-8-carboxylic acid amide (109 mg) as a white solid, m.p. 253–256° C.

$^1$H NMR [(CDCl$_3$]: δ 8.00 (d, 2H), 7.84 (d, 2H), 6.50–6.17 (bs, 1H), 5.71–5.29 (bs, 1H), 4.64 (s, 2H), 4.13 (t, 2H), 3.62 (t, 2H), 1.72–1.60 (m, 1H), 1.15–1.01 (m, 2H) and 0.98–0.85 (m, 2H).

EXAMPLE 33

7-Chloro-6-pyridin-3-yl-2-(4-trifluoromethylbenzenesulfonyl)-1,2,3,4-tetrahydropyrrolo[1,2-a]pyrazine-8-carboxylic acid amide

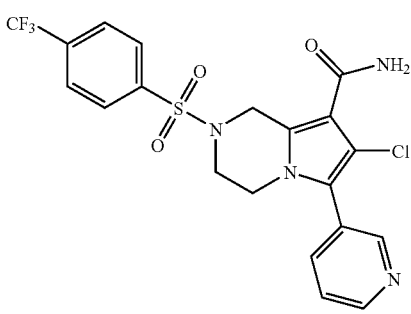

A suspension of 7-chloro-6-pyridin-3-yl-1,2,3,4-tetrahydropyrrolo[1,2-a]pyrazine-8-carboxylic acid amide bis trifluoroacetic acid salt (162 mg, Reference Example 1b) in dry acetonitrile (50 mL) was treated with dry triethylamine (0.19 mL), then 4-trifluoromethylbenzenesulfonyl chloride (82 mg). After stirring at 60° C. for 2.5 hours the reaction mixture was allowed to cool to room temperature and evaporated. The residue was treated with ethyl acetate (40 mL) and water (40 ml). The organic phase was separated, dried over sodium sulfate and evaporated. The residue was subjected to column chromatography on silica eluting with a mixture of ethyl acetate and pentane (4:1, v/v) to give 7-Chloro-6-pyridin-3-yl-2-(4-trifluoromethylbenzenesulfonyl)-1,2,3,4-tetrahydropyrrolo[1,2-a]pyrazine-8-carboxylic acid amide (61 mg) as a white solid, m.p. 205–206° C. [Elemental analysis: C, 47.90; H, 3.22; N, 10.96%; Calculated for $C_{20}H_{16}ClF_3N_4O_3S.0.9H_2O$: C, 47.94; H, 3.58; N, 11.18%].

EXAMPLE 34

(a) 7-Chloro-2-(5-pyridin-2-ylthiophene-2-sulfonyl)-1,2,3,4-tetrahydropyrrolo[1,2-a]pyrazine-8-carboxylic acid amide

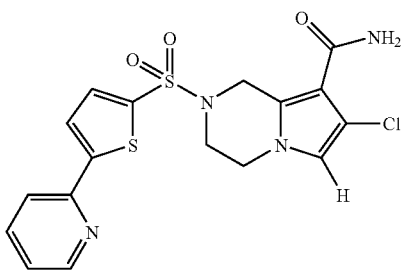

A suspension of 7-chloro-1,2,3,4-tetrahydropyrrolo[1,2-a]pyrazine-8-carboxylic acid amide trifluoroacetic acid salt (156 mg, Reference Example 24) in dry acetonitrile (13 mL) was treated with dry triethylamine (0.28 mL), then with 5-(pyrid-2-yl)thiophene-2-sulfonyl chloride (127 mg). After stirring at 60° C. for 4 hours the reaction mixture was allowed to cool to room temperature and evaporated. The residue was subjected to column chromatography on silica eluting with ethyl acetate to give 7-chloro-2-(5-pyridin-2-ylthiophene-2-sulfonyl)-1,2,3,4-tetrahydropyrrolo[1,2-a]pyrazine-8-carboxylic acid amide (51 mg) as a white solid, m.p. 213–214° C. [Elemental analysis: C, 47.99; H, 3.44; N, 12.97%; Calculated for $C_{17}H_{15}ClN_4O_3S_2$: C, 48.28; H, 3.58; N, 13.25%].

(b) 7-chloro-2-(4-trifluoromethylbenzenesulfonyl)-1,2,3,4-tetrahydro-pyrrolo[1,2-a]pyrazine-8-carboxylic acid amide

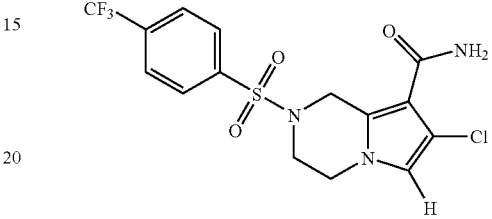

By proceeding in a similar manner to Example 34(a) above but using 4-trifluoromethyl-benzenesulfonyl chloride there was prepared 7-chloro-2-(4-trifluoromethylbenzenesulfonyl)-1,2,3,4-tetrahydro-pyrrolo[1,2-a]pyrazine-8-carboxylic acid amide as a white solid, m.p. 159–160° C. $^1$H NMR [$(CD_3)_2SO$]: δ 8.09–7.98 (m, 4H), 7.39–7.18 (bs, 1H), 6.94 (s, 1H), 6.76–6.57 (bs, 1H), 4.49 (s, 2H), 3.97 (t, 2H) and 3.60 (t, 2H).

EXAMPLE 35

(a) 7-Chloro-6-phenyl-2-phenylsulfamoyl-1.2,3,4-tetrahydropyrrolo[1,2-a]pyrazine-8-carboxylic acid amide

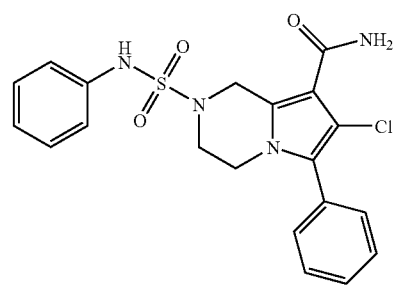

A suspension of 7-chloro-6-phenyl-1,2,3,4-tetrahydropyrrolo[1,2-a]pyrazine-8-carboxylic acid amide trifluoroacetic acid salt (100 mg, Reference Example 1) in dry acetonitrile (5 mL) was treated with dry triethylamine (0.20 mL), then with phenylsulfamoyl chloride (100 mg Reference Example 44). After stirring at room temperature for a further 1 hour the reaction mixture was evaporated and the residue then treated with water and dichloromethane. The organic phase was separated, then dried over magnesium sulfate and evaporated. The residue was subjected to column chromatography on silica eluting with a mixture of ethyl acetate and dichloromethane (1:1 v/v) to give 7-chloro-6-phenyl-2-phenylsulfamoyl-1,2,3,4-tetrahydropyrrolo[1,2-a]pyrazine-8-carboxylic acid amide (85 mg) as a white solid, m.p.

(b) 7-chloro-2-(4-methoxyphenylsulfamoyl)-6-phenyl-1,2,3,4-tetrahydropyrrolo[1,2-a]pyrazine-8-carboxylic acid amide

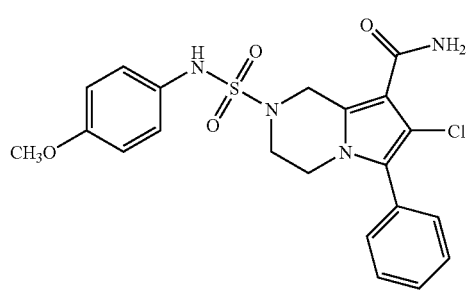

By proceeding in a similar manner to Example 35(a) above but using 4-methoxyphenylsulfamoyl chloride (Reference Example 44a) there was prepared 7-chloro-2-(4-methoxyphenylsulfamoyl)-6-phenyl-1,2,3,4-tetrahydropyrrolo[1,2-a]pyrazine-8-carboxylic acid amide as a white solid, m.p. 152–154° C. MS: 463 [MH]$^+$, 461 [MH]$^+$.

(c) 7-chloro-2-(4-trifluoromethylphenylsulfamoyl)-6-phenyl-1,2,3,4-tetrahydropyrrolo-[1,2-a]pyrazine-8-carboxylic acid amide

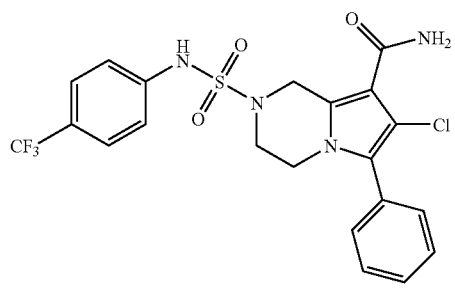

By proceeding in a similar manner to Example 35(a) above but using 4-trifluoromethylphenylsulfamoyl chloride (Reference Example 44b) there was prepared 7-chloro-2-(4-trifluoromethylphenylsulfamoyl)-6-phenyl-1,2,3,4-tetrahydropyrrolo[1,2-a]pyrazine-8-carboxylic acid amide as a white solid, m.p. 209–211° C. $^1$H NMR [(CD$_3$)$_2$SO]: δ 10.74 (s, 1H), 7.60 (d, 2H), 7.50–7.22 (m, 8H), 6.68 (s, 1H), 4.68 (s, 2H), 3.71 (t, 2H) and 3.58 (t, 2H).

(d) 7-chloro-2-(4-fluorophenylsulfamoyl)-6-phenyl-1,2,3,4-tetrahydropyrrolo[1,2-a]pyrazine-8-carboxylic acid amide

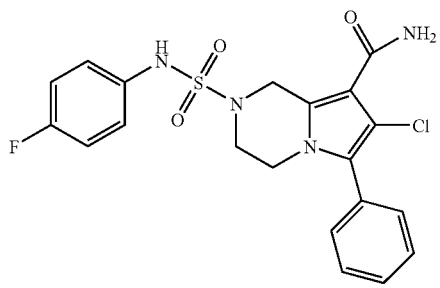

By proceeding in a similar manner to Example 35(a) above but using 4-fluorophenylsulfamoyl chloride (Reference Example 44c) there was prepared 7-chloro-2-(4-fluorophenylsulfamoyl)-6-phenyl-1,2,3,4-tetrahydropyrrolo[1,2-a]pyrazine-8-carboxylic acid amide as a white solid, m.p. 183–185° C. $^1$H NMR [(CD$_3$)$_2$SO]: δ 10.21 (s, 1H), 7.53–7.28 (m, 6H), 7.22–7.08 (m, 4H), 6.77 (s, 1H), 4.67 (s, 2H), 3.69 (t, 2H) and 3.53

(e) 7-chloro-2-methylsulfamoyl-6-phenyl-1,2,3,4-tetrahydropyrrolo[1,2-a]pyrazine-8-carboxylic acid amide

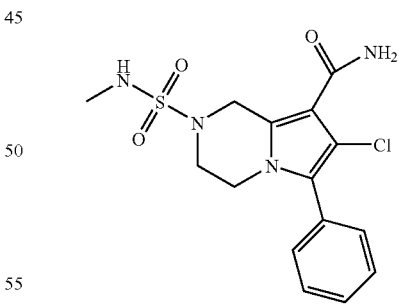

By proceeding in a similar manner to Example 35(a) above but using methylsulfamoyl chloride (prepared according to the procedure of Matier et. al, J. Med. Chem. 1972, 15, 538) there was prepared 7-chloro-2-methylsulfamoyl-6-phenyl-1,2,3,4-tetrahydropyrrolo[1,2-a]pyrazine-8-carboxylic acid amide as a white solid, m.p. 193–196° C. MS: 371 [MH]$^+$, 369 [MH]$^+$.

EXAMPLE 37

8-Carbamoyl-7-chloro-6-phenyl-3,4-dihydro-1H-pyrrolo[1,2-a]pyrazine-2-carboxylic acid phenyl ester

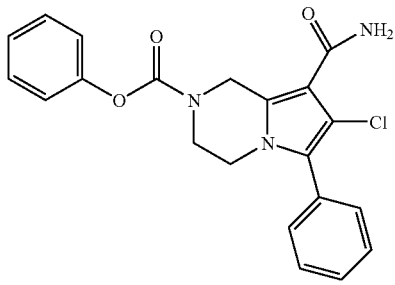

A suspension of 7-chloro-6-phenyl-1,2,3,4-tetrahydropyrrolo[1,2-a]pyrazine-8-carboxylic acid amide trifluoroacetic acid salt (100 mg, Reference Example 1) in dry dichloromethane (5 mL) was treated with dry triethylamine (0.11 mL). The resulting solution was then cooled to −40° C. and treated with a solution of phenyl chloroformate (32 μL, redistilled) in dry dichloromethane (5 mL) whilst maintaining the temperature at 40° C. After stirring at −40° C. for a further 30 minutes the reaction mixture was allowed to warm to room temperature and then washed three times with water (20 mL). The organic phase was dried over magnesium sulfate and the solvent then removed under reduced pressure. The residue was subjected to column chromatography on silica eluting with a mixture of pentane and ethyl acetate (9:11, v/v) to give 8-carbamoyl-7-chloro-6-phenyl-3,4-dihydro-1H-pyrrolo[1,2-a]pyrazine-2-carboxylic acid phenyl ester (40 mg) as a white solid, m.p. 196–198° C. [Elemental analysis: C, 63.52; H, 4.45; N, 10.31%; Calculated for $C_{21}H_{18}ClN_3O_3$: C, 63.72; H, 4.58; N, 10.62%].

EXAMPLE 38

7-Chloro-2-(4-methoxyphenylthiocarbamoyl)-6-phenyl-1,2,3,4-tetrahydropyrrolo[1,2-a]pyrazine-8-arboxylic acid amide

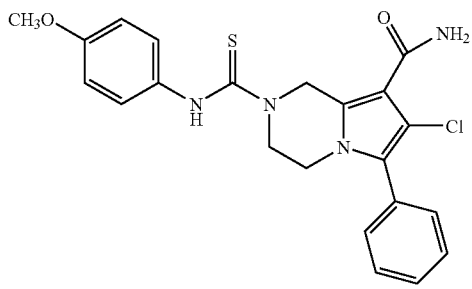

A suspension of 7-chloro-6-phenyl-1,2,3,4-tetrahydropyrrolo[1,2-a]pyrazine-8-carboxylic acid amide trifluoroacetic acid salt (50 mg, Reference Example 1) in dry dichloromethane (5 mL) was treated with dry triethylamine (54 μL), then with a solution of 4-methoxyphenyl isothiocyanate (18 μL) in dry dichloromethane (5 mL). After stirring at room temperature for a further 3 hours the reaction mixture was further treated with dichloromethane (10 mL) and then washed three times with water (5 mL). The organic phase was dried over magnesium sulfate and evaporated. The residue was subjected to column chromatography on silica eluting with a mixture of pentane and ethyl acetate (1:1, v/v) to give 7-chloro-2-(4-methoxyphenylthiocarbamoyl)-6-phenyl-1,2,3,4-tetrahydropyrrolo[1,2-a]pyrazine-8-carboxylic acid amide (40 mg) as a white solid, m.p. 176–178° C. MS: 443 [MH]⁺, 441 [MH]⁺.

EXAMPLE 39

2-[(Cyanoimino)(4-methoxyphenylamino)methyl]-7-chloro-6-phenyl-1,2,3,4-tetrahydro-pyrrolo[1,2-a]pyrazine-8-carboxylic acid amide

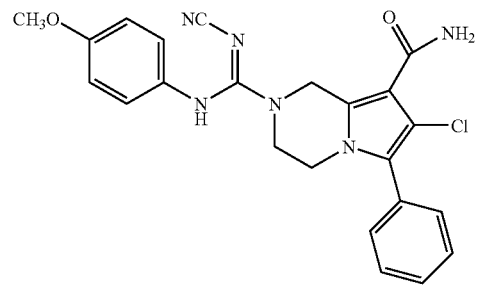

A suspension of 7-chloro-6-phenyl-1,2,3,4-tetrahydropyrrolo[1,2-a]pyrazine-8-carboxylic acid amide trifluoroacetic acid salt (100 mg, Reference Example 1) in dry dichloromethane (2 mL) under a blanket of nitrogen was treated with dry triethylamine (35 μL), then with a 2M solution of trimethylaluminum in toluene (0.30 mL) dropwise. After stirring at room temperature for a further 30 minutes the reaction mixture was treated with N-4-methoxyphenyl-N'-cyano-O-phenylisourea (64 mg, Reference Example 46) and then further stirred at room temperature for 3 hours. The reaction mixture was then heated overnight at 50° C. and then allowed to cool to room temperature. The reaction mixture was further treated with dichloromethane and then washed with a 0.5M aqueous solution of sodium carbonate. The organic phase was dried over magnesium sulfate and evaporated. The residue was subjected to column chromatography on silica eluting with a mixture of pentane and ethyl acetate (1:1, v/v) then ethyl acetate to give 2-[(cyanoimino)(4-methoxyphenylamino)methyl]-7-chloro-6-phenyl-1,2,3,4-tetrahydropyrrolo[1,2-a]pyrazine-8-carboxylic acid amide (10 mg) as a white solid, m.p. 170° C. MS: 451 [MH]⁺, 449 [MH]⁺.

EXAMPLE 40

6-Phenyl-3,4-dihydro-1H-pyrrolo[1,2-a]pyrazine-2,8-dicarboxylic acid 8-amide 2-[(4-methoxyphenyl)amide]

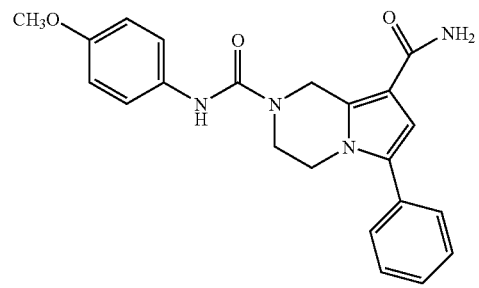

A suspension of 6-phenyl-1,2,3,4-tetrahydropyrrolo[1,2-a]pyrazine-8-carboxylic acid amide trifluoroacetic acid salt (107 mg, Reference Example 21) in dry dichloromethane (7 mL) was treated with dry triethylamine (0.13 mL), then with a solution of 4-methoxyphenyl isocyanate (49 mg) in dry dichloromethane (3 mL). After stirring at room temperature for a further 4 hours the reaction mixture was then allowed to stand overnight and then evaporated. The residue was subjected to column chromatography on silica eluting with a mixture of ethyl acetate and pentane (1:1, v/v) to give 6-phenyl-3,4-dihydro-1H-pyrrolo[1,2-a]pyrazine-2,8-dicarboxylic acid 8-amide 2-[(4-methoxyphenyl)amide] (40 mg) as a pale yellow solid, m.p. 170–173° C. MS: 391 [MH]$^+$.

EXAMPLE 41

7-Chloro-6-pyridin-3-yl-8-thiocarbamoyl-3,4-dihydro-1H-pyrrolo[1,2-a]pyrazine-2-carboxylic acid (4-fluorophenyl)amide

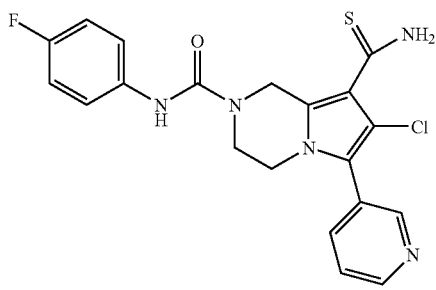

A suspension of 7-chloro-6-pyrid-3-yl-1,2,3,4-tetrahydropyrrolo[1,2-a]pyrazine-8-thiocarboxylic acid amide trifluoroacetic acid salt (283 mg, Reference Example 22) in dry dichloromethane (25 mL) was treated with dry triethylamine (0.32 mL), then with a solution of 4-fluorophenyl isocyanate (67 mg) in dry dichloromethane (3 mL). After stirring at room temperature overnight the reaction mixture was treated with concentrated ammonia (5 drops) and then evaporated. The residue was subjected to column chromatography on silica eluting with ethyl acetate to give, after trituration with diethyl ether and recrystallisation from a mixture of dichloromethane and diethyl ether, 7-chloro-6-pyridin-3-yl-8-thiocarbamoyl-3,4-dihydro-1H-pyrrolo[1,2-a]pyrazine-2-carboxylic acid (4-fluorophenyl)amide (15 mg) as off white solid, m.p. 214–216° C. $^1$H NMR [(CD$_3$)$_2$SO]: δ 9.69 (s, 1H), 8.84 (s, 2H), 8.68 (s, 1H), 8.63 (d, 1H), 7.93 (d, 1H), 7.55 (dd, 1H), 7.45 (dd, 2H), 7.10 (t, 2H), 4.96 (s, 2H), 3.93 (t, 2H) and 3.82 (t, 2H).

EXAMPLE 42

7-Chloro-6-phenyl-3,4-dihydro-1H-pyrrolo[1,2-a]pyrazine-2,8-dicarboxylic acid 8-amide 2-{[4-(morpholine-4-carbonyl)phenyl]amide}

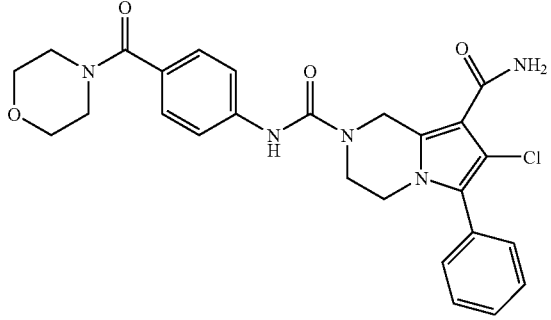

A vigorously stirred solution of 4-[(8-carbamoyl-7-chloro-6-phenyl-3,4-dihydro-1H-pyrrolo[1,2-a]pyrazine-2-carbonyl)amino]benzoic acid (59 mg, Example 28(b)) in dry dimethylformamide (4 mL) was treated with dry triethylamine (37 µL), then with 1-(3-dimethylaminopropyl)-3-ethylcarbodiimide hydrochloride (26 mg) and 1-hydroxybenzotriazole hydrate (18 mg). After stirring at room temperature for a further 15 minutes the reaction mixture was treated with morpholine (12 µL). The reaction mixture was then heated at 60° C. for 3 hours, allowed to cool to room temperature and then evaporated. The residue was treated with ethyl acetate (20 mL) and water (5 mL). The organic phase was separated and washed with aqueous solution of sodium hydroxide (10 mL, 1M), then three times with water (5 mL), then with brine (5 mL), then dried over magnesium sulfate and then evaporated. The residue was triturated with pentane to give 7-chloro-6-phenyl-3,4-dihydro-1H-pyrrolo[1,2-a]pyrazine-2,8-dicarboxylic acid 8-amide 2-{[4-(morpholine-4-carbonyl) phenyl]amide} as a white solid, m.p. 180–182° C. $^1$H NMR [(CD$_3$)$_2$SO]: δ 9.00 (s, 1H), 7.55–7.22 (m, 10H), 6.89–6.71 (bs, 1H), 4.93 (s, 2H), 3.85 (t, 2H), 3.77 (t, 2H) and 3.67–3.30 (m, 8H).

EXAMPLE 43

7-Cyano-6-cyclopropyl-3,4-dihydro-1H-pyrrolo[1,2-a]pyrazine-2,8-dicarboxylic acid 8-amide 2-{[4-(2-morpholin-4-ylethylcarbamoyl)phenyl]amide}

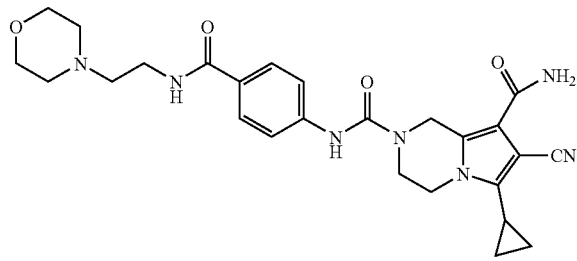

A vigorously stirred solution of 4-[(8-carbamoyl-7-cyano-6-cyclopropyl-3,4-dihydro-1H-pyrrolo[1,2-a]pyrazine-2-carbonyl)amino]benzoic acid (131 mg, Example 28(c)) in dry dimethylformamide (15 mL) was treated with dry triethylamine (93 µL), then with 1-(3-dimethylaminopropyl)-3-ethylcarbodiimide hydrochloride (64 mg) and 1-hydroxybenzotriazole hydrate (45 mg). After stirring at room temperature for a further 15 minutes the reaction mixture was treated with 4-(2-aminoethyl)morpholine (44 μL). The reaction mixture was then heated at 50° C. for 2 hours, allowed to cool to room temperature and then evaporated. The residue was triturated with a saturated aqueous solution of sodium hydrogen carbonate. The insoluble material was then recrystallised from acetonitrile to give 7-cyano-6-cyclopropyl-3,4-dihydro-1H-pyrrolo[1,2-a]pyrazine-2,8-dicarboxylic acid 8-amide 2-{[4-(2-morpholin-4-ylethylcarbamoyl)phenyl]amide} as a white solid, m.p. 197–199° C. [Elemental analysis: C, 60.09; H, 5.99; N, 18.91%; Calculated for $C_{26}H_{31}N_7O_4 \cdot 0.75H_2O$: C, 60.16; H, 6.31; N, 18.89%].

EXAMPLE 44

(a) 7-Chloro-6-cyclopropyl-1,2,34-tetrahydropyrrolo [1,2-a]pyrazine-8-carboxylic acid amide trifluoroacetic acid salt

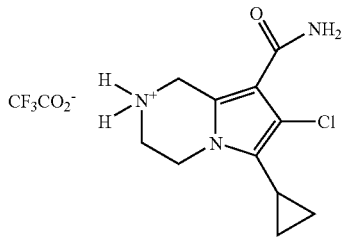

A stirred solution of 8-carbamoyl-7-chloro-6-cyclopropyl-3,4-dihydro-1H-pyrrolo[1,2-a]pyrazine-2-carboxylic acid tert-butyl ester (100 mg, Reference Example 25) in dry dichloromethane (2 ml) was treated with trifluoroacetic acid (1 ml). After stirring at room temperature for 18 hours the reaction mixture was evaporated to afford oil, which was azeotroped with toluene and then triturated with diethyl ether to give 7-chloro-6-cyclopropyl-1,2,3,4-tetrahydropyrrolo[1,2-a]pyrazine-8-carboxylic acid amide trifluoroacetic acid salt (42 mg) as white solid, m.p. 237–239° C. MS: 242 [MH]$^+$, 240 [MH]$^+$.

(b) 7-cyano-6-cyclopropyl-1,2,3,4-tetrahydropyrrolo [1,2-a]pyrazine-8-carboxylic acid amide trifluoroacetic acid salt

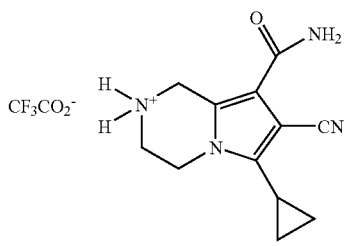

By proceeding in a similar manner to that described in Example 44(a) but using 8-carbamoyl-7-cyano-6-cyclopropyl-3,4-dihydro-1H-pyrrolo[1,2-a]pyrazine-2-carboxylic acid tert-butyl ester (3.73 g, Reference Example 7) there was prepared 7-cyano-6-cyclopropyl-1,2,3,4-tetrahydropyrrolo [1,2-a]pyrazine-8-carboxylic acid amide trifluoroacetic acid salt_(3.52 g) as a white solid, m.p. 195–197° C. $^1$H NMR [(CD$_3$)$_2$SO]: δ 9.65–9.37 (bs, 2H), 7.56–7.26 (bs, 1H), 7.16–6.84 (brs, 1H), 4.48 (s, 2H), 4.20 (t, 2H), 3.60 (t, 2H), 1.97–1.88 (m, 1H), 1.08–1.01 (m, 2H) and 0.84–0.79 (m, 2H).

EXAMPLE 45

(a) 2-Benzooxazol-2-yl-7-chloro-6-phenyl-1,2,3,4-tetrahydro-pyrrolo[1,2-a]-pyrazine-8-carboxylic acid amide

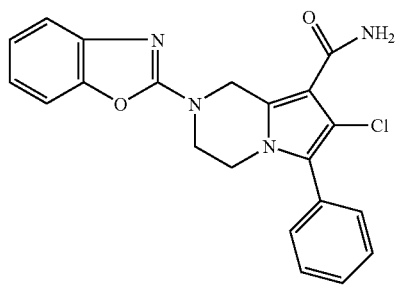

A mixture of sodium bicarbonate (76 mg) and 7-chloro-6-phenyl-1,2,3,4-tetrahydropyrrolo[1,2a]pyrazine-8-carboxylic acid amide trifluoroacetic acid salt (117 mg, Reference Example 1) in isopropanol (1.75 ml) and water (0.25 ml) was heated at reflux temperature for 30 minutes, then treated with a solution of 2-chlorobenzooxazole (47 mg) in isopropanol (0.125 ml). After heating at reflux temperature for a further 5 hours the reaction mixture was cooled to room temperature and then treated with water (2.5 ml). The resulting solid was filtered and then dried to give 2-benzooxazol-2-yl-7-chloro-6-phenyl-1,2,3,4-tetrahydropyrrolo [1,2-a]-pyrazine-8-carboxylic acid amide (94 mg) as an off white solid. MS: 393 [MH]$^+$.

(b) 2-Benzothiazol-2-yl-7-chloro-6-phenyl-1,2,3,4-tetrahydro-pyrrolo[1,2-a]pyrazine-8-carboxylic acid amide

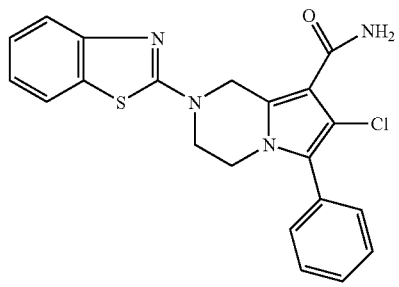

By proceeding in a similar manner to that described in Example 45(a) but using 2-chlorobenzothiazole and recrystallising the crude product from methanol there was prepared 2-benzothiazol-2-yl-7-chloro-6-phenyl-1,2,3,4-tetrahydro-pyrrolo[1,2-a]pyrazine-8-carboxylic acid amide (40 mg) as white solid. MS: 409 [MH]$^+$.

REFERENCE EXAMPLE 1

7-Chloro-6-phenyl-1,2,3,4-tetrahydropyrrolo[1,2-a]pyrazine-8-carboxylic acid amide trifluoroacetic acid salt A solution of 8-carbamoyl-7-chloro-6-phenyl-3,4-dihydro-1H-pyrrolo[1,2-a]pyrazine-2-carboxylic acid tert-butyl ester (2.75 g, Reference Example 2) in dichloromethane (60 mL) was treated with trifluoroacetic acid (5.64 mL). After stirring at room temperature for a further 3 hours the reaction mixture was further treated with trifluoroacetic acid (0.5 mL) and then further stirred for 1 hour. The reaction mixture was evaporated to afford an oil, which was azeotroped with toluene and then triturated with diethyl ether to give the title compound (2.61 g) as a white solid, m.p. 205–208° C. [Elemental Analysis: C, 49.32; H, 3.88; N, 10.78%. Calculated for $C_{16}H_{15}ClF_3N_3O_3$: C, 49.30; H, 3.88; N, 10.78%].

Similarly prepared were:

REFERENCE EXAMPLE 1a

7-Chloro-6-(tetrahydropyran-4-yl)-1,2,3,4-tetrahydropyrrolo[1,2-a]pyrazine-8-carboxylic acid amide trifluoroacetic acid salt (36 mg) as a white solid.

Using 8-carbamoyl-7-chloro-6-(tetrahydropyran-4-yl)-3,4-dihydro-1H-pyrrolo[1,2-a]pyrazine-2-carboxylic acid tert-butyl ester (44 mg, Reference Example 2a).

REFERENCE EXAMPLE 1b

7-Chloro-6-pyridin-3-yl-1,2,3,4-tetrahydropyrrolo[1,2-a]pyrazine-8-carboxylic acid amide bis trifluoroacetic acid salt (299 mg) as a white solid, m.p. 194–196° C. $^1$H NMR [$(CD_3)_2SO$]: δ 9.44–9.24 (bs, 2H), 8.66 (d, 1H), 8.64 (s, 1H), 7.90 (d, 1H), 7.60 (dd, 1H), 7.53–7.48 (bs, 1H), 7.00–6.82 (bs, 1H), 4.55 (s, 2H), 4.00 (t, 2H) and 3.51 (t, 2H).

Using 8-carbamoyl-7-chloro-6-pyridin-3-yl-3,4-dihydro-H-pyrrolo[1,2-a]pyrazine-2-carboxylic acid tert-butyl ester (214 mg, Reference Example 2b).

REFERENCE EXAMPLE 1c

7-Chloro-6-methyl-1,2,3,4-tetrahydropyrrolo[1,2-a]pyrazine-8-carboxylic acid amide trifluoroacetic acid salt (87 mg) as a white solid.

Using 8-carbamoyl-7-chloro-6-methyl-3,4-dihydro-1H-pyrrolo[1,2-a]pyrazine-2-carboxylic acid tert-butyl ester (78 mg, Reference Example 2c).

REFERENCE EXAMPLE 2

8-Carbamoyl-7-chloro-6-phenyl-3,4-dihydro-1H-pyrrolo[1,2-a]pyrazine-2-carboxylic acid tert-butyl ester A solution of 8-carbamoyl-6-phenyl-3,4-dihydro-1H-pyrrolo[1,2-a]pyrazine-2-carboxylic acid tert-butyl ester (8.0 g, Reference Example 3) in dichloromethane (300 mL) was treated with N-chlorosuccinimide (3.12 g). After stirring at room temperature for a further 16 hours the reaction mixture was washed four times with water (50 mL) and then once with brine (50 mL). The organic phase was then dried over magnesium sulfate and evaporated. The residue was subjected to column chromatography on silica eluting with a mixture of ethyl acetate and pentane (3:7, v/v) to give the title compound (4.3 g) as a white solid, m.p. 183–185° C. $^1$H NMR [$(CD_3)_2SO$]: δ 7.52–7.40 (m, 5H), 7.30 (bs, 1H), 6.80 (bs, 1H), 4.81 (s, 2H), 3.82 (t, 2H), 3.66 (t, 2H), 1.43 (s, 9H).

Similarly prepared were:

REFERENCE EXAMPLE 2a

8-Carbamoyl-7-chloro-6-(tetrahydropyran-4-yl)-3,4-dihydro-1H-pyrrolo[1,2-a]pyrazine-2-carboxylic acid tert-butyl ester (55 mg) as a white solid, m.p. 229–230° C. $^1$H NMR [$(CDCl_3)$]: δ 6.80–6.62 (bs, 1H), 5.50–5.34 (bs, 1H), 4.92 (s, 2H), 4.09 (dd, 2H), 3.91 (t, 2H), 3.83 (t, 2H), 3.47 (t, 2H), 3.02–2.93 (m, 1H), 2.35–2.22 (m, 2H), 1.50 (s, 9H) and 2H masked by $H_2O$ absorption.

Using 8-carbamoyl-6-(tetrahydropyran-4-yl)-3,4-dihydro-1H-pyrrolo[1,2-a]pyrazine-2-carboxylic acid tert-butyl ester (620 mg, Reference Example 3a) in acetonitrile (25 mL) at 50° C.

REFERENCE EXAMPLE 2b

8-Carbamoyl-7-chloro-6-pyridin-3-yl-3,4-dihydro-1H-pyrrolo[1,2-a]pyrazine-2-carboxylic acid tert-butyl ester (247 mg) as a white solid, MS: 379 [MH]$^+$, 377 [MH]$^+$. $^1$H NMR [$(CD_3)_2SO$]: δ 8.68 (s, 1H), 8.64 (d, 1H), 7.92 (d, 1H), 7.52 (dd, 1H), 7.40–7.26 (bs, 1H), 6.88–6.76 (bs, 1H), 4.80 (s, 2H), 3.84 (t, 2H), 3.68 (t, 2H) and 1.44 (s, 9H).

Using 8-carbamoyl-6-pyridin-3-yl-3,4-dihydro-1H-pyrrolo[1,2-a]pyrazine-2-carboxylic acid tert-butyl ester (962 mg, Reference Example 3b) in acetonitrile (36 mL) at 50° C.

REFERENCE EXAMPLE 2c

8-Carbamoyl-7-chloro-6-methyl-3,4-dihydro-1H-pyrrolo[1,2-a]pyrazine-2-carboxylic acid tert-butyl ester (83 mg) as a white solid, Rf 0.08 (cyclohexane:ethyl acetate 2:1). $^1$H NMR [$CDCl_3$] δ 6.75–6.65 (bs, 1H), 5.59–5.49 (bs, 1H), 4.91 (s, 2H), 3.86–3.78 (m, 4H), 2.18 (s, 3H), 1.49 (s, 9H).

Using 8-carbamoyl-6-methyl-3,4-dihydro-1H-pyrrolo[1,2-a]pyrazine-2-carboxylic acid tert-butyl ester (550 mg, Reference Example 3c).

REFERENCE EXAMPLE 3

8-Carbamoyl-6-phenyl-3,4-dihydro-1H-pyrrolo[1,2-a]pyrazine-2-carboxylic acid tert-butyl ester A solution of 8-cyano-6-phenyl-3,4-dihydro-1H-pyrrolo[1,2-a]pyrazine-2-carboxylic acid tert-butyl ester (3.87 g, Reference Example 4(a)) in methanol (200 mL) was treated with a 10M aqueous solution of sodium hydroxide (10.45 mL), then with a 27.5% w/w aqueous solution of hydrogen peroxide (0.74 mL). After stirring at 50° C. for 0.75 hour the reaction mixture was further treated with a 27.5% w/w aqueous solution of hydrogen peroxide (0.74 mL). After further stirring at 50° C. for 2 hours the reaction mixture was then further treated with a 27.5% w/w aqueous solution of hydrogen peroxide (0.74 mL). After further stirring at 50° C. for 1.5 hours the reaction mixture was allowed to cool to room temperature and treated with a saturated aqueous solution of sodium thiosulfate (20 mL). After stirring at room temperature for 15 minutes the reaction mixture was evaporated and then treated with ethyl acetate (650 mL) and water (150 mL). The organic phase was separated, washed with water (150 mL) and then dried over sodium sulfate. The organic phase was then evaporated to give the title compound (4.06 g) as a white solid, m.p. 208–210° C. MS: 342 [MH]⁺.

Similarly prepared were:

REFERENCE EXAMPLE 3a

8-Carbamoyl-6-(tetrahydropyran-4-yl)-3,4-dihydro-1H-pyrrolo[1,2-a]pyrazine-2-carboxylic acid tert-butyl ester (2.30 g) as a white solid, m.p. 247–248° C. [Elemental Analysis: C, 62.06; H, 7.87; N, 11.92%. Calculated for $C_{18}H_{27}N_3O_4$: C, 61.87; H, 7.79; N, 12.02%].

Using 8-cyano-6-(tetrahydropyran-4-yl)-3,4-dihydro-1H-pyrrolo[1,2-a]pyrazine-2-carboxylic acid tert-butyl ester (3.00 g, Reference Example 4a).

REFERENCE EXAMPLE 3b

8-Carbamoyl-6-pyridin-3-yl-3,4-dihydro-1H-pyrrolo[1,2-a]pyrazine-2-carboxylic acid tert-butyl ester (4.60 g) as a white solid, MS: 343 [MH]⁺. ¹H NMR [$(CD_3)_2SO$]: δ 8.68 (s, 1H), 8.52 (d, 1H), 7.88 (d, 1H), 7.46 (dd, 1H), 7.40–7.32 (bs, 1H), 6.86–6.76 (bs, 1H), 6.84 (s, 1H), 4.84 (s, 2H), 4.02 (t, 2H), 3.68 (t, 2H) and 1.44 (s, 9H).

Using 8-cyano-6-pyridin-3-yl-3,4-dihydro-1H-pyrrolo[1,2-a]pyrazine-2-carboxylic acid tert-buty ester (6.64 g, Reference Example 4b(a)).

REFERENCE EXAMPLE 3c

8-Carbamoyl-6-methyl-3,4-dihydro-1H-pyrrolo[1,2-a]pyrazine-2-carboxylic acid tert-butyl ester (570 mg) as a white solid, MS: 280 [MH]⁺. ¹H NMR [$CDCl_3$]: δ 6.01 (s, 1H), 5.62 (bs, 2H), 4.90 (s, 2H), 3.85–3.78 (m, 4H), 2.18 (s, 3H), 1.48 (s, 9H).

Using 8-Cyano-6-methyl-3,4-dihydro-1H-pyrrolo[1,2-a]pyrazine-2-carboxylic acid tert-butyl ester (820 mg, Reference Example 4c).

REFERENCE EXAMPLE 4

(a) 8-Cyano-6-phenyl-3,4-dihydro-1H-pyrrolo[1,2-a]pyrazine-2-carboxylic acid tert-butyl ester A solution of 4-benzoylpiperazine-1,3-dicarboxylic acid 1-tert-butyl ester 3-ethyl ester (22.25 g, Reference Example 5) in ethanol was treated with a 10M aqueous solution of sodium hydroxide (6.71 mL). After stirring at room temperature for a further 5 hours the reaction mixture was evaporated and the residue azeotroped with toluene to give a pale yellow solid (21.95 g), which was then dissolved in dichloromethane (350 mL) and treated with p-toluenesulfonyl chloride (12.79 g). After stirring for a further 10 minutes the reaction mixture was treated with 2-chloroacrylonitrile (4.87 mL) and then triethylamine (8.5 mL). After stirring for a further 45 minutes the reaction mixture was further treated with triethylamine (8.5 mL) and stirring was continued for a further 60 hours. The reaction mixture was then treated with water (160 mL), the layers were separated and the aqueous phase was further extracted three times with dichloromethane (160 mL). The combined organics were dried over magnesium sulfate and then evaporated. The residue was subjected to column chromatography on silica eluting with a mixture of ethyl acetate and pentane (1:9, v/v). The first eluted product was collected to give the title compound (5.30 g) as a white solid, m.p. 124–126° C. [Elemental Analysis: C, 70.65; H, 6.63; N, 12.81%. Calculated for $C_{19}H_{21}N_3O_2$: C, 70.57; H, 6.55; N, 12.99%].

Eluted second was (b) 7-Cyano-6-phenyl-3,4-dihydro-1H-pyrrolo[1,2-a]pyrazine-2-carboxylic acid tert-butyl ester (5.94 g) as a yellow solid, m.p. 109–111° C. MS: 324 [MH]⁺.

Similarly prepared were:

REFERENCE EXAMPLE 4a

8-Cyano-6-(tetrahydropyran-4-yl)-3,4-dihydro-1H-pyrrolo[1,2-a]pyrazine-2-carboxylic acid tert-butyl ester (8.72 g) as a yellow solid, m.p. 144–146° C. MS: 332 [MH]⁺.

Using 4-(tetrahydropyran-4-carbonyl)piperazine-1,3-dicarboxylic acid 1-tert-butyl ester 3-ethyl ester (19.05 g, Reference Example 5a).

REFERENCE EXAMPLE 4b (a) 8-Cyano-6-pyridin-3-yl-3,4-dihydro-1H-pyrrolo[1,2-a]pyrazine-2-carboxylic acid tert-butyl ester (1.75 g) as a white solid, Rf 0.16 (ethyl acetate). ¹H NMR [$CDCl_3$]: δ 8.68–8.60 (m, 2H), 7.68 (d, 1H), 7.40 (dd, 1H), 6.56 (s, 1H), 4.84 (s, 2H), 3.96 (t, 2H), 3.80 (t, 2H), 1.52 (s, 9H) and (b) 7-Cyano-6-pyridin-3-yl-3,4-dihydro-1H-pyrrolo[1,2-a]pyrazine-2-carboxylic acid tert-butyl ester (994 mg) as a brown solid, Rf 0.23 (ethyl acetate). ¹H NMR [$CDCl_3$]: δ 8.76–8.64 (m, 2H), 7.84 (d, 2H), 7.46 (dd, 1H), 6.36 (s, 1H), 4.68 (s, 2H), 3.96 (t, 2H), 3.78 (t, 2H) and 1.50 (s, 9H).

Using 4-(pyridine-4-carbonyl)piperazine-1,3-dicarboxylic acid 1-tert-butyl ester 3-ethyl ester (8.17 g, Reference Example 5b).

REFERENCE EXAMPLE 4c

8-Cyano-6-methyl-3,4-dihydro-1H-pyrrolo[1,2-a]pyrazine-2-carboxylic acid tert-butyl ester (850 mg) as an amber gum, Rf 0.14 (cyclohexane:ethyl acetate, 3:1). ¹H NMR [$CDCl_3$]: δ 6.12 (s, 1H), 4.70 (s, 2H), 3.85–3.78 (m, 4H), 2.17 (s, 3H) and 1.51 (s, 9H).

Using 4-acetylpiperazine-1,3-dicarboxylic acid 1-tert-butyl ester 3-ethyl ester (2.77 g, Reference Example 5c).

REFERENCE EXAMPLE 5

4-Benzoylpiperazine-1,3-dicarboxylic acid
1-tert-butyl ester 3-ethyl ester

A solution of piperazine-1,3-dicarboxylic acid 1-tert-butyl ester 3-ethyl ester (1.84 g, prepared according to the procedure described in WO 96/31478 Step B page 94) in dry dichloromethane (50 mL) was treated with triethylamine (1.1 mL), then benzoyl chloride (0.91 mL). After stirring at room temperature for a further 5 hours the reaction mixture was treated with further dichloromethane (150 mL) and then washed twice with a saturated aqueous solution of sodium hydrogen carbonate (50 mL) and twice with brine (50 mL). The organic phase was then dried over magnesium sulfate and evaporated to give the title compound (2.58 g) as an orange oil, MS: 363 [MH]⁺. ¹H NMR [$(CD_3)_2SO$]: δ 7.50–7.34 (m, 5H), 5.20–5.00 (s, 1H), 4.44–4.36 (m, 1H), 4.21–4.13 (m, 2H), 3.87–3.78 (m, 1H), 3.73–3.69 (bs, 1H), 3.30–3.20 (m, 2H), 2.98–2.90 (m, 1H), 1.45–1.38 (s, 9H) and 1.27–1.20 (m, 3H).

Similarly prepared were:

REFERENCE EXAMPLE 5a 4-(Tetrahydropyran-4-carbonyl)piperazine-1,3-dicarboxylic acid 1-tert-butyl ester 3-ethyl ester (3.71 g) as an orange oil, MS: 371 [MH]$^+$. $^1$H NMR [(CDCl$_3$]: δ 5.20–5.16 (m, 1H), 4.61 (d, 1H), 4.29–4.09 (m, 4H), 4.08–3.97 (m, 2H), 3.79–3.70 (m, 1H), 3.62–3.36 (m, 3H), 3.03 (dd, 1H), 2.84–2.78 (m, 1H), 2.04–1.54 (m, 4H), 1.45 (s, 9H) and 1.28 (t, 3H).

Using tetrahydropyran-4-carbonyl chloride (3.18 g, prepared according to the procedure of Gibson and Johnson, J. Chem. Soc., 1930, 2525).

REFERENCE EXAMPLE 5b 4-(Pyridine-4-carbonyl)piperazine-1,3-dicarboxylic acid 1-tert-butyl ester 3-ethyl ester (65.5 g) as an orange oil, Rf 0.20 (ethyl acetate). $^1$H NMR [(CDCl$_3$]: δ 8.74–8.64 (m, 2H), 7.82–7.72 (m, 1H), 7.42–7.28 (m, 1H), 5.28 (s, 1H), 4.80–2.64 (m, 8H), 1.44 (s, 9H) and 1.26 (t, 3H).

Using pyridine-3-carbonyl chloride hydrochloride (53.8 g).

REFERENCE EXAMPLE 5c

4-Acetylpiperazine-1,3-dicarboxylic acid 1-tert-butyl ester 3-ethyl ester (2.97 g) as a yellow oil, Rf 0.05 (methylene chloride:methanol, 99:1). MS: 301 [MH]$^+$.

Using acetyl chloride (1.88 g).

REFERENCE EXAMPLE 6a

7-Cyano-6-(2-methylpyridin-3-yl)-1,2,3,4-tetrahydropyrrolo[1,2-a]pyrazine-8-carboxylic acid amide bistrifluoroacetic acid salt By proceeding in a similar manner to that described in Reference Example 1 but using 8-carbamoyl-7-cyano-6-(2-methylpyridin-3-yl)-3,4-dihydro-1H-pyrrolo[1,2-a]pyrazine-2-carboxylic acid tert-butyl ester (327 mg, Reference Example 7a) there was prepared 7-cyano-6-(2-methylpyridin-3-yl)-1,2,3,4-tetrahydropyrrolo[1,2-a]pyrazine-8-carboxylic acid amide bistrifluoroacetic acid salt (438 mg) as a white solid, MS: 282 [MH]$^+$. $^1$H NMR [(CD$_3$)$_2$SO]: δ 9.50–9.27 (brs, 2H), 8.69 (d, 1H), 7.78 (d, 1H), 7.62–7.42 (bs, 1H), 7.48 (dd, 1H), 7.35–7.11 (bs, 1H), 4.63 (d, 1H), 4.56 (d, 1H), 3.95–3.86 (m, 1H), 3.85–3.77 (m, 1H), 3.63–3.47 (m, 2H) and 2.39 (s, 3H).

Similarly prepared was:

REFERENCE EXAMPLE 6b

7-Cyano-6-pyridin-3-yl-1,2,3,4-tetrahydropyrrolo[1,2-a]pyrazine-8-carboxylic acid amide bistrifluoroacetic acid salt (438 mg) as a white solid, MS: 268 [MH]$^+$. $^1$H NMR [(CD$_3$)$_2$SO]: δ 9.74–9.40 (bs, 2H), 8.95–8.65 (bs, 2H), 8.04 (d, 1H), 7.80–7.15 (2×bs and dd overlapping, 3H), 4.61 (s, 2H), 4.17 (t, 2H) and 3.55 (t, 2H).

Using 8-carbamoyl-7-cyano-6-pyridin-3-yl-3,4-dihydro-1H-pyrrolo[1,2-a]pyrazine-2-carboxylic acid tert-butyl ester (1.0 g, Reference Example 7b).

REFERENCE EXAMPLE 7

8-Carbamoyl-7-cyano-6-cyclopropyl-3,4-dihydro-1H-pyrrolo[1,2-a]pyrazine-2-carboxylic acid tert-butyl ester By proceeding in a similar manner to that described in Reference Example 3 but using 7,8-dicyano-6-cyclopropyl-3,4-dihydro-1H-pyrrolo[1,2-a]pyrazine-2-carboxylic acid tert-butyl ester (4.97 g, Reference Example 8) and performing the reaction at room temperature there was prepared 8-carbamoyl-7-cyano-6-cyclopropyl-3,4-dihydro-1H-pyrrolo[1,2-a]pyrazine-2-carboxylic acid tert-butyl ester (3.22 g) as a white solid, m.p. 221–222° C. $^1$H NMR [(CD$_3$)$_2$SO]: δ 7.35–7.15 (bs, 1H), 6.95–6.65 (bs, 1H), 4.69 (s, 2H), 4.02 (t, 2H), 3.74 (t, 2H), 1.90–1.82 (m, 1H), 1.43 (s, 9H), 1.02–0.96 (m, 2H) and 0.85–0.80 (m, 2H).

REFERENCE EXAMPLE 7a

8-Carbamoyl-7-cyano-6-(2-methylpyridin-3-yl)-3,4-dihydro-1H-pyrrolo[1,2-a]pyrazine-2-carboxylic acid tert-butyl ester By proceeding in a similar manner to that described in Reference Example 3 but using 7,8-dicyano-6-(2-methylpyridin-3-yl)-3,4-dihydro-1H-pyrrolo[1,2-a]pyrazine-2-carboxylic acid tert-butyl ester (2.00 g, Reference Example 8a) there was prepared the title compound (987 mg) as a white solid, MS: 382 [MH]$^+$. $^1$H NMR [(CDCl$_3$]: δ 8.65 (d, 1H), 7.55 (d, 1H), 7.25 (dd, 1H), 6.50–6.19 (bs, 1H), 5.70–5.32 (bs, 1H), 5.01 (s, 2H), 3.77 (t, 2H), 3.69–3.55 (m, 2H), 2.43 (s, 3H) and 1.47 (s, 9H).

Similarly prepared was:

REFERENCE EXAMPLE 7b

8-Carbamoyl-7-cyano-6-pyridin-3-yl-3,4-dihydro-1H-pyrrolo[1,2-a]pyrazine-2-carboxylic acid tert-butyl ester (790 mg) as a white solid, m.p. 196–200° C. [Elemental Analysis: C, 62.44; H, 5.92; N, 18.68%. Calculated for C$_{19}$H$_{21}$N$_5$O$_3$: C, 62.11; H, 5.76; N, 19.06%].

Using 7,8-dicyano-6-pyridin-3-yl-3,4-dihydro-1H-pyrrolo[1,2-a]pyrazine-2-carboxylic acid tert-butyl ester (2.43 g, Reference Example 8b)

REFERENCE EXAMPLE 8

7,8-Dicyano-6-cyclopropyl-3,4-dihydro-1H-pyrrolo[1,2-a]pyrazine-2-carboxylic acid tert-butyl ester A stirred solution of a mixture of 8-cyano-6-cyclopropyl-3,4-dihydro-1H-pyrrolo[1,2-a]pyrazine-2-carboxylic acid tert-butyl ester and 7-cyano-6-cyclopropyl-3,4-dihydro-1H-pyrrolo[1,2-a]pyrazine-2-carboxylic acid tert-butyl ester (6.67 g, Reference Example 9) in dry acetonitrile (370 mL) under a blanket of nitrogen at 0° C. was treated with chlorosulfonyl isocyanate (2.75 mL) dropwise whilst maintaining the temperature below 5° C. After stirring below 5° C. for a further 2.5 hours the reaction mixture was treated with dimethylformamide (18.5 mL), allowed to warm to room temperature and then stirred for a further 1 hour. The reaction mixture was then treated with triethylamine (21.7 mL), stirred for a further 1 hour and then left to stand overnight. The reaction mixture was evaporated and the residue treated with dichloromethane (200 mL) and water (80 mL). The organic phase was separated, further washed with water (80 mL), then dried over magnesium sulfate and evaporated. The residue was subjected to column chromatography on silica eluting with a mixture of ethyl acetate and pentane (2:3, v/v) to give the title compound (4.97 g) as a yellow oil, Rf 0.29 (ethyl acetate:pentane, 2:3). $^1$H NMR [(CDCl$_3$)]: δ 4.70 (s, 2H), 4.03 (t, 2H), 3.87 (t, 2H) 1.73–1.65 (m, 1H), 1.51 (s, 9H), 1.14–1.07 (m, 2H) and 0.99–0.93 (m, 2H).

Similarly prepared was:

REFERENCE EXAMPLE 8a 7,8-Dicyano-6-(2-methylpyridin-3-yl)-3,4-dihydro-1H-pyrrolo[1,2-a]pyrazine-2-carboxylic acid tert-butyl ester (2.00 g) as a white solid, MS: 364 [MH]$^+$. $^1$H NMR [(CDCl$_3$)]: δ 8.67 (d, 1H), 7.54 (d, 1H), 7.27 (dd, 1H), 4.79 (s, 2H), 3.78 (t, 2H), 3.71–3.58 (m, 2H), 2.42 (s, 3H) and 1.48 (s, 9H).

Using a mixture of 8-cyano-6-(2-methylpyridin-3-yl)-3,4-dihydro-1H-pyrrolo[1,2-a]pyrazine-2-carboxylic acid tert-butyl ester and 7-cyano-6-(2-methylpyridin-3-yl)-3,4-dihydro-1H-pyrrolo[1,2-a]pyrazine-2-carboxylic acid tert-butyl ester (9.29 g, Reference Example 9a).

REFERENCE EXAMPLE 8b 7,8-Dicyano-6-pyridin-3-yl-3,4-dihydro-1H-pyrrolo[1,2-a]pyrazine-2-carboxylic acid tert-butyl ester (4.89 g) as a white solid, m.p. 195–197° C. [Elemental Analysis: C, 65.37; H, 5.54; N, 20.06%. Calculated for C$_{19}$H$_{19}$N$_5$O$_2$: C, 65.32; H, 5.48; N, 20.04%].

Using a mixture of 8-cyano-6-pyridin-3-yl-3,4-dihydro-1H-pyrrolo[1,2-a]pyrazine-2-carboxylic acid tert-butyl ester and 7-cyano-6-pyridin-3-yl-3,4-dihydro-1H-pyrrolo[1,2-a]pyrazine-2-carboxylic acid tert-butyl ester (18.1 g, Reference Example 4b)

REFERENCE EXAMPLE 9

8-Cyano-6-cyclopropyl-3,4-dihydro-1H-pyrrolo[1,2-a]pyrazine-2-carboxylic acid tert-butyl ester and 7-cyano-6-cyclopropyl-3,4-dihydro-1H-pyrrolo[1,2-a]pyrazine-2-carboxylic acid tert-butyl ester By proceeding in a similar manner to that described in Reference Example 4 but using 4-cyclopropanecarbonylpiperazine-1,3-dicarboxylic acid 1-tert-butyl ester 3-ethyl ester (33.17 g, Reference Example 10) there was prepared a 10.4:1 mixture of the title compounds as a yellow oil (5.29 g).

Similarly prepared was:

REFERENCE EXAMPLE 9a

8-Cyano-6-(2-methylpyridin-3-yl)-3,4-dihydro-1H-pyrrolo[1,2-a]pyrazine-2-carboxylic acid tert-butyl ester and 7-cyano-6-(2-methylpyridin-3-yl)-3,4-dihydro-1H-pyrrolo[1,2-a]pyrazine-2-carboxylic acid tert-butyl ester as a yellow oil (10.52 g) in the ratio 5:4.

Using 4-(2-methylpyridine-3-carbonyl)piperazine-1,3-dicarboxylic acid 1-tert-butyl ester 3-ethyl ester (17.93 g, Reference Example 10a).

REFERENCE EXAMPLE 10

4-Cyclopropanecarbonylpiperazine-1,3-dicarboxylic acid 1-tert-butyl ester 3-ethyl ester By proceeding in a similar manner to that described in Reference Example 5 but using cyclopropanecarbonyl chloride (24.44 g) the title compound (68.1 g) was prepared as a yellow oil, Rf 0.73 (Et$_2$O). MS: 327 [MH]$^+$.

Similarly prepared was:

REFERENCE EXAMPLE 10a 4-(2-Methylpyridine-3-carbonyl)piperazine-1,3-dicarboxylic acid 1-tert-butyl ester 3-ethyl ester Using 2-methylnicotinoyl chloride (36.50 g).

REFERENCE EXAMPLE 11

7-Cyano-6-(1-methanesulfonylpiperidin-4-yl)-1,2,3,4-tetrahydropyrrolo[1,2-a]pyrazine-8-carboxylic acid amide trifluoroacetic acid salt By proceeding in a similar manner to that described in Reference Example 1 but using 8-carbamoyl-7-cyano-6-(1-methanesulfonylpiperidin-4-yl)-3,4-dihydro-1H-pyrrolo[1,2-a]pyrazine-2-carboxylic acid tert-butyl ester (317 mg, Reference Example 12) the title compound (352 mg) was prepared as an off white solid, m.p. 208–210° C. MS: 352 [MH]$^+$.

REFERENCE EXAMPLE 12

8-Carbamoyl-7-cyano-6-(1-methanesulfonylpiperidin-4-yl)-3,4-dihydro-1H-pyrrolo[1,2-a]pyrazine-2-carboxylic acid tert-butyl ester A stirred solution of 6-(1-benzyloxycarbonylpiperidin-4-yl)-8-carbamoyl-7-cyano-3,4-dihydro-1H-pyrrolo[1,2-a]pyrazine-2-carboxylic acid tert-butyl ester (600 mg, Reference Example 13) in industrial methylated spirit (100 mL) was treated with 5% Pd/C (100 mg), then placed under a blanket of hydrogen. After stirring at room temperature for a further 7 hours the reaction mixture was allowed to stand overnight. The reaction mixture was filtered through celite and then evaporated to give a glass (411 mg). A small quantity of the glass (268 mg) was suspended in dry acetonitrile (20 mL) and under a blanket of nitrogen treated with dry triethylamine (200 μL), then with a solution of methanesulfonyl chloride (58 μL) in acetonitrile (1 mL). After stirring at 40° C. for 3 hours the reaction mixture was further treated with a solution of methanesulfonyl chloride (10 μL) in acetonitrile (1 mL) and stirring continued at 40° C. for a further 1 hour. The reaction mixture was then allowed to cool to room temperature and evaporated. The residue was subjected to column chromatography on silica eluting with a mixture of ethyl acetate and methanol (19:1, v/v) to give the title compound (260 mg) as a white solid, m.p. 220° C. [Elemental analysis: C, 53.16; H, 6.90; N, 15.22%; Calculated for C$_{20}$H$_{29}$N$_5$O$_5$S: C, 53.20; H, 6.47; N, 15.51%].

REFERENCE EXAMPLE 13

6-(1-Benzyloxycarbonylpiperidin-4-yl)-8-carbamoyl-7-cyano-3,4-dihydro-1H-pyrrolo[1,2-a]pyrazine-2-arboxylic acid tert-butyl ester By proceeding in a similar manner to that described in Reference Example 3 but using 6-(1-benzyloxycarbonylpiperidin-4-yl)-7,8-dicyano-3,4-dihydro-H-pyrrolo[1,2-a]pyrazine-2-carboxylic acid tert-butyl ester (4.71 g, Reference Example 14) the title compound (1.23 g) was prepared as a white solid, m.p. 90° C. $^1$H NMR [(CDCl$_3$]: δ 7.41–7.30 (m, 5H), 6.52–6.34 (bs, 1H), 5.60–5.40 (bs, 1H), 5.16 (s, 2H), 4.93 (s, 2H), 4.50–4.28 (bs, 2H), 3.91 (t, 2H), 3.85 (t, 2H), 2.96–2.72 (m, 3H), 2.17–1.96 (brs, 2H), 1.82 (d, 2H) and 1.49 (s, 9H).

REFERENCE EXAMPLE 14

6-(1-Benzyloxycarbonylpiperidin-4-yl)-7,8-dicyano-3,4-dihydro-1H-pyrrolo[1,2-a]pyrazine-2-carboxylic acid tert-butyl ester By proceeding in a similar manner to that described in Reference Example 8 but using a mixture of 6-(1-benzyloxycarbonylpiperidin-4-yl)-8-cyano-3,4-dihydro-1H-pyrrolo[1,2-a]pyrazine-2-carboxylic acid tert-butyl ester and 6-(1-benzyloxycarbonylpiperidin-4-yl)-7-cyano-3,4-dihydro-1H-pyrrolo[1,2-a]pyrazine-2-carboxylic acid tert-butyl ester (5.00 g, Reference Example 15) the title compound (4.71 g) was prepared as a yellow oil, MS: 490 [MH]$^+$. $^1$H NMR [(CDCl$_3$]: δ 7.42–7.30 (m, 5H), 5.15 (s, 2H), 4.71 (s, 2H), 4.50–4.28 (bs, 2H), 3.92 (t, 2H), 3.86 (t, 2H), 2.93–2.72 (m, 3H), 2.20–1.93 (bs, 2H), 1.80 (d, 2H) and 1.51 (s, 9H).

REFERENCE EXAMPLE 15

6-(1-Benzyloxycarbonylpiperidin-4-yl)-8-cyano-3,4-dihydro-1H-pyrrolo[1,2-a]pyrazine-2-carboxylic acid tert-butyl ester and 6-(1-benzyloxycarbonylpiperidin-4-yl)-7-cyano-3,4-dihydro-1H-pyrrolo[1,2-a]pyrazine-2-carboxylic acid tert-butyl ester By proceeding in a similar manner to that described in Reference Example 4 but using 4-[(1-benzyloxycarbonylpiperidine-4-carbonyl)piperazine-1,3-dicarboxylic acid 1-tert-butyl ester 3-ethyl ester (25.02 g, Reference Example 16) there was prepared a 3:2 mixture of the title compounds as a yellow oil (14.44 g).

REFERENCE EXAMPLE 16

4-[(1-Benzyloxycarbonylpiperidine-4-carbonyl)piperazine-1,3-dicarboxylic acid 1-tert-butyl ester 3-ethyl ester By proceeding in a similar manner to that described in Reference Example 5 but using [1-(carbobenzoxy)4-piperidine]carbonyl chloride (12.31 g; prepared according to the procedure of Gueremy et. al. J. Med. Chem. 1980, 23, 1306) the title compound (14.85 g) was prepared as a yellow oil, Rf 0.54 (ethyl acetate). $^1$H NMR [(CDCl$_3$]: δ 7.39–7.28 (m, 5H), 5.17 (d, 1H), 5.13 (s, 2H), 4.61 (d, 1H), 4.29–4.06 (m, 5H), 3.72 (d, 1H), 3.60–3.45 (bs, 1H), 3.04 (d, 1H), 2.97–2.67 (m, 4H), 1.88–1.59 (m, 4H), 1.46 (s, 9H) and 1.27 (t, 3H).

REFERENCE EXAMPLE 17

7-Cyano-6-phenyl-1,2,3,4-tetrahydropyrrolo[1,2-a]pyrazine-8-carboxylic acid amide trifluoroacetic acid salt By proceeding in a similar manner to that described in Reference Example 1 but using 8-carbamoyl-7-cyano-6-phenyl-3,4-dihydro-1H-pyrrolo[1,2-a]pyrazine-2-carboxylic acid tert-butyl ester (1.80 g, Reference Example 18) the title compound (1.80 g) was prepared as a cream solid, m.p. 171–176° C. $^1$H NMR [(CD$_3$)$_2$SO]: δ 9.70–9.40 (bs, 2H), 7.77–7.46 (m, 6H), 7.27–7.06 (bs, 1H), 4.55 (s, 2H), 4.07 (t, 2H) and 3.50 (t, 2H).

REFERENCE EXAMPLE 18

8-Carbamoyl-7-cyano-6-phenyl-3,4-dihydro-1H-pyrrolo[1,2-a]pyrazine-2-carboxylic acid tert-butyl ester A stirred solution of triethylamine (3.34 mL), 1-(3-dimethylaminopropyl)-3-ethylcarbodiimide hydrochloride (2.30 g) and 1-hydroxybenzotriazole hydrate (1.62 g) in dry dimethylformamide (120 mL) was treated with 7-cyano-6-phenyl-3,4-dihydro-1H-pyrrolo[1,2-a]pyrazine-2,8-dicarboxylic acid 2-tert-butyl ester (4.40 g, Reference Example 19). After stirring at room temperature for a further 15 minutes the reaction mixture was treated with ammonium chloride (1.28 g) and then heated at 80° C. for 5 hours. The reaction mixture was allowed to cool to room temperature and then evaporated. The residue was treated with water and ethyl acetate. The organic phase was separated, washed with a 1M aqueous solution of sodium hydroxide (20 mL) and then water (20 mL). The organic phase was then dried over magnesium sulfate and evaporated to give a brown gum. The gum was triturated with diethyl ether to give the title compound (3.80 g) as a white solid, m.p. 214–215° C. $^1$H NMR [(CD$_3$)$_2$SO]: δ 7.59–7.50 (m, 5H), 7.41–7.27 (bs, 1H), 7.08–6.93 (bs, 1H), 4.75 (s, 2H), 3.92 (t, 2H), 3.62 (t, 2H) and 1.40 (s, 9H).

REFERENCE EXAMPLE 19

7-Cyano-6-phenyl-3,4-dihydro-1H-pyrrolo[1,2-a]pyrazine-2,8-dicarboxylic acid 2-tert-butyl ester A mechanically stirred mixture of bis(triphenylphosphine)palladium (II) chloride (425 mg), triphenylphosphine (425 mg), 4-methylanisole (125 mL) and poly(ethylene glycol) (Average M$_n$ ca 4600, 850 g) was treated with 7-cyano-8-iodo-6-phenyl-3,4-dihydro-1H-pyrrolo[1,2-a]pyrazine-2-carboxylic acid 2-tert-butyl ester (7.5 g, Reference Example 20), then placed under a blanket of carbon monoxide. The reaction mixture was heated to 80° C. and then treated with a solution of sodium hydroxide (10.6 g) in water (125 mL) dropwise over 30 minutes whilst maintaining the temperature at 80° C. After vigorously stirring at 80° C. for a further 6 hours the reaction mixture was allowed to cool to room temperature and then left to stand overnight. The reaction mixture was treated with diethyl ether, the layers separated and the basic aqueous fraction filtered through celite. The filtrate was acidified to pH 1 with concentrated hydrochloric acid and then extracted with ethyl acetate. The organic extract was dried over magnesium sulfate and evaporated. The residue was triturated with diethyl ether to give the title compound (4.40 g) as an off white solid, m.p. 212–215° C. $^1$H NMR [(CD$_3$)$_2$SO]: δ 7.62–7.50 (m, 5H), 4.83 (s, 2H), 3.95 (t, 2H), 3.68 (t, 2H) and 1.45 (s, 9H).

REFERENCE EXAMPLE 20

7-Cyano-8-iodo-6-phenyl-3,4-dihydro-1H-pyrrolo[1,2-a]pyrazine-2-carboxylic acid 2-tert-butyl ester A solution of 7-cyano-6-phenyl-3,4-dihydro-1H-pyrrolo[1,2-a]pyrazine-2-carboxylic acid tert-butyl ester (8.6 g, Reference Example 4(b)) in dry dimethylformamide (80 mL) was treated with N-iodosuccinamide (6.07 g) over 10 minutes. After stirring at room temperature for a further 4 hours the reaction mixture was treated with water and ethyl acetate. The organic phase was separated, further washed with water, then dried over magnesium sulfate and evaporated. The residue was triturated with diethyl ether to give the title compound (7.50 g) as a buff solid, m.p. 174–178° C. $^1$H NMR [(CD$_3$)$_2$SO]: δ 7.58–7.48 (m, 5H), 4.43 (s, 2H), 3.97 (t, 2H), 3.65 (t, 2H) and 1.46 (s, 9H).

REFERENCE EXAMPLE 21

6-Phenyl-1,2,3,4-tetrahydropyrrolo[1,2-a]pyrazine-8-carboxylic acid amide trifluoroacetic acid salt By proceeding in a similar manner to that described in Reference Example 1 but using 8-carbamoyl-6-phenyl-3,4-dihydro-1H-pyrrolo[1,2-a]pyrazine-2-carboxylic acid tert-butyl ester (400 mg, Reference Example 3) the title compound (390 mg) was prepared as a pale yellow solid, m.p. 206–209° C. MS: 242 [MH]$^+$.

REFERENCE EXAMPLE 22

7-Chloro-6-pyrid-3-yl-1,2,3,4-tetrahydro-pyrrolo[1,2-a]pyrazine-8-carbothioic acid amide trifluoroacetic acid salt By proceeding in a similar manner to that described in Reference Example 1 but using 7-chloro-6-pyridin-3-yl-8-thiocarbamoyl-3,4-dihydro-1H-pyrrolo[1,2-a]pyrazine-2-carboxylic acid tert-butyl ester (112 mg, Reference Example 23) there was prepared the title compound (175 mg) as a pale yellow solid.
$^1$H NMR [(CD$_3$)$_2$SO]: δ 9.84 (s, 1H), 9.42–9.20 (bs, 2H), 8.94 (s, 1H), 8.69 (d, 1H), 8.66 (d, 1H), 7.91 (d, 1H), 7.62 (dd, 1H), 4.63 (s, 2H), 4.02 (t, 2H) and 3.56 (t, 2H)

REFERENCE EXAMPLE 23

7-Chloro-6-pyridin-3-yl-8-thiocarbamoyl-3,4-dihydro-1H-pyrrolo[1,2-a]pyrazine-2-carboxylic acid tert-butyl ester A stirred suspension of 8-carbamoyl-7-chloro-6-pyridin-3-yl-3,4-dihydro-1H-pyrrolo[1,2-a]pyrazine-2-carboxylic acid tert-butyl ester (486 mg, Reference Example 2b) in toluene (25 mL) was treated with 4-methoxyphenylthionophosphine sulfide dimer (513 mg). After stirring at 80° C. for 2 hours the reaction mixture was allowed to cool to room temperature and then evaporated. The residue was subjected to column chromatography on silica eluting with dichloromethane, then with a mixture of methanol and dichloromethane (1:99, v/v) and then with a mixture of methanol and dichloromethane (1:49, v/v) to give the title compound (129 mg) as a off white solid, m.p. 220–221° C. [Elemental Analysis: C, 54.79; H, 5.10; N, 13.86%. Calculated for C$_{18}$H$_{21}$ClN$_4$O$_2$S: C, 55.03; H, 5.39; N, 14.26%].

REFERENCE EXAMPLE 24

7-Chloro-1,2,3,4-tetrahydropyrrolo[1,2-a]pyrazine-8-carboxylic acid amide trifluoroacetic acid salt By proceeding in a similar manner to that described in Reference Example 1 but using 8-carbamoyl-7-chloro-3,4-dihydro-1H-pyrrolo[1,2-a]pyrazine-2-carboxylic acid tert-butyl ester (3.96 g, Reference Example 25a) there was prepared 7-chloro-1,2,3,4-tetrahydropyrrolo[1,2-a]pyrazine-8-carboxylic acid amide trifluoroacetic acid salt (3.31 g) as a white solid, m.p. 227–228° C. MS: 202 [MH]$^+$, 200 [MH]$^+$.

REFERENCE EXAMPLE 25

8-Carbamoyl-7-chloro-6-cyclopropyl-3,4-dihydro-1H-pyrrolo[1,2-a]pyrazine-2-carboxylic acid tert-butyl ester By proceeding in a similar manner to that described in Reference Example 3 but using 7-chloro-8-cyano-6-cyclopropyl-3,4-dihydro-1H-pyrrolo[1,2-a]pyrazine-2-carboxylic acid tert-butyl ester (5.39 g, Reference Example 26) the title compound (4.91 g) was prepared as a white solid, m.p. 102–104° C. MS: 342 [MH]$^+$, 340 [MH]$^+$.

Similarly prepared was:

REFERENCE EXAMPLE 25a

8-Carbamoyl-7-chloro-3,4-dihydro-1H-pyrrolo[1,2-a]pyrazine-2-carboxylic acid tert-butyl ester (4.74 g) as a white solid, m.p. 168–170° C. $^1$H NMR [(CDCl$_3$)]: δ 6.85–6.54 (bs and s overlapping, 2H), 5.90–5.50 (bs, 1H), 4.91 (s, 2H), 3.90 (t, 2H), 3.81 (t, 2H) and 1.48 (s, 9H).

Using 7-chloro-8-cyano-3,4-dihydro-1H-pyrrolo[1,2-a]pyrazine-2-carboxylic acid tert-butyl ester (5.02 g, Reference Example 26a).

REFERENCE EXAMPLE 26

7-Chloro-8-cyano-6-cyclopropyl-3,4-dihydro-1H-pyrrolo[1,2-a]pyrazine-2-carboxylic acid tert-butyl ester By proceeding in a similar manner to that described in Reference Example 4 but using 4-cyclopropanecarbonylpiperazine-1,3-dicarboxylic acid 1-tert-butyl ester 3-ethyl ester (142 g, Reference Example 10) and substituting 2-chloroacrylonitrile with 2,3-dichloroacrylonitrile the title compound (7.65 g) was prepared as a white solid, m.p. 132–134° C. $^1$H NMR [(CDCl$_3$)]: δ 4.66 (s, 2H), 3.97 (t, 2H), 3.82 (t, 2H), 1.58–1.44 (m and s overlapping, 10H), 1.05–0.90 (m, 2H) and 0.85–0.70 (m, 2H).

Similarly prepared was:

REFERENCE EXAMPLE 26a

7-Chloro-8-cyano-3,4-dihydro-1H-pyrrolo[1,2-a]pyrazine-2-carboxylic acid tert-butyl ester (6.28 g) as an off white solid, m.p. 118–120° C. $^1$H NMR [(CDCl$_3$)]: δ 6.57 (s, 1H), 4.67 (s, 2H), 3.91 (t, 2H), 3.82 (t, 2H) and 1.49 (s, 9H).

Using 4-formylpiperazine-1,3-dicarboxylic acid 1-tert-butyl ester 3-ethyl ester (13.50 g, Reference Example 27)

REFERENCE EXAMPLE 27

4-Formylpiperazine-1,3-dicarboxylic acid 1-tert-butyl ester 3-ethyl ester

A solution of piperazine-1,3-dicarboxylic acid 1-tert-butyl ester 3-ethyl ester (38.22 g, prepared according to the procedure described in WO 96/31478 Step B page 94) in dry dichloromethane (400 mL) was treated with pentafluorophenyl formate (43.32 g, prepared according to the procedure of Kisfaludy and Otvos, Synthesis, 1987, 510). After stirring at room temperature overnight the reaction mixture was treated with N,N-dimethylethylenediamine (32.5 mL) and stirring continued for a further 1.5 hours. The reaction mixture was then washed with 1 M hydrochloric acid (400 mL), then a saturated solution of sodium hydrogen carbonate (400 mL), then water (400 mL), dried over sodium sulfate and then evaporated. The residue was triturated with a mixture of diethyl ether and pentane to give the title compound (27.21 g) as an off white solid, MS: 309 [MNa]$^+$.

REFERENCE EXAMPLE 28

7-Chloro-6-(4-methylpyridin-3-yl)-1,2,3,4-tetrahy-dropyrrolo[1,2-a]pyrazine-8-carboxylic acid amide bistrifluoroacetic acid salt By proceeding in a similar manner to that described in Reference Example 1 but using 8-arbamoyl-7-chloro-6-(4-methylpyridin-3-yl)-3,4-dihydro-1H-pyrrolo[1,2-a]pyrazine-2-carboxylic acid tert-butyl ester (1.60 g, Reference Example 29) the title compound (1.99 g) was prepared as an off white solid, MS: 293 [MH]$^+$, 291 [MH]$^+$. $^1$H NMR [(CD$_3$)$_2$SO]: δ 9.66–9.28 (bs, 2H), 8.64 (s, 1H), 8.00 (d, 1H), 7.64 (d, 1H), 7.60–7.40 (bs, 1H), 7.08–6.82 (bs, 1H), 4.60 (s, 2H), 4.01 (t, 2H), 3.56 (t, 2H) and 2.62 (s, 3H).

REFERENCE EXAMPLE 29

8-Carbamoyl-7-chloro-6-(4-methylpyridin-3-yl)-3,4-dihydro-1H-pyrrolo[1,2-a]pyrazine-2-carboxylic acid tert-butyl ester By proceeding in a similar manner to that described in Reference Example 2 but using 8-carbamoyl-6-(4-methylpyridin-3-yl)-3,4-dihydro-H-pyrrolo[1,2-a]pyrazine-2-carboxylic acid tert-butyl ester (3.47 g, Reference Example 30(a)) and performing the reaction in acetonitrile (400 mL) at 50° C. the title compound (1.60 g) was prepared as an off white solid, Rf 0.29 (ethyl acetate). $^1$H NMR [(CD$_3$)$_2$SO]: δ 8.52 (s, 1H), 7.79 (d, 1H), 7.38 (d, 1H), 7.37–7.25 (bs, 1H), 6.91–6.74 (bs, 1H), 4.80 (s, 2H), 3.82 (t, 2H), 3.66 (t, 2H), 2.52 (s, 3H) and 1.43 (s, 9H).

REFERENCE EXAMPLE 30

(a) 8-Carbamoyl-6-(4-methylpyridin-3-yl)-3,4-dihy-dro-1H-pyrrolo[1,2-a]pyrazine-2-carboxylic acid tert-butyl ester A solution of a 2:3 mixture of 8-cyano-6-(4-methylpyridin-3-yl)-3,4-dihydro-1H-pyrrolo[1,2-a]pyrazine-2-carboxylic acid tert-butyl ester and 7-cyano-6-(4-methylpyridin-3-yl)-3,4-dihydro-1H-pyrrolo[1,2-a]pyrazine-2-carboxylic acid tert-butyl ester (18.30 g, Reference Example 31) in methanol (538 mL) at 10° C. was treated with a solution of sodium hydroxide (21.35 g) in water (4 mL) dropwise. The reaction mixture was then treated with a 27.5% w/w aqueous solution of hydrogen peroxide (9 mL). After stirring at 50° C. for 2 hours the reaction mixture was allowed to cool to room temperature. The insoluble material collected was washed with ethyl acetate to give the title compound (3.47 g) as a white solid, Rf 0.09 (ethyl acetate). $^1$H NMR [(CD$_3$)$_2$SO]: δ 8.51 (s, 1H), 7.77 (d, 1H), 7.40–7.25 (bs and d overlapping, 2H), 6.85–6.74 (bs and s overlapping, 2H), 4.83 (s, 2H), 3.98 (t, 2H), 3.66 (t, 2H), 2.50 (s, 3H) and 1.44 (s, 9H).

The filtrate was then extracted four times with ethyl acetate (100 mL), the combined extracts dried over magnesium sulfate and then evaporated. The residue was subjected to column chromatography on silica eluting with ethyl acetate.

Eluted first was (b) 7-Cyano-6-(4-methylpyridin-3-yl)-3,4-dihydro-1H-pyrrolo[1,2-a]pyrazine-2-carboxylic acid tert-butyl ester (3.43 g) as a white solid, Rf 0.39 (ethyl acetate). $^1$H NMR [(CD$_3$)$_2$SO]: δ 8.60 (s, 1H), 7.87 (d, 1H), 7.43 (d, 1H), 6.52 (s, 1H), 4.60 (s, 2H), 4.00 (t, 2H), 3.66 (t, 2H), 2.54 (s, 3H) and 1.44 (s, 9H).

Eluted second was further quantities of the title compound (1.73 g).

REFERENCE EXAMPLE 31

8-Cyano-6-(4-methylpyridin-3-yl)-3,4-dihydro-1H-pyrrolo[1,2-a]pyrazine-2-carboxylic acid tert-butyl ester and 7-cyano-6-(4-methylpyridin-3-yl)-3,4-dihydro-1H-pyrrolo[1,2-a]pyrazine-2-carboxylic acid tert-butyl ester By proceeding in a similar manner to that described in Reference Example 4 but using 4-(4-methylpyridine-3-carbonyl)piperazine-1,3-dicarboxylic acid 1-tert-butyl ester 3-ethyl ester (41.0 g, Reference Example 32) there was prepared a 2:3 mixture of the title compounds as a light yellow gum (19.30 g).

REFERENCE EXAMPLE 32

4-(4-Methylpyridine-3-carbonyl)piperazine-1,3-di-carboxylic acid 1-tert-butyl ester 3-ethyl ester A stirred suspension of 6-methylnicotinic acid (29 g) in dry dichloromethane (400 mL) was treated with piperazine-1,3-dicarboxylic acid 1-tert-butyl ester 3-ethyl ester (57.58 g, prepared according to the procedure described in WO 96/31478 Step B page 94), then with 1-(3-dimethylaminopropyl)-3-ethylcarbodiimide hydrochloride (40.7 g). After stirring at room temperature for a further 1 hour the reaction mixture was treated with 4-dimethylaminopyridine (3.00 g) and stirring continued overnight. The reaction mixture was then further treated with dimethylaminopyridine (1.00 g). After stirring for a further 7 hours the reaction mixture was washed with a saturated aqueous solution of sodium hydrogen carbonate and then water. The organic phase was dried over magnesium sulfate and evaporated. The residue was subjected to column chromatography on silica eluting with a mixture of ethyl acetate and pentane (2:1, v/v) to give the title compound (54.0 g) as a yellow oil, Rf 0.31 (ethyl acetate).

REFERENCE EXAMPLE 33

7-Cyano-6-(4-methylpyridin-3-yl)-1,2,3,4-tetrahy-dropyrrolo[1,2-a]pyrazine-8-carboxylic acid amide bistrifluoroacetic acid salt By proceeding in a similar manner to that described in Reference Example 1 but using 8-carbamoyl-7-cyano-6-(4-methylpyridin-3-yl)-3,4-dihydro-1H-pyrrolo[1,2-a]pyrazine-2-carboxylic acid tert-butyl ester (310 mg, Reference Example 34) the title compound (340 mg) was prepared as an off white solid, $^1$H NMR [(CD$_3$)$_2$SO]: δ 9.72–9.23 (bs, 2H), 8.63 (s, 1H), 7.94 (d, 1H), 7.62–7.15 (two bs and d overlapping, 3H), 4.60 (s, 2H), 4.14 (t, 2H), 3.52 (t, 2H) and 2.60 (s, 3H).

REFERENCE EXAMPLE 34

8-Carbamoyl-7-cyano-6-(4-methylpyridin-3-yl)-3,4-dihydro-1H-pyrrolo[1,2-a]pyrazine-2-carboxylic acid tert-butyl ester By proceeding in a similar manner to that described in Reference Example 3 but using 7,8-dicyano-6-(4-methylpyridin-3-yl)-3,4-dihydro-1H-pyrrolo[1,2-a]pyrazine-2-carboxylic acid tert-butyl ester (1.60 g, Reference Example 35) and performing the reaction at room temperature the title compound (310 mg) was prepared as an off white solid, Rf 0.22 (ethyl acetate). $^1$H NMR [(CD$_3$)$_2$SO]: δ 8.62 (s, 1H), 7.90 (d, 1H), 7.52–7.32 (bs and d overlapping, 2H), 7.18–7.00 (bs, 1H), 4.80 (s, 2H), 3.98 (t, 2H), 3.67 (t, 2H), 2.55 (s, 3H) and 1.44 (s, 9H).

REFERENCE EXAMPLE 35

7,8-Dicyano-6-(4-methylpyridin-3-yl)-3,4-dihydro-1H-pyrrolo[1,2-a]pyrazine-2-carboxylic acid tert-butyl ester By proceeding in a similar manner to that described in Reference Example 8 but using 7-cyano-6-(4-methylpyridin-3-yl)-3,4-dihydro-1H-pyrrolo[1,2-a]pyrazine-2-carboxylic acid tert-butyl ester (3.40 g, Reference Example 30(b)) the title compound (1.60 g) was prepared as an off white solid, MS: 364 [MH]$^+$. $^1$H NMR [(CD$_3$)$_2$SO]: δ 8.64 (s, 1H), 7.95 (d, 1H), 7.49 (d, 1H), 4.77 (s, 2H), 4.00 (t, 2H), 3.69 (t, 2H), 2.56 (s, 3H) and 1.44 (s, 9H).

REFERENCE EXAMPLE 36

7-Cyano-6-(tetrahydropyran-4-yl)-1,2,3,4-tetrahydropyrrolo[1,2-a]pyrazine-8-carboxylic acid amide trifluoroacetic acid salt By proceeding in a similar manner to that described in Reference Example 1 but using 8-carbamoyl-7-cyano-6-(tetrahydropyran-4-yl)-3,4-dihydro-1H-pyrrolo[1,2-a]pyrazine-2-carboxylic acid tert-butyl ester (1.43 g, Reference Example 37) the title compound (1.46 g) was prepared as an off white solid, m.p. 237–242° C. MS: 275 [MH]$^+$.

REFERENCE EXAMPLE 37

8-Carbamoyl-7-cyano-6-(tetrahydropyran-4-yl)-3,4-dihydro-1H-pyrrolo[1,2-a]pyrazine-2-carboxylic acid tert-butyl ester By proceeding in a similar manner to that described in Reference Example 3 but using 7,8-dicyano-6-tetrahydropyran-4-yl-3,4-dihydro-1H-pyrrolo[1,2-a]pyrazine-2-carboxylic acid tert-butyl ester (1.91 g, Reference Example 38) and performing the reaction at room temperature the title compound (1.45 g) was prepared as an off white solid, m.p. 212–221° C. $^1$H NMR [(CD$_3$)$_2$SO]: δ 7.45–7.16 (bs, 1H), 7.07–6.78 (bs, 1H), 4.69 (s, 2H), 4.01 (t, 2H), 3.94 (dd, 2H), 3.71 (t, 2H), 3.40 (t, 2H), 3.14–3.01 (m, 1H), 2.03–1.88 (m, 2H), 1.71 (d, 2H) and 1.42 (s, 9H).

REFERENCE EXAMPLE 38

7,8-Dicyano-6-(tetrahydropyran-4-yl)-3,4-dihydro-1H-pyrrolo[1,2-a]pyrazine-2-carboxylic acid tert-butyl ester Method A: By proceeding in a similar manner to that described in Reference Example 4 but using 4-(tetrahydropyran-4-carbonyl)piperazine-1,3-dicarboxylic acid 1-tert-butyl ester 3-ethyl ester (28.51 g, Reference Example 5a) and substituting 2-chloroacrylonitrile with chloromaleic acid dinitrile (10.22 g, prepared according to the procedure of Morgan et. al. Eur. J. Med. Chem. 1997, 32, 21) there was prepared the title compound (2.80 g) as a brown gum, Rf 0.60 (dichloromethane:methanol, 19:1). $^1$H NMR [(CD$_3$)$_2$SO]: δ 4.64 (s, 2H), 4.08 (t, 2H), 3.94 (dd, 2H), 3.75 (t, 2H), 3.40 (t, 2H), 3.20–3.05 (m, 1H), 1.93–1.67 (m, 4H) and 1.43 (s, 9H).

Method B: A mixture of 4-(tetrahydropyran-4-carbonyl)-piprazine-1,3-dicarboxylic acid 1-tert-butyl ester (31.2 g, Reference Example 62), triethylamine (46 g) and acetic anhydride (14 g) in toluene (200 ml) was heated at 60° C. for 15 minutes then treated with a solution of 2-chlorobut-2-ene-dinitrile (23 g) in toluene (100 ml) over 1 hour via a syringe pump whilst maintaining the temperature at 55–60° C. The reaction mixture was stirred for a further 15 minutes, then cooled to room temperature and then partitioned between aqueous sodium bicarbonate (100 ml), water (700 ml) and ethyl acetate (700 ml). The organic phase was separated, then washed with water and then evaporated under reduced pressure. The residue was subjected to column chromatography on silica, eluting with a mixture of dichloromethane and methanol (98.5:1.5, v/v) to give the title compound (25.8 g) as tan solid.

REFERENCE EXAMPLE 39

7-Cyano-6-trifluoromethyl-1,2,3,4-tetrahydropyrrolo[1,2-a]pyrazine-8-carboxylic acid amide trifluoroacetic acid salt By proceeding in a similar manner to that described in Reference Example 1 but using 8-carbamoyl-7-cyano-6-trifluoromethyl-3,4-dihydro-1H-pyrrolo[1,2-a]pyrazine-2-carboxylic acid tert-butyl ester (240 mg, Reference Example 40) the title compound (249 mg) was prepared as an off white solid, $^1$H NMR [(CD$_3$)$_2$SO]: δ 9.63–9.07 (bs, 2H), 7.74–7.40 (2 bs overlapping, 2H), 4.53 (s, 2H), 4.27 (t, 2H) and 3.60 (t, 2H).

REFERENCE EXAMPLE 40

8-Carbamoyl-7-cyano-6-trifluoromethyl-3,4-dihydro-1H-pyrrolo[1,2-a]pyrazine-2-carboxylic acid tert-butyl ester By proceeding in a similar manner to that described in Reference Example 3 but using 7,8-dicyano-6-trifluoromethyl-3,4-dihydro-1H-pyrrolo[1,2-a]pyrazine-2-carboxylic acid tert-butyl ester (376 mg, Reference Example 41) and performing the reaction at room temperature the title compound (200 mg) was prepared as an off white solid, Rf 0.32 (ethyl acetate:pentane 1:1). MS: 359 [MH]$^+$.

REFERENCE EXAMPLE 41

7,8-Dicyano-6-trifluoromethyl-3,4-dihydro-1H-pyrrolo[1,2-a]pyrazine-2-carboxylic acid tert-butyl ester A suspension of piperazine-2-carboxylic acid dihydrochloride (12.03 g) in N-methylpyrrolidinone (150 mL) was treated with triethylamine (16.45 mL) and trifluoroacetic anhydride (41.70 mL). After stirring at room temperature for 1 hour the reaction mixture was treated with chloromaleic acid dinitrile (7.38 g, prepared according to the procedure of Morgan et. al. Eur. J. Med. Chem. 1997, 32, 21) and then heated at 70° C. for 19 hours. The reaction mixture was allowed to cool to room temperature and then evaporated. The residue was treated with dichloromethane (100 mL) and water (100 mL). The organic phase was separated and the aqueous phase further extracted twice with dichloromethane (100 mL). The combined organic extracts were dried over magnesium sulfate and evaporated. The residue was subjected to column chromatography on silica eluting with a mixture of ethyl acetate and pentane (1:4, v/v), then with a mixture of ethyl acetate and pentane (1:1, v/v) to give an off white solid (7.93 g). A solution of the off white solid (7.93 g) in methanol (200 mL) was then treated with a solution of potassium carbonate (6.50 g) in water (20 mL). After stirring at room temperature for 1 hour the reaction mixture was filtered and the filtrate evaporated. The residue was treated with water (50 mL) and dichloromethane (100 mL). The organic phase was separated and the aqueous phase further extracted five times with dichloromethane (100 mL). The combined organic extracts were dried over magnesium sulfate and evaporated. The residue in dimethylformamide (120 mL) was then treated with di-tert-butyl dicarbonate (4.70 g) and triethylamine (2.78 mL). After stirring at room temperature for 4 hours the reaction mixture was left to stand 48 hours, then evaporated. The residue was subjected to column chromatography on silica eluting with a mixture of ethyl acetate and pentane (1:4, v/v) to give an off white solid, which was triturated with a mixture of diethyl ether and pentane to give the title compound (376 mg) as a white solid, $^1$H NMR [(CDCl$_3$)]: δ 4.80 (s, 2H), 4.14 (t, 2H), 3.92 (t, 2H) and 1.50 (s, 9H).

REFERENCE EXAMPLE 42

Cyclopentylmethyl isocyanate

A solution of cyclopentylacetyl chloride (1.00 g) in dry acetonitrile (10 mL), under a blanket of nitrogen, was treated with sodium azide (488 mg). After stirring at reflux for 1.5 hours the reaction mixture was allowed to cool to room temperature and then left to stand overnight. The reaction mixture was then filtered and the filtrate evaporated at room temperature to give title compound (0.50 g) as a pale yellow oil, which was used without further purification.

REFERENCE EXAMPLE 43

5-(Pyrid-2-yl)thiophene-2-carbonyl chloride

A suspension of 5-(pyrid-2-yl)thiophene-2-carboxylic acid (48 mg) in dry toluene (10 mL) was treated with thionyl chloride (269 μL). After stirring at 100° C. for 2.5 hours the reaction mixture was allowed to cool to room temperature and then evaporated. The residue was azeotroped with toluene to give the title compound (61 mg), which was used without further purification.

REFERENCE EXAMPLE 44

Phenylsulfamoyl chloride

A suspension of sodium phenylsulfamate (200 mg, prepared according to the procedure of Audrieth and Sveda, J. Org. Chem., 1944, 9, 89) in dry toluene (5 mL), under a blanket of nitrogen, was treated with PCl$_5$ (267 mg). After stirring at 80° C. for 20 hours the reaction mixture was allowed to cool to room temperature and then evaporated to give the title compound (100 mg) as a brown oil, which was used without further purification.

Similarly prepared were:

REFERENCE EXAMPLE 44a 4-methoxyphenylsulfamoyl chloride (47 mg) as a yellow oil.

Using sodium 4-methoxyphenylsulfamate (72 mg, Reference Example 45).

REFERENCE EXAMPLE 44b 4-(trifluoromethyl)phenylsulfamoyl chloride (200 mg) as a yellow oil.

Using sodium 4-(trifluoromethyl)phenylsulfamate (260 mg, Reference Example 45a).

REFERENCE EXAMPLE 44c

4-Fluorophenylsulfamoyl chloride (26 mg) as a yellow oil.

Using sodium 4-fluorophenylsulfamate (82 mg, Reference Example 45b).

REFERENCE EXAMPLE 45

Sodium 4-methoxyphenylsulfamate

A stirred solution of 4-methoxyaniline (13.95 g) in dry dichloromethane (100 mL) was treated with chlorosulfonic acid (3.33 mL) dropwise. After stirring at room temperature for a further 1 hour the reaction mixture was filtered. The insoluble material was treated with a solution of sodium carbonate (7.95 g) in water (250 mL). The aqueous solution was washed with diethyl ether (50 mL) and then evaporated. The residue was triturated with ethanol and the insoluble material then recrystallised from ethanol/water (95:5) to give the title compound (3.30 g).

Similarly prepared were:

REFERENCE EXAMPLE 45a

Sodium 4-(trifluoromethyl)phenylsulfamate (260 mg) as a white solid.

Using 4-(trifluoromethyl)aniline (2 mL).

REFERENCE EXAMPLE 45b

Sodium 4-fluorophenylsulfamate (82 mg) as a white solid.

Using 4-fluoroaniline (14 mL).

REFERENCE EXAMPLE 46

N-4-Methoxyphenyl-N'-cyano-O-phenylisourea

A slurry of diphenyl cyancarbonimidate (1 g) in isopropanol (10 mL) was treated with 4-methoxyaniline (517 mg). After stirring at room temperature for a further 2.5 hours the reaction mixture was filtered. The insoluble material was washed with isopropanol to give the title compound (778 mg) as a white solid, which was used without further purification.

REFERENCE EXAMPLE 47

4-Morpholin-4-ylmethylphenylamine

A stirred suspension of 4-(4-nitrobenzyl)morpholine (500 mg) (prepared according to a modified procedure described by Leffler and Volwiler, JACS, 1938, 60, 896) in water (4.15 mL) was treated with glacial acetic acid (0.5 mL). The reaction mixture was heated to gentle reflux and then treated with iron powder (500 mg) over 10 minutes. After stirring at reflux for a further 10 minutes the reaction mixture was allowed to cool to room temperature. The reaction mixture was treated with water (10 mL) and then basified to pH 12 with a 4 M aqueous solution of sodium hydroxide. The aqueous was extracted three times with diethyl ether (1×40 mL, 2×10 mL). The combined organic extracts were dried over magnesium sulfate and then evaporated to give the title compound (370 mg) as a white solid, m.p. 96–97° C. MS: 193 [MH]$^+$.

REFERENCE EXAMPLE 48

1-(4-Aminobenzoyl)4-methylpiperazine

A mixture of iron powder (30.0 g) and concentrated hydrochloric acid (1.5 mL) was shaken and dried at 70° C. for 1 hour under high vacuum. The activated iron powder was then allowed to cool to room temperature. A solution of 1-methyl-4-(4-nitrobenzoyl)piperazine (15.0 g, Reference Example 49) in toluene (75 mL) was treated with the activated iron powder. The reaction mixture was heated to 125° C. and treated with water (7.5 mL) dropwise over 1.25 hours. Stirring was continued for a further 45 minutes. On cooling to 60° C. the reaction mixture was further treated with toluene (75 mL) and dichloromethane (75 mL), and then allowed to cool to room temperature. The reaction mixture was treated with potassium carbonate (5.0 g), dried over magnesium sulfate, and then evaporated to low bulk and treated with pentane (120 mL). The insoluble material collected was washed with pentane to give the title compound (11.9 g) as a pale cream crystalline solid, m.p. 149–150° C. $^1$H NMR [(CDCl$_3$]: δ 7.26 (d, 2H), 6.65 (d, 2H), 3.99–3.82 (bs, 2H), 3.81–3.54 (bs, 4H), 2.52–2.37 (brs, 4H) and 2.33 (s, 3H).

REFERENCE EXAMPLE 49

1-Methyl-4-(4-nitrobenzoyl)piperazine

A stirred solution of 1-methylpiperazine (14.6 mL) and triethylamine (19.2 mL) in dry dichloromethane (132 mL) at 10° C. was treated with 4-nitrobenzoyl chloride (23.2 g) portion wise whilst maintaining the temperature below 15° C. After stirring at 10° C. for a further 1 hour the reaction mixture was allowed to warm to room temperature and treated with water (100 mL). The organic phase was then separated and the aqueous phase further extracted with dichloromethane (50 mL). The combined organic extracts were washed with a 0.5 M aqueous solution of sodium carbonate (100 mL), then with brine (100 mL), and then evaporated to low bulk and treated with petroleum ether (80–100° C.) (100 mL). After removal of further solvent, and trituration, the insoluble material collected was washed with petroleum ether (40–60° C.) to give the title compound (30.4 g) as pale orange crystalline solid, m.p. 100–101° C. $^1$H NMR [(CDCl$_3$]: δ 8.29 (d, 2H), 7.59 (d, 2H), 3.94–3.71 (bs, 2H), 3.52–3.29 (bs, 2H) and 2.58–2.30 (2×brs and s overlapping, 7H).

Similarly prepared were:

REFERENCE EXAMPLE 49a

Morpholin-4-yl(4-nitrophenyl)methanone (3.84 g) as a white solid, m.p. 101–103° C. $^1$H NMR [(CD$_3$)$_2$SO]: δ 8.24 (d, 2H), 7.65 (d, 2H), 3.72–3.39 (2 bs overlapping, 6H) and 3.35–3.14 (bs, 2H).

Using morpholine (1.74 mL).

REFERENCE EXAMPLE 49b

1-Methyl-4-(3-nitrobenzoyl)piperazine (860 mg) as a white solid, $^1$H NMR [(CDCl$_3$]: δ 8.34–8.27 (s and d overlapping, 2H), 7.76 (d, 1H), 7.64 (t, 1H), 4.15–3.30 (2×bs overlapping, 4H) and 2.84–2.37 (2×bs and s overlapping, 7H).

Using 3-nitrobenzoyl chloride (1.0 g).

REFERENCE EXAMPLE 49c

1-Isopropyl-4-(4-nitrobenzoyl)piperazine (1.00 g) as a yellow solid, $^1$H NMR [(CD$_3$)$_2$SO]: δ 8.28 (d, 2H), 7.66 (d, 2H), 3.67–3.57 (bs, 2H), 3.28–3.18 (bs, 2H), 2.75–2.65 (m, 1H), 2.56–2.47 (bs, 2H), 2.45–2.35 (bs, 2H) and 0.97 (d, 6H). MS: 278 [MH]$^+$.

Using 1-isopropylpiperazine (800 mg, prepared according to the procedure of Renau et. al, J. Med. Chem. 1996, 39, 729)

REFERENCE EXAMPLE 49d

1-Isopropyl-4-(4-nitrobenzoyl)[1,4]diazepane (1.00 g) as a light yellow oil, Rf 0.25 (methanol:ethyl acetate, 1:9). MS: 292 [MH]$^+$.

Using 1-isopropyl[1,4]diazepane (1.00 g, prepared by adaptation of the method described by Renau et. al, J. Med. Chem. 1996, 39, 729)

REFERENCE EXAMPLE 50

4-(4-Methylpiperazin-1-ylmethyl)phenylamine

A mixture of 6 M hydrochloric acid (38.0 mL) and N-(4-methylpiperazin-1-ylmethylphenyl)acetamide (3.80 g, Reference Example 51) was heated at 95° C. for 2 hours, then allowed to cool to room temperature and left to stand overnight. The reaction mixture was evaporated and the residue treated with a 4M aqueous solution of sodium hydroxide (15 mL) and diethyl ether (200 mL). The organic phase was separated and the aqueous further extracted twice with diethyl ether (50 mL). The combined organic extracts were dried over magnesium sulfate and then evaporated to give the title compound (3.01 g) as a pale yellow crystalline solid, m.p. 97–99° C. ¹H NMR [(CDCl₃]: δ 7.05 (d, 2H), 6.60 (d, 2H), 3.68–3.50 (bs, 2H), 3.37 (s, 2H), 2.63–2.29 (bs, 8H) and 2.26 (s, 3H).

REFERENCE EXAMPLE 51

N-(4-Methylpiperazin-1-ylmethylphenyl)acetamide

A stirred solution of formic acid (3.77 mL) at −10° C. was treated with 1-methylpiperazine (11.10 mL) dropwise whilst maintaining the temperature at −10° C. The reaction mixture was then allowed to warm to room temperature and treated with 4-acetamidobenzaldehyde (4.08 g). After stirring at 130° C. for 15 minutes the temperature was increased to 155° C. and stirring continued for 2.5 hours. The reaction mixture was allowed to cool to room temperature and treated with diisopropyl ether (50 mL). The insoluble material was washed with diethyl ether to give the title compound (3.98 g) as buff crystalline solid, m.p. 106–108° C. MS: 248 [MH]⁺.

REFERENCE EXAMPLE 52

3-Morpholin-4-ylmethylphenylamine

A stirred solution of 4-(3-nitrobenzyl)morpholine (1.0 g, Reference Example 33) in ethanol (25 mL) was treated with 5% Pd/C (15 mg), then placed under a blanket of hydrogen. After stirring at room temperature for a further 2 hours the reaction mixture was filtered through celite and then evaporated. The residue was subjected to column chromatography on silica eluting with ethyl acetate to give the title compound (700 mg) as a light brown oil, Rf 0.08 (ethyl acetate). ¹H NMR [(CDCl₃]: δ 7.09 (t, 1H), 6.73–6.67 (m, 2H), 6.58 (d, 1H), 3.84–3.45 (t and bs overlapping, 6H), 3.41 (s, 2H) and 2.45 (t, 4H).

Similarly prepared were:

REFERENCE EXAMPLE 52a 4-(2-Morpholin-4-ylethoxy)phenylamine (610 mg) as a white solid, m.p. 55–56° C. MS: 223 [MH]⁺.

Using 4-(2-(4-nitrophenoxy)ethyl)morpholine (1.13 g, prepared according to a modified procedure described by Kaye et. al., JOC, 1951, 16, 1421).

REFERENCE EXAMPLE 52b (4-Aminophenyl)morpholin-4-ylmethanone (0.99 g) as a white solid, m.p. 133–136° C. MS: 207 [MH]⁺.

Using morpholin-4-yl(4-nitrophenyl)methanone (1.18 g, Reference Example 49a).

REFERENCE EXAMPLE 52c 1-(3-Aminobenzoyl)-4-methylpiperazine (625 mg) as an off white solid, m.p. 112–114° C. ¹H NMR [(CDCl₃]: δ 7.16 (t, 1H), 6.75–6.68 (m, 3H), 3.96–3.37 (2×bs overlapping, 6H) and 2.66–2.25 (2×bs and s overlapping, 7H).

Using 1-methyl-4-(3-nitrobenzoyl)piperazine (800 mg, Reference Example 49b).

REFERENCE EXAMPLE 52d 1-(4-Aminobenzoyl)-4-methyl[1.4]diazepane (1.01 g) as a white solid, m.p. 153–156° C. MS: 234 [MH]⁺.

Using 1-methyl-4-(4-nitrobenzoyl)[1,4]diazepane (1.26 g, Reference Example 54).

REFERENCE EXAMPLE 52e 1-(3-Aminobenzoyl)-4-methyl[1,4]diazepane (1.15 g) as a white solid, m.p. 91–93° C. MS: 234 [MH]⁺.

Using 1-methyl-4-(3-nitrobenzoyl)[1,4]diazepane (1.5 g, Reference Example 54a)

REFERENCE EXAMPLE 52f 1-(4-Aminophenyl)-2-morpholin-4-ylethanone (462 mg) as a yellow solid, m.p. 78–80° C. MS: 221 [MH]⁺.

Using 2-morpholin-4-yl-1-(4-nitrophenyl)ethanone (700 mg, Reference Example 55)

REFERENCE EXAMPLE 52g 4-(4-Fluorophenoxy)phenylamine (727 mg) as an off white solid, m.p. 62–64° C. MS: 204 [MH]⁺.

Using 4-fluoro-4'-nitrodiphenyl ether (1.00 g, prepared according to the procedure of Rarick et. al, JACS, 1933, 55, 1289)

REFERENCE EXAMPLE 52h 1-(4-Aminobenzoyl)-4-isopropylpiperazine (320 mg) as a yellow oil, ¹H NMR [(CD₃)₂SO]: δ 7.10 (d, 2H), 6.53 (d, 2H), 5.50 (s, 2H), 3.45 (t, 4H), 2.72–2.60 (m, 1H), 2.41 (t, 4H) and 0.96 (d, 6H). MS: 248 [MH]⁺.

Using 1-isopropyl-4-(4-nitrobenzoyl)piperazine (500 mg, Reference Example 49c)

REFERENCE EXAMPLE 52i 1-(4-Aminobenzoyl)-4-isopropyl[1,4]diazepane (250 mg) as a light yellow oil, Rf 0.11 (methanol:ethyl acetate 1:9). MS: 262 [MH]⁺.

Using 1-isopropyl-4-(4-nitrobenzoyl)[1,4]diazepane (1.00 g, Reference Example 49d)

REFERENCE EXAMPLE 53

4-(3-Nitrobenzyl)morpholine

A solution of morpholine (4.57 mL) in toluene (10 mL) at 5° C. was treated with a solution of 3-nitrobenzyl chloride (4.29 g) in toluene (10 mL). After stirring at 85° C. for 2 hours the reaction mixture was allowed to cool to room temperature and then left to stand overnight. The reaction mixture was treated with diethyl ether (100 mL), then washed three times with water (50 mL), then three times with brine (50 mL), dried over magnesium sulfate and then evaporated. The residue was subjected to column chromatography on silica eluting with ethyl acetate to give the title compound (2.86 g) as a white solid, m.p. 48–50° C. ¹H NMR [(CDCl₃]: δ 8.24 (s, 1H), 8.13 (d, 1H), 7.70 (d, 1H), 7.50 (t, 1H), 3.74 (t, 4H), 3.60 (s, 2H) and 2.48 (s, 4H).

REFERENCE EXAMPLE 54

1-Methyl-4-(4-nitrobenzoyl)[1,4]diazepane

A stirred solution of 1-methyl-[1,4]diazepane (2.19 mL) in dry dichloromethane (30 mL) was treated with a solution of 4-nitrobenzoyl chloride (3.6 g) in dry dichloromethane (30 mL) dropwise over 10 minutes. After stirring at room temperature for a further 10 minutes the reaction mixture was treated with triethylamine (2.8 mL) and then stirred for a further 3 hours. The reaction mixture was then treated with water (10 mL), the organic phase separated and further washed twice with a 2 M aqueous solution of sodium hydroxide (20 mL), then four times with water (15 mL). The organic phase was then dried over magnesium sulfate and evaporated to give the title compound (4.4 g) as brown oil, Rf 0.64 (dichloromethane:methanol, 4:1). MS: 264 [MH]$^+$.

Similarly prepared were:

REFERENCE EXAMPLE 54a

1-Methyl-4-(3-nitrobenzoyl)[1,4]diazepane (4.2 g) as an orange oil after purification by column chromatography on silica eluting with a mixture of ethyl acetate and methanol and triethylamine (43:5:2, v/v/), Rf 0.52 (dichloromethane:methanol:triethylamine, 40:10:1). MS: 264 [MH]$^+$.

Using 3-nitrobenzoyl chloride (3.5 g)

REFERENCE EXAMPLE 55

2-Morpholin-4-yl-1-(4-nitrophenyl)ethanone

A stirred solution of 2-bromo-4'-nitroacetophenone (4.0 g) in dry tetrahydrofuran (60 mL) was treated with morpholine (2.84 mL). After stirring at room temperature for a further 30 minutes the reaction mixture was treated with water (100 mL) and ethyl acetate (100 mL). The organic phase was separated, washed with brine (100 mL), then dried over magnesium sulfate and evaporated. The residue was triturated with diethyl ether to give the title compound (2.72 g) as a yellow solid, Rf 0.60 (dichloromethane:methanol:triethylamine, 85:10:5). $^1$H NMR [(CD$_3$)$_2$SO]: δ 8.32 (d, 2H), 8.20 (d, 2H), 3.90 (s, 2H), 3.58 (t, 4H) and 2.48 (t, 4H).

REFERENCE EXAMPLE 56

2-Trifluoromethylpyridine-4-carbonyl azide

A suspension of 6-trifluoromethylnicotinic acid (2.90 g) in toluene (130 mL) was treated with diphenylphosphoryl azide (3.30 mL), then triethylamine (2.30 mL). After stirring at room temperature for 3.5 hours the reaction mixture was treated with water (80 mL). The organic phase was separated and the aqueous phase further extracted three times with ethyl acetate (40 mL). The combined organics were dried over magnesium sulfate and then evaporated under reduced pressure at room temperature such as to give the title compound as a 0.3M solution in toluene, which was used without further purification.

REFERENCE EXAMPLE 57

2-Isocyanoto-5-methylthiophene

A solution of 5-methythiophene-2-carbonyl azide (167 mg, prepared according to the procedure of Binder et. al, Synthesis 1977, 225) in toluene (3 mL) was heated to 100° C. for 1 hour under a stream of nitrogen. The reaction mixture was then allowed to cool to room temperature to give the title compound as a 0.3M solution in toluene, which was used without further purification.

REFERENCE EXAMPLE 58

5-(Pyrid-2-yl)thiophene-2-carbonyl azide

A solution of 5-(pyrid-2-yl)thiophene-2-carbonyl chloride (254 mg, Reference Example 43) in acetone (3 mL) was treated with a solution of sodium azide (128 mg) in a water and acetone mixture (3.5 mL, 1:6, v/v). After stirring at room temperature for a further 75 minutes the reaction mixture was treated with water (4 mL). The insoluble material was collected and washed with water to give the title compound (217 mg) as a white solid, which was used without further purification.

REFERENCE EXAMPLE 59

(4-Amino-piperidin-1-yl)-morpholin-4-yl-methanone, trifluoroacetic acid salt

A solution of diphosgene (0.99 g) in dry dichloromethane (20 mL), under a blanket of nitrogen and at 0° C., was treated dropwise with morpholine (0.87 mL), then triethylamine (3.48 mL) whilst maintaining the temperature at 0° C. The resulting reaction mixture was stirred at 0° C. for a further 30 minutes, then treated dropwise with a solution of 4-tert-butoxycarbonylaminopiperidine (2.0 g, prepared according to a modified procedure described in WO94/10146 step j page 27) in dry dichloromethane (20 mL) whilst maintaining the temperature at 0° C. After stirring at 0° C. for a further 1 hour the reaction mixture was allowed to warm to room temperature and stand overnight. The reaction mixture was then treated with water (50 mL) and the organic phase separated. The aqueous phase was then extracted twice with dichloromethane (75 mL). The combined organic extracts were dried over magnesium sulfate and evaporated. A solution of the residue in dry dichloromethane (170 mL) was then treated with trifluoroacetic acid (10.37 mL). After stirring at room temperature for a further 7 hours the reaction mixture was left to stand overnight and then evaporated to give the title_compound (2.99 g) as a brown oil, which was used without further purification.

REFERENCE EXAMPLE 60

4-Amino-piperidine-1-carboxylic acid isopropyl ester, trifluoroacetic acid salt

A solution of 4-tert-butoxycarbonylaminopiperidine (5.0 g, prepared according to a modified procedure described in WO94/10146 step j page 27) in dry dichloromethane (150 mL) was treated with triethylamine (6.46 mL), then isopropyl chloroformate (24.9 mL). After stirring at room temperature for a further 6 hours the reaction mixture was allowed to stand for 48 hours. The reaction mixture was then washed three times with a saturated aqueous solution of sodium bicarbonate (50 mL), then three times with water (50 mL), then dried over magnesium sulfate and evaporated. A solution of the residue in dry dichloromethane (30 mL) was then treated with trifluoroacetic acid (10.8 mL). After stirring at room temperature for a further 5 hours the reaction mixture was evaporated to give the title compound (5.36 g) as a colourless oil, which was used without further purification.

REFERENCE EXAMPLE 61

(4-Amino-piperidin-1-yl)-phenyl-methanone, trifluoroacetic acid salt

A solution of 4-tert-butoxycarbonylaminopiperidine (2.0 g, prepared according to a modified procedure described in WO94/10146 step j page 27) in dry dichloromethane (150 mL) was treated with triethylamine (2.78 mL), then benzoyl chloride (1.48 mL). After stirring at room temperature for 3.5 hours the reaction mixture was washed once with water (50 mL), then once with a saturated aqueous solution of sodium hydrogen carbonate (30 mL), then dried over sodium sulfate and then evaporated. The residue was triturated with diethyl ether and the insoluble white solid was dissolved in dichloromethane (50 mL). This solution was then treated with trifluoroacetic acid (5.9 mL) and after stirring at room temperature for 2 hours and then standing at room temperature overnight the mixture was evaporated to give the title compound (2.00 g) as a colourless oil, which was used without further purification.

REFERENCE EXAMPLE 62

4-(Tetrahydropyran-4-carbonyl)-piprazine-1,3-dicarboxylic acid 1-tert-butyl ester Tetrahydropyran-4-carbonyl chloride was added drop wise to a mixture of piperazine-1,3-dicarboxylicacid 1-tert-butyl ester (123 g, Reference Example 63) and triethylamine (150 g) in dichloromethane (2000 ml) over a period of 0.45 hours. After stirring at room temperature for 3 days the reaction mixture was treated with water (1500 ml) and then acidified to pH 2 by addition of hydrochloric acid (37%). The organic phase was separated, then washed with aqueous sodium chloride solution (1%) and then evaporated under reduced pressure to give a yellow foam (157 g) which was recrystallised from diethyl ether and then from ethyl acetate to give the title compound (67.9 g) as white solid.

REFERENCE EXAMPLE 63

Piperazine-1,3-dicarboxylicacid 1-tert-butyl ester

A mixture of piperazine-2-carboxylic acid dihydrochloride in dioxan (1000 ml) and water (500 ml), at 10–15° C., was treated with aqueous sodium hydroxide solution (50%) over 15 minutes to adjust the pH to 9.1. This mixture was then treated portionwise (0.1 equivalent portions) with tert-butyl dicarbonate (114.6 g) over a period of 1 hour whilst maintaining the temperature at 5° C. and the pH around 8.8. After stirring at room temperature overnight the reaction mixture was cooled to 10° C., then the pH of the mixture was adjusted to 2 by the addition of hydrochloric acid (37%) and then the mixture was concentrated at 40° C. under reduced pressure. The resulting solid was treated with methanol (1500 ml) and this mixture was heated at reflux temperature and then filtered to remove the insoluble inorganics. The filtrate was evaporated to give the title compound (126 g) as an off white solid. MS: 231 [MH]$^+$.

The compounds of the Examples 64, 65, 66, 67, 68 and 69 have been prepared as indicated above for the Examples of the present application using the appropriated substituents.

In Vitro and In Vivo Test Procedures

I) In Vitro Test Procedures for IGF1R

1. Inhibitory Effects of Compounds on IGF1R

Inhibitory effects of compounds on IGF1R—autophosphorylation activity—were determined using a time-resolved fluorescent assay.

The cytoplasmic domain of human IGF1R has been cloned as glutathione S-transferase (GST) fusion into the pFastBac-GST tagged baculovirus expression vector. The protein has been expressed in SF21 cells and purified to about 80% homogeneity.

Kinase activity was determined in 50 mM Hepes pH 7.5 containing 5 mM $MnCl_2$, 50 mM NaCl, 3% Glycerol, 0.025% Tween 20, 120 µM adenosine triphosphate. Enzyme reactions were terminated by the addition of 100 mM Hepes buffer pH 7.0, containing 0.4 M KF, 133 mM EDTA, BSA 0.1% containing an anti-GST antibody labelled with XL665 and an anti-phosphotyrosine antibody conjugated to a europium cryptate (Eu—K). Features of the two fluorophores, XL-665 and Eu—K are given in G. Mathis et al., Anticancer Research, 1997, 17, pages 3011–3014. The specific long time signal of XL-665, produced only when the IGF1R enzyme is autophosphorylated, was measured on a Victor analyser (Perkin-elmer). Inhibition of IGF1R kinase activity with compounds of the invention was expressed as percentage inhibition of control activity exhibited in the absence of test compounds.

2. Proliferation/Viability of Human Breast Carcinoma MCF-7 Cells as Measured by [$^{14}$C] Thymidine Uptake 2.1 Cell Culture, Labelling of MCF-7 Cells and Performance of Assay.

The antiproliferative effect of the molecules on MCF-7 cells was evaluated by [$^{14}$C]-thymidine uptake 72 hours after IGF1-induced cell proliferation.

MCF-7 cells were seeded at 25,000 cells per well in Cytostar 96-multiwell plates (Amersham) at 37° C., 5% $CO_2$, at day 1, left overnight in EMEM medium supplemented with 10% of FCS to allowed cell attachment. At day 2, the medium culture was changed for EMEM/HamF12, 50/50 in order to deprivated the cells for 24 H. On day 3, cell medium was replaced by fresh EMEM with 1% of sodium pyruvate, penicillin, streptamicin and 50 ng/ml final concentration of IGF1. Then, 0.1 µCi of [$^{14}$C]-Thymidine and 3 µl of compounds were added in 213 µl final volume. Cells were incubated at 37° C., 5% $CO_2$ for 72 hours. [$^{14}$C]-Thymidine uptake was quantified by counting the radioactivity 72 hours after IGF1-induced proliferation (Microbeta trilux counter, Perkin-elmer). IC50 determination were performed in duplicate with 10 increasing concentrations.

2.2 Calculation of Results (i) The mean±s.e.m. of each set of duplicate wells was calculated.

(ii) Maximum response signal value was calculated from the positive control wells containing cells stimulated by IGF1 but no compound.

(iii) Minimum response signal value was calculated from the control wells containing cells unstimulated by IGF1 and no compound.

(iv) Using these values as the maximum (100%) and minimum (0%) values respectively, the data were normalized to give a percentage of the maximum response.

(v) A dose response curve of 10 points was plotted and the $IC_{50}$ (the concentration of drug that induces a 50% decrease in specific signal) of the compound was calculated by non-linear regression analysis.

3. IGF1R Autophosphorylation in MCF7 Cell Line After IGF1 Stimulation 3.1 Cell Culture and Performance of Assay.

IGF1-induced IGF1R autophosphorylation in cells was evaluated by ELISA technique. MCF-7 cells were seeded at 600 000 cells per well in 6-multiwell plates, left over night in 10% serum and then serum-starved for 24 h. Compounds are added to medium 1 h before IGF1 stimulation. After 10 min of IGF1 stimulation, cells are lysed with Hepes 50 mM pH7.6, Triton X100 1%, Orthovanadate 2 mM, proteases inhibitors. Cell lysates are incubated on 96-multiwell plates pre-coated with anti-IGF1R antibody, followed by incubation with an anti-phosphotyrosine antibody coupled to peroxydase enzyme. Peroxidase activity level (measured by OD with a luminescent substrate) reflects receptor phosphorylation status.

3.2 Calculation of Results (i) The mean±s.e.m. of each set of duplicate wells was calculated.

(ii) Maximum response signal value was calculated from positive control wells containing lysates of cells stimulated by IGF1 but no compound.

(iii) Minimum response signal value was calculated from the control wells containing lysates of unstimulated cells and no compounds.

(iv) Using these values as the maximum (100%) and minimum (0%) values respectively, the data were normalized to give a percentage of the maximum response.

(v) A dose response curve was plotted and the $IC_{50}$ (the concentration of drug that induces a 50% decrease in OD measure) of the compound was calculated.

II) In Vitro Test Procedures for Fak

1. Inhibitory Effects of Compounds on Fak

Inhibitory effects of compounds on Fak kinase—autophosphorylation assay—were determined using a time-resolved fluorescent assay.

The full length cDNA of human enzyme has been cloned into the pFastBac HTc baculovirus expression vector. The protein has been expressed and purified to about 70% homogeneity.

Kinase activity was determined in 50 mM Hepes pH 7.2 containing 10 mM $MgCl_2$, 100 µM $Na_3VO_4$, 15 µM adenosine triphosphate. Enzyme reactions were terminated by the addition of Hepes buffer pH 7.0, containing 0.4 M KF, 133 mM EDTA, BSA 0.1% containing an anti-6His antibody labelled with XL665 (Fak is His-tagged) and a monoclonal tyrosine phosphospecfic antibody conjugated to a europium cryptate (Eu—K). Features of the two fluorophores, XL-665 and Eu—K are given in G. Mathis et al., Anticancer Research, 1997, 17, pages 3011–3014. The specific long time signal of XL-665, produced only when the Fak enzyme is autophosphorylated, was measured on a Packard Discovery Microplate analyzer. Inhibition of Fak activity with compounds of the invention was expressed as percentage inhibition of control activity exhibited in the absence of test compounds.

2 Migration of Human Cervical Hela Cells on Fibronectin Matrix 2.1 Cell Culture and Performance of Assay.

Hela (100,000 cells) were stained with DiIC12 (Interchim, catalog number D-383) for 2 h at 37° C., 5% $CO_2$, pretreated with increasing concentrations of compounds for 30 min at 37° C., 5% $CO_2$. They were then loaded in presence of the compound on the upper side of 8 µm 24-multiwell chemotaxis Boyden chambers (Becton Dickinson Falcon HTS FluoroBlock insert systems, catalog number 351158) and allowed to migrate to the lower chamber containing fibronectin (10 µg/ml) as chemoattractant in basal DMEM culture medium for 24 hours at 37° C., 5% $CO_2$. Cell migration was quantified by fluorescence measurement. Assays were performed in three replicate wells.

2.2 Calculation of Results (i) The mean±s.e.m. of each set of triplicate wells was calculated.

(ii) Maximum response was positive control wells containing cells but no compound and allowed to migrate on fibronectin.

(iii) Minimum response was the control wells containing cells but no compound and allowed to migrate on basal culture medium w/o chemoattractant.

(iv) Using these values as the maximum (100%) and minimum (0%) values respectively, the data were normalized to give a percentage of the maximum response.

(v) A dose response curve was plotted and the $IC_{50}$ (the concentration of drug that induces a 50% decrease in cell migration) of the compound was calculated.

III) 1. In Vitro Enzyme Assays 1.1 JNK Enzyme Assays 1.1.1 $[^{33}P]$-ATP Method Compounds were assessed for their abilities to suppress JNK1 activity in a filtration assay in which incorporation of the γ-phosphate from $[\gamma\text{-}^{33}P]$ ATP into GST-c-Jun substrate was measured. Compounds (0.001 µM–30 µM) were incubated with GST-c-Jun (0.5 µM), JNK1 (0.1 µM) and $[\gamma\text{-}^{33}P]$ ATP (6 µM) for 30 min in 96 well phosphocellulose microtitre plates (Millipore, MAPH NOB 10) before addition of phosphoric acid (1%) to stop the incubation. The plates were incubated at room temperature for a further 5 min before vacuum was applied to draw the assay mix through the filter. The filters were then washed five times with 100 µl phosphoric acid (1%), blotted dry on tissue paper and dried completely in a Millipore adapter cassette. Twenty-five microlitres of Microscint scintillant (Packard) were added to each well and the plate sealed with a plate sealer. The incorporation of $[^{33}P]$-ATP into c-Jun was measured on a Packard Topcount.

1.1.2 Homogenous Time-Resolved Fluorescence Method

The assay is based on homogeneous time resolved fluorescence (HTRF) technology, which relies on the non-radioactive energy transfer between a europium cryptate donor and an XL665 acceptor. GST-ATF2 substrate is incubated with JNK3 enzyme, and the addition of ATP initiates the enzymatic reaction. A mixture of XL665 labeled anti-GST antibody and cryptate labeled anti-phospho-ATF2 antibody is added to determine the extent of substrate phosphorylation. The interaction between the XL665 labeled anti-GST antibody/phosphorylated GST-ATF2 complex and the cryptate labeled anti-Phospho-ATF2 antibody induces a resonance energy transfer from cryptate to XL665, which is proportional to the phosphorylation of the substrate. The fluorescent emissions are read on an LJL Acquest at 665 nm and 620 nm, and the ratio of the two values is reported. Active compounds inhibit the enzymatic activity of JNK3, which is reflected by a decrease of the 665 nm/620 nm ratio. The enzyme reaction is run in 15 µl final volume in 384-well format. Each well contains 1.75 µg/ml JNK3, 25 mM Hepes (pH 7.4), 100 µM magnesium chloride, 0.05% Triton-X-100, 10 mM DTT, 5% glycerol, 18.2 uM ATP, and 96 nM GST-ATF2 substrate. The enzyme used was human $(His)_6$-

JNK3α2, produced in yeast by Aventis Core Biotech, Vitry, France (Batch # HUM414, 0.685 mg/ml). The enzyme had an apparent molecular weight of 56,600 Da. Following incubation for 30 minutes at 37° C., 24µl of 2.5 µg/ml anti-GST-XL and 0.10 µg/ml of anti-phospho-ATF2-cryptate antibodies are added and the plates are incubated for a further 2 hours at room temperature. GST-ATF2 was produced in E. Coli (molecular weight of 38,867 Da) by Aventis Core Biotech, Vitry, France, Batch # JCE3224, 1.1 mg/ml). Antibodies were obtained from CIS Bio as follows: anti-phospho-ATF2-cryptate antibody, Lot # 004, 310 ug/ml; anti-GST-XL665 antibody, Lot # 012, 250 µg/ml.

HTRF readings were taken on the LJL Acquest reader. In cases where inhibitory activities of compounds are to be measured, the desired concentrations of the test compound are included in the enzyme reaction (usually $10^{-4}$ to $10^{-9}$ M). Potency of test compounds is represented by their $IC_{50}$ values as determined by non-linear regression analysis using Activity Base Software (IDBS Ltd).

2. cJun Phosphorylation Assay

Compounds were assessed for their abilities to suppress phosphorylation of the transcription factor c-Jun using previously published methodology (Hazzalin et al., 1996). Phosphorylation on two serine residues ($Ser^{63}$ and $Ser^{73}$) results in reduced electrophoretic mobility on polyacrylamide gels. Thus, the non-phosphorylated and phosphorylated c-Jun species migrate differently and this can be detected following polyacrylamide gel electrophoresis by Western blotting with an anti-c-Jun specific antibody.

Compounds were tested on C3H10T1/2 mouse fibroblasts which were grown in Dulbecco's modified Eagle's medium (DMEM) with 10% (vol/vol) foetal calf serum (FCS). Confluent cells were made quiescent by incubation for 18 to 24 hours in DMEM containing 0.5%. Serum-starved C3H10T1/2 cells were pretreated with compounds (0.01–10 µM) or vehicle (dimethyl sulfoxide) for 30 minutes prior to stimulation with anisomycin (50 ng/ml) for a further 30 minutes. Whole cell extracts were prepared and resolved on 15% polyacrylamide gels (without SDS). Non-phosphorylated and phosphorylated cJun was detected by Western blotting and enhanced chemoluminescence with anti-phospho c-Jun antibody (Santa Cruz).

3. Measurement of Cellular JNK Inhibition in 3T3 Fibroblasts

The fibroblast cell line (3T3 cells) was obtained from the American Type Tissue Collection and grown in monolayer culture as directed by the supplier. On the day of the experiment, the JNK pathway was activated by exposing cells to 15 ng/mL anisomycin for 2 hours in the cell culture incubator. Test compounds were assessed by preincubating indicated concentrations (1 nM to 30 µM) for 1 hour prior to anisomycin addition. The reaction was terminated by aspirating the culture media, followed by solubilizing the cell monolayer in electrophoresis sample loading buffer.

A portion of each sample (7.5–15 µl) was loaded on a Novex polyacrylamide Tris-glycine 4–12% gradient gel (#EC60355). Gels were run at 150–200V for 1–1.5 hours until the lowest molecular weight marker runs off gel. The protein of interest (c-Jun) migrates at approximately 39 kDa. The proteins were transferred to a PVDF membrane (Imobilon P, Fisher Scientific catalog # 1PVH15150) using a Hoeffer semi-dry transfer protocol for 1 hour with voltage to maximum and current set to 200 mA. After transfer, membranes were washed for 5' in Tris buffered saline (TBS) containing 1% Tween. The membranes were blocked for 1 hour at room temperature in block buffer (5% Carnation's non-fat dry milk-1% tween 20-TBS). The block buffer was then removed and blots were incubated with primary antibody (Santa Cruz Biotechnology #sc-822) 1:2000 dilution (diluted in block buffer) overnight at 4° C. This primary is a mouse monoclonal directed against a peptide corresponding to amino acids 56–69 of c-Jun of human origin. After primary antibody incubation, membranes were washed twice at room temperature for 30 minutes in TBS containing 1% Tween. Membranes were then incubated for 1 hour with the secondary antibody (Cell Signaling goat anti-mouse IgG #7076) at 1:10,000 dilution in block buffer. The membranes were washed twice for 30 minutes each in TBS containing 1% Tween. Blots were then developed using Pierce Super Signal West Femto luminol/enhancer solution (Pierce#1856189 and #1856190) at 1:1 dilution for 5 minutes. Excess solution was removed; membranes were placed between two transparencies, exposed to film and developed.

4. In Vitro Inhibitory Effects on TNF-Alpha Release by Human Monocytes

The effects of compounds on TNF-alpha production by human peripheral blood monocytes (PBMs) are examined as follows.

4.1 Preparation of Human Peripheral Blood Monocytes

Freshly drawn blood from normal healthy donors was mixed (4:1, v/v) with sodium citrate (3.8%, w/v). Mononuclear cells were prepared by centrifugation of the blood on Histopaque-1077 (Sigma Diagnostics) according to manufacturers instructions. The fraction enriched with mononuclear cells was washed and resuspended in Hank's balanced salts solution (HBSS) supplemented with deoxyribonuclease (37.5 U/ml) and human serum albumin (0.3%). Differential (cytospin) cell counts revealed that the monouclear cell fraction routinely comprised 70–80% monocytes.

Cells from the mononuclear leukocyte fraction were centrifuged (200 g, 10 min, 20° C.), resuspended, at a density of $10^6$ cells/ml, in RPMI 1640 containing foetal calf serum (FCS) (1%), penicillin (50 U/ml) and streptomycin (50 µg/ml) and allowed to adhere in 96 well plates. Following incubation (5% $CO_2$, 37° C.) for 90 min, medium containing non-adherent cells was removed and the cells were washed once with fresh medium.

4.2 Measurement of Monocyte TNF-Alpha Release

Adherent cells in culture medium were incubated for 1 h (5% $CO_2$, 37° C.) with fresh medium containing compounds or vehicle (0.1% dimethylsulfoxide). Compounds were tested within the concentration range of $3\times10^{-9}$M to $3\times10^{-6}$M. LPS (10 ng/ml) was then added to the cells and the incubation continued for a further 18 hours. Cell supernatants were removed into 96 well, 0.22 µm filtration plates for storage at −20° C.

TNF-alpha concentrations in cell supernatants were quantified by sandwich ELISA. Briefly, ELISA plates were coated overnight with 2 µg/ml of mouse anti-human TNF-alpha antibody in bicarbonate buffer (pH 9.9). After washing the wells with wash buffer (0.05% (v/v) Tween in PBS), and blocking unoccupied sites (1% BSA in), monocyte supernatant samples or human recombinant TNF-alpha standards were vacuum filtered into the corresponding wells of the ELISA plate. Biotinylated rabbit polyclonal anti-human TNF-alpha antibody (3 µg/ml) was used as the second antibody and streptavidin-horseradish peroxidase was used as the detection antibody. The peroxidase substrate was 3,3',5,5'-tetramethylbenzidine (TMB), in the presence of hydrogen peroxide.

TNF-alpha concentrations in supernatants from control and LPS-stimulated monocyte incubations were calculated by interpolation from a standard (log/log) curve (0.125–16 ng/ml) fitted by linear regression using a Multicalc software program (Wallac U.K., Ltd).

5. Inhibitory Effects of Compounds on Serum TNF-Alpha Levels in LPS-Challenged Mice 5.1 Treatment of Animals and Measurement of Murine TNF-Alpha Female Balb/c mice (age 6–8 weeks, weight 20–22 g from Charles River, U.K.) in groups of five or more animals are dosed p.o. with compounds (1 to 100 mg/kg) suspended in 1.5% (w/v) carboxymethyl cellulose then challenged after a minimum period of 30 minutes with 30 mg of LPS i.p. After 90 minutes the animals are killed by carbon dioxide asphyxiation and bled by cardiac puncture. Blood is allowed to clot at 4° C., centrifuged (12,000 g for 5 minutes) and serum taken for TNF-alpha analysis. TNF-alpha levels are measured using a commercially available murine TNF-alpha ELISA kit, purchased from Genzyme (Cat. no. 1509.00), as recommended by the manufacturer. Values for TNF-alpha are calculated from a recombinant murine TNF-alpha standard curve.

6. Inhibitory Effects on IgE Release from Human Tonsillar B-Lymphocytes 6.1 Isolation of Human B-Lymphocytes Human tonsils were obtained from patients undergoing routine tonsillectomy in a local hospital. They were than dissected and mononuclear cells isolated by buoyant density centrifugation over Histopaque. Isolated cells were 70–80% B-lymphocytes, 20–30% T-lymphocytes and <2% NK cells. T-lymphocytes were depleted by rosetting with sheep red blood cells, leaving the remaining cell population as being >98% pure B cells.

6.2 B-Lymphocyte Incubations and Measurement of IgE

B-lymphocytes were cultured at $1 \times 10^5$ cells/well and resuspended in 200 µl IMDM/10% FCS together with interleukin (IL)-4 (200 U/ml) and anti-CD40 (0.5 µg/ml) for 7 days at 37° C. Samples from the incubations were removed, cell debris removed by centrifugation (1000 g, 5 min) and IgE in the supernatants was measured by sandwich ELISA.

6.3 Detection of IgE

Micrititre plates (Costar EIA/RIA) were coated overnight at 4° C. with 5 µg/ml of anti-IgE (clone 577 C1) in carbonate buffer (pH 9.6). Plates were then washed (PBS/0.1% Tween) and subsequently blocked for 30 min. at room temperature, with PBS/3% BSA (200 µl/well). After washing, IgE standards (0–1000 I.U/ml: 1 I.U is equivalent to 2.4 ng/ml IgE) and cell culture supernatents (diluted 1:10) were added (100 µl/well: 1.5 h at 37° C.). The secondary antibody (alkaline phosphatase conjugated goat anti human IgE) was then added (1:500) and incubated for 1 h at 37° C. (100 µl/well). After a final wash, the substrate solution (p-Nitrophenyl phosphate) was added (100 µl/well: 1 mg/ml) and incubated for 30 min at room temperature. Finally, the reaction was stopped by the addition of 3M NaOH and the absorbance was read at 405 nm using the Labsystems Multiskan MCC/340 plate reader.

7. Effect of JNK Inhibitors on Cytotoxicity in Cerebellar Granule Cells

Recent results (*Dev. Br. Res.* 112, 245–253, 1999) have suggested that activation of the PI3K-Akt signaling pathway prevents neuronal death in cerebellar granule cells by inhibiting the activation of JNK and the expression of c-jun. LY294002 is a reversible inhibitor of PI3K and activates JNKs with subsequent cell death. We have investigated the ability of the JNK inhibitors to protect against LY294002-induced cell death in a cerebellar granule cell preparation.

Primary cerebellar cell cultures were prepared from 7-day-old Sprague-Dawley rats. Cerebella were carefully collected, dissected free of meninges and cut into 5–7 parts. Tissues were gently mechanically dissociated after digestion with VERSENE (5 minutes, 37° C.). The cells were seed onto 96-well plates pre-coated with poly-D-lysine (Becton-Dickinson) at a final density of $10^5$ cells per well. Cultures were maintained at 37° C. in a humidified atmosphere with 5% $CO_2$ and used after the $9^{th}$ day of culture in DMEM medium complemented with 5% fetal calf serum, 5% horse serum and 30 mM potassium chloride in the presence of an anti-mitotic (10 µM cytosine arabinoside). The drugs were directly added to the culture at the indicated concentrations for 24 hours. Neuronal viability was assessed quantitatively by the colorimetric measurement of Mosmann or MTT assay (1983, J. Immunol. Methods, 65, 55–63). Each condition was tested in sextuplicate or triplicate and the mean values obtained analyzed statistically by one-way ANOVA, followed by Dunnett's multiple comparison test.

LY294002, an inhibitor of PI3K, induced neuronal death when added to rat cerebellar granule neurons cultured in medium containing high potassium (FIG. 1). LY294002-induced cell death is more reproducible in cells that were maintained in culture for 8 or more days. The dose response for LY294002-induced toxicity was examined by adding 3–100 µM of LY294002 to cultured cerebellar granule cells (FIG. 1). To observe a neuroprotective effect with Example 9(a), cerebellar granule cells must be used after 9 days of culture. This is consistent with the increase of the expression of JNK during postnatal development. Example 9(a) produces a dose-dependent protection against LY294002 (30 µM)-induced toxicity with an $IC_{50}$ of 7 µM (FIG. 2).

8. Measurement of JNK Inhibition In Vivo

Male Wistar Rats are housed individually until the start of the experiments, at which point animals are housed in groups of 5 on a 12 hour light/dark schedule. Water and food were available ad libitum. All experimental procedures were performed with approved institutional animal research protocols. Drugs or vehicle can be administered s.c., i.p., or i.v. at varying timepoints before, after, or both before and after administration of kainic acid (10 mg/kg in sterile water, i.p). In certain cases drugs were administered directly into the brain by means of cannulae are implanted into the left lateral ventricle. Animals are observed, scored for seizure severity and then euthanized at different timepoints for evaluation of the amount of total and phosphorylated c-Jun.

This method can also be performed in mice. Male C57BL/6 mice (20–25 g) were purchased from Charles River Laboratories. All mice were housed in groups of 5 on a 12 hour light/dark schedule. Water and food were available ad libitum until the day of the experiment. All experimental procedures were performed with approved institutional animal research protocols. Kainic acid is dissolved in water and injected I.P. at 30 mg/kg. Compound or vehicle can be administered s.c., i.p., i.v., or i.c.v., before, after, or both before and after kainic acid administration. Animals are scored for seizure severity, and then euthanized at different timepoints after administration of kainic acid to evaluate the amount of total and phosphorylated c-Jun.

After euthanasia, hippocampi are rapidly dissected out, weighed, and flash frozen on dry ice. Hippocampi are then disrupted by sonication at a tissue concentration of 120 mg dry weight per ml for rat, 60 mg/ml for mice using 50 mM Tris pH 7.4, 1% tween-20, plus a protease inhibitor cocktail (Boehringer). Samples are then incubated on ice for 30 minutes, then spun for 13,500 rpm, 30 minutes at 4° C. Samples are pooled (60 mg for rats, or 30 mg for mice) to a total volume of 500 µl per sample. Total c-Jun is immunoprecipitated with 5 µg mouse anti c-Jun (Becton Dickenson) and protein A Sepharose (Amersham) overnight. Similarly, phosphorylated c-Jun is immunoprecipitated with 5 µg mouse anti-phospho(serine 63) c-Jun (Santa Cruz) and protein A Sepharose (Amersham) overnight. The following morning, samples are washed 3 times with 20 mM HEPES pH 7.4, 2 mM magnesium chloride, 1 mM EDTA. Samples are then denatured in 4× NuPAGE LDS sample buffer (Invitrogen) by heating for 10 minutes at 70° C. Samples are then resolved by electrophoresis on 10% Tris-Bis NuPAGE gels in MOPS buffer at 200 volts for 1 hour. The proteins are then transferred onto PVDF membranes in Tris-glycine-methanol for 1.5 hours. Membranes are blocked in 5% milk in PBS, 0.5% tween-20 for 1 hour, then incubated overnight at 4° C. with 1:1000 anti c-Jun antibody (Cell Signaling Technologies). Blots are washed 3 times with PBS-Tween and incubated for 1 hour with 1:10,000 anti rabbit HPR. Finally, the blots are washed 3 times with PBS-Tween and the images developed using West Femto Maximum Luminol reagent. Images are captured and analyzed on a Kodak Image Station (NEN).

9. Models of Focal Cerebral Ischemia

Rats (Charles River) are housed 3 per cage with water and food freely available 3 days before use. All surgical procedures are carried out using aseptic conditions and sterilized instruments. Rats weighing 250–350 g, are initially anaesthetized with 5% (v v$^{-1}$) isoflurane, 30% (v v$^{-1}$) oxygen and 70% (v v$^{-1}$) nitrous oxide and maintained with 1–2% isoflurane by means of a nose cone. Body temperature is maintained at 37° C. by a heating pad placed under the animal and the temperature is monitored (BAT-10 thermometer, Physitemp, Clifton, U.S.A.) throughout the surgery with a rectal temperature probe.

9.1 Permanent Middle Cerebral Artery Occlusion (MCAo) by Coagulation

This model of permanent MCAo is performed based on a modified technique described by Tamura et al., 1981. Rats are placed in a lateral position under an operating microscope. A curved vertical incision approximately 3 mm in length is made between the animal's right orbit and external auditory canal. The temporalis muscle is deflected to allow access for the craniotomy, which is made 3 mm anterior and 1 mm lateral to the foramen ovale with a dental drill. The dura is incised and the right middle cerebral artery (MCA) exposed and coagulated approximately 2 mm proximal to the olfactory tract by bipolar electrocoagulation with fine forceps (Vetroson, V-10 Bi-polar electrosurgical unit, Summit Hill Laboratories, Navesink, N.J., U.S.A.). After coagulation, the artery is cut to avoid re-canulization. The craniotomy is covered with bone wax, the muscle allowed to fall back into place and the wound is sutured.

9.2 Model of Transient Focal Cerebral Ischemia by Intraluminal Filament

The transient model of MCAo is performed based on the technique described by Belayev et al., 1996. The rats are anesthetized as described above. The right common, internal and external carotid arteries are isolated with 5-0 silk suture (Deknatel, Fall River, Mass. 02720, U.S.A.). During surgery the pressure on the right common artery is released to allow reperfusion every 2–4 minutes. The right superior thyroid artery is isolated and cauterized, while the external carotid is ligated distally with a 5-0 silk suture. Another 5-0 silk suture is loosely tided around the base of external carotid artery. The occipital artery is isolated next ligated with two 5-0 silk sutures and cauterized. The internal carotid and pterygopalatine arteries are then isolated and the pterygopalatine artery about 1 mm below the bifurcation of the internal carotid artery is ligated with a 5-0 silk suture. With the common and external carotid arteries immobilized, an aneurysm clip is placed onto the internal carotid artery. A small incision is made at the distal end of the external carotid. A 3-0 or 4-0 nylon suture approximately 30 mm long, coated with poly-L-lysine (Sigma St. Louis, Mo. 63178, U.S.A.) is then inserted into the external carotid artery and extended into the common carotid artery. The loosely tied 5-0 silk suture around the external carotid is now gently tightened around the monofilament. The remaining piece of the external carotid artery with the filament is rotated so that the monofilament could be inserted into the lumen of the internal carotid artery. After the insertion of 18 to 22 mm of the monofilament into the lumen of the internal carotid artery (dependent upon the weight of the animal) the blood flow to the MCA is blocked. The neck incision is then closed with 5-0 silk suture using an interrupted stitch. After removal of the temperature probe and discontinuation of the anesthesia, the animal is allowed to awaken. Two hours after MCAo the rat is then re-anesthetized with the same anesthetic combination used initially and placed back into the nose cone. The neck incision is re-opened to expose the external and common carotid artery as described above. The restoration of blood flow is accomplished by completely withdrawing the intraluminal monofilament from the external carotid artery and tightening the suture around the external carotid artery. The incision is then sutured closed with 5-0 silk with an interrupted stitch as before. The rat is allowed to awaken from anesthesia and returned to the cage.

9.3 Model of Permanent Focal Cerebral Ischemia Using an Intraluminal Filament

This model of permanent MCAo, originally described by Longa et al., 1989 and modified by Belayev et al., 1996, is similar in technique to that described above for the transient MCAo model. The difference is that once the monofilament is inserted into the internal carotid artery to occlude the MCA, the animal is sutured and allowed to awaken. The filament is never removed and animals are sacrificed 24 hours after MCAo.

Determination of Infarct Volume

Animals are euthanized under isofluorane anesthesia (5% in 70% $N_2O$ and 30% $O_2$) for 5 minutes. Following decapitation, the brains are rapidly removed, cut into seven 2 mm coronal sections by use of a rat brain matrix (RBM 4000C, ASI Instruments), stained with 2,3,5-triphenyltetrazolium chloride and then fixed in buffered formalin. The slices are individually captured electronically as digitized images using the MCID Imaging software (MCID M5+, Imaging Research, Inc.). Infarction areas of the digitized images are calculated using AIS software (Analytic Imaging Software, Imaging Research Inc.). The 7 slice areas per brain are summed for volumetric analysis as both a direct infarction volume (mm$^3$) or indirect volume (% Infarction) to compensate for edema formation in the ipsilateral hemisphere (Swanson et al., 1990).

What is claimed is:

1. A compound of general formula (I):

$$\text{(I)}$$

optionally further substituted in the saturated ring by one or more alkyl substituents, in which:

$R^1$ represents hydrogen, $R^4$, —C(=Y)—NHR$^4$, —SO$_2$NHR$^4$, —C(=Z$^1$)-R$^4$, —SO$_2$—R$^4$ or —C(=Z$^1$)-OR$^4$;

$R^2$ represents hydrogen, cyano, halogen or —C≡C—R$^5$;

$R^3$ represents hydrogen, acyl, alkoxycarbonyl, alkyl, aroyl, aryl, aryloxycarbonyl, carboxy, cycloalkenyl, cycloalkyl, heteroaroyl, heteroaryl, heterocycloalkyl or —C(=O)—NY$^1$Y$^2$;

$R^4$ represents alkyl, cycloalkyl, cycloalkenyl or heterocycloalkyl each optionally substituted by one or more groups selected from aryl, cycloalkenyl, cycloalkyl, heteroaryl, heterocycloalkyl, —C(=O)—OR$^8$, —C(=O)—R$^9$, —C(=O)—NY$^3$Y$^4$, —NY$^1$Y$^2$, —N(R$^{10}$)—C(=O)—R$^9$, —N(R$^{10}$)—C(=O)—OR$^9$, —N(R$^{10}$)—SO$_2$—R$^9$ or -Z$^2$R$^8$; or R$^4$ represents aryl or heteroaryl each optionally substituted by one or more groups selected from alkylenedioxy, alkenyl, alkenyloxy, alkynyl, aryl, cyano, halo, hydroxy, heteroaryl, heterocycloalkyl, nitro, R$^7$, —C(=O)—NY$^3$Y$^4$, —C(=O)—OR$^8$, —C(=O)—R$^{11}$, —NY$^3$Y$^4$, —N(R$^{10}$)—C(=O)—R$^9$, —N(R$^{10}$)—C(=O)—NY$^5$Y$^6$, —N(R$^{10}$)—C(=O)—OR$^9$, —N(R$^{10}$)—SO$_2$—R$^9$, —N(R$^{10}$)—SO$_2$—NY$^5$Y$^6$, —SO$_2$—NY$^3$Y$^4$ and -Z$^2$R$^{12}$;

$R^5$ represents hydrogen or alkyl;

$R^6$ represents alkyl, acyl, alkoxycarbonyl, alkylsulfonyl, aryl, arylsulfonyl, aroyl, cycloalkyl, cycloalkenyl, heteroaryl, heteroarylsulfonyl, heteroaroyl and heterocycloalkyl;

$R^7$ represents alkyl, cycloalkyl or cycloalkylalkyl each optionally substituted by one or more substituents selected from aryl, cycloalkyl, cyano, halo, heteroaryl, heterocycloalkyl, hydroxy, —CHO (or a 5-, 6- or 7-membered cyclic acetal derivative thereof), —C(=O)—NY$^1$Y$^2$, —C(=O)—OR$^8$, —NY$^3$Y$^4$, —N(R$^{10}$)—C(=O)—R$^9$, —N(R$^{10}$)—C(=O)—NY$^3$Y$^4$, —N(R$^{10}$)—SO$_2$—R$^9$, —N(R$^{10}$)—SO$_2$—NY$^3$Y$^4$ and —OR$^9$;

$R^8$ represents hydrogen, alkyl, alkenyl, aryl, arylalkyl, heteroaryl or heteroarylalkyl;

$R^9$ represents alkyl, aryl, arylalkyl, cycloalkyl, cycloalkylalkyl, heteroaryl, heteroarylalkyl, heterocycloalkyl or heterocycloalkylalkyl;

$R^{10}$ represents hydrogen or lower alkyl;

$R^{11}$ represents alkyl, aryl, arylalkyl, cycloalkyl, cycloalkylalkyl, heteroaryl, heteroarylalkyl, heterocycloalkyl or heterocycloalkylalkyl; or alkyl optionally substituted by —NY$^1$Y$^2$;

$R^{12}$ represents aryl or heteroaryl; or alkyl, cycloalkyl, cycloalkylalkyl, heterocycloalkyl or heterocycloalkylalkyl each optionally substituted by one or more substituents selected from aryl, cycloalkyl, cyano, halo, heteroaryl, heterocycloalkyl, hydroxy, —CHO (or a 5-, 6- or 7-membered cyclic acetal derivative thereof), —C(=O)—NY$^1$Y2, —C(=O)—OR$^8$, —NY$^1$Y$^2$, —N(R$^{10}$)—C(=O)—R$^9$, —N(R$^{10}$)—C(=O)—NY$^3$Y$^4$, —N(R$^{10}$)—SO$_2$—R$^9$, —N(R$^{10}$)—SO$_2$—NY$^3$Y$^4$ and —OR$^9$;

Y represents O, S or NCN;

$Y^1$ and $Y^2$ are independently hydrogen, alkyl, aryl, cycloalkyl, cycloalkenyl, heteroaryl or heterocycloalkyl; or the group —NY$^1$Y$^2$ may form 5–7 membered ring which optionally contains an additional heteroatom selected from O, S or NR$^6$;

$Y^3$ and $Y^4$ are independently hydrogen, alkenyl, aryl, cycloalkyl, heteroaryl or alkyl optionally substituted by one or more groups selected from aryl, halo, heteroaryl, hydroxy, —C(=O)—NY$^5$Y$^6$, —C(=O)—OR$^8$, —NY$^5$Y$^6$, —N(R$^6$)—C(=O)—R$^9$, —N(R$^6$)—C(=O)—NY$^5$Y$^6$, —N(R$^6$)—SO$_2$—R$^9$, —N(R$^6$)—SO$_2$—NY$^5$Y$^6$ and —OR$^9$; or the group —NY$^3$Y$^4$ may form a cyclic amine;

$Y^5$ and $Y^6$ are independently hydrogen, alkenyl, alkyl, aryl, arylalkyl, cycloalkyl, heteroaryl or heteroarylalkyl; or the group —NY$^5$Y$^6$ may form a cyclic amine;

Z represents O or S;

$Z^1$ represents O or S;

$Z^2$ represents O or S(O)$_p$;

n is zero or an integer 1 or 2;

m is 1 or 2;

p is 1 or 2;

and the corresponding N-oxides, and the prodrug esters and the pharmaceutically acceptable salts and hydrates of compounds of formula (I) and their N-oxides and their prodrug esters.

2. The compound according to claim 1, of formula (Ia):

$$\text{(Ia)}$$

in which R$^2$, R$^3$, R$^4$ and Y are as hereinbefore defined; and the corresponding N-oxides, and the prodrug esters; and pharmaceutically acceptable salts and solvates of compounds of formula (Ia) and their N-oxides and their prodrugs esters.

3. The compound according to claim 1, of formula (Ib):

$$\text{(Ib)}$$

in which R$^2$, R$^3$ and R$^4$ are as hereinbefore defined; and the corresponding N-oxides, and the prodrugs esters; and pharmaceutically acceptable salts and solvates of compounds of formula (Ib) and their N-oxides and their prodrugs esters.

4. The compound according to claim 1, of formula (Ic):

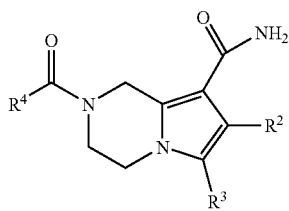

(Ic)

in which $R^2$, $R^3$ and $R^4$ are as hereinbefore defined; and the corresponding N-oxides, and the prodrugs esters; and pharmaceutically acceptable salts and solvates of compounds of formula (Ic) and their N-oxides and their prodrugs esters.

5. The compound according to claim 1, of formula (ICC):

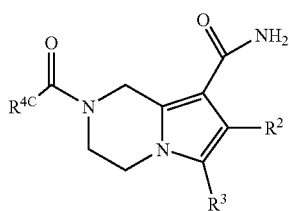

(ICC)

in which $R^2$, $R^3$ and $R^{4C}$ represent NHR4 with $R^4$ as hereinbefore defined; and the corresponding N-oxides, and the prodrugs esters; and pharmaceutically acceptable salts and hydrates of compounds of formula (Ic) and their N-oxides and their prodrugs esters.

6. The compound according to claim 1, of formula (Id):

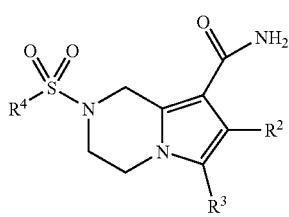

(Id)

in which $R^2$, $R^3$ and $R^4$ are as hereinbefore defined; and the corresponding N-oxides, and the prodrugs esters; and pharmaceutically acceptable salts and solvates of compounds of formula (Id) and their N-oxides and their prodrugs esters.

7. The compound according to claim 1, of formula (Ie):

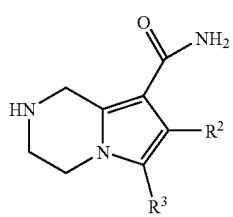

(Ie)

in which $R^2$ and $R^3$ are as hereinbefore defined; and the corresponding N-oxides, and the prodrugs esters; and pharmaceutically acceptable salts and solvates of compounds of formula (Ie) and their N-oxides and their prodrugs esters.

8. The compound according to claim 1, of formula (If):

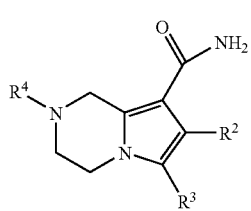

(If)

in which $R^2$, $R^3$ and $R^4$ are as hereinbefore defined; and the corresponding N-oxides, and the prodrugs esters; and pharmaceutically acceptable salts and solvates of compounds of formula (If) and their N-oxides and their prodrugs esters.

9. A pharmaceutical composition comprising, as active principle, at least one compound according to claim 1.

10. A method of treating asthma, comprising: administering to a patient in need thereof an effective dose of a compound according to claim 1.

* * * * *